US007638526B2

(12) United States Patent  
McKittrick et al.

(10) Patent No.: US 7,638,526 B2
(45) Date of Patent: Dec. 29, 2009

(54) AZETIDINE DERIVATIVES USEFUL IN TREATING PAIN, DIABETES AND DISORDERS OF LIPID METABOLISM

(75) Inventors: Brian A. McKittrick, New Vernon, NJ (US); Elizabeth M. Smith, Verona, NJ (US); Chad E. Bennett, Metuchen, NJ (US); Joel M. Harris, Summit, NJ (US); Eugenia Y. Kiselgof, Flemington, NJ (US); Chad E. Knutson, Garwood, NJ (US); Peter Korakas, Bound Brook, NJ (US); Deen Tulshian, Lebanon, NJ (US); Hyunjin Kim, Livingston, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/854,600

(22) Filed: Sep. 13, 2007

(65) Prior Publication Data

US 2008/0089858 A1    Apr. 17, 2008

Related U.S. Application Data

(60) Provisional application No. 60/845,077, filed on Sep. 15, 2006.

(51) Int. Cl.
*A61K 31/438*   (2006.01)
*C07D 471/10*   (2006.01)

(52) U.S. Cl. ........................ 514/278; 546/16
(58) Field of Classification Search ............ 514/210.16, 514/226.5, 278; 544/230, 70; 546/16
See application file for complete search history.

(56) References Cited

U.S. PATENT DOCUMENTS

| | | | |
|---|---|---|---|
| 5,624,920 | A | 4/1997 | McKittrick et al. |
| 5,633,246 | A | 5/1997 | McKittrick et al. |
| 5,656,624 | A | 8/1997 | Vaccaro et al. |
| 5,688,787 | A | 11/1997 | Burnett et al. |
| 5,698,548 | A | 12/1997 | Dugar et al. |
| 5,756,470 | A | 5/1998 | Yumibe et al. |
| 5,767,115 | A | 6/1998 | Rosenblum |
| 5,846,966 | A | 12/1998 | Rosenblum et al. |
| 6,992,067 | B2 | 1/2006 | Glombik et al. |
| 7,045,515 | B2 | 5/2006 | Tomiyama et al. |
| 2005/0096307 | A1 | 5/2005 | Graziano |
| 2005/0282858 | A1 | 12/2005 | Yao et al. |
| 2008/0070888 | A1 | 3/2008 | McKittrick et al. |
| 2008/0070889 | A1 | 3/2008 | Burnett et al. |
| 2008/0070890 | A1* | 3/2008 | Burnett et al. ......... 514/210.05 |
| 2008/0070892 | A1 | 3/2008 | Harris et al. |
| 2008/0076750 | A1 | 3/2008 | Aslanian et al. |
| 2008/0076751 | A1 | 3/2008 | Aslanian et al. |

FOREIGN PATENT DOCUMENTS

| | | |
|---|---|---|
| EP | 0553682 | 8/1993 |
| WO | WO 94/17038 | 8/1994 |
| WO | WO 96/19450 | 6/1996 |
| WO | WO 99/00393 | 1/1999 |
| WO | WO 99/61424 | 12/1999 |
| WO | WO 02/066464 | 8/2002 |
| WO | WO 2004/005293 | 1/2004 |
| WO | WO 2004/071454 | 8/2004 |
| WO | WO 2004/110375 | 12/2004 |
| WO | WO 2005/000217 | 1/2005 |
| WO | WO 2005/040167 | 5/2005 |
| WO | WO 2005/116009 | 12/2005 |

OTHER PUBLICATIONS

PCT International Search Report mail date Feb. 25, 2008 for corresponding PCT Application No. PCT/US2007/019918.
Cignarella et al., "Synthesis of a new series of 2,7-diazaspiro[3.5]nonan-1-ones and study of their cholinergic properties", Eur J Med Chem 29:115-120, (1994).
Clayden et al., "Cyclization of Lithiated Pyridine and Quinoline Carboxamides: Synthesis of Partially Saturated Pyrrolopyridines and Spirocyclic β-Lactams", Organic Letters 7 (17):3673-3676, (2005).
Alonso et al., "Spiro β-Lactams as β-Turn Mimetics. Design, Synthesis, and NMR Conformational Analysis", J. Org. Chem. 66(19):6333-6338, (2001).
Bittermann et al., "Chirospecific Synthesis of Spirocyclic β-Lactams and Their Characterization as Potent Type II β-Turn Inducing Peptide Mimetics", J. Org. Chem. 71:97-102, (2006).
Khasanov et al., "Novel Asymmetric Approach to Proline-Derived Spiro-β-Lactams", J. Org. Chem. 69(17):5766-5769, (2004).

(Continued)

*Primary Examiner*—Kamal A Saeed
*Assistant Examiner*—Kristin Bianchi
(74) *Attorney, Agent, or Firm*—Henry C. Jeanette

(57) ABSTRACT

Disclosed are compounds of the formula:

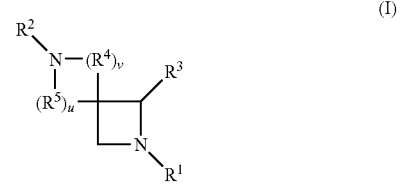

(I)

and compounds of the formula:

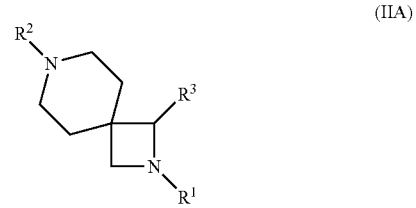

(IIA)

wherein $R^1$, $R^2$, $R^3$, $R^4$, $R^5$, u and v are as defined herein. Also disclosed are methods of treating pain (e.g., inflammatory pain, chronic pain, and neuropathic pain), methods of treating diabetes, and methods of inhibiting the absorption of cholesterol using compounds of formula I or IIA.

6 Claims, No Drawings

OTHER PUBLICATIONS

Macias et al., "Diastereoselective [2+2]-Cycloaddition Reactions of Unsymmetrical Cyclic ketens with Imines: Synthesis of Modified Prolines and Theoretical Study of the Reaction Mechanism", J. Org. Chem. 69:7004-7012, (2004).

Macias et al., "Synthesis of Enantiopure Pyrrolidine-Derived Peptidomimetics and Oligo-β-peptides via Nucleophilic Ring-Opening of β-Lactams", J. Org. Chem. 71:7721-7730, (2004).

Overman et al., "A Convenient Synthesis of 4-Unsubstituted β-Lactams", J. Am. Chem. Soc. 107:1698-1701, (1985).

Database WPI, Thomson Scientific, 1985-138995 & JP 60075457A, Osaka Soda Co. Ltd., Apr. 17, 1985, Abstract.

PCT International Search Report dated Mar. 31, 2008 for corresponding PCT Application No. PCT/US2007/019930.

PCT International Search Report dated Feb. 25, 2008 for corresponding PCT Application No. PCT/US2007/019931.

PCT International Search Report dated Feb. 14, 2008 for corresponding PCT Application No. PCT/US2007/019871.

PCT International Search Report date Feb. 28, 2008 for corresponding PCT Application No. PCT/US2007/019901.

PCT International Search Report mailed Jun. 5, 2008 for counterpart PCT Application No. PCT/US2007/019934.

PCT International Search Report dated Dec. 12, 2008 for corresponding PCT Application No. PCT/US2007/019925.

* cited by examiner

AZETIDINE DERIVATIVES USEFUL IN TREATING PAIN, DIABETES AND DISORDERS OF LIPID METABOLISM

REFERENCE TO RELATED APPLICATION

This application claims the benefit of Provisional Application No. 60/845,077 filed on Sep. 15, 2006.

BACKGROUND

Treatment of chronic pain, particularly inflammatory and neuropathic pain, is an area of high unmet medical need. Neuropathic pain is nerve injury resulting in hyperexcitability of neurons involved in pain sensation. T-currents are present in neurons of pain pathways. T-type calcium channel blockers are effective in preclinical models of neuropathic pain.

Type II diabetes, also known as non-insulin dependent diabetes mellitus, is a progressive disease characterized by impaired glucose metabolism resulting in elevated blood glucose levels. Patients with type II diabetes exhibit impaired pancreatic beta-cell function resulting in failure of the pancreatic beta-cells to secrete an appropriate amount of insulin in response to a hyperglycemic signal, and resistance to the action of insulin at its target tissues (insulin resistance).

Current treatments of type II diabetes aim to reverse insulin resistance, control intestinal glucose absorption, normalise hepatic glucose production, and improve beta-cell glucose sensing and insulin secretion. The sulfonylurea class of oral antihyperglycemic agents promote insulin secretion from pancreatic beta-islet cells, but have the potential to cause hypoglycemia as their action is independent of glucose levels. Antihyperglycemic agents include: insulin sensitizers that reduce hepatic glucose production by inhibiting gluconeogenesis; α-glucosidase inhibitors that inhibit breakdown of complex carbohydrates thus delaying glucose absorption and dampening postprandial glucose and insulin peaks; and thiazolidinediones that improve the action of insulin and reduce insulin resistance. Over time approximately one-half of type II diabetes patients lose their response to these agents. Because of the shortcomings of current treatments, new treatments for type II diabetes are highly desirable.

GPR119 is a constitutively active G-protein coupled receptor expressed predominantly in pancreatic beta-islet cells. Activation of GPR119 by an agonist increases insulin release from pancreatic beta-islet cells in a glucose dependent manner. Thus an agonist of GPR119 offers the potential to normalize blood glucose levels in a type II diabetic patient in response to post-prandial blood glucose elevation, but would not be expected to stimulate insulin release in the pre-prandial or fasted state.

WO 2004/110375 describes combination therapies for the treatment of diabetes comprising the administration of a combination of an anti-obesity agent and an anti-diabetic agent.

Niemann-Pick C1-like (NPC1L1) has been identified as a critical mediator of cholesterol absorption. It has been determined that the cholesterol absorption inhibitor ezetimibe targets NPC1L1.

The treatment of disorders of lipid metabolism, diabetes, vascular conditions, demyelination and nonalcoholic fatty liver disease with Spirocyclic Azetidinone Derivatives has been disclosed. Spirocyclic Azetidinone Derivatives that inhibit cholesterol absorption in the small intestine are well known in the art and are described, for example, in U.S. Pat. No. RE 37,721; U.S. Pat. No. 5,631,356; U.S. Pat. No. 5,767,115; U.S. Pat. No. 5,846,966; U.S. Pat. No. 5,698,548; U.S. Pat. No. 5,633,246; U.S. Pat. No. 5,656,624; U.S. Pat. No. 5,624,920; U.S. Pat. No. 5,688,787; U.S. Pat. No. 5,756,470; US Publication No. 2002/0137689; WO 02/066464; WO 95/08522 and WO96/19450. Each of the aforementioned publications is incorporated by reference. The art indicates that these compounds are useful in treating, for example, atherosclerotic coronary disease, either by administrating these compounds alone or with a second compound such as a cholesterol biosynthesis inhibitor.

WO 2005/000217 describes combination therapies for the treatment of dyslipidemia comprising the administration of a combination of an anti-obesity agent and an anti-dyslipidemic agent. WO 2004/110375 describes combination therapies for the treatment of diabetes comprising the administration of a combination of an anti-obesity agent and an anti-diabetic agent. US 2004/0122033 describes combination therapies for the treatment of obesity comprising the administration of a combination of an appetite suppressant and/or metabolic rate enhancers and/or nutrient absorption inhibitors. US 2004/0229844 describes combination therapies for treating atherosclerosis comprising the administration of a combination of nicotinic acid or another nicotinic acid receptor agonist and a DP receptor antagonist. Also known is a method for treating nonalcoholic fatty liver disease in a mammal by administering an effective amount of therapeutic composition comprising at least one cholesterol lowering agent and/or at least one $H_3$ receptor antagonist/inverse agonist.

A welcome contribution to the art would be compounds useful for the treatment of pain, compounds useful for the treatment of diabetes (e.g., type II diabetes), and compounds useful for the treatment of disorders of lipid metabolism. This invention provides such a contribution.

SUMMARY OF THE INVENTION

The present invention claims compounds of formula I (e.g., compounds that are T-calcium channel blockers, agonists of GPR119, or NPC1L1 antagonists):

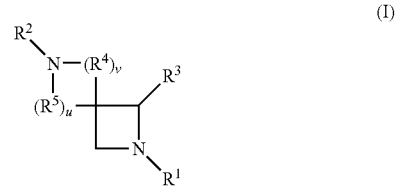

or a pharmaceutically acceptable salt, solvate, hydrate, ester, prodrug or stereoisomer thereof, wherein:

$R^1$ is selected from the group consisting of: (1) H, (2) alkyl, (3) substituted alkyl, (4) cycloalkyl, (5) aryl, (6) substituted aryl, (7) arylalkyl, (8) heteroaryl, (9) substituted heteroaryl, (10) heteroarylalkyl, (11) diphenylmethyl, (12) cycloalkylalkyl, (13) alkenyl, (14) —C(O)NQ$^B$ (wherein Q$^B$ is selected from the group consisting of substituted aryl (e.g., substituted phenyl)), and (15) -alkylene-C(O)N(alkyl)$_2$; and wherein:

the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$, the substituted aryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl; and the substituted heteroaryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl;

$R^2$ is selected from the group consisting of: (1) H, (2) alkyl, (3) substituted alkyl, (3) cycloalkyl, (4) aryl, (5) substituted aryl, (6) arylalkyl, (7) heteroarylalkyl, (8) heterocycloalkyl, (9) heterocycloalkylalkyl, (10) $R^6$-A-, (11) alkyl-O—C(O)—, (12) (alkyl)$_2$-N-alkylene-C(O)—, (13) (alkyl)$_2$-N—C(O)-alkylene-C(O)—, (14) CN-alkylene-C(O)—, (15) alkyl-O-alkylene-C(O)—, (16) alkyl-C(O)-alkylene-C(O)—, (17) alkyl-C(O)—NH-alkylene-C(O)—, (18) alkyl-NH—C(O)—, (19) alkyl-O—C(O)-alkylene-C(O)—, (20) alkyl-O—C(O)-cycloalkylene-alkylene-, (21) NH$_2$—C(O)—NH-alkylene-C(O)—, (22) NH$_2$—C(O)-alkylene-C(O)—, (23) alkyl-C(O)—NH-alkylene-S-alkylene-C(O)—, (24) alkyl-O—C(O)-alkylene-C(O)—, (25) alkyl-S-alkylene-C(O)—, (26) alkyl-C(O)-cycloalkylene-alkylene-C(O)—, (27) alkyl-S-alkylene-(—NHC(O)alkyl)-C(O)—, (28) alkyl(-C(O)Oalkyl)-NH—C(O)—, (29) alkyl-S-alkylene(—NHC(O)alkyl)-C(O)—, (30) —C(O)NHQ$^A$ wherein Q$^A$ is selected from the group consisting of: (a) cycloalkyl, (b) alkyl substituted with —C(O)—O-alkyl, (c) substituted aryl, (d) alkyl, (e) substituted arylalkyl, (f) substituted heterocycloalkenylbenzo, and (g) heteroaryl, (31) —C(O)NQ$^C$Q$^D$ wherein Q$^C$ and Q$^D$ are each independently selected from the group consisting of: (a) H, (b) Q$^A$ (wherein Q$^A$ is as previously defined), (c) substituted aryl, and (d) arylalkyl, (32) substituted heteroarylalkyl, and (33)

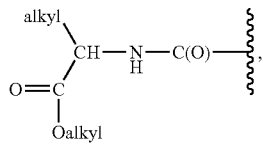

wherein $Z^A$ is selected from the group consisting of: H and alkyl (e.g., C$_1$ to C$_4$ alkyl), and Q$^F$ is selected from the group consisting of: —C(O)Oalkyl (e.g., —C(O)O(C$_1$ to C$_4$ alkyl)) and —C(O)N(X$^A$)$_2$ wherein each X$^A$ is independently selected from the group consisting of: H and alkyl (e.g., C$_1$ to C$_4$ alkyl), and wherein examples of the group (33) include, for example, alkyl(—C(O)Oalkyl)-NH—C(O)— (such as, for example,

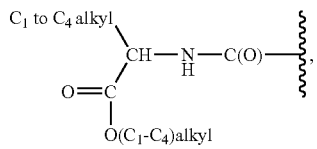

such as, for example,

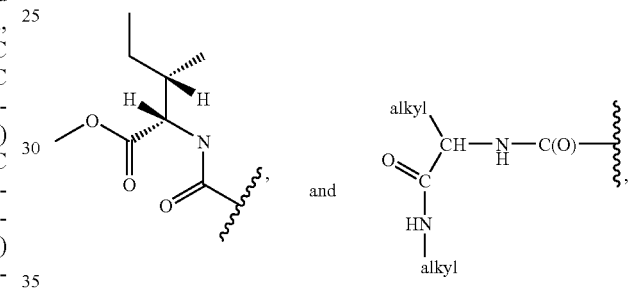

such as, for example,

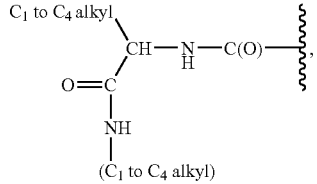

such as, for example,

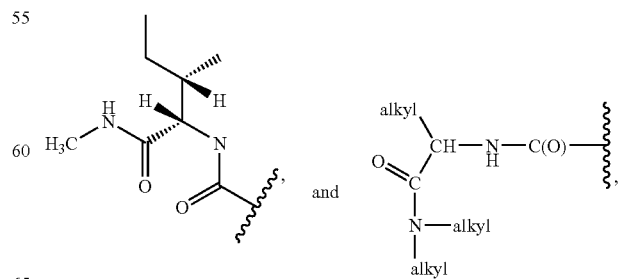

such as, for example,

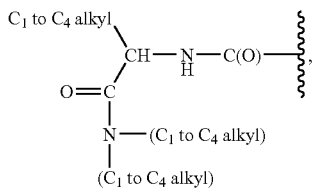

such as, for example,

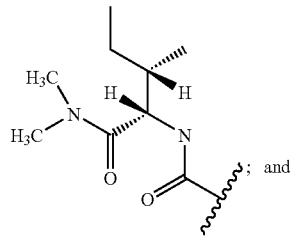

wherein:
the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$;

the substituted aryl moieties are each independently substituted with one or more (i.e., at least one, e.g. 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$, and (q) alkyl; and the substituted heteroarylalkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl, and wherein the heteroaryl portion is substituted, or the alkyl portion is substituted, or both the heteroaryl and alkyl portions are substituted; and $R^3$ is selected from the group consisting of: (1) H, (2) alkyl, (3) substituted alkyl, (4) cycloalkyl, (5) aryl, (6) substituted aryl, (7) arylalkyl, (8) arylalkenyl, (9) arylalkynyl (10) heteroaryl, (11) substituted heteroaryl, (12) heteroarylalkyl, (13) heteroarylalkenyl, and (14) heteroarylalkynyl; and wherein:
the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$;

the substituted aryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl; and the substituted heteroaryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, (p) —P(O)(O-alkyl)$_2$, and (q) alkyl; and Each occurrence of $R^4$ is independently selected from the group consisting of: —CH$_2$—, —CH(alkyl)- and —C(alkyl)$_2$ wherein each alkyl for each $R^4$ is independently selected, and wherein examples of said alkyl group include, for example, $C_1$ to $C_4$ alkyl, and $C_1$ to $C_2$ alkyl;

Each occurrence of $R^5$ is independently selected from the group consisting of: —CH$_2$—, —CH(alkyl)- and —C(alkyl)$_2$ wherein each alkyl for each $R^5$ is independently selected, and wherein examples of said alkyl group include, for example, $C_1$ to $C_4$ alkyl, and $C_1$ to $C_2$ alkyl; or $R^4$ and $R^5$ are as defined above, and a ring carbon of said $R^4$ is bound to a ring carbon of said $R^5$ by a —CH$_2$—CH$_2$— group (i.e., there is a $C_2$ bridge joining a $R^4$ ring carbon and a $R^5$ ring carbon, and those skilled in the art will appreciate that the bridged carbons for $R^4$ and $R^5$ are each independently selected from the group consisting of: —CH— and —C(alkyl)-);

u is an integer from 0 to 3;

v is an integer from 0 to 3, such that the sum of u and v is from 3 to 5;

$R^6$ is selected from the group consisting of: (1) alkyl, (2) substituted alkyl, (3) aryl, (4) substituted aryl, (4) heteroaryl, (5) substituted heteroaryl, (6) cycloalkyl, (7) cycloalkylalkyl, (8) heterocycloalkyl, (9) cycloalkenyl, (10) heterocycloalkenyl, (11) benzofused cycloalkyl, (12) benzofused heterocycloalkyl, and (13) benzofused heterocycloalkenyl; and wherein
the substituted alkyl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NO(O)NH(alkyl), (d) —NC(O)N(alkyl)$_2$, (e) —SO$_2$NH$_2$, (f) —SO$_2$NH(alkyl), (g) —SO$_2$N(alkyl)$_2$, (h) —CF$_3$, (i) —OH, (j) -halo, (k) —CN, (l) -alkoxy, (m) —C(O)O-alkyl, (n) —S(O)alkyl, (o) —SO$_2$-alkyl, and (p) —P(O)(O-alkyl)$_2$;

the substituted aryl moieties are each independently substituted with one or more (i.e., at least one, e.g., 1 to 3) substituents independently selected from the group consisting of: (a) —(C=N—O-alkyl)CH$_3$, (b) —NC(O)NH$_2$, (c) —NC(O)NH(alkyl), (d) —NC(O)N(alkyl)$_2$, (e) —SO$_2$NH$_2$, (f) —SO$_2$NH(alkyl), (g)

—SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl; and the substituted heteroaryl moieties are each independently substituted with one or more (i.e., at least one, e.g., 1 to 3) substituents independently selected from the group consisting of: (a) —(C═N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl;

A is selected from the group consisting of: (1) —C(O)—, (2) —C(O)-alkylene-, (3) —C(O)-alkylene-O—, (4) —C(O)—(CH₂)₀₋₂—C(O)—, (5) —C(O)—CH₂—NH—C(O)—, (6) —C(O)—CH₂—N(alkyl)-C(O)—, (7) -alkylene-, (8) -alkenylene-, (9) —C(O)-alkenylene-, (10) —O—C(O)-alkylene-C(O)—, (11) —C(O)—NH-cycloalkylene-, (12) —C(O)—NH—, (13) —C(O)—NH-alkylene-, (14) —C(O)-alkylene(—NHC(O)alkyl)-, (15) —C(O)-alkylene-NH—C(O)-alkylene-, (16) —C(O)-alkylene-NH—C(O)—, (17) —C(O)-alkylene-O-alkylene-, (18) —C(O)-alkylene(alkoxy)-, (19) —C(O)-alkylene-S—, (20) —C(O)-alkylene(—N(alkyl)₂)—, and

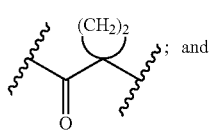

(21); and wherein the compounds defined by an "X" in Tables 3a, 3b, 3c, and 3d, and the compounds defined in Table 4a are excluded from the definition of the compounds of formula I.

The definitions for the numbers for R² and/or R¹ in Tables 3a, 3b, 3c, 3d, and 4a are given in Tables 1 and 2. Thus, (1) the compounds defined by the formulas assigned to Tables 3a, 3b, 3c, 3d, having the R¹ and R² definitions indicated by an "X" in the box formed by the intersection of the R² column and the R¹ row are not within the scope of the compounds of formula I (boxes without an "X" define compounds that are within the scope of the invention), and (2) the compounds defined in Table 4a are not within the scope of the compounds of formula I. The numbers in the first column in Tables 3a, 3b, 3c, and 3d represent the R² groups defined in Table 2. The numbers in top row of Tables 3a, 3b, 3c, and 3d, as well as the numbers in Table 4a, represent the R¹ groups defined in Table 1.

In another aspect, this invention relates to compounds of formula I having the structure represented by formula IIA:

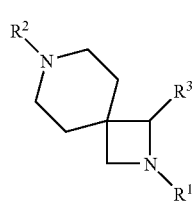

(IIA)

wherein the compounds defined by the "X" in Tables 3a, 3b, 3c, 3d, and the compounds defined in Table 4a are excluded from the compounds of formula IIA.

In another aspect, the present invention relates to compounds of formula I.

In another aspect, the present invention relates to compounds of formula I wherein R¹, R² and R³ are the R¹, R² and R³ moieties on the compounds in any one of Tables 5, 6, 7, 8, and 8A, and Examples 1 to 6.

In another aspect, the present invention relates to compounds of formula IIA wherein R¹, R² and R³ are the R¹, R² and R³ moieties on the compounds in any one of Tables 5, 6, 7 and 8, and 8A, and Examples 1 to 6.

In another aspect, the present invention relates to the final compounds of Examples 1 to 6.

In another aspect, the present invention relates to the compounds in Tables 5, 6, 7, 8, 8A, 9, and 10.

In another aspect, the present invention relates to a pharmaceutically acceptable salt of the compounds of formula I.

In another aspect, the present invention relates to a solvate of the compounds of formula I.

In another aspect, the present invention relates to compounds of formula I in pure and isolated form.

The compounds of the present invention are T-type calcium channel blockers. The T-calcium channel blocker compounds of formula I are useful in the treatment of pain (such as, for example, such as for example, inflammatory pain, chronic or neuropathic pain).

Thus, in another aspect, the present invention relates to a method of treating pain (such as for example, inflammatory pain, chronic or neuropathic pain) comprising administering to a patient in need of such treatment an effective amount of at least one compound of formula I.

In another aspect, the present invention relates to a method of treating pain (such as for example, inflammatory pain, chronic pain or neuropathic pain) comprising administering to a patient in need of such treatment an effective amount of a compound of formula I.

In another aspect, the present invention relates to a method of treating chronic pain comprising administering to a patient in need of such treatment an effective amount at least one (e.g., one) compound of formula I.

More particularly, in another aspect, the present invention relates to a method of treating inflammatory pain comprising administering to a patient in need of such treatment an effective amount of at least one (e.g., one) compound of formula I.

Also, more particularly, in another aspect, the present invention relates to a method of treating neuropathic pain comprising administering to a patient in need of such treatment an effective amount of at least one (e.g., one) compound of formula I.

In another aspect, the present invention relates to a method of treating pain (such as for example, inflammatory pain, chronic pain or neuropathic pain) comprising administering to a patient in need of such treatment an effective amount of at least one (e.g., one) compound of formula I selected from the group consisting of the compounds in Table 5.

In another aspect, the present invention relates to a method of treating pain (such as for example, inflammatory pain, chronic pain or neuropathic pain) comprising administering to a patient in need of such treatment an effective amount of at least one (e.g., one) compound of formula I selected from the group consisting of the compounds in Table 10.

In another aspect, the present invention relates to a method of treating neuropathic pain comprising administering to a patient in need of such treatment an effective amount of at least one (e.g., one) compound of formula I.

In another aspect, the present invention relates to a method of blocking T-calcium channels comprising administering to a patient in need of such treatment an effective amount of at least one (e.g., one) compound of formula I.

Compounds of formula I are agonists of GPR119. Compounds of formula I that are agonists of GPR119 are useful for the treatment of, for example, diabetes (e.g., type II diabetes).

Thus, in another aspect, the invention relates to a method of treating a disease mediated by a GPR119 receptor (such as diabetes, such as type II diabetes) comprising administering to a patient in need of such treatment an effective amount of at least one compound of formula I.

In another aspect, the invention relates to a method of treating a disease mediated by a GPR119 receptor (such as diabetes, such as type II diabetes) comprising administering to a patient in need of such treatment an effective amount of a compound of formula I.

In another aspect, the present invention relates to a method of treating a disease mediated by a GPR119 receptor (such as diabetes, such as type II diabetes) comprising administering to a patient in need of such treatment an effective amount of at least one compound of formula I selected from the group consisting of the compounds in Table 6.

In another aspect, the present invention relates to a method of treating a disease mediated by a GPR119 receptor (such as diabetes, such as type II diabetes) comprising administering to a patient in need of such treatment an effective amount of at least one compound of formula I selected from the group consisting of the compounds in Table 9.

More particularly, the compounds of formula I are useful in treating diabetes.

In another aspect, the invention relates to the treatment of diabetes comprising administering to a patient in need of such treatment an effective amount of at least one (e.g., one) GPR119 agonist of formula I to a patient in need of such treatment.

In another aspect, the invention relates to the method of treating pain comprising administering to a patient in need of such treatment an effective amount of a combination of at least one compound of formula I and at least one additional agent for treating pain.

In another aspect, the invention relates to the method of treating chronic pain comprising administering to a patient in need of such treatment an effective amount of a combination of at least one compound of formula I and at least one additional agent for treating chronic pain.

More particularly, in another aspect, the invention relates to the method of treating inflammatory pain comprising administering to a patient in need of such treatment an effective amount of a combination of at least one compound of formula I and at least one additional agent for treating inflammatory pain.

More particularly, in another aspect, the invention relates to the method of treating neuropathic pain comprising administering to a patient in need of such treatment an effective amount of a combination of at least one compound of formula I and at least one additional agent for treating neuropathic pain.

In particular, in another aspect, the invention relates to the method of treating diabetes comprising administering to a patient in need of such treatment an effective amount of a combination of at least one compound of formula I and at least one additional agent for treating diabetes.

In another aspect the present invention is directed to a method of treating a disorder of lipid metabolism comprising administering to a patient in need of such treatment an effective amount of a combination of at least one compound of formula I.

In another aspect the present invention is directed to a method of inhibiting the absorption of cholesterol comprising administering to a patient in need of such treatment an effective amount of at least one compound of formula I.

In another aspect the present invention is directed to a method of inhibiting cholesterol absorption comprising administering to a patient in need of such treatment an effective amount of at least one NPC1L1 antagonist compound of formula I.

In another aspect the present invention is directed to a method of inhibiting the absorption of cholesterol comprising administering to a patient in need of such treatment an effective amount of at least one compound of formula I in combination with an effective amount of at least one additional agent useful for treating a disorder of lipid metabolism (such as, at least one additional agent useful in lowering cholesterol).

In another aspect the present invention is directed to a method of inhibiting cholesterol absorption comprising administering to a patient in need of such treatment an effective amount of at least one NPC1L1 antagonist compound of formula I in combination with an effective amount of at least one additional agent useful for treating a disorder of lipid metabolism (such as at least one additional agent useful in lowering cholesterol).

In another aspect the present invention is directed to the inhibition of the absorption of cholesterol comprising administering to a patient in need of such treatment an effective amount of at least one compound of formula I in combination with an effective amount of at least one inhibitor of HMG-CoA reductase (e.g., statins, such as, for example, simvastatin, atorvastatin calcium, and rosuvastatin calcium).

In another aspect the present invention is directed to the inhibition of the absorption of cholesterol comprising administering to a patient in need of such treatment an effective amount of at least one compound of formula I in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula I in combination with an effective amount of at least one inhibitor of CETP (e.g., torcetrapib).

Another embodiment of the invention is directed to the inhibition of the absorption of cholesterol comprising administering to a patient in need of such treatment an effective amount of at least one compound of formula I in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula I in combination with an effective amount of at least one inhibitor of HMG-CoA reductase (e.g., statins, such as, for example, simvastatin, atorvastatin calcium, and rosuvastatin calcium), and in combination with an effective amount of at least one NPC1L1 antagonist (such as, for example, ezetimibe, such as the Zetia® brand of ezetimibe). An example of a medicament already comprising a combination of a HMG-CoA reductase and a NPC1L1 antagonist that can be used in this embodiment is the Vytorin® brand of the combination of ezetimibe and simvastatin.

Another embodiment of the present invention is directed to a kit comprising in a single package at least one compound of formula I in a pharmaceutical composition, and at least one separate pharmaceutical composition comprising at least one additional therapeutic agent (such as, for example, at least one of the additional agents useful in the treatment of pain, or at least one additional agent useful in the treatment of lipid disorders (such as at least one additional agent useful in lowering cholesterol), or one of the additional agents useful in treating diabetes).

DETAILED DESCRIPTION

Current chronic pain therapies provide only partial relief in responsive patients and are either not tolerated or ineffective in others. Chronic pain may arise as a consequence of tissue inflammation, viral infection (HIV, Herpes zoster) direct tissue injury or trauma, as a result of chemotherapy (e.g., taxol, vincristine), lesions of the central nervous system (e.g. stroke, MS) or as a consequence of diabetes. When chronic pain is associated with somatic or visceral tissue injury, symptoms usually include severe sensory disturbances characterized by spontaneous pain (often described as stabbing, burning, electric-shock-like or throbbing), hyperalgesia (exaggerated responsiveness to painful stimuli) and allodynia (perception of non noxious stimuli as painful). Prevalent symptoms in human patients include cold hyperalgesia, tactile allodynia and less commonly, heat hyperalgesia. Symptoms may present in isolation or in combination and there is often appreciable variation in the symptomatology associated with different disease states and typically between patients presenting with the same condition. In cases of somatic or visceral tissue injury/diseases, these distorted sensory perceptions have been linked to inappropriate activity (pathological hyperexcitability) in the peripheral nerves innervating the affected area. Neuronal hyperexcitability may arise as a result of altered ion channel function or activity.

Chronic pain is a true disease. It is believed to be a result, at least in part, of the plasticity at synapses in nociceptive processing centers, a phenomenon referred to as "central sensitization" which consists of increased excitability of spinal cord dorsal horn neurons. Maintenance of central sensitization is believed to require sustained peripheral neuronal activity (hyperexcitability) in sensory afferent nerves and such activity may be generated as a result of ectopic foci. Large T-type calcium currents can be found in sensory afferent neurons of the dorsal root ganglia (DRG). T-type calcium channels have been implicated as a causal factor in establishing such abnormal hyperexcitability, due to their known ability to function as neuronal pacemakers. Pharmacological and antisense oligonucleotide evidence supports a key role for DRG T-type calcium channels preclinical models of chronic pain.

T-type calcium channels are voltage-gated channels that can be opened with relatively small depolarizations from the resting potential of excitable cells. There are three distinct genes for T-type calcium currents that encode for $Ca_v3.1$, $Ca_v3.2$ and $Ca_v3.3$. The individual subtypes have unique patterns of distribution and are expressed in peripheral and central portions of pain pathways. T-type calcium channels are found in small and medium sized DRG neurons ($Ca_v3.2$) and regions of the CNS involved in pain processing including the dorsal horn of the spinal cord an the thalamus (Talley et al, *J Neurosci*, 1999, 19:1895-1911). T-type calcium currents have been shown to play a role in neuronal burst firing via low-threshold calcium spikes that permit rapid burst of neuronal action potentials (Suzuki and Rogwoski, Proc Natl Acad Sci USA, 1989, 86:7228-7232; White et al., *Proc Natl Acad Sci USA*, 1989, 86:6802-6806).

Inhibition of T-type calcium channel function in vivo through either the use of pharmacological blockers or antisense oligonucleotide mediated knockdown strongly implicate T-type channels in normal and pathological pain processing. Mibefradil and/or ethosuximide are selective for T-type calcium channel and have been shown to be effective in a number of preclinical pain models including: acute thermal and mechanical pain, phase I and II of the formalin model, the rat spinal nerve ligation model, capsaicin-induced mechanical hyperalgesia, rat tail flick, paclitaxil- and vincristine-induced chemoneuropathy (Barton et al., *Eur J Pharmacol*, 2005, 521:79-8; Dogrul et al *Pain*, 2003, 105:159:168; Flatters and Bennett, *Pain*, 2004, 109:150-161; Todorovic et al., *Brain Res*, 2002, 951:336-340).

Pain relief in response to ethosuximide could be due to either central or peripheral actions. However efficacy in response to mibefradil can be attributed to peripheral effects for two reasons. First systemically administered mibefradil does not enter the brain. In addition intrathecal administration of mibefradil is ineffective (Dogrul et al *Pain*, 2003, 105:159: 168). Further evidence supporting efficacy from block of peripheral T-type channels comes from studies with antisense oligonucleotide directed against on type of T-type channel, $Ca_v3.2$. Intrathecal injection of hCaV3.2 specific oligonucleotides decreased T-type calcium currents in DRG neurons and produced antinociceptive, anti-hyperalgesic and anti-allodynic effects. In these studies the uptake of oligonucleotide and the antisense mediated knockdown of T-type currents occurred in DRG neurons close to the site of injection but not in spinal cord (Bourinet et al., *EMBO J*, 2005 24:315-324).

The compounds of formula I of this invention are T-type calcium channel blockers. Accordingly, the present compounds are useful in the treatment or prevention of conditions that are treatable or preventable by administering T-type calcium channel blockers. Such conditions include the treatment or prevention of neuropathic pain.

Neuropathic pain as used herein refers to an abnormal state of pain sensation, in which a reduction of pain threshold and the like are continued, due to functional abnormalities accompanying damage or degeneration of a nerve, plexus or perineural soft tissue, which is caused by wound (e.g., lacerations, contusions, nerve avulsion injuries, amputation of a limb), compression (carpal tunnel syndrome, trigeminal neuralgia, tumor activity), infection, cancer, ischemia and the like, or metabolic disorders such as diabetes mellitus and the like, Neuropathic pain includes pain caused by either central or peripheral nerve damage. It also includes the pain caused by either mononeuropathy or polyneuropathy. In some embodiments, the neuropathic pain is induced by diabetes.

Other examples of neuropathic pain treatable or preventable by the present compounds include, but are not limited to, allodynia (a pain sensation induced by mechanical or thermal stimulus that does not normally provoke pain), hyperalgesia (an excessive response to a stimulus that is normally painful), hyperesthesia (an excessive response to a contact stimulus), diabetic polyneuropathy, entrapment neuropathy, cancer pain, central pain, labor pain, myocardial infarction pain, post-stroke pain, pancreatic pain, colic pain, muscle pain, post-operative pain, post-stroke pain, pain associated with Parkinson's disease, pain associated with intensive care, pain associated with a periodontal disease (including gingivitis and periodontitis), menstrual pain, migraine pain, persistent headaches (e.g., cluster headache or chronic tension headache), persistent pain states (e.g., fibromyalgia or myofascial pain), trigeminal neuralgia, postherpetic neuralgia, bursitis, pain associated with AIDS, pain associated with multiple sclerosis, pain due to spinal trauma and/or degeneration, burn pain, referred pain, enhanced memory of pain and neuronal mechanisms involved in coping with pain. Inflammatory pain may arise as a result of soft tissue injury including that involving the musculature (myositis) and viscera (colitis and inflammatory bowel disease, pancreatitis, cystitis, ileitis, Crohn's disease), nerves (neuritis, radiculopathies, radioculogangionitis), arthritic conditions (e.g. rheumatoid disease and related conditions such as ankylosing spondylitis), joint disease (including osteoarthritis). The compounds of the present invention are particularly useful for treating or preventing allodynia and hyperalgesia.

Additional agents for treating neuropathic pain include non-opioid analgesics, opioid analgesics, antimigraine agents, Cox-II inhibitors, antiemetics, β-adrenergic blockers, anticonvulsants, antidepressants, other $Ca^{2+}$-channel blockers, sodium channel blockers, anticancer agents, agents for treating or preventing UI, agents for treating hypertension, agents for treating or preventing angina pectoris, agents for treating atrial fibrillation, agents for treating insomnia, agents for treating renal failure, agents for treating Alzheimer's disease, agents for treating or preventing IBD, agents for treating or preventing IBS, agents for treating Parkinson's disease and parkinsonism, agents for treating anxiety, agents for treating epilepsy, agents for treating a stroke, agents for treating psychosis, agents for treating Huntington's chorea, agents for treating ALS, agents for treating vomiting, agents for treating dyskinesia, and agents for treating depression.

Preferred additional agents for treating neuropathic pain include those selected from the group consisting of: non-opioid analgesics and opioid analgesics.

Additional agents for treating inflammatory pain include corticosteroids, non-sterodial anti-inflammatory agents, COX-I and COX-II inhibitors, agents useful for treating inflammatory bowel disease and agents useful for treating rheumatoid arthritis.

Diabetes mellitus, commonly called diabetes, refers to a disease process derived from multiple causative factors and characterized by elevated levels of plasma glucose, referred to as hyperglycemia. Premature development of atherosclerosis and increased rate of cardiovascular and peripheral vascular diseases are characteristic features of patients with diabetes. There are two major forms of diabetes: Type I diabetes (also referred to as insulin-dependent diabetes or IDDM) and Type II diabetes (also referred to as noninsulin dependent diabetes or NIDDM). Compounds of formula I are useful in treating Type II diabetes.

Type I diabetes is the result of an absolute deficiency of insulin, the hormone that regulates glucose utilization. This insulin deficiency is usually characterized by β cell destruction in the pancreas, which usually leads to absolute insulin deficiency.

Type I diabetes has two forms: Immune-Mediated Diabetes Mellitus, which results from a cellular mediated autoimmune destruction of the β cells of the pancreas; and Idiopathic Diabetes Mellitus, which refers to forms of the disease that have no known etiologies.

Type II diabetes is a disease characterized by insulin resistance accompanied by relative, rather than absolute, insulin deficiency. Type II diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequately control glucose, a state of impaired glucose tolerance develops. Insulin secretion may further decline over time.

Type II diabetes can be due to a resistance to insulin stimulating regulatory effects on glucose and lipid metabolism in the main insulin-sensitive tissues, such as muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type II diabetes, free fatty acid levels are often elevated in obese and some non-obese patients and lipid oxidation is increased.

In particular, Type II diabetes can be treated by treatment with a GPR119 agonist of formula II, alone or in combination with one or more additional agents for treating diabetes.

Other therapies for the treatment of type II diabetes that can be used in combination with compounds of formula II of this invention for treating Type II diabetes include sulfonylureas, insulin sensitizers, PPAR agonists, α-glucosidase inhibitors, insulin secretagogues, hepatic glucose output lowering compounds, and insulin.

In another aspect, the invention relates to compounds of formula I wherein:

(A) $R^1$ is selected from the group consisting of: H, alkyl, substituted alkyl, cycloalkyl, aryl, substituted aryl, arylalkyl, heteroaryl, substituted heteroaryl, heteroarylalkyl, diphenylmethyl, cycloalkylalkyl and -alkylene-C(O)N(alkyl)$_2$;

(B) $R^2$ is selected from the group consisting of: H, alkyl, substituted alkyl, cycloalkyl, aryl, substituted aryl, arylalkyl, heteroarylalkyl, substituted heteroarylalkyl, heterocycloalkyl, heterocycloalkylalkyl, $R^6$-A-, alkyl-O—C(O)—, (alkyl)$_2$-N-alkylene-C(O)—, CN-alkylene-C(O)—, alkyl-O-alkylene-C(O)—, alkyl-C(O)-alkylene-C(O)—, alkyl-NH—C(O)—, alkyl-O—C(O)-alkylene-C(O)—, and

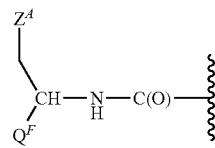

wherein $Z^A$ and $Q^F$ are as defined above, and wherein examples of said

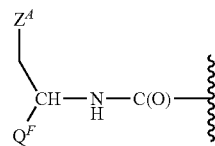

include for example,

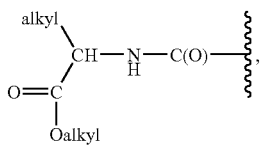

such as, for example,

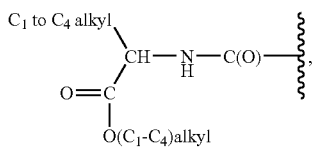

such as, for example,

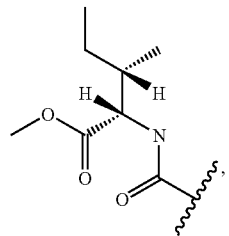

such as, for example,

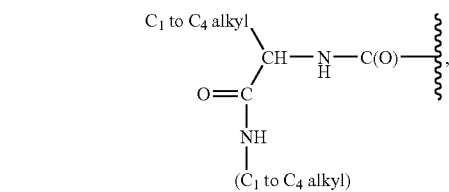

such as, for example,

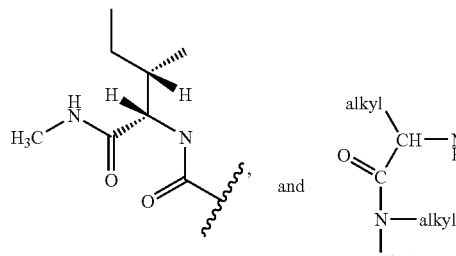

such as, for example,

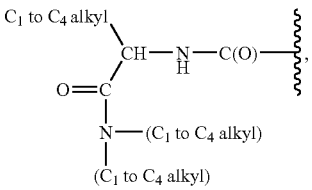

such as, for example,

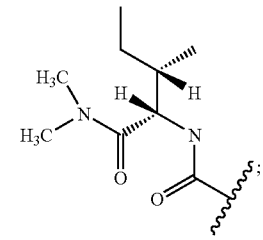

(C) $R^3$ is selected from the group consisting of: H, alkyl, substituted alkyl, cycloalkyl, aryl, substituted aryl, arylalkyl, arylalkenyl, arylalkynyl, arylalkyl-NH—, heteroaryl, substituted heteroaryl, heteroarylalkyl, heteroarylalkenyl, heteroarylalkynyl;

(D) Each occurrence of $R^4$ is independently selected from the group consisting of: —CH$_2$—, —CH(alkyl)- and —C(alkyl)$_2$ wherein each alkyl for each $R^4$ is independently selected, and wherein examples of said alkyl group include, for example, $C_1$ to $C_4$ alkyl, and $C_1$ to $C_2$ alkyl;

(E) Each occurrence of $R^5$ is independently selected from the group consisting of: —CH$_2$—, —CH(alkyl)- and —C(alkyl)$_2$ wherein each alkyl for each $R^5$ is independently selected, and wherein examples of said alkyl group include, for example, $C_1$ to $C_4$ alkyl, and $C_1$ to $C_2$ alkyl; or (F) $R^4$ and $R^5$ are as defined above, and a ring carbon of said $R^4$ is bound to a ring carbon of said $R^5$ by a —CH$_2$—CH$_2$— group (i.e., there is a $C_2$ bridge joining a $R^4$ ring carbon and a $R^5$ ring carbon, and those skilled in the art will appreciate that the bridged carbons for $R^4$ and $R^5$ are each independently selected from the group consisting of: —CH— and —C(alkyl)-);

(G) u is an integer from 0 to 3;

(H) v is an integer from 0 to 3, such that the sum of u and v is from 3 to 5;

(I) $R^6$ is selected from the group consisting of: alkyl, substituted alkyl, aryl, substituted aryl, heteroaryl, substituted heteroaryl, cycloalkyl, cycloalkylalkyl, heterocycloalkyl, cycloalkenyl, heterocycloalkenyl, benzofused cycloalkyl, benzofused heterocycloalkyl, and benzofused heterocycloalkenyl;

(J) A is selected from the group consisting of: —C(O)—, —C(O)-alkylene-, —C(O)-alkylene-O—, —C(O)—CH$_2$—N(alkyl)-C(O)—, -alkylene-, -alkenylene-, —C(O)-alkenylene-, —C(O)—NH—, —C(O)—NH-alkylene-, and

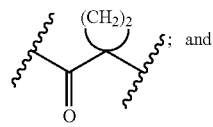

(K) wherein the compounds defined by an "X" in Tables 3a, 3b, 3c, and 3d, and the compounds defined in Table 4a are excluded from the definition of the compounds of formula I.

In another aspect, this invention relates to compounds of formula I wherein $R^1$ is selected from the group consisting of the $R^1$ groups in Table 1, $R^2$ is selected from the group consisting of $R^2$ groups in Table 2, and wherein the compounds defined by the "X" in Tables 3a, 3b, 3c, 3d and the compounds in Table 4a are excluded from the compounds of formula I.

In another aspect, this invention relates to compounds of formula I wherein $R^3$ is selected from the group consisting of: (A) phenyl, (B) substituted phenyl (e.g., wherein there are 1 to 3 substituents (e.g., 1 or 2, or 1) independently selected from the group consisting of: halo (e.g., Br, F, and Cl) and —CN, (C) heteroaryl (such as, for example, pyridyl and pyrimidinyl), and (D) substituted heteroaryl (e.g., substituted pyridyl and substituted pyrimindinyl) wherein there are 1 to 3 (e.g., 1 or 2, or 1) substituents independently selected from the group consisting of: halo (e.g., Br, F, and Cl) and —CN.

In another aspect, this invention relates to compounds of formula I wherein $R^3$ is selected from the group consisting of:

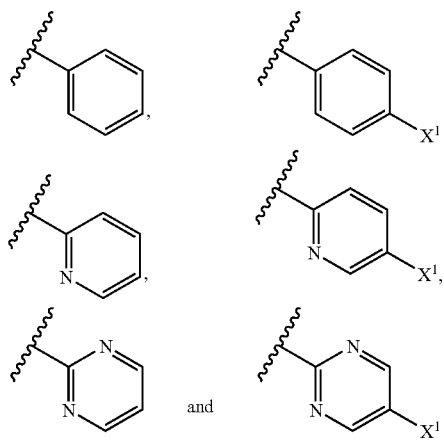

wherein $X^1$ is selected from the group consisting of: halo (e.g., Br, F, and Cl), —$CF_3$ and —CN.

In another aspect, this invention relates to compounds of formula IIA wherein $R^3$ is selected from the group consisting of: (A) phenyl, (B) substituted phenyl (e.g., wherein there are 1 to 3 substituents (e.g., 1 or 2, or 1) independently selected from the group consisting of: halo (e.g., Br, F, and Cl) and —CN, (C) heteroaryl (such as, for example, pyridyl and pyrimidinyl), and (D) substituted heteroaryl (e.g., substituted pyridyl and substituted pyrimindinyl) wherein there are 1 to 3 (e.g., 1 or 2, or 1) substituents independently selected from the group consisting of: halo (e.g., Br, F, and Cl) and —CN.

In another aspect, this invention relates to compounds of formula IIA wherein $R^3$ is selected from the group consisting of:

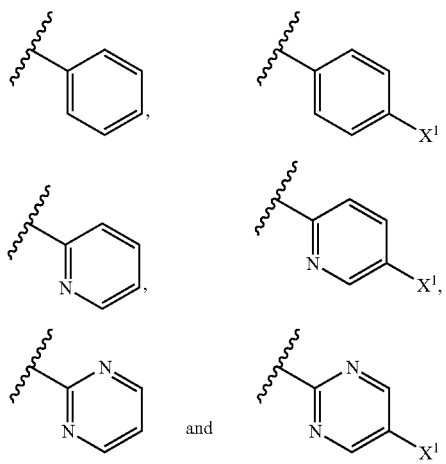

wherein $X^1$ is selected from the group consisting of: halo (e.g., Br, F, and Cl), —$CF_3$ and —CN.

In another aspect, this invention relates to compounds of formula I wherein $R^3$ is selected from the group consisting of:

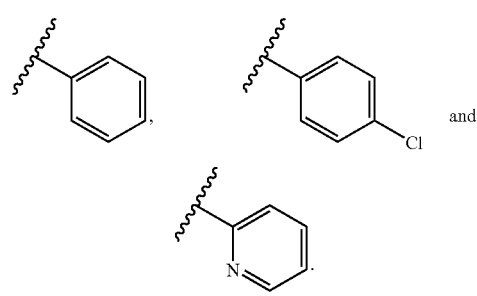

In another aspect, this invention relates to compounds of formula IIA wherein $R^3$ is selected from the group consisting of:

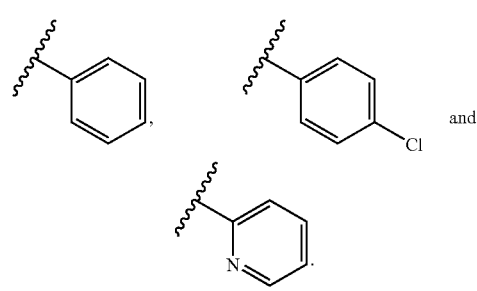

In another aspect, this invention relates to compounds of formula I wherein $R^1$ is selected from the group consisting of the $R^1$ groups in Table 1, $R^2$ is selected from the group consisting of $R^2$ groups in Table 2, $R^3$ is selected from the group consisting of:

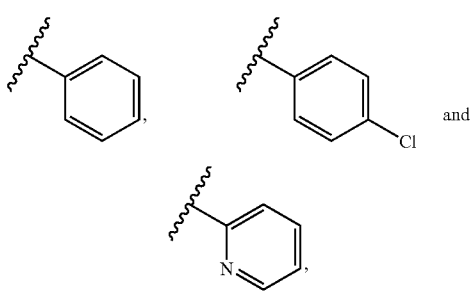

and wherein the compounds defined by the "X" in Tables 3a, 3b, 3c, 3d and the compounds in Table 4a are excluded from the compounds of formula I.

In another aspect, this invention relates to compounds of formula I having the structure represented by formula IIA:

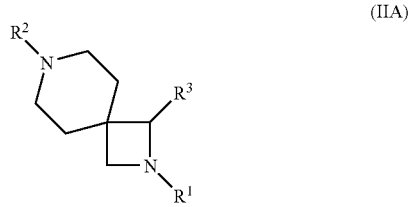

(IIA)

wherein $R^1$ is selected from the group consisting of the $R^1$ groups in Table 1, $R^2$ is selected from the group consisting of $R^2$ groups in Table 2, $R^3$ is as defined for formula I, and wherein the compounds defined by the "X" in Tables 3a, 3b, 3c, 3d and the compounds in Table 4a are excluded from the compounds of formula IIA.

In another aspect, this invention relates to compounds of formula I having the structure represented by formula IIA:

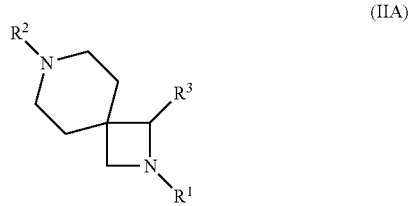

(IIA)

wherein $R^1$ is selected from the group consisting of the $R^1$ groups in Table 1, $R^2$ is selected from the group consisting of $R^2$ groups in Table 2, $R^3$ is selected from the group consisting of:

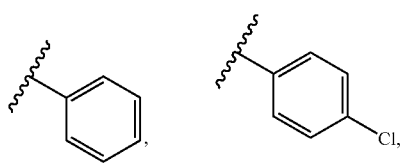

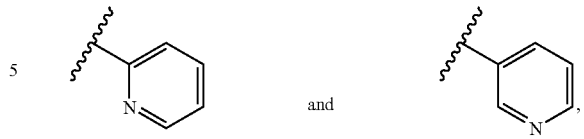

and wherein the compounds defined by the "X" in Tables 3a, 3b, 3c, 3d and the compounds in Table 4a are excluded from the compounds of formula IIA.

In another aspect, the present invention relates to compounds of formula I wherein $R^1$ is any one of the $R^1$ moieties on the compounds in any one of Tables 5, 6, 7, 8 and 8A, and Examples 1 to 6.

In another aspect, the present invention relates to compounds of formula I wherein $R^2$ is any one of the $R^2$ moieties on the compounds in any one of Tables 5, 6, 7, 8 and 8A, and Examples 1 to 6.

In another aspect, the present invention relates to compounds of formula I wherein $R^3$ is any one of the $R^3$ moieties on the compounds in any one of Tables 5, 6, 7, 8 and 8A, and Examples 1 to 6.

In another aspect, the present invention relates to compounds of formula IIA wherein $R^1$ is any one of the $R^1$ moieties on the compounds in any one of Tables 5, 6, 7, 8 and 8A, and Examples 1 to 6.

In another aspect, the present invention relates to compounds of formula IIA wherein $R^2$ is any one of the $R^2$ moieties on the compounds in any one of Tables 5, 6, 7, 8 and 8A, and Examples 1 to 6.

In another aspect, the present invention relates to compounds of formula IA wherein $R^3$ is any one of the $R^3$ moieties on the compounds in any one of Tables 5, 6, 7, 8 and 8A, and Examples 1 to 6.

In another aspect, the present invention relates to the compounds in Table 5.

In another aspect, the present invention relates to the compounds in Table 6.

In another aspect, the present invention relates to the compounds in Table 7.

In another aspect, the present invention relates to the compounds in Table 8.

In another aspect, the present invention relates to the compounds in Table 8A.

In another aspect, the present invention relates to the compounds in Table 9.

In another aspect, the present invention relates to the compounds in Table 10.

In another aspect, the present invention relates to compounds of formula I in pure form.

In another aspect, the present invention relates to compounds of formula I in isolated form.

In another aspect, the present invention relates to compounds of formula IIA in pure form.

In another aspect, the present invention relates to compounds of formula IIA in isolated form.

In another aspect, the invention relates to a method of treating pain (such as for example, inflammatory pain, chronic or neuropathic pain) comprising administering to a patient in need of such treatment an effective amount of at least one compound of formula IIA.

In another aspect, the present invention relates to a method of treating pain (such as for example, inflammatory pain, chronic pain or neuropathic pain) comprising administering to a patient in need of such treatment an effective amount of a compound of formula IIA.

In another aspect, the present invention relates to a method of treating chronic pain comprising administering to a patient in need of such treatment an effective amount at least one (e.g., one) compound of formula IIA.

More particularly, in another aspect, the present invention relates to a method of treating inflammatory pain comprising administering to a patient in need of such treatment an effective amount of at least one (e.g., one) compound of formula IIA.

Also, more particularly, in another aspect, the present invention relates to a method of treating neuropathic pain comprising administering to a patient in need of such treatment an effective amount of at least one (e.g., one) compound of formula IIA.

In another aspect, the present invention relates to a method of treating pain (such as for example, inflammatory pain, chronic pain or neuropathic pain) comprising administering to a patient in need of such treatment an effective amount of at least one (e.g., one) compound of formula IIA selected from the group consisting of the compounds in Table 5.

In another aspect, the present invention relates to a method of treating pain (such as for example, inflammatory pain, chronic pain or neuropathic pain) comprising administering to a patient in need of such treatment an effective amount of at least one (e.g., one) compound of formula IIA selected from the group consisting of the compounds in Table 10.

In another aspect, the present invention relates to a method of treating neuropathic pain comprising administering to a patient in need of such treatment an effective amount of at least one (e.g., one) compound of formula IIA.

In another aspect, the present invention relates to a method of blocking T-calcium channels comprising administering to a patient in need of such treatment an effective amount of at least one (e.g., one) compound of formula IIA.

Compounds of formula I are agonists of GPR119. Compounds of formula IIA that are agonists of GPR119 are useful for the treatment of, for example, diabetes (e.g., type II diabetes).

Thus, in another aspect, the invention relates to a method of treating a disease mediated by a GPR119 receptor (such as diabetes, such as type II diabetes) comprising administering to a patient in need of such treatment an effective amount of at least one compound of formula IIA.

In another aspect, the invention relates to a method of treating a disease mediated by a GPR119 receptor (such as diabetes, such as type II diabetes) comprising administering to a patient in need of such treatment an effective amount of a compound of formula IIA.

In another aspect, the present invention relates to a method of treating a disease mediated by a GPR119 receptor (such as diabetes, such as type II diabetes) comprising administering to a patient in need of such treatment an effective amount of at least one compound of formula IIA selected from the group consisting of the compounds in Table 6.

In another aspect, the present invention relates to a method of treating a disease mediated by a GPR119 receptor (such as diabetes, such as type II diabetes) comprising administering to a patient in need of such treatment an effective amount of at least one compound of formula IIA selected from the group consisting of the compounds in Table 9.

In another aspect, the invention relates to the use of the compounds of formula IIA to treat diabetes (e.g., type II diabetes).

In another aspect, the invention relates to the treatment of diabetes comprising administering to a patient in need of such treatment an effective amount of at least one (e.g., one) GPR119 agonist of formula IIA to a patient in need of such treatment.

In another aspect, the invention relates to the method of treating pain comprising administering to a patient in need of such treatment an effective amount of a combination of at least one compound of formula IIA and at least one additional agent for treating pain.

In another aspect, the invention relates to the method of treating chronic pain comprising administering to a patient in need of such treatment an effective amount of a combination of at least one compound of formula IIA and at least one additional agent for treating chronic pain.

More particularly, in another aspect, the invention relates to the method of treating inflammatory pain comprising administering to a patient in need of such treatment an effective amount of a combination of at least one compound of formula IIA and at least one additional agent for treating inflammatory pain.

More particularly, in another aspect, the invention relates to the method of treating neuropathic pain comprising administering to a patient in need of such treatment an effective amount of a combination of at least one compound of formula IIA and at least one additional agent for treating neuropathic pain.

In particular, in another aspect, the invention relates to the method of treating diabetes comprising administering to a patient in need of such treatment an effective amount of a combination of at least one compound of formula IIA and at least one additional agent for treating diabetes.

The compounds of formula I (e.g., at least one compound of formula I or IIA) of this invention are NPC1L1 antagonists and are therefore useful for treating disorders of lipid metabolism, in particular for inhibiting absorption of cholesterol.

The compounds of this invention are useful for treating disorders of lipid metabolism. The compounds of this invention are NPC1L1 antagonists. In one embodiment, the compounds of this invention are therefore useful for treating disorders of lipid metabolism, in particular for inhibiting absorption of cholesterol. It is to be understood that when the compounds of this invention are administered for inhibiting the absorption of cholesterol in a patient, the inhibition may be partial or complete. Accordingly, in one embodiment, the absorption of cholesterol in a patient is partially inhibited. In another embodiment, the absorption of cholesterol in a patient is completely inhibited.

Methods of treating disorders of lipid metabolism include treating hyperlipidemia, hypercholesterolaemia, hypertriglyceridaemia, sitosterolemia and arteriosclerotic symptoms; inhibiting absorption of cholesterol from the intestine; reducing blood plasma or serum concentrations of LDL cholesterol; reducing the concentrations of cholesterol and cholesterol ester in blood plasma or serum; reducing blood plasma or serum concentrations of C-reactive protein (CRP); reducing blood plasma or serum concentrations of triglycerides; reducing blood plasma or serum concentrations of apolipoprotein B; increasing blood plasma or serum concentrations of high density lipoprotein (HDL) cholesterol; increasing the fecal excretion of cholesterol; treating a clinical condition for which a cholesterol absorption inhibitor is indicated; reducing the incidence of cardiovascular disease-related events; reducing plasma or tissue concentration of at least one non-cholesterol sterol or 5α-stanol; treating or preventing vascular inflammation; preventing, treating or ameliorating symptoms of Alzheimer's Disease; regulating the production or level of at least one amyloid β peptide in the bloodstream and/or brain of a patient; regulating the amount of ApoE isoform 4 in the bloodstream and/or brain; preventing and/or treating obesity; and preventing or decreasing the incidence of xanthomas.

A method of treating a disorder of lipid metabolism comprises administering a cholesterol absorption inhibitor of formula I (e.g., at least one compound of formula I or IIA).

Additional agents for treating a disorder of lipid metabolism include inhibitors of cholesterol absorption (e.g., NPC1L1 antagonists, such as, for example, ezetimibe (such as the Zetia® brand of ezetimibe)), inhibitors of cholesterol biosynthesis, including, but not limited to HMG CoA reductase inhibitors (such as statins, such as, for example, simvastatin (such as the Zocor® brand of simvastatin), atorvastatin calcium (such as the Lipitor® brand of atorvastatin calcium), and rosuvastatin calcium (such as the Crestor® brand of rosuvastatin calcium)), inhibitors of cholesterol biosynthesis, cholesterol ester transfer protein (CETP) inhibitors (e.g., torcetrapib), bile acid sequesterants, a nicotinic acid receptor agonist such as nicotinic acid or a derivative thereof (e.g., Niacin (nicotinic acid), and the Niaspan® brand of niacin extended release tablets), peroxisome proliferator-activator receptor (PPAR) alpha agonists or activators, acylcoenzyme A:cholesterol acyltransferase (ACAT) inhibitors; obesity control medications, hypoglycemic agents, antioxidants, antihypertensive agents, ileal bile acid transport ("IBAT") inhibitors (or apical sodium co-dependent bile acid transport ("ASBT") inhibitors, probucol or derivatives thereof; low-density lipoprotein ("LDL") receptor activators, omega 3 fatty acids ("3-PUFA"); natural water soluble fibers; plant sterols, and plant stanols and/or fatty acid esters of plant stanols.

U.S. Provisional Application 60/752,710, filed Dec. 20, 2005, and U.S. Provisional Application 60/77048, filed Mar. 29, 2006, disclose the use of cholesterol absorption inhibitors.

Classes of cholesterol lowering agents useful in the present methods for treating disorders of lipid metabolism include the following non-limiting classes of agents: NPC1L1 inhibitors such as ezetimibe; HMG-CoA reductase inhibitors; bile acid sequestrants; PPAR agonists or activators; ileal bile acid transport ("IBAT") inhibitors (or apical sodium co-dependent bile acid transport ("ASBT") inhibitors; nicotinic acid (niacin) and/or nicotinic acid receptor agonists; acylCoA:cholesterol O-acyltransferase ("ACAT") inhibitors; cholesteryl ester transfer protein ("CETP") inhibitors; probucol or derivatives thereof; low-density lipoprotein ("LDL") receptor activators; omega 3 fatty acids ("3-PUFA"; natural water soluble fibers; plant sterols, plant stanols and/or fatty acid esters of plant stanols.

Non-limiting examples of suitable cholesterol biosynthesis inhibitors useful in the present methods include competitive inhibitors of HMG-CoA reductase, the rate-limiting step in cholesterol biosynthesis, squalene synthase inhibitors, squalene epoxidase inhibitors and mixtures thereof. Non-limiting examples of suitable HMG-CoA reductase inhibitors useful in the present methods include statins such as lovastatin, pravastatin, fluvastatin, simvastatin, atorvastatin, cerivastatin, CI-981, resuvastatin, rivastatin and pitavastatin, rosuvastatin; HMG-CoA reductase inhibitors, for example L-659, 699 ((E,E)-11-[3'R-(hydroxy-methyl)-4'-oxo-2'R-oxetanyl]-3,5,7R-trimethyl-2,4-undecadienoic acid); squalene synthesis inhibitors, for example squalestatin 1; and squalene epoxidase inhibitors, for example, NB-598 ((E)-N-ethyl-N-(6,6-dimethyl-2-hepten-4-ynyl)-3-[(3,3'-bithiophen-5-yl) methoxy]benzene-methanamine hydrochloride) and other sterol biosynthesis inhibitors such as DMP-565. Preferred HMG-CoA reductase inhibitors include lovastatin, pravastatin and simvastatin. The most preferred HMG-CoA reductase inhibitor is simvastatin.

Generally, a total daily dosage of cholesterol biosynthesis inhibitor(s) can range from about 0.1 to about 160 mg per day. In one embodiment, the dosage is from about 0.2 to about 80 mg/day, administered in a single dose or in 2-3 divided doses.

Bile acid sequestrants bind bile acids in the intestine, interrupting the enterohepatic circulation of bile acids and causing an increase in the faecal excretion of steroids.

Non-limiting examples of suitable bile acid sequestrants useful in the present methods include cholestyramine (a styrene-divinylbenzene copolymer containing quaternary ammonium cationic groups capable of binding bile acids, such as QUESTRAN® or QUESTRAN LIGHT® cholestyramine which are available from Bristol-Myers Squibb), colestipol (a copolymer of diethylenetriamine and 1-chloro-2,3-epoxypropane, such as COLESTID® tablets which are available from Pharmacia), colesevelam hydrochloride (such as WelChol® Tablets (poly(allylamine hydrochloride) cross-linked with epichlorohydrin and alkylated with 1-bromodecane and (6-bromohexyl)-trimethylammonium bromide) which are available from Sankyo), water soluble derivatives such as 3,3-ioene, N-(cycloalkyl) alkylamines and poliglusam, insoluble quaternized polystyrenes, saponins and mixtures thereof. Suitable inorganic cholesterol sequestrants include bismuth salicylate plus montmorillonite clay, aluminum hydroxide and calcium carbonate antacids.

The activators or agonists of PPAR act as agonists for the peroxisome proliferator-activated receptors. Three subtypes of PPAR have been identified, and these are designated as peroxisome proliferator-activated receptor alpha (PPARα), peroxisome proliferator-activated receptor gamma (PARRγ) and peroxisome proliferator-activated receptor delta (PPARδ). It should be noted that PPARδ is also referred to in the literature as PPARβ and as NUC1, and each of these names refers to the same receptor.

PPARα regulates the metabolism of lipids. PPARα is activated by fibrates and a number of medium and long-chain fatty acids, and it is involved in stimulating β-oxidation of fatty acids. The PPARγ receptor subtypes are involved in activating the program of adipocyte differentiation and are not involved in stimulating peroxisome proliferation in the liver. PPARδ has been identified as being useful in increasing high density lipoprotein (HDL) levels in humans. See, e.g., WO 97/28149.

PPARα activator compounds are useful for, among other things, lowering triglycerides, moderately lowering LDL levels and increasing HDL levels. Useful examples of PPARα activators include fibrates.

Non-limiting examples of suitable fibric acid derivatives ("fibrates") useful in the present methods include clofibrate; gemfibrozil; ciprofibrate; bezafibrate; clinofibrate; binifibrate; lifibrol; fenofibrate and mixtures thereof. These compounds can be used in a variety of forms, including but not limited to acid form, salt form, racemates, enantiomers, zwitterions and tautomers.

Other examples of PPARα activators useful in the present methods include suitable fluorophenyl compounds as disclosed in U.S. Pat. No. 6,028,109 which is incorporated herein by reference; certain substituted phenylpropionic compounds as disclosed in WO 00/75103 which is incorporated herein by reference; and PPARα activator compounds as disclosed in WO 98/43081 which is incorporated herein by reference.

Non-limiting examples of suitable PPARγ activators useful in the present methods include derivatives of glitazones or thiazolidinediones, such as, troglitazone; rosiglitazone and pioglitazone. Other useful thiazolidinediones include ciglitazone, englitazone, darglitazone and BRL 49653 as disclosed in WO 98/05331 which is incorporated herein by reference; PPARγ activator compounds disclosed in WO 00/76488 which is incorporated herein by reference; and PPARγ activator compounds disclosed in U.S. Pat. No. 5,994,554 which is incorporated herein by reference.

Other useful PPARγ activator compounds useful in the present methods include certain acetylphenols as disclosed in U.S. Pat. No. 5,859,051 which is incorporated herein by reference; certain quinoline phenyl compounds as disclosed in WO 99/20275 which is incorporated herein by reference; aryl compounds as disclosed by WO 99/38845 which is incorporated herein by reference; certain 1,4-disubstituted phenyl compounds as disclosed in WO 00/63161; certain aryl compounds as disclosed in WO 01/00579 which is incorporated herein by reference; benzoic acid compounds as disclosed in WO 01/12612 & WO 01/12187 which are incorporated herein by reference; and substituted 4-hydroxy-phenylalconic acid compounds as disclosed in WO 97/31907 which is incorporated herein by reference.

PPARδ compounds are useful for, among other things, lowering triglyceride levels or raising HDL levels. Non-limiting examples of PPARδ activators useful in the present methods include suitable thiazole and oxazole derivatives, such as C.A.S. Registry No. 317318-32-4, as disclosed in WO 01/00603 which is incorporated herein by reference); certain fluoro, chloro or thio phenoxy phenylacetic acids as disclosed in WO 97/28149 which is incorporated herein by reference; suitable non-β-oxidizable fatty acid analogues as disclosed in U.S. Pat. No. 5,093,365 which is incorporated herein by reference; and PPARδ compounds as disclosed in WO 99/04815 which is incorporated herein by reference.

Moreover, compounds that have multiple functionality for activating various combinations of PPARα, PPARγ and PPARδ are also useful in the present methods. Non-limiting examples include certain substituted aryl compounds as disclosed in U.S. Pat. No. 6,248,781; WO 00/23416; WO 00/23415; WO 00/23425; WO 00/23445; WO 00/23451; and WO 00/63153, all of which are incorporated herein by reference, are described as being useful PPARα and/or PPARγ activator compounds. Other non-limiting examples of useful PPARα and/or PPARγ activator compounds include activator compounds as disclosed in WO 97/25042 which is incorporated herein by reference; activator compounds as disclosed in WO 00/63190 which is incorporated herein by reference; activator compounds as disclosed in WO 01/21181 which is incorporated herein by reference; biaryl-oxa(thia)zole compounds as disclosed in WO 01/16120 which is incorporated herein by reference; compounds as disclosed in WO 00/63196 and WO 00/63209 which are incorporated herein by reference; substituted 5-aryl-2,4-thiazolidinediones compounds as disclosed in U.S. Pat. No. 6,008,237 which is incorporated herein by reference; arylthiazolidinedione and aryloxazolidinedione compounds as disclosed in WO 00/78312 and WO 00/78313G which are incorporated herein by reference; GW2331 or (2-(4-[difluorophenyl]-1heptylureido)ethyl]phenoxy)-2-methylbutyric compounds as disclosed in WO 98/05331 which is incorporated herein by reference; aryl compounds as disclosed in U.S. Pat. No. 6,166,049 which is incorporated herein by reference; oxazole compounds as disclosed in WO 01/17994 which is incorporated herein by reference; and dithiolane compounds as disclosed in WO 01/25225 and WO 01/25226 which are incorporated herein by reference.

Other useful PPAR activator compounds useful in the present methods include substituted benzylthiazolidine-2,4-dione compounds as disclosed in WO 01/14349, WO 01/14350 and WO/01/04351 which are incorporated herein by reference; mercaptocarboxylic compounds as disclosed in WO 00/50392 which is incorporated herein by reference; ascofuranone compounds as disclosed in WO 00/53563 which is incorporated herein by reference; carboxylic compounds as disclosed in WO 99/46232 which is incorporated herein by reference; compounds as disclosed in WO 99/12534 which is incorporated herein by reference; benzene compounds as disclosed in WO 99/15520 which is incorporated herein by reference; o-anisamide compounds as disclosed in WO 01/21578 which is incorporated herein by reference; and PPAR activator compounds as disclosed in WO 01/40192 which is incorporated herein by reference.

The peroxisome proliferator-activated receptor(s) activator(s) are administered in a therapeutically effective amount to treat the specified condition, for example in a daily dose preferably ranging from about 50 to about 3000 mg per day. In one embodiment, the daily dose is from about 50 to about 2000 mg per day, administered in a single dose or in 2-4 divided doses. The exact dose, however, is determined by the attending clinician and is dependent on such factors as the potency of the compound administered, the age, weight, condition and response of the patient.

In an alternative embodiment, the present invention includes the use of one or more IBAT inhibitors or ASBT inhibitors. The IBAT inhibitors can inhibit bile acid transport to reduce LDL cholesterol levels. Non-limiting examples of suitable IBAT inhibitors useful in the present methods include benzothiepines such as therapeutic compounds comprising a 2,3,4,5-tetrahydro-1-benzothiepine 1,1-dioxide structure such as are disclosed in PCT Patent Application WO 00/38727 which is incorporated herein by reference.

Generally, a total daily dosage of IBAT inhibitor(s) can range from about 0.01 to about 1000 mg/day. In one embodiment, the dosage is from about 0.1 to about 50 mg/day, administered in a single dose or in 2-4 divided doses.

In another alternative embodiment, the methods of the present invention can further comprise nicotinic acid (niacin) and/or nicotinic acid receptor ("NAR") agonists as lipid lowering agents.

As used herein, "nicotinic acid receptor agonist" means any compound comprising that will act as an agonist to the nicotinic acid receptor. Compounds include those that have a pyridine-3-carboxylate structure or a pyrazine-2-carboxylate structure, including acid forms, salts, esters, zwitterions and tautomers, where available. Examples of nicotinic acid receptor agonists useful in the present methods include niceritrol, nicofuranose and acipimox. Nicotinic acid and NAR agonists inhibit hepatic production of VLDL and its metabolite LDL and increases HDL and apo A-1 levels. An example of a suitable nicotinic acid product is NIASPAN® (niacin extended-release tablets) which are available from Kos Pharmaceuticals, Inc. (Cranbury, N.J.).

Generally, a total daily dosage of nicotinic acid can range from about 500 to about 10,000 mg/day. In one embodiment, the dosage is from about 1000 to about 8000 mg/day. In another embodiment, the dosage is from about 3000 to about 6000 mg/day, administered in a single dose or in divided doses. Generally, the total daily dosage of a NAR agonist can range from about 1 to about 100 mg/day.

In another alternative embodiment, the methods of the present invention can further comprise one or more ACAT inhibitors as lipid lowering agents. ACAT inhibitors reduce LDL and VLDL levels. ACAT is an enzyme responsible for esterifying excess intracellular cholesterol and may reduce the synthesis of VLDL, which is a product of cholesterol esterification, and overproduction of apo B-100-containing lipoproteins.

Non-limiting examples of useful ACAT inhibitors useful in the present methods include avasimibe, HL-004, lecimibide and CL-277082 (N-(2,4-difluorophenyl)-N-[[4-(2,2-dimethylpropyl)phenyl]-methyl]-N-heptylurea). See P. Chang et al., "Current, New and Future Treatments in Dyslipidaemia and Atherosclerosis", *Drugs* 2000 July; 60 (1); 55-93, which is incorporated by reference herein.

Generally, a total daily dosage of ACAT inhibitor(s) can range from about 0.1 to about 1000 mg/day, administered in a single dose or in 2-4 divided doses.

In another alternative embodiment, the compositions used in the methods of the present invention can further comprise one or more Cholesteryl Ester Transfer Protein ("CETP") Inhibitors coadministered with or in combination with one of more Spirocyclic Azetidinone Compounds. CETP is responsible for the exchange or transfer of cholesteryl ester carrying HDL and triglycerides in VLDL.

Non-limiting examples of suitable CETP inhibitors useful in the present methods are disclosed in PCT Patent Application No. WO 00/38721 and U.S. Pat. No. 6,147,090, which are incorporated herein by reference. Pancreatic cholesteryl ester hydrolase (pCEH) inhibitors such as WAY-121898 also can be co-administered with or in combination with the fibric acid derivative(s) and sterol absorption inhibitor(s) discussed above.

Generally, a total daily dosage of CETP inhibitor(s) can range from about 0.01 to about 1000 mg/day, and preferably about 0.5 to about 20 mg/kg body weight/day, administered in a single dose or in 2 or more divided doses.

In another alternative embodiment, the methods of the present invention can further comprise probucol or derivatives thereof (such as AGI-1067 and other derivatives disclosed in U.S. Pat. Nos. 6,121,319 and 6,147,250), which can reduce LDL and HDL levels, as cholesterol lowering agents.

Generally, a total daily dosage of probucol or derivatives thereof can range from about 10 to about 2000 mg/day. In one embodiment, the dosage is from about 500 to about 1500 mg/day, administered in a single dose or in 2-4 divided doses.

In another alternative embodiment, the methods of the present invention can further comprise one or more low-density lipoprotein (LDL) receptor activators, as lipid lowering agents. Non-limiting examples of suitable LDL-receptor activators useful in the present methods include HOE-402, an imidazolidinyl-pyrimidine derivative that directly stimulates LDL receptor activity. See M. Huettinger et al., "Hypolipidemic activity of HOE-402 is Mediated by Stimulation of the LDL Receptor Pathway", *Arterioscler Thromb.* 1993; 13:1005-12.

Generally, a total daily dosage of LDL receptor activator(s) can range from about 1 to about 1000 mg/day, administered in a single dose or in 2-4 divided doses.

In another alternative embodiment, the methods of the present invention can further comprise fish oil, which contains Omega 3 fatty acids (3-PUFA), which can reduce VLDL and triglyceride levels, as a lipid lowering agent. Generally, a total daily dosage of fish oil or Omega 3 fatty acids can range from about 1 to about 30 grams per day, administered in a single dose or in 2-4 divided doses.

In another alternative embodiment, the methods of the present invention can further comprise natural water-soluble fibers, such as psyllium, guar, oat and pectin, which can reduce cholesterol levels. Generally, a total daily dosage of natural water soluble fibers can range from about 0.1 to about 10 grams per day, administered in a single dose or in 2-4 divided doses.

In another alternative embodiment, methods of the present invention can further comprise plant sterols, plant stanols and/or fatty acid esters of plant stanols, such as sitostanol ester used in BENECOL® margarine, which can reduce cholesterol levels. Generally, a total daily dosage of plant sterols, plant stanols and/or fatty acid esters of plant stanols can range from about 0.5 to about 20 grams per day, administered in a single dose or in 2-4 divided doses.

Thus, another aspect of the invention is directed to the inhibition of the absorption of cholesterol comprising administering to a patient in need of such treatment an effective amount of at least one compound of formula I.

Another aspect of the invention is directed to the inhibition of the absorption of cholesterol comprising administering to a patient in need of such treatment an effective amount of at least one compound of formula IIA.

Another aspect of the invention is directed to the inhibition of the absorption of cholesterol comprising administering to a patient in need of such treatment an effective amount of at least one compound of formula I in combination with an effective amount of at least one additional agent for treating a disorder of lipid metabolism.

Another aspect of the invention is directed to the inhibition of the absorption of cholesterol comprising administering to a patient in need of such treatment an effective amount of at least one compound of formula IIA in combination with an effective amount of at least one additional agent for treating a disorder of lipid metabolism.

Another aspect of the invention is directed to the inhibition of the absorption of cholesterol comprising administering to a patient in need of such treatment an effective amount of at least one compound of formula I in combination with an effective amount of at least one nicotinic acid receptor agonist (e.g., nicotinic acid).

Another embodiment of the invention is directed to the inhibition of the absorption of cholesterol comprising administering to a patient in need of such treatment an effective amount of at least one compound of formula IIA in combination with an effective amount of at least one nicotinic acid receptor agonist (e.g., nicotinic acid).

Another aspect of the invention is directed to the inhibition of the absorption of cholesterol comprising administering to a patient in need of such treatment an effective amount of at least one compound of formula I in combination with an effective amount of at least one inhibitor of HMG-CoA reductase (e.g., statins, such as, for example, simvastatin, atorvastatin calcium, and rosuvastatin calcium).

Another embodiment of the invention is directed to the inhibition of the absorption of cholesterol comprising administering to a patient in need of such treatment an effective amount of at least one compound of formula IIA in combination with an effective amount of at least one inhibitor of HMG-CoA reductase (e.g., . statins, such as, for example, simvastatin, atorvastatin calcium, and rosuvastatin calcium).

Another aspect of the invention is directed to the inhibition of the absorption of cholesterol comprising administering to a patient in need of such treatment an effective amount of at least one compound of formula I in combination with an effective amount of at least one inhibitor of CETP (e.g., torcetrapib).

Another aspect of the invention is directed to the inhibition of the absorption of cholesterol comprising administering to a patient in need of such treatment an effective amount of at least one compound of formula IIA in combination with an effective amount of at least one inhibitor of CETP (e.g., torcetrapib).

Another aspect of the invention is directed to the inhibition of the absorption of cholesterol comprising administering to a patient in need of such treatment an effective amount of at least one compound of formula I in combination with an effective amount of at least one NPC1L1 antagonist (such as, for example, ezetimibe, such as the Zetia® brand of ezetimibe).

Another aspect of the invention is directed to the inhibition of the absorption of cholesterol comprising administering to a patient in need of such treatment an effective amount of at least one compound of formula IIA in combination with an effective amount of at least one NPC1L1 antagonist (such as, for example, ezetimibe, such as the Zetia® brand of ezetimibe).

Another embodiment of the invention is directed to the inhibition of the absorption of cholesterol comprising administering to a patient in need of such treatment an effective amount of at least one compound of formula I (e.g., a compound of formula I or IIA) in combination with an effective amount of at least one inhibitor of HMG-CoA reductase (e.g., statins, such as, for example, simvastatin, atorvastatin calcium, and rosuvastatin calcium), and in combination with an effective amount of at least one NPC1L1 antagonist (such as, for example, ezetimibe, such as the Zetia® brand of ezetimibe). An example of a medicament already comprising a combination of a HMG-CoA reductase and a NPC1L1 antagonist that can be used in this embodiment is the Vytorin® brand of the combination of ezetimibe and simvastatin.

For compounds of formula I, $R^4$ and $R^5$ are preferably each —$CH_2$— and u and v are preferably each 2, i.e., $R^4$ and are $R^5$ are preferably each —$CH_2$—$CH_2$—.

In another aspect this invention relates to compounds of formula I wherein $R^1$ is selected from the group consisting of: H, alkyl, substituted alkyl, aryl, substituted aryl, arylalkyl, heteroaryl, substituted heteroaryl and -alkylene-C(O)N(alkyl)$_2$. In another aspect this invention relates to compounds of formula I wherein $R^1$ is selected from the group consisting of: H, $C_1$-$C_4$ alkyl, phenyl, pyrimidyl, pyridyl, halo substituted pyridyl, benzyl substituted by halo, and phenyl substituted with 1 or 2 substituents selected from the group consisting of: phenyl, halo substituted phenyl, F, Cl, Br, CN and —$CF_3$.

In another aspect this invention relates to compounds of formula IIA wherein $R^1$ for formula IIA is selected from the group consisting of: methyl, i-propyl, —$CH_2CH(CH_3)_2$, $CH_2CH_2(CH_3)_2$,

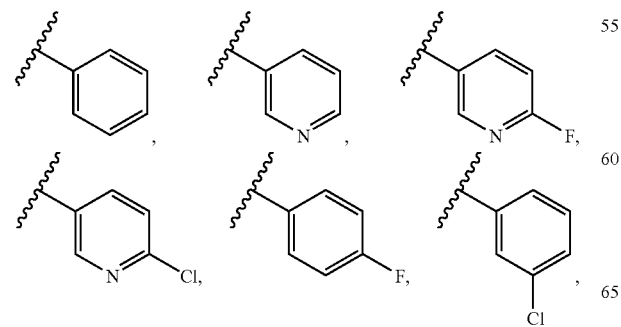

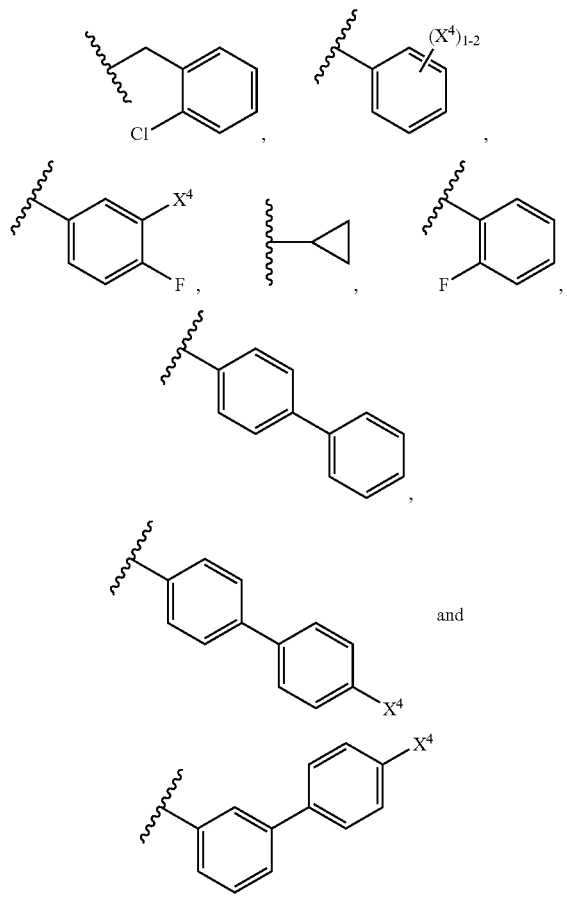

wherein each $X^4$ is independently selected from the group consisting of: Br, Cl, F, CN and —$CF_3$. An Example of the $R^1$ moiety:

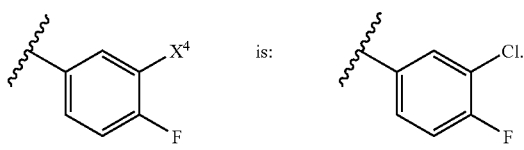

In another aspect this invention relates to compounds of formula I wherein $R^2$ is selected from the group consisting of:

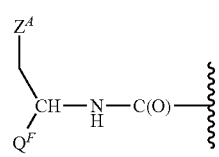

wherein $Z^A$ and $Q^F$ are as defined above, and wherein examples of said

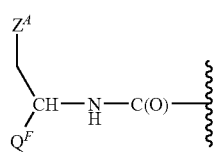

include for example,

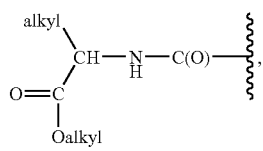

such as for example,

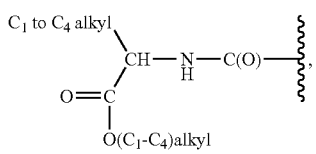

such as, for example,

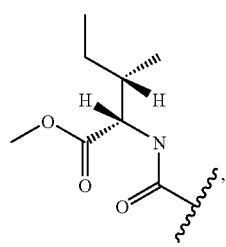

such as, for example,

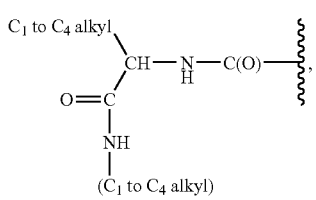

such as, for example,

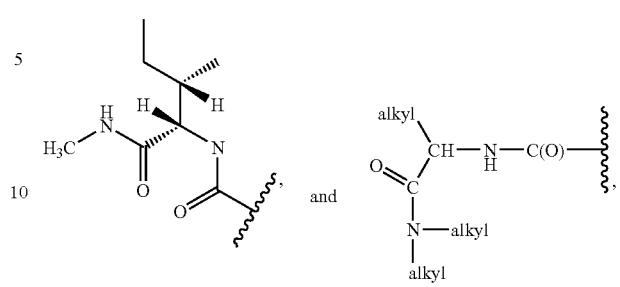

such as, for example,

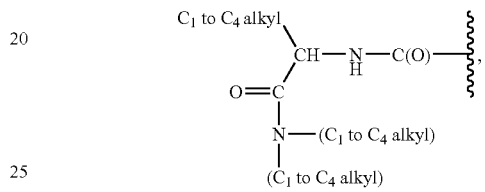

such as, for example,

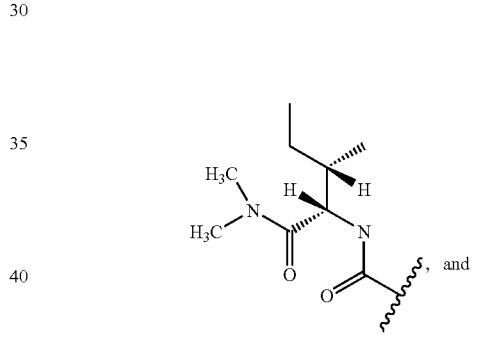

$R^6$-A- wherein A is —C(O)—NH—, —C(O)— or —C(O)-alkylene- and $R^6$ is an optionally substituted group selected from aryl, heteroaryl, cycloalkyl, cycloalkylalkyl, heterocycloalkyl, cycloalkenyl, heterocycloalkenyl, benzofused cycloalkyl, benzofused heterocycloalkyl, and benzofused heterocycloalkenyl.

In another aspect this invention relates to compounds of formula I wherein said aryl groups for $R^6$ in $R^2$ in formula I are phenyl, and said heteroaryl groups for $R^6$ are pyridyl.

In another aspect this invention relates to compounds of formula I wherein said substituted aryl (e.g., substituted phenyl and substituted naphthyl) groups for $R^6$ in $R^2$ are substituted with 1 to 3 (e.g., 1 or 2, or 1) substituents independently selected from the group consisting of: alkyl, halo (e.g., F, Cl, and Br), —$CF_3$, CN, alkoxy, phenoxy and —$CO_2$alkyl. In another aspect this invention relates to compounds of formula I wherein said substituted aryl $R^6$ groups in $R^2$ are substituted with 1 to 3 (e.g., 1 or 2, or 1) substituents independently selected from the group consisting of: F, Cl, Br and CN. Examples of substituted phenyls include:

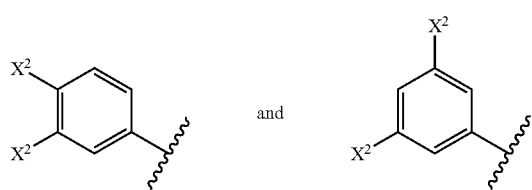

wherein each $X^2$ is independently selected from the group consisting of: alkyl, halo (e.g., F, Cl, and Br), —$CF_3$, CN, alkoxy, phenoxy and —$CO_2$alkyl. In another aspect, each $X^2$ is independently selected from the group consisting of: F, Cl, Br and CN. Examples of substituted phenyl $R^6$ groups include

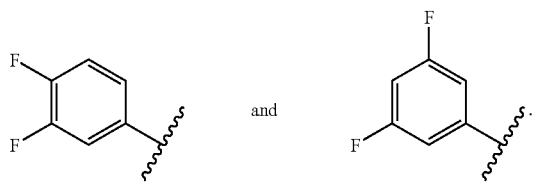

In another aspect this invention relates to compounds of formula I wherein said substituted heteroaryl (e.g., substituted pyridyl) groups for $R^6$ in $R^2$ are substituted with 1 to 3 (e.g., 1 or 2, or 1) substituents independently selected from the group consisting of: alkyl, halo (e.g., F, Cl, and Br), —$CF_3$, CN, alkoxy, phenoxy and —$CO_2$alkyl. In another aspect this invention relates to compounds of formula I wherein said substituted heteroaryl groups for $R^6$ in $R^2$ are substituted with 1 to 3 (e.g., 1 or 2, or 1) substituents independently selected from the group consisting of: F, Cl, Br and CN. Examples of substituted pyridyls include:

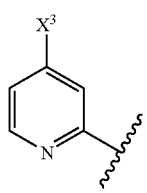

wherein $X^3$ is independently selected from the group consisting of: alkyl, halo (e.g., F, Cl, and Br), —$CF_3$, CN, alkoxy, phenoxy and —$CO_2$alkyl. In another aspect, $X^3$ is independently selected from the group consisting of F, Cl, Br and CN. Examples of substituted heteroaryl $R^6$ groups include

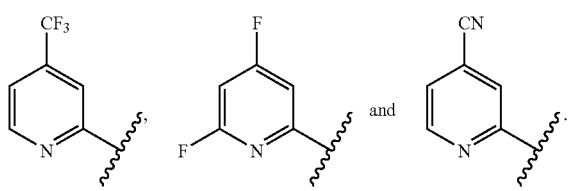

In another aspect this invention relates to compounds of formula I wherein said cycloalkyl groups for $R^6$ in $R^2$ in formula I are selected from the group consisting of: cyclopentyl, cyclohexyl, and cycloheptyl.

In another aspect this invention relates to compounds of formula I wherein said cycloalkenyl groups for $R^6$ in $R^2$ in formula I is dihydropyran.

In another aspect this invention relates to compounds of formula I for use as T-type calcium channel blockers wherein:

$R^1$ is selected from the group consisting of: H, alkyl, substituted alkyl, cycloalkyl, aryl, and substituted aryl;

$R^3$ is selected from the group consisting of aryl and substituted aryl; and $R^2$ is selected from the group consisting of: H, aryl-NH—C(O)—, alkyl-NH—C(O)—, alkyl-O—C(O)—, alkyl-O—C(O)-alkylene-NH—C(O)—, and

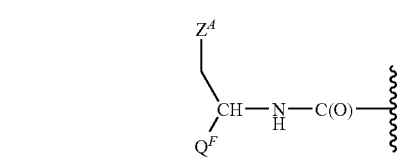

wherein $Z^A$ and $Q^F$ are as defined above, and wherein examples of said

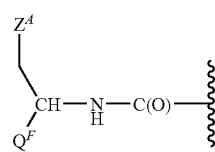

include for example,

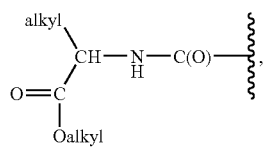

such as, for example,

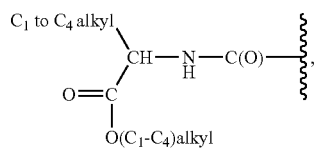

such as, for example,

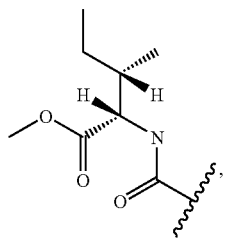

such as, for example,

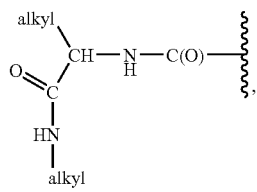

and such as, for example,

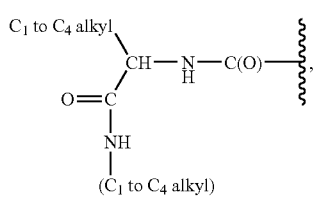

such as, for example,

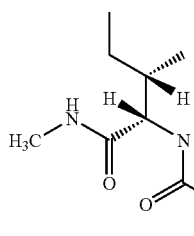

and

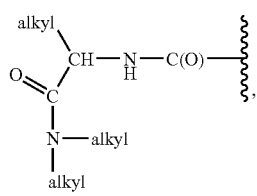

such as for example,

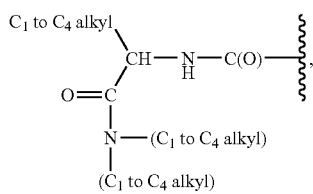

such as, for example,

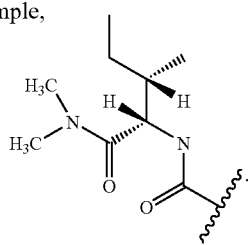

In another aspect this invention relates to compounds of formula I wherein said "Aryl" in $R^1$, $R^2$ and $R^3$ is optionally substituted phenyl.

In another aspect this invention relates to compounds of formula I for use as T-type calcium channel blockers wherein:

$R^1$ is selected from the group consisting of: H, isopropyl, methyl, phenyl, 4-fluorophenyl, 2-chlorophenyl and cyclopropyl;

$R^3$ is selected from the group consisting of: 4-chlorophenyl, phenyl, 4-bromophenyl, and 4-benzyloxy-phenyl; and $R^2$ is selected from the group consisting of: H, 3,5-dichloro-phenyl-NH—C(O)—, 3,4-di-fluoro-phenyl-NH—C(O)—, 4-chloro-phenyl-NH—C(O)—, 3,5-difluoro-phenyl-NH—C(O)—, 4-fluoro-phenyl-NH—C(O)—, $(CH_3)_2$—C—$CH_2$—$C(CH_3)_2$—NH—C(O)—, phenyl-NH—C(O)—, 2-methyl-phenyl-NH—C(O)—, 4-($CH_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—, 2-$CF_3$-phenyl-NHC(O)—, 2-chloro-6-methyl-phenyl-NHC(O)—, 2,6-dichloro-phenyl-NHC(O)—, t-Bu-phenyl-NHC(O)—, In the aryl, heteroaryl, heterocycloalkyl, heterocycloalkenyl, cycloalkyl, cycloalkenyl, benzofused cycloalkyl, benzofused heterocycloalkyl and benzofused cycloalkenyl groups ring system substituents can be present. In another aspect this invention relates to compounds of formula I wherein said ring system substituents are selected from the group consisting of: alkyl, alkoxy, —C(O)alkyl, halo, —C(O)Oalkyl, —$CF_3$, —$OCF_3$, optionally substituted phenyl, phenoxy, benzyl, benzyloxy, piperidinyl, piperazinyl, N-methylpiperazinyl, morpholinyl, —CN, —$SO_2$alkyl, OH, —NHC(O)alkyl, —N(alkyl)-alkylene-CN, —C(=$CH_2$)$CH_3$, —O-alkylene-N(alkyl)$_2$, —N(alkyl)$_2$, optionally substituted heteroaryl, and heteroarylalkyl, wherein heteroaryl is selected from the group consisting of pyrrolyl, triazolyl, thienyl, pyridyl, pyrazolyl, and ozazolyl. Optionally, for said heterocycloalkyl group and said benzofused heterocycloalkyl group, a —$CH_2$— group can be replaced by a —C(=N)— or —C(O)— group. Optionally, for said aryl group and for said heteroaryl group, two adjacent ring carbons can be joined by a —$(CH_2)_3$—, —$(CH_2)_4$—, —O—$CH_2$—O—, —$O(CH_2)_2$—O—, or —$O(CH_2)_3$—O— group.

In another aspect this invention relates to compounds of formula I wherein $R^1$ for formula I is any one of the $R^1$ moieties in the formulas in any one of Examples 1 to 6, or in any one of the formulas in Tables 5, 6, 7, 8, or 8A.

In another aspect this invention relates to compounds of formula I wherein $R^2$ for formula I is any one of the $R^2$ moieties in the formulas in any one of Examples 1 to 6, or in any one of the formulas in Tables 5, 6, 7, 8 or 8A.

In another aspect this invention relates to compounds of formula I wherein $R^3$ for formula I is any one of the $R^3$ moieties in the formulas in any one of Examples 1 to 6, or in any one of the formulas in Tables 5, 6, 7, 8 or 8A.

In another aspect this invention relates to compounds of formula I wherein $R^1$ for formula I is any one of the $R^1$ moieties in the formulas in any one of Examples 1 to 6, or in any one of the formulas in Tables 5, 6, 7, 8 or 8A, and $R^2$ for formula I is any one of the $R^2$ moieties in the formulas in any one of Examples 1 to 6, or in any one of the formulas in Tables 5, 6, 7, 8 or 8A, and $R^3$ for formula I is any one of the $R^3$ moieties in the formulas in any one of Examples 1 to 6, or in any one of the formulas in Tables 5, 6, 7, 8 or 8A.

In another aspect this invention relates to compounds of formula I wherein $R^1$ for formula IIA is any one of the $R^1$ moieties in the formulas in any one of Examples 1 to 6, or in any one of the formulas in Tables 5, 6, 7, 8 or 8A.

In another aspect this invention relates to compounds of formula I wherein $R^2$ for formula IIA is any one of the $R^2$ moieties in the formulas in any one of Examples 1 to 6, or in any one of the formulas in Tables 5, 6, 7, 8 or 8A.

In another aspect this invention relates to compounds of formula I wherein $R^3$ for formula IIA is any one of the $R^3$ moieties in the formulas in any one of Examples 1 to 6, or in any one of the formulas in Tables 5, 6, 7, 8 or 8A.

In another aspect this invention relates to compounds of formula I wherein $R^1$ for formula IIA is any one of the $R^1$ moieties in the formulas in any one of Examples 1 to 6, or in any one of the formulas in Tables 5, 6, 7, 8 or 8A, and $R^2$ for formula IIA is any one of the $R^2$ moieties in the formulas in any one of Examples 1 to 6, or in any one of the formulas in Tables 5, 6, 7, 8 or 8A, and $R^3$ for formula IIA is any one of the $R^3$ moieties in the formulas in any one of Examples 1 to 6, or in any one of the formulas in Tables 5, 6, 7, 8 or 8A.

In another aspect this invention relates to compounds of formula I (e.g., compounds of formula I or IIA, useful, for example, as T-calcium channel blockers, and useful, for example, for the treatment of pain) wherein:

(A) $R^1$ is selected from the group consisting of: (1) alkyl (such as, for example, i-propyl, methyl, —$(CH_2)_2CH(CH_3)_2$), —$CH_2CH(CH_3)_2$), (2) alkenyl (such as, for example, —$CH_2CH=CH_2$), (3) cycloalkyl (such as, for example, cyclopropyl), (4) aryl (such as, for example, phenyl), (5) halo substituted phenyl (such as, for example, p-F-phenyl), (6) arylalkyl- (such as, for example, benzyl), and (7) —$C(O)NQ^B$ wherein $Q^B$ is selected from the group consisting of: substituted phenyl (such as, for example, phenyl substituted with halo (such as, for example, o,p-di-F-phenyl))

(B) $R^2$ is selected from the group consisting of:
(1) —$C(O)NHQ^A$ wherein $Q^A$ is selected from the group consisting of:
(a) cycloalkyl (such as, for example, adamantyl (a multicyclic cycloalkyl) and cycloheptyl),
(b) alkyl substituted with —C(O)—O-alkyl (such as, for example, —$CH(C(O)OCH_3)CH(CH_3)_2$, —$CH(C(O)OCH_3)CH(CH_3)CH_2CH_3$, —$CH(C(O)Ot-butyl)CH(CH_3)CH_2CH_3$, —$CH(C(O)OCH_3)CH(CH_3)_2$, and —$CH_2C(O)OCH_2CH_3$),
(c) substituted aryl, e.g., substituted phenyl, such as, for example, halo substituted phenyl (such as, for example 3,5-di-F-phenyl, 3-F-phenyl, p-Cl-phenyl, m-Cl-phenyl, o-Cl-phenyl, m-Br-phenyl, p-Br-phenyl, m,p-di-F-phenyl, p-F-phenyl, o-F-phenyl, o,p-di-F-phenyl, o,m-di-F-phenyl), m-CN-phenyl, p-CN-phenyl, m-$CF_3$-phenyl, p-$CF_3$-phenyl, m-methoxyphenyl, m-$CH_3CH_2OC(O)$-phenyl, m-methylphenyl, m-$CH_3O$-phenyl, p-methylphenyl, o-methylphenyl, o-methoxyphenyl, p-methoxyphenyl, and m-F-p-methyl-phenyl),
(d) alkyl (such as, for example, —$CH(CH_3)_2CH_2C(CH_3)_3$, and t-butyl),
(e) substituted arylalkyl, such as, for example, a halo substituted arylalkyl, such as, for example, a halo substituted benzyl, such as, for example, m-F-benzyl,
(f) substituted heterocycloalkenylbenzo, such as, for example, oxo substituted heterocycloalkenylbenzo, such as, for example,

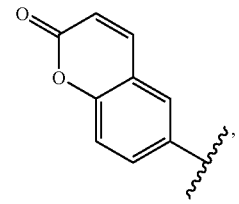

(g) heteroaryl, such as, for example, pyridyl, such as, for example, m-pyridyl
(2) H,
(3) substituted benzoheterocycloakyl-C(O)—, such as, for example,
(a) halo substituted benzoheterocycloalkyl-C(O)—, such as, for example,

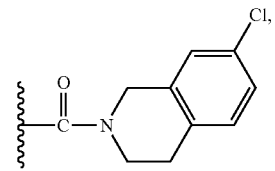

(b) alkoxy substituted benzoheterocycloalkyl-C(O)— such as, for example,

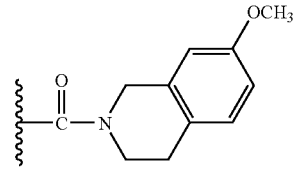

(4) —C(O)O-alkyl, such as, for example, —C(O)Ot-butyl,
(5) heterocycloalkyl (such as, for example, morpholinyl), and
(6) —$C(O)NQ^CQ^D$ wherein $Q^C$ and $Q^D$ are each independently selected from the group consisting of: H, $Q^A$ (as defined above), substituted aryl (such as, for example, substituted phenyl, such as, for example, halo substituted phenyl, such as, for example, m,m-di-F-phenyl), and arylalkyl (such as, for example, phenylalkyl- such as, for example, benzyl); and wherein, in one example, $Q^C$ and $Q^D$ are selected as follows: $Q^C$ is substituted aryl (such as, for example, substituted phenyl, such as, for example, halo substituted phenyl, such as, for example, as m,m-di-F-phenyl), and $Q^D$ is arylalkyl (such as phenylalkyl-, such as, for example, benzyl); and
(C) $R^3$ is selected from the group consisting of:
(1) substituted phenyl, such as, for example, (a) halo substituted phenyl, (such as, for example, p-Cl-phenyl, p-Br-phenyl, and p-F-phenyl), (b) phenyl substituted phenyl (i.e., phenyl-phenyl-), (c) phenyl substituted with heteroaryl (such as, for example, pyridyl-phenyl-, such as, for example,

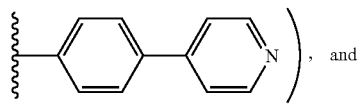

(d) cyano substituted phenyl (such as, for example, p-CN-phenyl), and
    (2) heteroaryl (such as, for example, pyridyl such as, for example, m-pyridyl and o-pyridyl).

In another aspect this invention relates to compounds of formula I (e.g., compounds of formula I or IIA, useful, for example, as T-calcium channel blockers, and useful, for example, for the treatment of pain) wherein:
(A) $R^1$ is selected from the group consisting of: (1) alkyl (such as, for example, i-propyl, methyl, —$(CH_2)_2CH(CH_3)_2$), —$CH_2CH(CH_3)_2$), (2) alkenyl (such as, for example, —$CH_2CH=CH_2$), (3) cycloalkyl (such as, for example, cyclopropyl), (4) aryl (such as, for example, phenyl), (5) halo substituted phenyl (such as, for example, p-F-phenyl), (6) arylalkyl- (such as, for example, benzyl), and (7) —$C(O)NQ^B$ wherein $Q^B$ is selected from the group consisting of: substituted phenyl (such as, for example, phenyl substituted with halo (such as, for example, o,p-di-F-phenyl))
(B) $R^2$ is selected from the group consisting of:
(1) —$C(O)NHQ^A$ wherein $Q^A$ is selected from the group consisting of:
    (a) cycloalkyl (such as, for example, adamantyl (a multicyclic cycloalkyl) and cycloheptyl),
    (b) alkyl substituted with —C(O)—O-alkyl (such as, for example, —$CH(C(O)OCH_3)CH(CH_3)_2$, —$CH(C(O)OCH_3)CH(CH_3)CH_2CH_3$, —$CH(C(O)Ot-butyl)CH(CH_3)CH_2CH_3$, —$CH(C(O)OCH_3)CH(CH_3)_2$, and —$CH_2C(O)OCH_2CH_3$),
    (c) substituted aryl, e.g., substituted phenyl, such as, for example, halo substituted phenyl (such as, for example 3,5-di-F-phenyl, 3-F-phenyl, p-Cl-phenyl, m-Cl-phenyl, o-Cl-phenyl, m-Br-phenyl, p-Br-phenyl, m,p-di-F-phenyl, p-F-phenyl, o-F-phenyl, o,p-di-F-phenyl, o,m-di-F-phenyl), m-CN-phenyl, p-CN-phenyl, m-$CF_3$-phenyl, p-$CF_3$-phenyl, m-methoxyphenyl, m-$CH_3CH_2OC(O)$-phenyl, m-methylphenyl, m-$CH_3O$-phenyl, p-methylphenyl, o-methylphenyl, o-methoxyphenyl, p-methoxyphenyl, and m-F-p-methyl-phenyl),
    (d) alkyl (such as, for example, —$CH(CH_3)_2CH_2C(CH_3)_3$, and t-butyl),
    (e) substituted arylalkyl, such as, for example, a halo substituted arylalkyl, such as, for example, a halo substituted benzyl, such as, for example, m-F-benzyl, and
    (f) heteroaryl, such as, for example, pyridyl, such as, for example, m-pyridyl (2) H,
(3) —C(O)O-alkyl, such as, for example, —C(O)Ot-butyl,
(4) heterocycloalkyl (such as, for example, morpholinyl), and
(5) —$C(O)NQ^CQ^D$ wherein $Q^C$ and $Q^D$ are each independently selected from the group consisting of: H, $Q^A$ (as defined above), substituted aryl (such as, for example, substituted phenyl, such as, for example, halo substituted phenyl, such as, for example, such as, for example, m,m-di-F-phenyl), and arylalkyl (such as, for example, phenylalkyl- such as, for example, benzyl); and wherein, in one example, $Q^C$ and $Q^D$ are selected as follows: $Q^C$ is substituted aryl (such as, for example, substituted phenyl, such as, for example, halo substituted phenyl, such as, for example, as m,m-di-F-phenyl), and $Q^D$ is arylalkyl (such as phenylalkyl-, such as, for example, benzyl); and
(C) $R^3$ is selected from the group consisting of:
(1) substituted phenyl, such as, for example, (a) halo substituted phenyl, (such as, for example, p-Cl-phenyl, p-Br-phenyl, and p-F-phenyl), (b) phenyl substituted phenyl (i.e., phenyl-phenyl-), (c) phenyl substituted with heteroaryl (such as, for example, pyridyl-phenyl-, such as, for example,

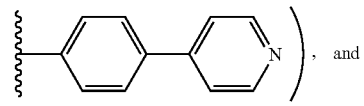

(d) cyano substituted phenyl (such as, for example, p-CN-phenyl), and
    (2) heteroaryl (such as, for example, pyridyl such as, for example, m-pyridyl and o-pyridyl).

In another aspect this invention relates to compounds of formula I (e.g., compounds of formula I or IIA, useful, for example, as GPR119 agonists, and useful, for example, for the treatment of diabetes (e.g., type II diabetes)):
(A) $R^1$ is selected from the group consisting of:
(1) alkyl (such as, for example, —$CH_2CH(CH_3)_2$),
(2) substituted arylalkyl, such as, for example,
    (a) halo substituted phenylalkyl-, such as, for example, o,p-di-F-benzyl, o-Cl-benzyl, and o,p-di-F-benzyl,
    (b) substituted aryl, such as, for example, (i) alkyl substituted phenyl (such as, for example, p-methylphenyl), (ii) alkoxy substituted phenyl (such as, for example, p-methoxyphenyl, and m-methoxyphenyl), (iii) haloalkyl substituted phenyl (such as, for example, p-$CF_3$-phenyl), and (iv) halo substituted phenyl (such as, for example, p-F-phenyl),
(3) cycloalkylalkyl (such as, for example, cyclopropyl-$CH_2$—), and
(4) substituted alkyl (such as, for example, aryl substituted alkyl, such as, for example, phenyl substituted alkyl, such as, for example, —$CH(phenyl)_2$)
(B) $R^2$ is selected from the group consisting of:
(1) —C(O)aryl wherein said aryl is substituted with 1 to 3 substituents independently selected from the group consisting of: alkoxy, alkyl-C(O)—, and —$SO_2$alkyl; and wherein examples of said substituted —C(O)aryl moiety include, for example, —C(O)(substituted phenyl), and examples of said —C(O)(substituted phenyl) moiety include, for example, (a) —C(O)

(alkoxy substituted phenyl), such as, for example, o,m,p-tri-methoxyphenyl-C(O)—, (b) —C(O)(alkyl-C(O)-phenyl), such as, for example, —C(O)-(p-CH₃C(O)phenyl), and (c) —C(O)(SO₂alkyl substituted phenyl)-, such as, for example, —C(O)-(p-SO₂CH₃-phenyl), (2) —C(O)benzoheterocycloalkyl, such as, for example,

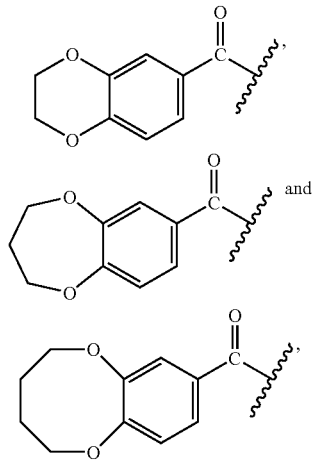

(3) substituted heterocycloalkyl, such as, for example,

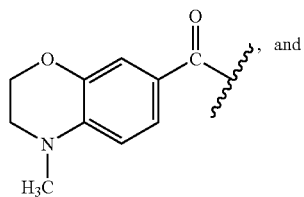

(4) substituted arylalkyl, such as, for example, substituted phenyl-alkyl-such as, for example, alkoxy substituted phenyl-alkyl-, such as, for example, p-methoxybenzyl; and (C) $R^3$ is selected from the group consisting of: H, aryl (such as phenyl), substituted aryl (such as, for example, substituted phenyl, such as, for example, halo substituted phenyl, such as, for example, p-F-phenyl, p-Cl-phenyl, and o,p-di-F-phenyl)

Tables 1, 2, 3a, 3b, 3c, 3d, and 4a are given below. Table 1 defines the $R^1$ moieties used in Tables 3a, 3b, 3c, 3d and 4a by assigning a number to the moieties which number is used in Tables 3a, 3b, 3c, 3d and 4a. Table 2 defines the $R^2$ moieties used in Tables 3a, 3b, 3c, and 3d by assigning a number to the moieties which number is used in Tables 3a, 3b, 3c, and 3d. With reference to the particular structure assigned to Tables 3a, 3b, 3c, and 3d, the compounds whose $R^1$ and $R^2$ moieties are defined by an "X" in the box formed by the intersection of the $R^2$ column and the $R^1$ row are excluded from the definition of formula I (and formula IIA). If there isn't an "X" in the box, the compounds having such $R^1$ and $R^2$ moieties are within the definition of formula I (and formula IIA). The compounds defined by the structure assigned to Table 4a having the $R^1$ moieties defined in Table 4a are excluded from the definition of the compounds of formula I (and formula IIA).

Tables 1, 2, 3a, 3b, 3c, 3d, and 4a are defining compounds of the formula (IIA):

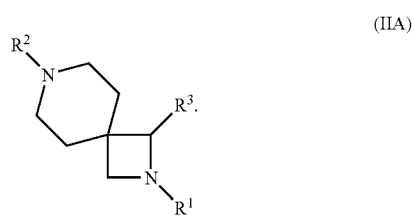

In Table 1 "#" represents number, which is the number assigned to the $R^1$ moiety, and is the number that is referenced in Tables 3a, 3b, 3c, 3d, and 4a.

In Table 2 "#" represents number, which is the number assigned to the $R^2$ moiety, and is the number that is referenced in Tables 3a, 3b, 3c, and 3d.

In Tables 1 and 2 "Z" represents the point of attachment to the rest of the molecule (i.e., "Z" represents where $R^1$ and $R^2$ are attached to the rest of the molecule). Thus, for example, for the compounds of formula IIA, when $R^1$ is Z-CH(CH₃)₂ (i.e., group number 50 in Table 1), the compound of formula IIA is:

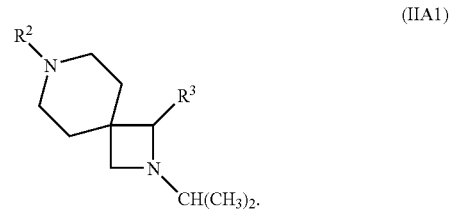

TABLE 1

| Definition of the $R^1$ Moieties | |
|---|---|
| R1 | # |
| Z-C(O)-(2-Cl-phenyl) | 2 |
| Z-C(O)-(3-pyridyl) | 3 |
| Z-C(O)-CH₂-CH(CH₃)₂ | 7 |
| Z-C(O)-CH₂-CH₂-phenyl | 8 |

TABLE 1-continued
Definition of the R¹ Moieties
| R1 | # |
|---|---|
| 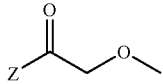 | 9 |
| 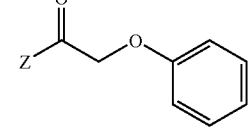 | 10 |
| 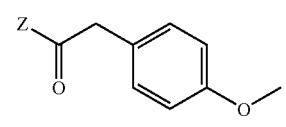 | 11 |
| 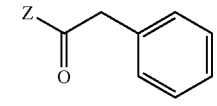 | 13 |
| 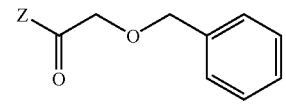 | 14 |
| 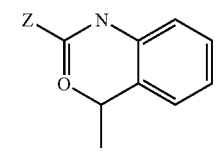 | 15 |
| 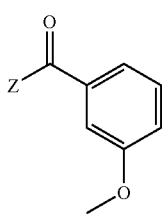 | 17 |
| 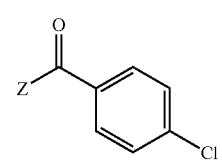 | 19 |
| 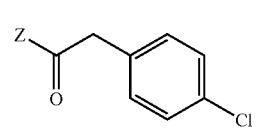 | 20 |
| 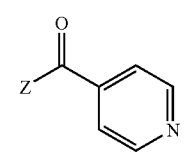 | 21 |
TABLE 1-continued
Definition of the R¹ Moieties
| R1 | # |
|---|---|
| 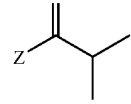 | 22 |
| 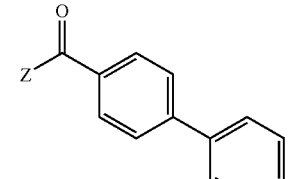 | 23 |
| 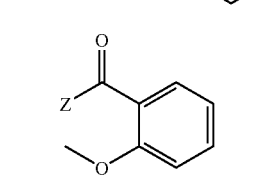 | 25 |
| 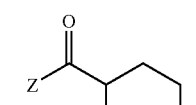 | 26 |
| 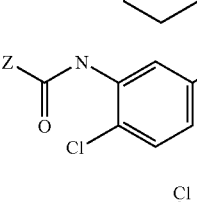 | 27 |
| 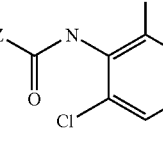 | 28 |
| 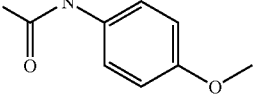 | 29 |
| 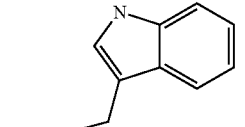 | 30 |
| 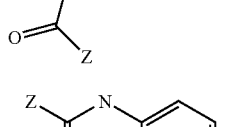 | 31 |
| 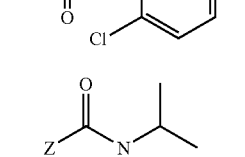 | 32 |

TABLE 1-continued

Definition of the R¹ Moieties

| R1 | # |
|---|---|
| (structure) | 33 |
| (structure) | 34 |
| (structure) | 35 |
| (structure) | 36 |
| (structure) | 37 |
| (structure) | 38 |
| (structure) | 39 |
| (structure) | 40 |
| (structure) | 41 |
| (structure) | 42 |
| (structure) | 43 |
| (structure) | 44 |
| (structure) | 45 |
| (structure) | 46 |
| (structure) | 47 |
| (structure) | 48 |
| (structure) | 49 |
| (structure) | 50 |
| (structure) | 51 |
| (structure) | 52 |

TABLE 1-continued
Definition of the R¹ Moieties
| R1 | # |
|---|---|
| 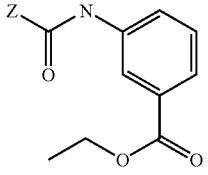 | 93 |
TABLE 2
Definition of the R² Moieties
| R2 | # |
|---|---|
| 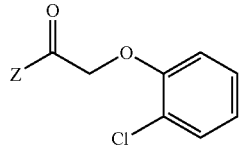 | 1 |
|  | 2 |
| 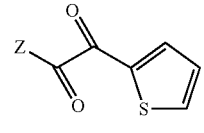 | 3 |
| 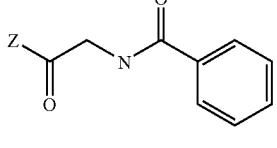 | 4 |
| 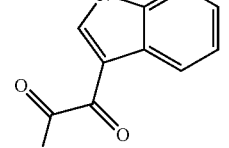 | 5 |
| 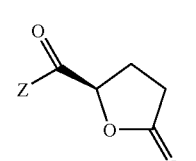 | 6 |
| 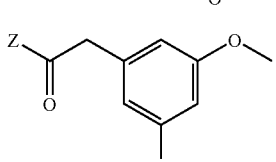 | 7 |
TABLE 2-continued
Definition of the R² Moieties
| R2 | # |
|---|---|
| 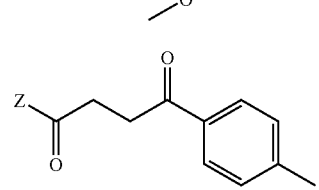 | 8 |
| 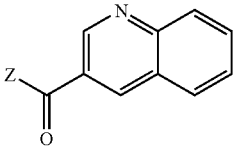 | 9 |
| 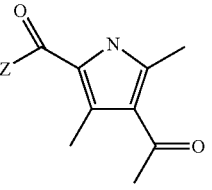 | 10 |
| 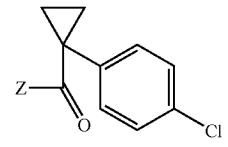 | 11 |
| 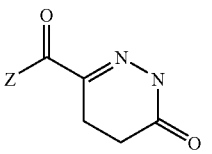 | 12 |
| 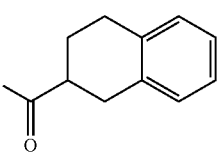 | 13 |
| 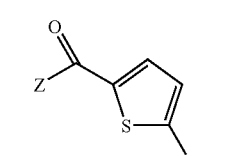 | 14 |
| 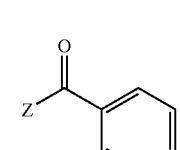 | 15 |

TABLE 2-continued

Definition of the R² Moieties

| R2 | # |
|---|---|
| (2,4-dimethylthiazol-5-yl-carbonyl, Z attached to C=O) | 16 |
| (N,N-dipropyl-alanyl, Z attached to C=O) | 17 |
| (2,7-dimethylpyrazolo[5,1-c][1,2,4]triazin-3-yl-carbonyl, Z attached to C=O) | 18 |
| (2,4,5-trifluorobenzoyl, Z attached to C=O) | 19 |
| (tetrahydrofuran-3-yl-carbonyl, Z attached to C=O) | 20 |
| (2,6-dimethoxypyridin-3-yl-carbonyl, Z attached to C=O) | 21 |
| (1-methylpyrrol-2-yl-carbonyl, Z attached to C=O) | 22 |
| (3-methyl-5-ethoxycarbonylmethyl-4-oxopentanoyl, Z attached to C=O) | 23 |
| (4-trifluoromethylpyridin-3-yl-carbonyl, Z attached to C=O) | 24 |
| (1-tert-butyl-3-methylpyrazol-5-yl-carbonyl, Z attached to C=O) | 25 |
| (5-phenyloxazol-4-yl-carbonyl, Z attached to C=O) | 26 |
| (N-(pyridin-3-yl)succinamoyl, Z attached to C=O) | 27 |
| (2-phenoxybutanoyl, Z attached to C=O) | 28 |
| (N-methyl-N-benzoyl-glycyl, Z attached to C=O) | 29 |
| (N-acetylglycyl, Z attached to C=O) | 30 |
| (pyrazin-2-yl-carbonyl, Z attached to C=O) | 31 |
| (3-methyl-2-phenylbutanoyl, Z attached to C=O) | 32 |
| (4-propoxybenzoyl, Z attached to C=O) | 33 |

TABLE 2-continued

Definition of the R² Moieties

| R2 | # |
|---|---|
| (7-methyl-1,8-naphthyridin-3-yl)carbonyl structure | 34 |
| (2,2-dimethyl-5-oxo-1,3-dioxolan-4-yl)acetyl structure | 35 |
| (1H-indazol-3-yl)carbonyl structure | 36 |
| (2,1,3-benzoxadiazol-5-yl)carbonyl structure | 37 |
| (4-chloro-2-methoxyphenyl)carbonyl structure | 38 |
| 3-(2,3-dihydro-1H-indol-1-yl)propanoyl structure | 39 |
| 3-(1,3-benzodioxol-5-yl)propanoyl structure | 40 |
| 2-(1H-benzimidazol-2-yl)propanoyl structure | 41 |

TABLE 2-continued

Definition of the R² Moieties

| R2 | # |
|---|---|
| 5-(methoxycarbonyl)pyridine-2-carbonyl structure | 42 |
| (3-methylisoxazol-5-yl)acetyl structure | 43 |
| 4-(dimethylamino)-4-oxobutanoyl structure | 44 |
| (2,1-benzisoxazol-3-yl)carbonyl structure | 45 |
| (1,3-benzothiazol-2-yl)carbonyl structure | 46 |
| [4-(1H-1,2,4-triazol-1-yl)phenyl]carbonyl structure | 47 |
| (1-acetylpyrrolidin-2-yl)carbonyl structure | 48 |
| (biphenyl-2-yl)carbonyl structure | 49 |

TABLE 2-continued
Definition of the R² Moieties
| R2 | # |
|---|---|
| 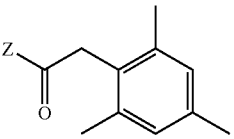 | 50 |
| 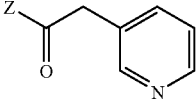 | 51 |
| 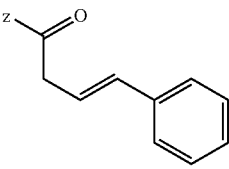 | 52 |
| 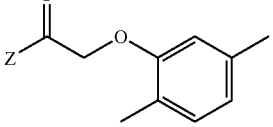 | 53 |
| 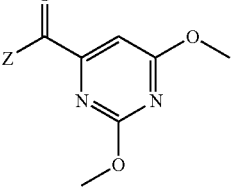 | 54 |
| 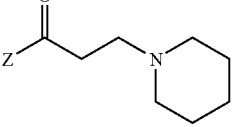 | 55 |
| 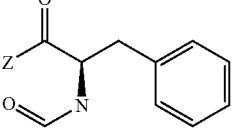 | 56 |
| 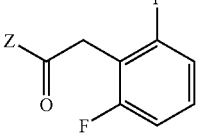 | 57 |
| 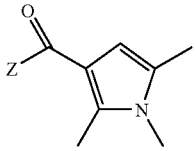 | 58 |
TABLE 2-continued
Definition of the R² Moieties
| R2 | # |
|---|---|
| 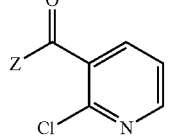 | 59 |
| 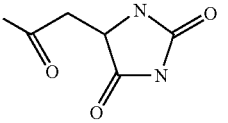 | 60 |
| 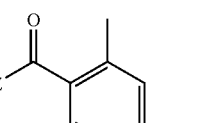 | 61 |
| 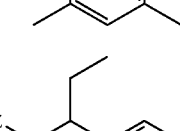 | 62 |
| 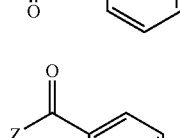 | 63 |
| 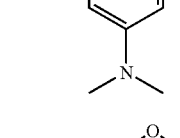 | 64 |
| 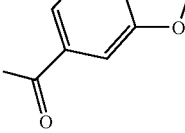 | 65 |
| 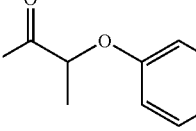 | 66 |
| 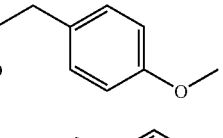 | 67 |
| 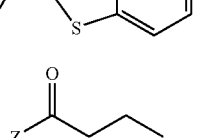 | 68 |

US 7,638,526 B2
TABLE 2-continued
Definition of the R² Moieties
| R2 | # |
|---|---|
| 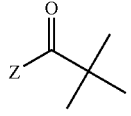 | 69 |
| 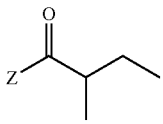 | 70 |
| 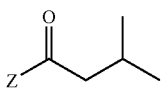 | 71 |
| 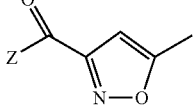 | 72 |
| 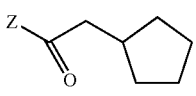 | 73 |
| 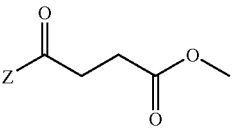 | 74 |
| 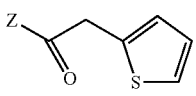 | 75 |
| 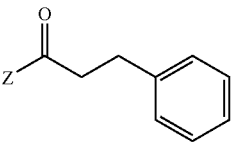 | 76 |
| 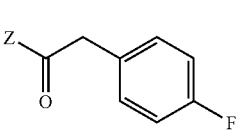 | 77 |
| 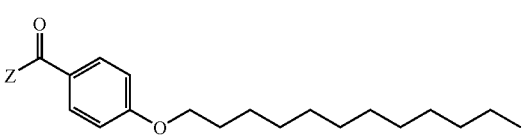 | 78 |
| 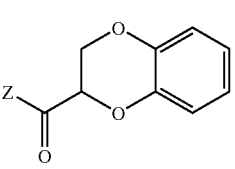 | 79 |
TABLE 2-continued
Definition of the R² Moieties
| R2 | # |
|---|---|
| 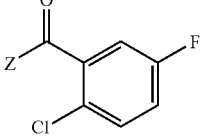 | 80 |
| 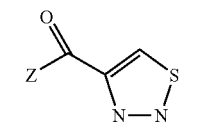 | 81 |
| 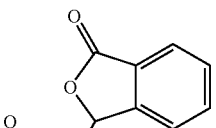 | 82 |
| 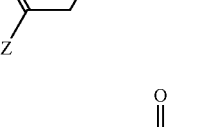 | 83 |
| 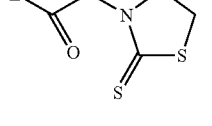 | 84 |
| 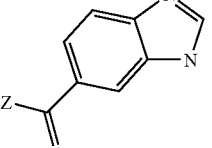 | 85 |
| 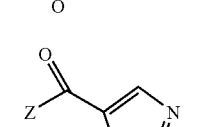 | 86 |
| 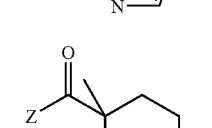 | 87 |
| 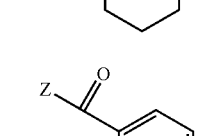 | 88 |

TABLE 2-continued

Definition of the R² Moieties

| R2 | # |
|---|---|
| (trans-2-phenylcyclopropyl carbamate, Z-NH-C(O)-) | 133 |
| (2-methoxyphenyl carbamate) | 134 |
| (4-methoxyphenyl carbamate) | 135 |
| (benzyl carbamate) | 136 |
| (tert-butyl carbamate) | 137 |
| (isopropyl carbamate) | 138 |
| (ethyl carbamate) | 139 |
| (propyl carbamate) | 140 |
| (4-ethylphenyl carbamate) | 141 |
| (phenethyl carbamate) | 142 |
| (2-(3-isopropenylphenyl)propan-2-yl carbamate) | 143 |
| (2,6-difluorophenyl carbamate) | 144 |
| (2,3-dichlorophenyl carbamate) | 145 |
| (2-ethoxyphenyl carbamate) | 146 |
| (2-trifluoromethylphenyl carbamate) | 147 |
| (2,6-dimethylphenyl carbamate) | 148 |
| (4-trifluoromethylphenyl carbamate) | 149 |
| ((S)-1-phenylethyl carbamate) | 150 |
| (2,3-dimethylphenyl carbamate) | 151 |
| (4-methoxy-2-methylphenyl carbamate) | 152 |
| (3-chloro-4-methylphenyl carbamate) | 153 |

TABLE 2-continued
Definition of the R² Moieties
| R2 | # |
|---|---|
| 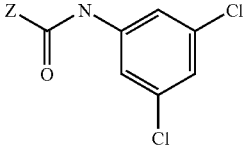 | 154 |
| 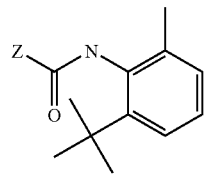 | 155 |
| 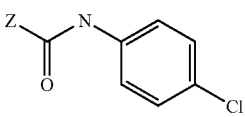 | 156 |
| 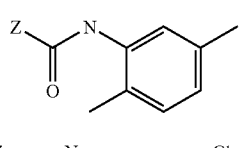 | 157 |
| 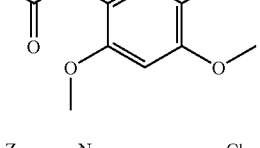 | 158 |
| 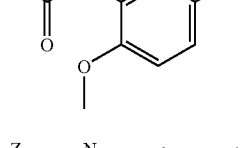 | 159 |
| 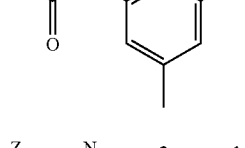 | 160 |
| 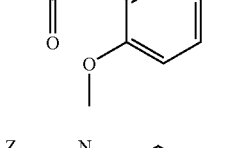 | 161 |
| 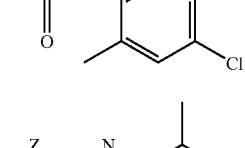 | 162 |
| 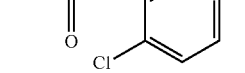 | 163 |
| 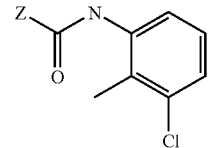 | 164 |
| 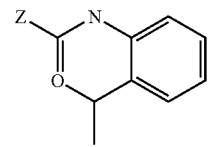 | 165 |
| 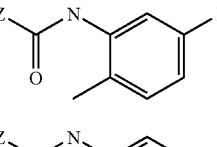 | 166 |
| 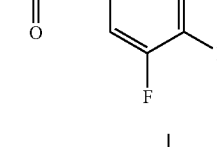 | 167 |
| 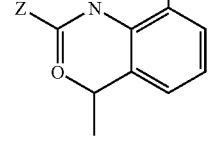 | 168 |
| 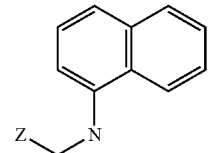 | 169 |
| 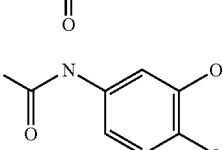 | 170 |
| 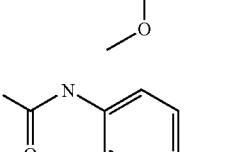 | 171 |
| 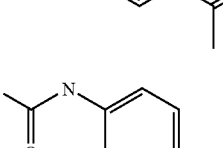 | 172 |

TABLE 2-continued
Definition of the R² Moieties
| R2 | # |
|---|---|
| 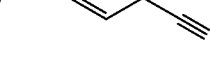 | 173 |
| 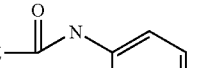 | 174 |
| 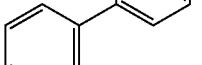 | 175 |
| 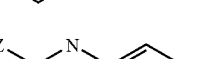 | 176 |
| 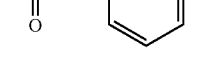 | 177 |
| 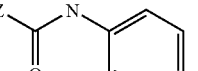 | 178 |
|  | 179 |
| 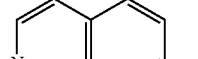 | 180 |
| 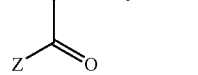 | 181 |
|  | 182 |
| 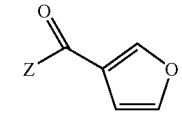 | 183 |
| 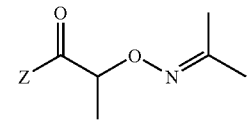 | 184 |
| 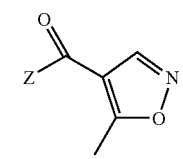 | 185 |
| 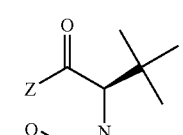 | 186 |
| 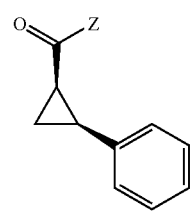 | 187 |
| 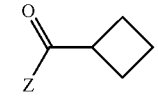 | 188 |
| 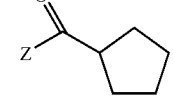 | 189 |
| 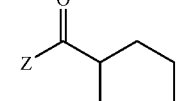 | 190 |
| 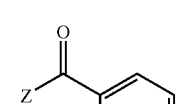 | 191 |
| 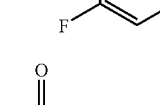 | 192 |

TABLE 2-continued

Definition of the R² Moieties

| R2 | # |
|---|---|
| (2-chlorobenzoyl) | 193 |
| (3-fluorobenzoyl) | 194 |
| (3-chlorobenzoyl) | 195 |
| (3-methylbenzoyl) | 196 |
| (cyclopropanecarbonyl) | 197 |
| (phenoxyacetyl) | 198 |
| (pent-4-enoyl) | 199 |
| (isoxazole-5-carbonyl) | 200 |
| (4-methyl-1,2,3-thiadiazole-5-carbonyl) | 201 |

TABLE 2-continued

Definition of the R² Moieties

| R2 | # |
|---|---|
| (methoxyacetyl) | 202 |
| (3,5-dimethylisoxazole-4-carbonyl) | 203 |
| (2-methylbenzoyl) | 204 |
| (thiophene-2-carbonyl) | 205 |
| (2-(2-methoxyethoxy)acetyl) | 206 |
| (phenylacetyl) | 207 |
| (4-fluoro-3-methylbenzoyl) | 208 |
| (3-methyl-1H-pyrazole-5-carbonyl) | 209 |
| (bicyclo[2.2.1]heptane-2-carbonyl) | 210 |
| (3-methylphenylacetyl) | 211 |

TABLE 2-continued

Definition of the R² Moieties

| R2 | # |
|---|---|
| (structure) | 212 |
| (structure) | 213 |
| (structure) | 214 |
| (structure) | 215 |
| (structure) | 216 |
| (structure) | 217 |
| (structure) | 218 |
| (structure) | 219 |
| (structure) | 220 |
| (structure) | 221 |
| (structure) | 222 |
| (structure) | 223 |
| (structure) | 224 |
| (structure) | 225 |
| (structure) | 226 |
| (structure) | 227 |
| (structure) | 228 |
| (structure) | 229 |
| (structure) | 230 |
| (structure) | 231 |

TABLE 2-continued
Definition of the R² Moieties
| R2 | # |
|---|---|
| 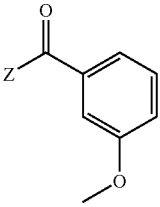 | 232 |
| 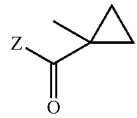 | 233 |
| 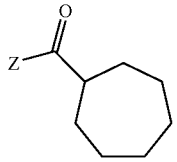 | 234 |
| 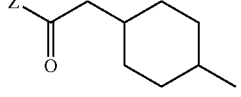 | 235 |
| 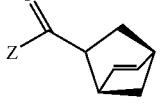 | 236 |
| 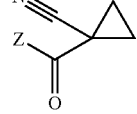 | 237 |
| 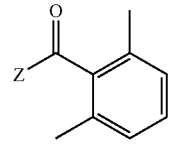 | 238 |
| 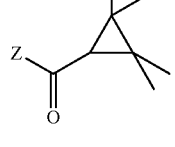 | 239 |
| 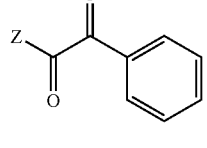 | 240 |
TABLE 2-continued
Definition of the R² Moieties
| R2 | # |
|---|---|
| 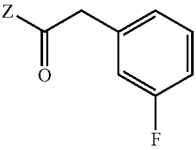 | 241 |
| 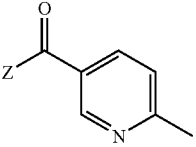 | 242 |
| 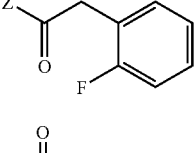 | 243 |
| 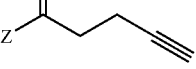 | 244 |
| 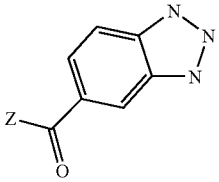 | 245 |
| 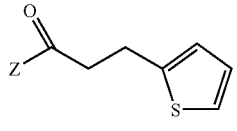 | 246 |
| 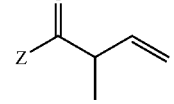 | 247 |
| 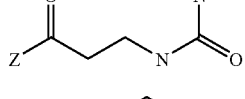 | 248 |
| 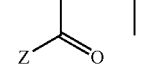 | 249 |
| 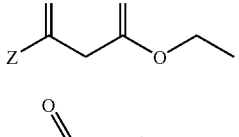 | 250 |
| 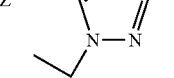 | 251 |

TABLE 2-continued
Definition of the R² Moieties
| R2 | # |
|---|---|
| 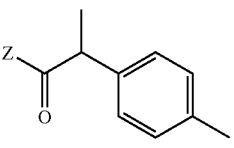 | 252 |
| 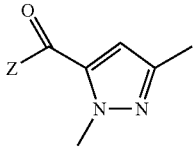 | 253 |
| 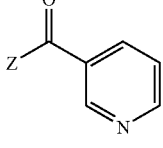 | 254 |
| 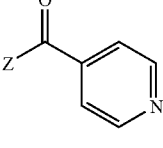 | 255 |
| 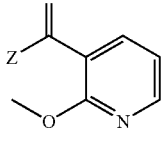 | 256 |
| 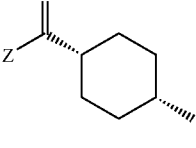 | 257 |
| 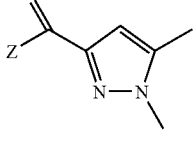 | 258 |
| 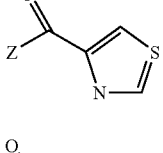 | 259 |
| 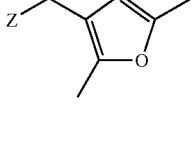 | 260 |
| 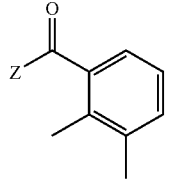 | 261 |
| 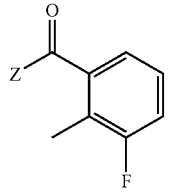 | 262 |
| 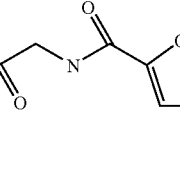 | 263 |
| 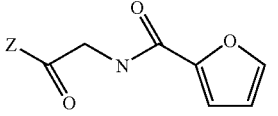 | 264 |
| 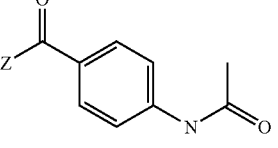 | 265 |
| 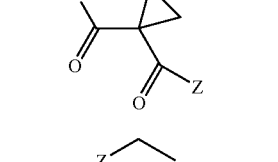 | 266 |
| 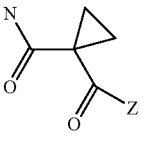 | 267 |
|  | 268 |
| 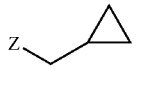 | 269 |
|  | 270 |
|  | 271 |
|  | 272 |
| 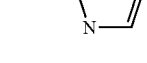 | 273 |

TABLE 2-continued

Definition of the R² Moieties

| R2 | # |
|---|---|
| Z-CH₂CH₂-CH(CH₃)-CH₂CH₃ | 274 |
| Z-CH₂-phenyl | 275 |
| Z-CH₂-(pyridin-4-yl) | 276 |
| Z-CH₂-(pyridin-3-yl) | 277 |
| Z-CH₂-(pyridin-2-yl) | 278 |
| Z-CH₂-(thiazol-2-yl) | 279 |
| Z-CH₂-(2-methylphenyl) | 280 |
| Z-CH₂-(4-methylphenyl) | 281 |
| Z-CH₂-(6-methylpyridin-2-yl) | 282 |
| Z-CH₂-(4-fluorophenyl) | 283 |
| Z-CH₂-(3-fluorophenyl) | 284 |
| Z-CH₂-(2,5-dimethylfuran-3-yl) | 285 |
| Z-CH₂-(5-methylthiophen-2-yl) | 286 |
| Z-CH₂-CH(CH₃)-phenyl | 287 |
| Z-CH₂-(3,5-dimethylphenyl) | 288 |
| Z-CH₂-(3-methoxyphenyl) | 289 |
| Z-CH₂-(2-methoxyphenyl) | 290 |
| Z-CH₂-(4-methoxyphenyl) | 291 |
| Z-CH₂-(2-chlorophenyl) | 292 |
| Z-CH₂-(3-chlorophenyl) | 293 |
| Z-CH₂-(4-chlorophenyl) | 294 |
| Z-CH₂-(2,6-difluorophenyl) | 295 |

TABLE 2-continued
Definition of the R² Moieties
| R2 | # |
|---|---|
| 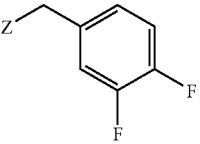 | 296 |
| 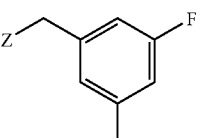 | 297 |
| 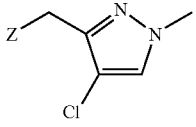 | 298 |
| 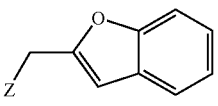 | 299 |
| 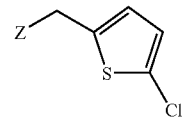 | 300 |
| 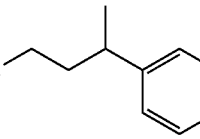 | 301 |
| 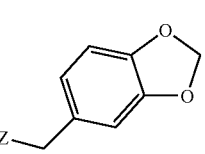 | 302 |
| 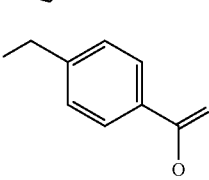 | 303 |
| 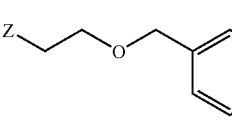 | 304 |
| 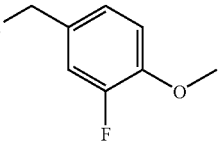 | 305 |
| 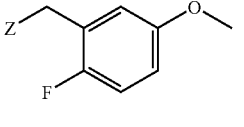 | 306 |
| 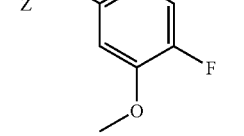 | 307 |
| 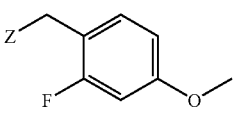 | 308 |
| 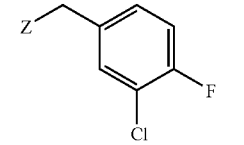 | 309 |
| 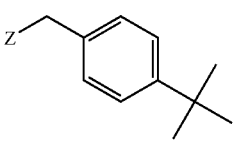 | 310 |
| 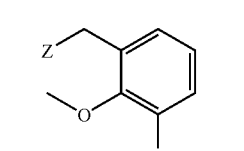 | 311 |
| 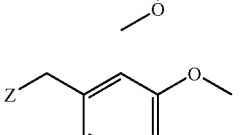 | 312 |
| 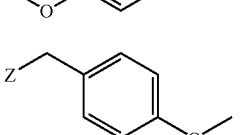 | 313 |
| 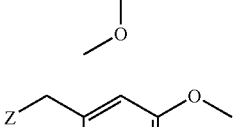 | 314 |
| 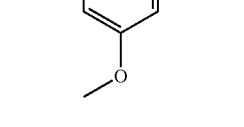 | 315 |

TABLE 2-continued
Definition of the R² Moieties
| R2 | # |
|---|---|
| 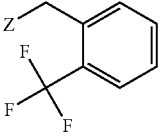 | 316 |
| 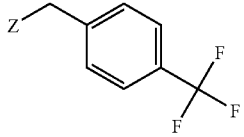 | 317 |
|  | 318 |
| 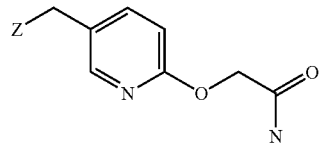 | 319 |
| 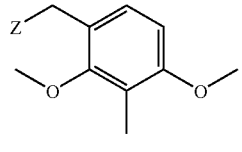 | 320 |
| 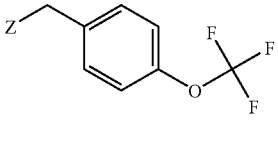 | 321 |
| 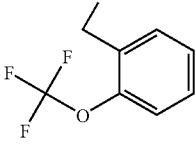 | 322 |
| 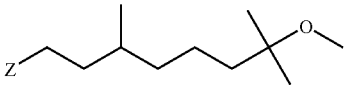 | 323 |
| 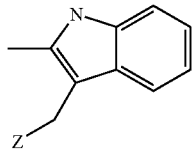 | 324 |
| 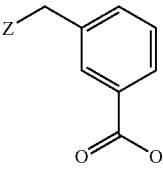 | 325 |
| 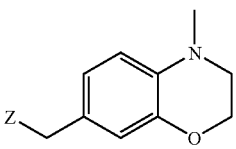 | 326 |
| 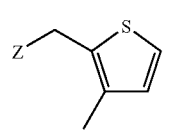 | 327 |
| 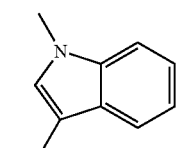 | 328 |
| 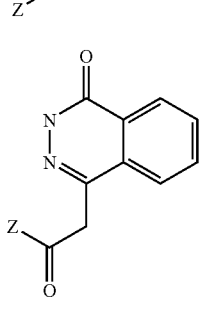 | 329 |
| 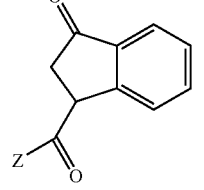 | 330 |
| 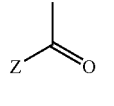 | 331 |
| 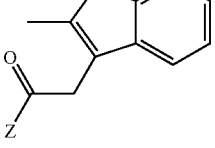 | 332 |
| 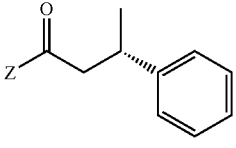 | 333 |
| 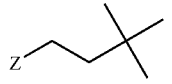 | 334 |

TABLE 2-continued
Definition of the R² Moieties
| R2 | # |
|---|---|
| 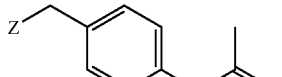 | 335 |
| 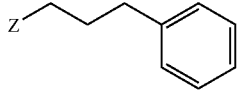 | 336 |
| 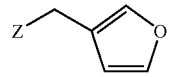 | 337 |
| 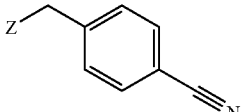 | 338 |
| 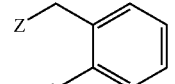 | 339 |
| 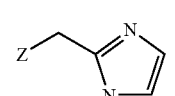 | 340 |
| 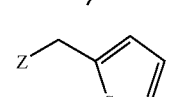 | 341 |
| 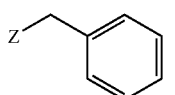 | 342 |
| 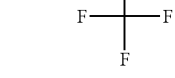 | 343 |
| 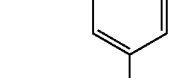 | 344 |
| 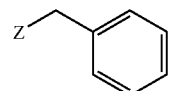 | 345 |
| 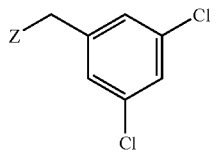 | 346 |
| 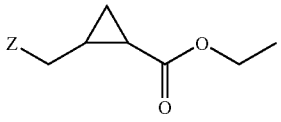 | 347 |
| 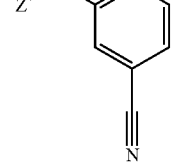 | 348 |
| 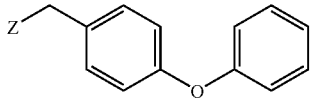 | 349 |
| 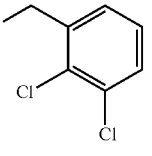 | 350 |
| 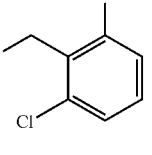 | 351 |
| 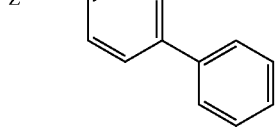 | 352 |
| 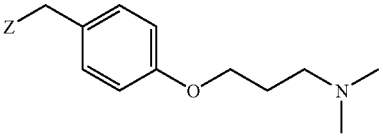 | 353 |
| 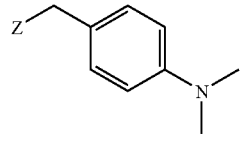 | 354 |

TABLE 2-continued

Definition of the R² Moieties

| R2 | # |
|---|---|
| (structure) | 355 |
| (structure) | 356 |
| (structure) | 357 |
| (structure) | 358 |
| (structure) | 359 |
| (structure) | 360 |
| (structure) | 361 |
| (structure) | 362 |
| (structure) | 363 |
| (structure) | 364 |
| (structure) | 365 |
| (structure) | 366 |
| (structure) | 367 |
| (structure) | 368 |
| (structure) | 369 |
| (structure) | 370 |
| (structure) | 371 |
| (structure) | 372 |
| (structure) | 373 |
| (structure) | 374 |

TABLE 2-continued
Definition of the R² Moieties
| R2 | # |
|---|---|
| 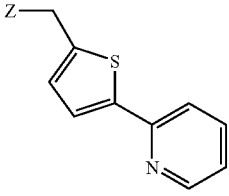 | 375 |
| 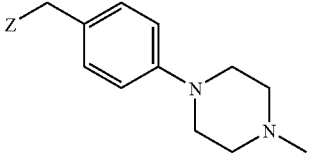 | 376 |
| 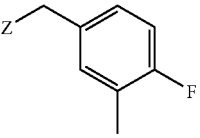 | 377 |
| 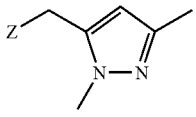 | 378 |
| 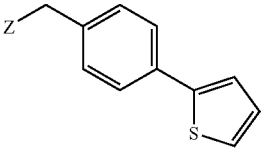 | 379 |
| 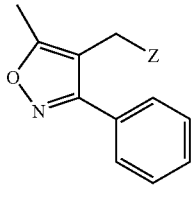 | 380 |
| 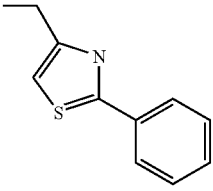 | 381 |
| 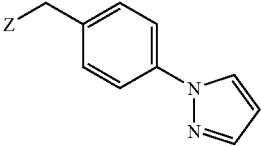 | 382 |
| 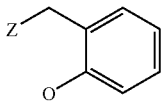 | 383 |
| 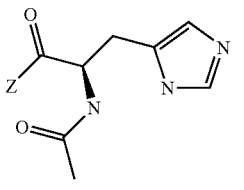 | 384 |
| 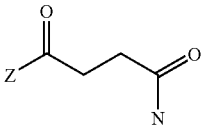 | 385 |
| 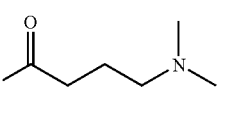 | 386 |
| 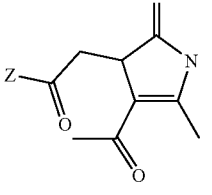 | 387 |
| 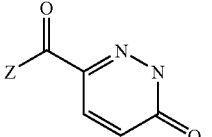 | 388 |
| 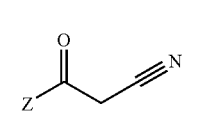 | 389 |
| 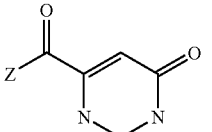 | 390 |
| 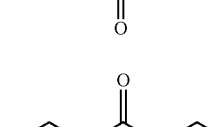 | 391 |
| 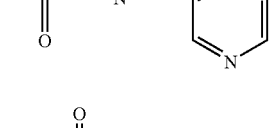 | 392 |

TABLE 2-continued
Definition of the R² Moieties
| R2 | # |
|---|---|
|  | 393 |
| 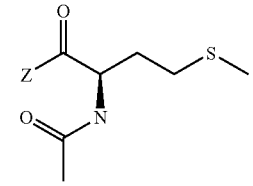 | 394 |
| 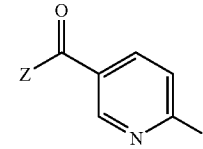 | 395 |
| 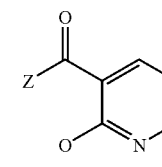 | 396 |
| 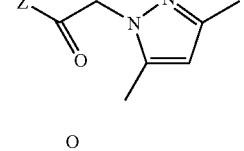 | 397 |
| 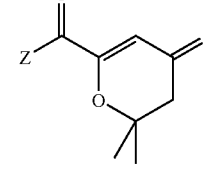 | 398 |
| 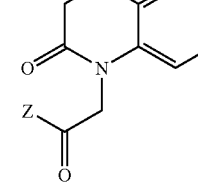 | 399 |
| 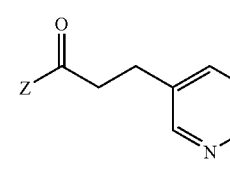 | 400 |
|  | 401 |
| | 402 |
| | 403 |
| | 404 |
| | 405 |
| | 406 |
| | 407 |
| | 408 |
| | 409 |
| | 410 |
| | 411 |

TABLE 2-continued

Definition of the R² Moieties

| R2 | # |
|---|---|
| (structure) | 412 |
| (structure) | 413 |
| (structure) | 414 |
| (structure) | 415 |
| (structure) | 416 |
| (structure) | 417 |
| (structure) | 418 |
| (structure) | 419 |
| (structure) | 420 |
| (structure) | 421 |
| (structure) | 422 |
| (structure) | 423 |
| (structure) | 424 |
| (structure) | 425 |
| (structure) | 426 |
| (structure) | 427 |
| (structure) | 428 |
| (structure) | 429 |

TABLE 2-continued
Definition of the R² Moieties
| R2 | # |
|---|---|
| 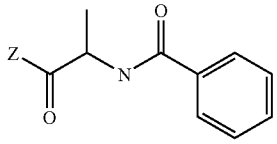 | 430 |
| 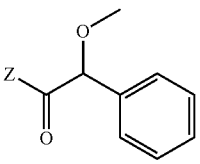 | 431 |
| 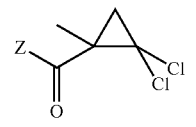 | 432 |
| 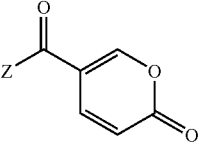 | 433 |
| 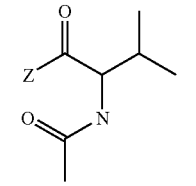 | 434 |
| 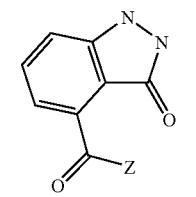 | 435 |
| 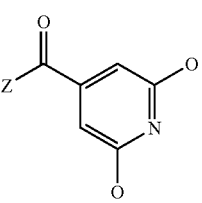 | 436 |
| 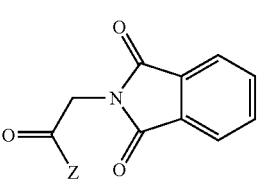 | 437 |
TABLE 2-continued
Definition of the R² Moieties
| R2 | # |
|---|---|
| 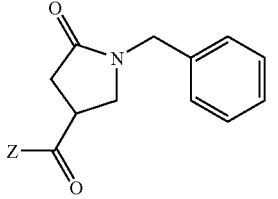 | 438 |
| 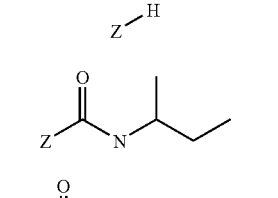 | 468 |
| 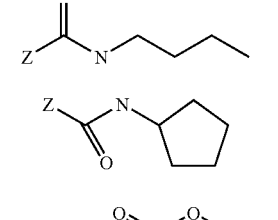 | 469 |
| 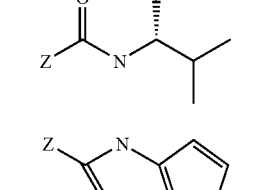 | 470 |
| 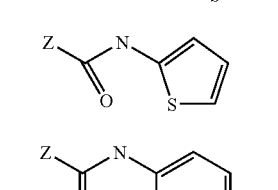 | 471 |
| 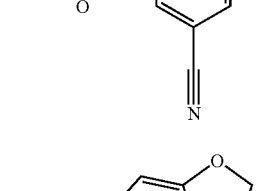 | 472 |
| 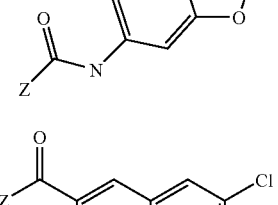 | 473 |
| 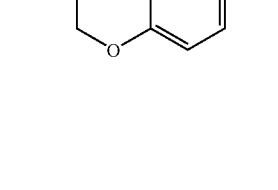 | 474 |
|  | 475 |
| 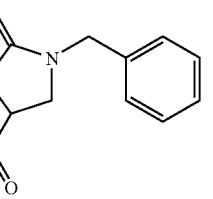 | 476 |
| 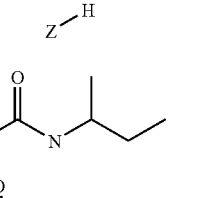 | 531 |

TABLE 2-continued

Definition of the R² Moieties

| R2 | # |
|---|---|
| 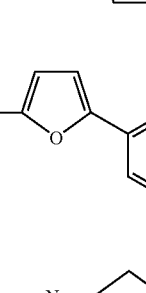 | 532 |
| 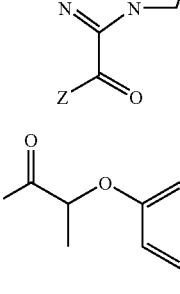 | 533 |
| 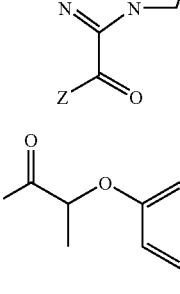 | 534 |
| 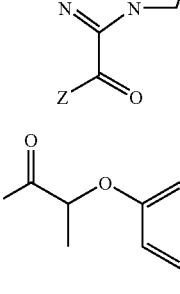 | 535 |
| 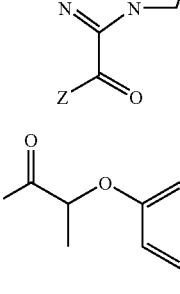 | 536 |

Table 3a

Table 3a is directed to compounds of the formula (IIIa):

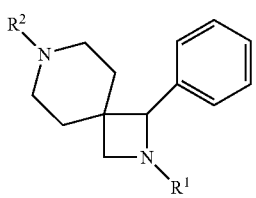

(IIIA)

wherein R¹ and R² are as defined in Table 3a.

An "X" in the box formed by the intersection of the R² and the R¹ row represents an R² and R¹ combination of a compound of formula IIIA that is excluded from the definition of the compounds of formula I (and formula IIA). For example, compounds of formula IIIA wherein R² is moiety 1 (see Table 2 for definition) and R¹ is moiety 2 (see Table 1 for definition) are excluded from the definition of formula I (and formula IIA) (there is an "X" in the box formed by the intersection of the R² column and the R¹ row).

If there is no "X" in the box, then that compound is within the definition of the compounds of formula I (and formula IIA). For example, compounds of formula IIIA wherein moiety R² is 2 and moiety R¹ is 23 (no "X" in the box formed by the intersection of the R² column and the R¹ row) are within the definition of the compounds of formula I (and formula IIA).

TABLE 3a

| R2 | \multicolumn{9}{c}{R1} |
|---|---|---|---|---|---|---|---|---|---|

| R2 | 2 | 3 | 9 | 10 | 11 | 14 | 15 | 23 | 20 |
|---|---|---|---|---|---|---|---|---|---|
| 1 | X | X | X | X | X | X | X | X | X |
| 2 | X | X | X | X | X | X | X |  | X |
| 3 |  | X | X | X | X | X | X | X | X |
| 4 | X | X | X | X | X | X | X | X | X |
| 5 | X | X |  |  |  |  |  | X | X |
| 6 | X | X | X | X | X | X | X | X | X |
| 7 | X | X | X | X | X | X | X |  | X |
| 8 | X | X | X | X | X | X | X | X | X |
| 9 | X | X | X | X | X | X | X |  | X |
| 10 | X | X | X | X | X | X | X | X | X |
| 11 | X | X | X | X | X | X | X | X | X |
| 12 | X | X | X | X | X | X | X | X | X |
| 13 | X | X | X | X |  | X | X | X | X |
| 14 | X | X | X | X | X | X | X | X | X |
| 15 | X | X | X | X | X | X | X | X | X |
| 16 | X | X | X | X | X | X | X | X | X |
| 17 | X | X | X | X | X | X | X | X | X |
| 18 | X | X | X | X | X | X | X | X | X |
| 19 | X | X | X | X | X | X | X | X | X |
| 20 | X | X | X | X | X | X | X |  | X |
| 21 | X | X | X | X | X | X | X | X | X |
| 22 | X | X | X | X | X | X | X | X | X |
| 23 | X | X | X | X | X | X | X | X | X |
| 24 | X | X | X | X | X | X | X | X | X |
| 25 | X | X | X | X | X | X | X | X | X |
| 26 | X | X | X | X | X | X | X | X | X |
| 27 | X | X |  | X | X | X | X |  |  |
| 28 | X | X | X | X | X | X | X | X | X |
| 29 | X | X | X | X | X | X | X | X | X |
| 30 | X | X | X | X | X | X | X | X | X |
| 31 | X | X | X | X |  | X | X | X | X |
| 32 | X | X | X | X | X | X | X | X | X |
| 33 | X | X | X | X | X | X | X | X | X |
| 34 | X | X | X | X | X | X | X | X | X |
| 35 | X |  | X | X | X | X | X | X | X |
| 36 | X | X | X | X | X | X | X | X | X |
| 37 | X | X | X | X | X | X | X | X | X |
| 38 | X | X | X | X | X | X | X | X | X |
| 39 | X | X | X | X | X |  | X | X | X |
| 40 | X | X | X | X | X | X | X | X | X |
| 41 | X |  |  | X | X |  | X | X | X |
| 42 | X | X | X | X | X | X | X | X | X |
| 43 | X | X | X | X | X | X | X | X | X |

| R2 | 22 | 27 | 38 | 39 | 40 | 41 | 42 | 31 | 32 | 34 | 35 | 36 | 37 |
|---|---|---|---|---|---|---|---|---|---|---|---|---|---|
| 1 | X | X | X | X | X | X | X | X | X | X | X | X | X |
| 2 | X | X | X | X | X | X | X | X | X | X | X | X | X |
| 3 | X | X | X | X | X | X | X | X | X | X | X | X | X |
| 4 | X | X | X | X | X |  | X | X | X | X | X | X | X |
| 5 | X | X | X | X | X |  | X | X |  | X | X | X | X |
| 6 | X | X | X | X | X | X | X | X | X | X | X | X | X |
| 7 | X | X | X | X | X | X | X | X | X | X | X | X | X |
| 8 | X | X | X | X | X | X | X | X | X | X | X | X | X |
| 9 | X |  | X | X | X | X | X | X | X | X | X | X | X |
| 10 | X | X | X | X | X | X | X | X | X | X | X | X | X |

TABLE 3a-continued

| R2 | | | | | | | | | | | | |
|---|---|---|---|---|---|---|---|---|---|---|---|---|
| 11 | X | X | X | X | X | X | X | X | X | X | X | X |
| 12 | X | X | X | X | X | X | X | X | X | X | X | X |
| 13 | X | X | X | X | X | X | X | X | X | X | X | X |
| 14 | X | X | X | X | X | X | X | X | X | X | X | X |
| 15 | X | X | X | X | X | X | X | X | X | X | X | X |
| 16 | X | X | X | X | X | X | X | X | X | X | X | X |
| 17 | X | X | X | X | X | X | X | X | X | X | X | X |
| 18 | X | X | X | X |   | X | X |   | X | X | X | X |
| 19 | X | X | X | X | X | X |   |   |   | X | X | X |
| 20 | X | X | X | X | X |   | X | X | X | X | X | X |
| 21 | X | X | X | X | X | X | X | X | X | X | X | X |
| 22 | X | X | X | X | X | X | X | X | X | X | X | X |
| 23 | X | X | X | X | X | X | X | X | X | X | X | X |
| 24 | X | X | X | X | X | X | X | X | X | X | X | X |
| 25 | X | X | X | X | X | X | X | X | X | X | X | X |
| 26 | X | X | X | X | X | X | X | X | X | X | X | X |
| 27 |   |   |   |   |   |   |   |   |   |   |   |   |
| 28 | X | X | X | X |   | X | X | X | X | X | X | X |
| 29 | X | X | X |   |   |   | X | X | X | X | X | X |
| 30 | X |   | X | X | X | X | X | X | X | X | X | X |
| 31 | X | X | X | X | X |   | X | X | X | X | X | X |
| 32 | X | X | X | X | X | X |   | X | X |   |   | X |
| 33 | X | X | X | X | X | X |   |   | X | X | X | X |
| 34 | X | X | X | X | X |   |   | X | X | X |   | X |
| 35 | X |   | X | X |   | X |   | X |   |   |   | X |
| 36 | X |   | X | X | X | X | X |   | X | X | X | X |
| 37 | X | X | X | X | X | X | X |   | X | X | X | X |
| 38 | X | X | X | X | X | X | X | X | X | X | X | X |
| 39 | X | X | X | X | X | X |   |   |   |   |   |   |
| 40 | X | X | X | X |   |   |   | X |   | X | X | X |
| 41 | X | X | X | X |   | X | X | X | X | X | X | X |
| 42 | X | X | X | X | X |   |   | X | X | X | X | X |
| 43 | X | X | X | X | X |   | X | X | X | X | X | X |

| | R1 | | | | | | | | | | |
|---|---|---|---|---|---|---|---|---|---|---|---|
| R2 | 30 | 44 | 45 | 47 | 49 | 50 | 51 | 52 | 7 | 8 | 13 |
| 1 |    |    |    |    |    |    |    |    |    |    |    |
| 2 | X  |    |    |    |    |    |    |    |    |    |    |
| 3 | X  | X  | X  | X  | X  | X  | X  | X  |    |    |    |
| 4 |    |    |    |    |    |    |    |    |    |    |    |
| 5 | X  | X  | X  | X  | X  | X  | X  | X  |    |    |    |
| 6 | X  |    |    |    |    |    |    |    | X  | X  | X  |
| 7 | X  |    |    |    |    |    |    |    | X  | X  | X  |
| 8 | X  |    |    |    |    |    |    |    | X  | X  | X  |
| 9 | X  |    |    |    |    |    |    |    | X  | X  | X  |
| 10 | X |    |    |    |    |    |    |    | X  | X  | X  |
| 11 | X |    |    |    |    |    |    |    | X  | X  | X  |
| 12 | X |    |    |    |    |    |    |    | X  | X  | X  |
| 13 | X |    |    |    |    |    |    |    | X  | X  | X  |
| 14 | X |    |    |    |    |    |    |    | X  | X  | X  |
| 15 | X |    |    |    |    |    |    |    | X  | X  | X  |
| 16 | X | X  | X  | X  | X  | X  | X  | X  | X  | X  | X  |
| 17 | X |    |    |    |    |    |    |    | X  | X  | X  |
| 18 | X |    |    |    |    |    |    |    | X  | X  | X  |
| 19 |   |    |    |    |    |    |    |    | X  | X  | X  |
| 20 | X | X  | X  | X  | X  | X  | X  | X  | X  | X  | X  |
| 21 | X |    |    |    |    |    |    |    | X  | X  | X  |
| 22 | X | X  |    | X  | X  | X  | X  | X  | X  | X  | X  |
| 23 | X |    |    |    |    |    |    |    | X  | X  | X  |
| 24 | X |    |    |    |    |    |    |    | X  | X  | X  |
| 25 | X |    |    |    |    |    |    |    | X  | X  | X  |
| 26 | X |    |    |    |    |    |    |    | X  | X  | X  |
| 27 |   |    |    |    |    |    |    |    | X  | X  | X  |
| 28 | X |    |    |    |    |    |    |    | X  | X  | X  |
| 29 | X |    |    |    |    |    |    |    | X  | X  | X  |
| 30 | X | X  | X  | X  | X  | X  | X  | X  | X  | X  | X  |
| 31 | X |    |    |    |    |    |    |    | X  | X  | X  |
| 32 | X |    |    |    |    |    |    |    | X  | X  | X  |
| 33 |   |    |    |    |    |    |    |    | X  | X  | X  |
| 34 | X |    |    |    |    |    |    |    | X  | X  | X  |
| 35 | X |    | X  | X  |    | X  | X  | X  | X  | X  | X  |
| 36 | X |    |    |    |    |    |    |    | X  | X  | X  |
| 37 |   |    |    |    |    |    |    |    | X  | X  | X  |
| 38 | X |    |    |    |    |    |    |    | X  | X  | X  |
| 39 | X |    |    |    |    |    |    |    | X  | X  | X  |
| 40 | X |    |    |    |    |    |    |    | X  | X  | X  |
| 41 | X |    |    |    |    |    |    |    | X  | X  | X  |
| 42 | X |    |    |    |    |    |    |    | X  | X  | X  |
| 43 | X |    |    |    |    |    |    |    | X  | X  | X  |

| | R1 | | | | | | | | |
|---|---|---|---|---|---|---|---|---|---|
| R2 | 2 | 3 | 9 | 10 | 11 | 14 | 15 | 23 | 20 |
| 44 | X | X | X | X | X | X | X |   | X |
| 45 | X | X | X | X | X | X | X | X | X |
| 46 |   |   |   | X |   | X | X | X | X |
| 47 | X | X | X | X | X | X | X | X | X |
| 48 | X | X | X | X | X | X | X | X | X |
| 49 | X | X | X |   | X | X | X | X | X |
| 50 | X | X | X | X | X | X | X | X | X |
| 51 | X | X |   |   | X | X | X | X |   |
| 52 | X | X | X | X | X | X | X | X | X |
| 53 | X | X | X | X | X | X | X | X | X |
| 54 | X | X | X | X | X | X | X | X | X |
| 55 | X | X | X | X | X | X | X | X | X |
| 56 | X | X | X | X | X | X | X | X | X |
| 57 | X | X | X | X | X | X | X | X | X |
| 58 | X | X | X | X | X | X | X | X | X |
| 59 | X | X | X | X | X | X | X | X | X |
| 60 | X | X | X | X | X | X | X | X | X |
| 61 | X | X | X | X | X | X | X | X | X |
| 62 | X | X | X | X | X | X | X | X | X |
| 63 | X | X | X | X | X | X | X | X | X |
| 64 | X | X | X | X |   | X | X | X | X |
| 65 | X | X | X | X | X | X | X | X | X |
| 66 | X | X | X | X | X | X | X | X | X |
| 67 | X | X | X | X | X | X | X | X | X |
| 68 | X | X | X | X | X | X | X | X | X |
| 69 | X | X | X | X | X | X | X | X | X |
| 70 | X | X | X | X | X | X | X | X | X |
| 71 | X | X | X | X |   | X | X | X | X |
| 72 | X | X | X | X | X | X | X | X | X |
| 73 | X | X | X | X | X | X | X | X | X |
| 74 | X | X | X | X | X | X | X | X | X |
| 75 | X | X | X | X |   | X | X | X | X |
| 76 | X | X | X | X | X | X | X | X | X |
| 77 | X | X | X | X |   | X | X | X | X |
| 78 | X | X | X | X | X | X | X |   |   |
| 79 | X | X | X | X | X | X | X |   | X |
| 80 | X | X | X | X | X | X | X | X | X |
| 81 | X | X | X | X |   | X | X |   | X |
| 82 | X | X | X | X |   | X |   | X | X |
| 83 |   | X |   |   | X | X |   | X | X |
| 84 |   |   | X | X | X | X |   | X | X |
| 85 |   |   | X |   | X |   |   | X | X |
| 86 |   |   |   |   | X |   |   |   | X |
| 87 |   |   | X |   | X |   |   |   | X |
| 88 |   |   |   |   | X |   |   | X | X |

| | R1 | | | | | | | | | | | | |
|---|---|---|---|---|---|---|---|---|---|---|---|---|---|
| R2 | 22 | 27 | 38 | 39 | 40 | 41 | 42 | 31 | 32 | 34 | 35 | 36 | 37 |
| 44 | X |   | X | X | X | X | X | X | X | X | X | X | X |
| 45 | X | X | X | X | X | X | X | X | X | X | X | X | X |
| 46 | X | X |   | X | X |   | X | X | X |   |   |   |   |
| 47 | X | X |   | X | X |   | X | X | X | X | X |   |   |
| 48 | X |   | X | X | X |   | X | X | X | X | X | X | X |
| 49 | X | X | X | X | X |   | X | X | X | X | X | X | X |
| 50 | X | X | X | X | X |   | X | X | X | X | X | X | X |
| 51 |   | X |   | X | X | X | X | X | X | X | X | X | X |
| 52 | X | X | X | X | X | X | X | X | X | X | X | X | X |
| 53 | X | X | X | X | X | X | X | X | X | X | X | X | X |
| 54 | X | X | X | X | X | X | X | X | X | X | X | X | X |
| 55 | X | X | X | X | X | X | X | X | X | X | X | X | X |
| 56 | X | X | X |   |   |   |   |   |   |   |   |   |   |
| 57 | X | X |   | X | X |   |   | X |   | X | X | X | X |
| 58 | X | X |   | X | X |   |   | X | X | X | X |   |   |
| 59 | X | X |   | X | X |   |   | X | X | X | X | X | X |
| 60 | X |   |   | X | X |   | X | X | X | X | X | X | X |
| 61 | X | X |   | X | X |   |   | X | X | X | X | X | X |
| 62 | X | X |   | X | X |   | X | X | X | X | X | X | X |
| 63 | X | X | X | X | X | X | X | X | X | X | X | X | X |
| 64 | X | X |   | X | X |   | X | X | X | X | X | X | X |
| 65 | X | X | X | X | X |   | X | X | X | X | X | X | X |

TABLE 3a-continued

| | | | | | | | | | | | |
|---|---|---|---|---|---|---|---|---|---|---|---|
| 66 | X | X | X | X | X |   | X | X | X | X | X | X |
| 67 | X | X | X | X | X |   | X | X | X | X | X | X |
| 68 | X | X | X | X | X |   | X | X | X | X | X |   |
| 69 | X | X |   |   | X | X |   | X | X | X | X |   |
| 70 | X | X |   |   | X |   | X | X | X | X | X | X |
| 71 | X | X |   |   | X |   | X | X | X | X | X |   |
| 72 | X | X | X |   | X |   | X | X | X | X | X |   |
| 73 | X | X | X | X | X |   | X | X | X | X |   | X |
| 74 | X | X | X | X | X |   | X | X | X | X | X |   |
| 75 | X | X | X | X | X |   | X | X | X | X | X | X |
| 76 | X | X | X | X | X |   | X | X | X | X | X | X |
| 77 | X | X | X | X | X | X | X | X | X | X | X | X |
| 78 |   |   |   |   |   |   |   |   |   |   |   |   |
| 79 | X | X | X | X | X |   | X | X | X | X | X | X |
| 80 | X | X | X | X | X |   | X | X | X | X | X | X |
| 81 | X | X | X | X | X | X | X |   | X | X | X | X |
| 82 | X | X | X | X | X | X | X |   |   | X | X | X |
| 83 | X |   | X | X |   | X |   | X |   |   |   | X |
| 84 | X | X | X | X | X |   | X |   | X |   | X | X | X |
| 85 | X | X | X | X |   | X |   | X |   |   | X | X |
| 86 | X | X | X | X |   | X |   |   |   | X |   | X |
| 87 | X |   | X | X |   | X |   | X |   |   |   | X |
| 88 | X | X | X | X |   | X |   | X |   |   |   | X |

| | R1 | | | | | | | | | | |
|---|---|---|---|---|---|---|---|---|---|---|---|
| R2 | 30 | 44 | 45 | 47 | 49 | 50 | 51 | 52 | 7 | 8 | 13 |
| 44 | X | X | X | X | X | X | X | X | X | X | X |
| 45 | X |   |   |   |   |   |   |   | X | X | X |
| 46 | X |   |   |   |   |   |   |   | X | X | X |
| 47 | X | X | X | X | X | X | X | X | X | X | X |
| 48 | X | X | X | X | X | X | X | X | X | X | X |
| 49 | X |   |   |   |   |   |   |   | X | X | X |
| 50 | X |   |   |   |   |   |   |   | X | X | X |
| 51 | X |   |   |   |   |   |   |   | X | X | X |
| 52 | X |   |   |   |   |   |   |   | X | X | X |
| 53 | X |   |   |   |   |   |   |   | X | X | X |
| 54 | X |   |   |   |   |   |   |   | X | X | X |
| 55 | X | X | X | X | X | X | X | X | X | X | X |
| 56 | X |   |   |   |   |   |   |   | X | X | X |
| 57 |   |   |   |   |   |   |   |   | X | X | X |
| 58 | X |   |   |   |   |   |   |   | X | X | X |
| 59 | X | X | X | X | X | X | X | X | X | X | X |
| 60 | X | X | X | X | X |   | X | X | X | X | X |
| 61 | X |   |   |   |   |   |   |   | X | X | X |
| 62 | X |   |   |   |   |   |   |   | X | X | X |
| 63 | X |   |   |   |   |   |   |   | X | X | X |
| 64 | X | X | X | X | X | X | X | X | X | X | X |
| 65 | X |   |   |   |   |   |   |   | X | X | X |
| 66 | X |   |   |   |   |   |   |   | X | X | X |
| 67 | X |   |   |   |   |   |   |   | X | X | X |
| 68 | X | X | X | X | X | X | X | X | X | X | X |
| 69 | X |   |   |   |   |   |   |   | X | X | X |
| 70 | X |   |   |   |   |   |   |   | X | X | X |
| 71 | X |   |   |   |   |   |   |   | X | X | X |
| 72 | X |   |   |   |   |   |   |   | X | X | X |
| 73 | X |   |   |   |   |   |   |   | X | X | X |
| 74 | X |   |   |   |   |   |   |   | X | X | X |
| 75 | X |   |   |   |   |   |   |   | X | X | X |
| 76 | X |   |   |   |   |   |   |   | X | X | X |
| 77 | X |   |   |   |   |   |   |   | X | X | X |
| 78 | X |   |   |   |   |   |   |   | X | X | X |
| 79 | X |   |   |   |   |   |   |   | X | X | X |
| 80 | X |   |   |   |   |   |   |   | X | X | X |
| 81 | X |   |   |   |   |   |   |   | X | X | X |
| 82 | X |   |   |   |   |   |   |   | X | X | X |
| 83 |   | X |   | X |   |   | X | X |   |   |   |
| 84 | X | X | X | X | X | X | X | X |   |   |   |
| 85 | X | X |   | X | X | X | X | X | X | X | X |
| 86 |   |   |   |   |   |   |   |   | X | X | X |
| 87 | X |   |   |   |   |   |   |   | X | X | X |
| 88 |   |   |   |   |   |   |   |   |   |   |   |

| | R1 | | | | | | | | |
|---|---|---|---|---|---|---|---|---|---|
| R2 | 2 | 3 | 9 | 10 | 11 | 14 | 15 | 20 | 22 |
| 133 | X | X | X | X | X | X |   | X | X |
| 134 | X | X | X | X | X | X |   | X | X |
| 135 | X | X | X | X | X | X |   | X | X |
| 136 | X | X | X | X | X | X |   | X | X |
| 137 | X | X | X | X | X | X |   | X | X |
| 138 | X | X | X | X | X | X |   | X | X |
| 139 | X | X | X | X | X |   |   |   | X |
| 140 | X | X | X | X | X | X |   |   | X |
| 141 | X | X | X | X |   |   |   |   | X |
| 142 | X | X | X | X | X | X |   | X | X |
| 143 | X | X | X | X | X | X |   | X | X |
| 144 | X | X | X | X | X | X |   | X | X |
| 145 | X | X | X | X | X | X |   | X | X |
| 146 | X | X | X | X | X | X |   | X | X |
| 147 | X | X | X | X | X |   |   |   | X |
| 148 | X | X | X | X | X | X |   | X | X |
| 149 | X | X | X | X | X | X |   | X | X |
| 150 | X | X | X | X | X | X |   | X | X |
| 151 | X | X | X | X | X | X |   | X | X |
| 152 | X | X | X | X | X | X |   | X | X |
| 153 | X | X | X | X | X | X |   | X | X |
| 154 | X | X | X | X | X | X |   | X | X |
| 155 | X | X | X | X | X | X |   | X | X |
| 156 | X | X | X | X | X | X |   | X | X |
| 157 | X | X | X | X | X | X |   | X | X |
| 158 | X | X | X | X | X | X |   | X | X |
| 159 | X | X | X | X | X | X |   | X | X |
| 160 | X | X | X | X | X | X |   | X | X |
| 161 | X | X | X | X | X | X |   | X | X |
| 162 | X | X | X | X | X | X |   | X | X |
| 163 | X | X | X | X | X | X |   | X | X |
| 164 | X | X | X | X | X | X |   | X | X |
| 165 | X | X | X | X | X | X |   | X | X |
| 166 | X | X | X | X | X | X |   | X | X |
| 167 | X | X | X | X | X | X |   | X | X |
| 168 | X | X | X | X | X | X |   | X | X |
| 169 | X |   |   | X |   |   |   |   | X |
| 170 | X |   |   | X |   |   |   |   | X |
| 171 | X |   |   | X |   |   |   |   | X |
| 172 | X |   |   | X | X | X | X |   | X | X |
| 173 | X |   |   | X |   | X | X |   | X | X |
| 174 | X |   |   | X |   |   |   |   | X |
| 175 | X |   |   | X |   | X | X |   | X | X |
| 176 | X |   |   | X | X | X | X |   | X | X |

| | R1 | | | | | | | | | | | | |
|---|---|---|---|---|---|---|---|---|---|---|---|---|---|
| R2 | 44 | 45 | 47 | 49 | 50 | 51 | 52 | 7 | 8 | 13 | 17 | 19 | 21 |
| 133 |   | X |   | X | X |   | X | X | X |   |   |   | X |
| 134 | X | X |   | X | X | X | X | X | X |   |   |   | X |
| 135 | X | X |   | X | X | X | X | X | X |   |   |   | X |
| 136 | X | X |   | X | X | X | X | X | X |   |   |   | X |
| 137 |   |   |   |   |   |   |   | X | X | X |   |   | X |
| 138 | X | X |   | X | X | X | X | X | X |   |   |   | X |
| 139 | X | X |   | X | X | X | X | X | X |   |   |   | X |
| 140 | X | X |   | X | X |   | X | X | X |   |   |   | X |
| 141 | X | X |   | X | X | X | X | X | X |   |   |   | X |
| 142 |   |   |   |   |   |   |   | X | X | X |   |   | X |
| 143 |   |   |   |   |   |   |   | X | X | X |   |   | X |
| 144 | X | X |   | X | X | X | X | X | X |   |   |   | X |
| 145 |   |   |   |   |   |   |   | X | X | X |   |   | X |
| 146 | X |   |   | X | X | X | X | X | X |   |   |   | X |
| 147 |   |   |   |   |   |   |   | X | X | X |   |   | X |
| 148 |   |   |   |   |   |   |   | X | X | X |   |   | X |
| 149 |   |   |   |   |   |   |   | X | X | X |   |   | X |
| 150 |   |   |   |   |   |   |   | X | X | X |   |   | X |
| 151 |   |   |   |   |   |   |   | X | X | X |   |   | X |
| 152 | X | X |   | X | X | X | X | X | X |   |   |   | X |
| 153 |   |   |   |   |   |   |   | X | X | X |   |   | X |
| 154 |   |   |   |   |   |   |   | X | X | X |   |   | X |
| 155 |   |   |   |   |   |   |   | X | X | X |   |   | X |
| 156 |   |   |   |   |   |   |   | X | X | X |   |   | X |
| 157 | X | X |   | X | X | X | X | X | X |   |   |   | X |
| 158 |   |   |   |   |   |   |   | X | X | X |   |   | X |

TABLE 3a-continued

| | 2 | 3 | 9 | 10 | 11 | 14 | 15 | 23 |
|---|---|---|---|---|---|---|---|---|
| 159 | | | | | X | X | X | X |
| 160 | | | | | | X | X | X |
| 161 | | | | | X | X | X | X |
| 162 | | | | | | X | X | X |
| 163 | | | | | | X | X | X |
| 164 | | | | | | X | X | X |
| 165 | | | | | | X | X | X |
| 166 | | | | | | X | X | X |
| 167 | X | X | | X | X | X | X | X | X |
| 168 | | | | | | X | X | X |
| 169 | | | | | | X | X | |
| 170 | | | | | | X | X | X |
| 171 | | | | | | X | X | |
| 172 | | | | | X | X | X | X |
| 173 | | | | | | X | X | X |
| 174 | | | | | | X | X | |
| 175 | X | X | | X | X | X | X | X | X |
| 176 | | | | | | X | X | X | X |

| | R1 | | | | | | | |
|---|---|---|---|---|---|---|---|---|
| R2 | 2 | 3 | 9 | 10 | 11 | 14 | 15 | 23 |
| 180 | X | | X | X | | X | X | X |
| 181 | X | | X | X | X | X | X | X |
| 182 | X | | X | X | | X | | X |
| 183 | X | | X | X | X | X | X | X |
| 184 | X | | X | X | X | X | X | X |
| 185 | X | | X | X | X | X | X | X |
| 186 | X | | X | | | X | | X |
| 187 | X | | X | X | X | X | X | X |
| 188 | X | | X | X | X | X | X | X |
| 190 | X | | X | | | X | X | X |
| 191 | X | | X | | | X | X | X |
| 192 | X | | X | X | | X | X | X |
| 193 | X | | X | | | X | X | X |
| 194 | X | | X | X | | X | X | X |
| 195 | X | | X | | | X | X | X |
| 196 | X | | X | X | | X | X | X |
| 197 | X | | X | X | | X | X | X |
| 199 | X | | X | X | X | X | | X |
| 201 | X | | X | X | | X | X | X |
| 203 | X | | X | X | | X | X | X |
| 204 | X | | X | X | | X | X | X |
| 205 | X | | X | X | | X | X | X |
| 206 | X | | X | X | | X | | X |
| 207 | X | | X | X | | X | X | X |
| 208 | X | | X | X | | X | X | X |
| 209 | X | | X | X | | X | X | X |
| 210 | X | | X | X | | X | | X |
| 211 | X | | X | X | | X | X | X |
| 212 | X | | X | X | | X | X | X |
| 213 | X | | X | X | | X | | X |
| 214 | X | | X | X | X | X | X | X |
| 215 | X | | X | | | X | X | X |
| 216 | X | | X | X | X | X | X | X |
| 220 | X | | X | X | X | X | X | X |
| 221 | X | | X | X | X | X | X | X |
| 222 | X | | X | | | X | X | X |
| 228 | X | | X | X | X | X | X | X |
| 229 | X | | X | X | | X | X | X |
| 231 | X | | X | X | | X | X | X |
| 232 | X | | X | X | | X | X | X |
| 233 | X | | X | X | | X | X | X |
| 234 | X | | X | X | | X | X | X |
| 235 | X | | X | X | X | X | X | X |

| | R1 | | | | | | | | | | | | |
|---|---|---|---|---|---|---|---|---|---|---|---|---|---|
| R2 | 20 | 22 | 27 | 38 | 39 | 40 | 41 | 42 | 31 | 32 | 34 | 35 | 36 | 37 |
| 180 | | X | | X | X | X | X | X | X | | | | X | X |
| 181 | | X | | X | X | X | X | X | X | | | | X | X |
| 182 | | X | | X | X | X | X | | | | | | X | X |
| 183 | | X | | X | X | X | X | X | | | | | X | X |
| 184 | | X | | X | X | X | X | X | X | | | | X | X |
| 185 | | | | | | | | | | | | | | |
| 186 | | | | X | X | X | X | X | X | | | | | |
| 187 | | X | | X | X | X | X | X | X | | | | X | X |

TABLE 3a-continued

| | | | | | | | | | | |
|---|---|---|---|---|---|---|---|---|---|---|
| 188 | X | | X | X | X | X | X | X | | X | X |
| 190 | X | | X | X | X | X | X | X | | X | X |
| 191 | X | | X | X | X | X | X | X | | X | X |
| 192 | X | | X | X | X | X | X | X | | X | X |
| 193 | X | | X | X | X | X | X | X | | X | X |
| 194 | X | | X | X | X | X | X | X | | X | X |
| 195 | X | | X | X | X | X | X | X | | X | X |
| 196 | X | | X | X | X | X | X | X | | X | X |
| 197 | X | | X | X | X | X | X | X | | X | X |
| 199 | X | | X | X | X | X | X | X | | X | X |
| 201 | X | | | X | | X | X | X | | X | X |
| 203 | X | | X | | X | | X | X | | X | X |
| 204 | X | | X | X | X | X | X | X | | X | X |
| 205 | X | | X | X | X | X | X | X | | X | X |
| 206 | X | | X | X | X | X | X | X | | X | X |
| 207 | X | | X | X | X | X | X | X | | X | X |
| 208 | X | | X | X | X | X | X | X | | X | X |
| 209 | X | | | X | | X | X | X | | | |
| 210 | X | | | X | | X | X | X | | X | X |
| 211 | X | | X | X | X | X | X | X | | X | X |
| 212 | X | | X | X | X | X | X | X | | | |
| 213 | X | | | X | | X | X | X | | | X |
| 214 | X | | X | | X | X | X | X | X | | |
| 215 | | | | | | | | | | | |
| 216 | X | | X | X | X | X | X | X | | X | |
| 220 | X | | X | X | X | X | X | X | | X | X |
| 221 | X | | X | X | X | X | X | X | | X | X |
| 222 | X | | X | X | X | X | X | X | | X | X |
| 228 | X | | X | X | X | X | X | X | | X | X |
| 229 | | | | | | | | | | | |
| 231 | | | X | X | X | X | X | X | | X | X |
| 232 | X | | X | X | X | X | X | X | | X | X |
| 233 | X | | X | X | X | X | X | X | | X | X |
| 234 | X | | X | X | X | | | X | X | X | X |
| 235 | | | X | X | X | X | X | X | | X | X |

| | R1 | | | | | | | | | |
|---|---|---|---|---|---|---|---|---|---|---|
| R2 | 7 | 8 | 13 | 17 | 19 | 21 | 25 | 33 | 43 | 26 |
| 180 | | X | | X | X | | X | | X | X |
| 181 | X | X | | X | X | X | | X | X | X |
| 182 | X | X | | | | | X | X | X | |
| 183 | X | X | | X | X | X | X | X | X | |
| 184 | X | X | | X | X | | | X | X | |
| 185 | | X | | | X | | | | | |
| 186 | | | | | | | X | | | |
| 187 | X | | X | | X | X | X | | X | X |
| 188 | X | | X | | X | X | X | | X | X |
| 190 | X | | | | X | | X | | X | X |
| 191 | X | | X | | X | | X | | X | X |
| 192 | X | | X | | X | | X | | X | X |
| 193 | X | | X | | X | X | X | | X | |
| 194 | X | | X | | X | X | X | | X | X |
| 195 | X | | X | | X | X | X | | X | X |
| 196 | X | | X | | X | X | X | | X | X |
| 197 | X | | X | | X | X | X | | X | X |
| 199 | X | | X | | X | X | X | | X | X |
| 201 | X | | X | | X | X | X | | X | X |
| 203 | X | | X | | X | X | X | | X | X |
| 204 | X | | X | | X | X | X | | X | X |
| 205 | X | | X | | X | X | X | | | X |
| 206 | X | | X | | X | X | X | | X | X |
| 207 | X | | X | | X | X | X | | X | X |
| 208 | X | | X | | X | X | X | | X | X |
| 209 | X | | X | | X | X | X | | | X |
| 210 | X | | | | X | X | X | | | X |
| 211 | X | | X | | X | X | X | | X | X |
| 212 | X | | X | | X | X | X | | X | X |
| 213 | X | | X | | X | X | X | | X | X |
| 214 | X | | X | | X | X | X | | | X |
| 215 | | | | | | | | | | X |
| 216 | X | | X | | X | | X | | X | X |
| 220 | X | | X | | X | | X | | X | X |
| 221 | X | | X | | X | X | X | | X | X |
| 222 | | | | | X | X | X | | X | X |
| 228 | X | | X | | X | X | X | | X | X |
| 229 | X | | X | | X | X | | | | X |
| 231 | X | | X | | | | X | | X | X |

TABLE 3a-continued

| | | | | | | | | |
|---|---|---|---|---|---|---|---|---|
| 232 | X | | X | | X | X | X | | X | X |
| 233 | X | | X | | X | | X | X | X | X |
| 234 | X | | X | | X | X | X | | X | X |
| 235 | X | | X | | X | X | X | X | | X |

| | R1 | | | | | | | |
|---|---|---|---|---|---|---|---|---|
| R2 | 2 | 3 | 9 | 10 | 11 | 14 | 15 | 23 |
| 237 | X | | X | X | X | X | X | X |
| 238 | X | | X | X | X | X | X | X |
| 239 | X | | X | X | X | X | X | X |
| 240 | X | | X | X | X | X | X | X |
| 241 | X | | X | X | X | X | X | X |
| 243 | X | | X | X | X | X | X | X |
| 244 | X | | X | X | X | X | X | X |
| 246 | X | | X | X | X | X | X | X |
| 247 | X | | X | X | X | X | X | X |
| 249 | X | | X | X | X | X | X | X |
| 250 | X | | X | X | X | X | X | X |
| 252 | X | | X | X | X | X | X | X |
| 253 | X | | X | X | X | X | X | X |
| 254 | X | | X | X | X | X | X | X |
| 255 | X | | X | X | X | X | X | X |
| 256 | X | | X | X | X | X | X | X |
| 257 | X | | X | X | X | X | X | X |
| 259 | X | | X | X | X | X | X | X |
| 261 | X | | X | X | X | X | X | X |
| 262 | X | | X | X | X | X | X | X |

| | R1 | | | | | | | | | | | | |
|---|---|---|---|---|---|---|---|---|---|---|---|---|---|
| R2 | 20 | 22 | 27 | 38 | 39 | 40 | 41 | 42 | 31 | 32 | 34 | 35 | 36 | 37 |
| 237 | | X | | | X | | X | X | X | | | X | X |
| 238 | | X | | X | X | X | X | | | | X | | X | X |
| 239 | | | | X | X | X | X | X | X | | | | X | X |
| 240 | X | | | X | X | X | X | | | | | | X | X |
| 241 | X | | | X | X | X | X | X | X | | | | X | X |
| 243 | X | | X | X | X | X | X | X | X | | | | X | X |
| 244 | X | | X | X | X | X | | | | | | | X | X |
| 246 | X | | X | X | | | X | X | X | | | | X | X |
| 247 | X | | X | X | | X | X | X | | | | | | |
| 249 | X | | X | X | X | X | X | X | | | | | X | X |
| 250 | X | | X | X | X | X | X | X | X | | | | X | X |
| 252 | X | | X | X | X | X | X | X | X | | | | X | X |
| 253 | | | | | X | | | X | X | X | | | | |
| 254 | X | | X | X | X | X | X | X | | | | | X | X |
| 255 | X | | X | X | X | X | X | X | X | | | | X | X |
| 256 | X | | X | X | X | X | X | X | X | | | | X | X |
| 257 | X | | X | X | X | X | X | X | X | | | | X | X |
| 259 | X | | | X | | X | | | X | X | | | X | X |
| 261 | X | | X | X | X | X | X | X | X | | | | X | X |
| 262 | X | | X | X | X | X | X | X | X | | | | X | X |

| | R1 | | | | | | | | | | | |
|---|---|---|---|---|---|---|---|---|---|---|---|---|
| R2 | 7 | 8 | 13 | 17 | 19 | 21 | 25 | 33 | 43 | 26 | 28 | 29 |
| 237 | X | | X | | X | X | X | X | X | | | |
| 238 | X | | X | | X | X | X | X | X | | | |
| 239 | X | | X | | X | X | X | | | | | X |
| 240 | X | | X | | X | X | X | | | | X | X |
| 241 | X | | X | | X | X | X | X | | | X | X |
| 243 | X | | X | | X | X | X | | | | X | X |
| 244 | X | | X | | X | X | X | | | | X | X |
| 246 | X | | X | | X | X | X | | X | | X | X |
| 247 | X | | X | | X | X | X | | | | X | X |
| 249 | X | | X | | X | X | X | | | | | X |
| 250 | X | | X | | X | X | X | | X | | X | X |
| 252 | X | | X | | X | X | X | | | | X | X |
| 253 | X | | X | | X | X | X | | | | X | X |
| 254 | X | | X | | X | X | X | | | | X | X |
| 255 | X | | X | | X | X | X | | X | | X | X |
| 256 | X | | X | | X | X | X | | | | X | X |
| 257 | X | | X | | X | X | X | | | | | X |
| 259 | X | | X | | X | X | X | X | | | | X |

| | | | | | | | | |
|---|---|---|---|---|---|---|---|---|
| 261 | X | | X | | X | X | X | X | X | X |
| 262 | X | | X | | X | X | X | X | | X |

| | R1 | | | | | | | |
|---|---|---|---|---|---|---|---|---|
| R2 | 2 | 3 | 9 | 10 | 11 | 14 | 15 | 23 |
| 265 | | | | | | | | |
| 266 | X | X | X | X | X | X | X | X |
| 267 | X | X | X | X | X | X | X | X |
| 268 | X | X | X | X | X | X | X | X |
| 269 | X | X | X | | | X | X | X |
| 270 | X | X | X | X | X | X | X | X |
| 271 | X | X | X | X | X | X | | X |
| 272 | X | X | X | X | X | X | | X |
| 273 | X | X | X | X | X | X | | X |
| 274 | | | X | | | | | |
| 275 | X | X | X | | X | X | | X | X |
| 276 | X | X | X | | X | X | X | | X |
| 277 | | | X | | X | X | X | X | X |
| 278 | X | X | X | X | X | X | X | X |
| 279 | X | X | X | X | X | X | X | X |
| 280 | X | X | X | | X | X | | X |
| 281 | X | X | X | X | X | X | | X |
| 282 | X | X | X | X | X | X | X | X |
| 283 | X | X | X | X | X | X | | X |
| 284 | X | X | X | X | X | X | X | X |
| 285 | X | X | X | | X | X | | X |
| 286 | X | X | X | X | X | | | |
| 287 | X | X | | X | X | | | X |
| 288 | X | X | X | X | X | X | | X |
| 289 | X | X | X | X | X | | | X |
| 290 | X | X | X | X | X | | | X |
| 291 | X | X | X | X | | | | X |
| 292 | X | X | X | X | X | X | | X |
| 293 | X | X | X | X | X | X | | X |
| 294 | X | X | X | X | X | | | X |
| 295 | X | X | X | X | X | | X | X |
| 296 | X | X | X | X | X | X | | X |
| 297 | X | X | X | X | X | X | X | X |
| 298 | X | X | X | X | X | | X | X |
| 299 | X | X | | | | | | X |

| | R1 | | | | | | | | | | | | |
|---|---|---|---|---|---|---|---|---|---|---|---|---|---|
| R2 | 20 | 22 | 27 | 38 | 39 | 40 | 41 | 42 | 31 | 32 | 34 | 35 | 36 | 37 |
| 265 | | | | | | | | | | | | | | |
| 266 | | | | X | X | X | X | X | | | | X | X | |
| 267 | | X | | X | X | X | X | X | X | | | | X | X |
| 268 | | X | | X | X | X | X | X | X | | | | X | X |
| 269 | | X | | X | X | X | X | X | X | | | | X | X |
| 270 | | X | | X | X | X | | | | | | | X | X |
| 271 | | X | | | X | | X | X | X | | | | X | X |
| 272 | | X | | X | | X | X | X | X | | | | X | X |
| 273 | | X | | X | X | X | X | X | X | | | X | X | X |
| 274 | | X | | | | | | | | | | | | |
| 275 | | X | | | X | X | X | X | X | | | | X | X |
| 276 | | X | | X | X | X | X | X | X | | | | X | X |
| 277 | | X | | | X | X | X | X | X | | | | X | X |
| 278 | | X | | | X | X | X | X | X | | | | X | X |
| 279 | | X | | X | X | X | X | X | X | | | | X | X |
| 280 | | X | | | X | X | X | X | X | | | | X | X |
| 281 | | X | | | X | X | X | X | X | | | | X | X |
| 282 | | X | | X | X | X | X | X | X | | | | X | X |
| 283 | | X | | X | X | X | X | X | X | | | | X | X |
| 284 | | X | | X | X | X | X | X | X | | | | X | X |
| 285 | | X | | X | X | | | X | X | | | | X | X |
| 286 | | X | | | | | | | X | | | X | X | X |
| 287 | | X | | | X | X | X | X | | | | | X | X |
| 288 | | X | | X | X | X | X | X | | | | | X | X |
| 289 | | X | | X | X | X | X | X | | | | | X | X |
| 290 | | X | | | X | X | X | X | X | | | | X | X |
| 291 | | X | | X | X | X | X | | X | | | | X | X |
| 292 | | X | | X | X | X | X | X | X | | | | X | X |
| 293 | | X | | X | X | X | X | X | X | | | | X | X |
| 294 | | X | | X | X | X | | | X | | | | X | X |
| 295 | | X | | X | X | X | X | X | X | | | | X | X |
| 296 | | X | | X | X | X | X | X | X | | | | X | X |

TABLE 3a-continued

| R2 | | | | | | | | | | | | |
|---|---|---|---|---|---|---|---|---|---|---|---|---|
| 297 | X | | X | X | X | X | X | X | X | X | X | X |
| 298 | X | | X | X | X | X | X | X | X | X | X | X |
| 299 | X | | | | | X | X | | X | | | |

| | R1 | | | | | | | | | | | |
|---|---|---|---|---|---|---|---|---|---|---|---|---|
| R2 | 7 | 8 | 13 | 17 | 19 | 21 | 25 | 33 | 43 | 26 | 28 | 29 | 30 |
| 265 | | | | | | | | | | | | |
| 266 | | X | X | X | | X | | | | X | | X |
| 267 | X | X | X | X | X | X | X | X | | X | X | X |
| 268 | X | X | X | X | X | X | X | X | | X | X | X |
| 269 | X | X | X | | X | X | X | X | | X | X | X |
| 270 | X | X | X | | X | X | X | X | | X | X | X |
| 271 | X | X | X | X | X | X | X | X | | | | X |
| 272 | X | X | X | X | X | X | X | X | | | | X |
| 273 | | X | X | | X | X | X | X | | X | X | X |
| 274 | | X | | | X | | | | | | | X |
| 275 | X | X | X | X | X | X | X | | | X | | X |
| 276 | | X | X | | X | X | X | X | | X | X | X |
| 277 | | | X | | X | X | X | X | | X | X | |
| 278 | | X | X | | X | X | X | X | | X | X | X |
| 279 | | X | X | | X | X | X | X | | X | X | X |
| 280 | X | X | X | X | X | X | X | X | | | | X |
| 281 | X | X | X | | X | X | X | X | | | | X |
| 282 | X | X | X | X | X | X | X | X | | X | X | X |
| 283 | X | X | X | X | X | X | | X | | | | X |
| 284 | X | | X | X | X | X | | X | | X | | X |
| 285 | | X | X | X | X | X | | | | | | X |
| 286 | X | X | X | | X | X | X | X | | | | X |
| 287 | | X | | X | X | | X | | | | | |
| 288 | X | X | X | X | X | X | X | | | | | X |
| 289 | X | X | X | X | X | X | | | | | | X |
| 290 | X | X | X | X | X | X | X | | | | | X |
| 291 | X | | X | X | X | X | | X | | | | X |
| 292 | X | X | X | X | X | | X | X | | | | X |
| 293 | X | X | X | X | X | | X | X | | | | X |
| 294 | X | X | X | X | X | | X | X | | | | X |
| 295 | X | X | X | X | X | X | X | X | | | | X |
| 296 | X | X | X | X | X | X | X | X | | X | | X |
| 297 | X | X | X | X | X | X | X | X | | X | X | X |
| 298 | X | X | X | X | X | X | X | X | | X | | X |
| 299 | X | X | | | X | X | | | | X | X | |

| | R1 | | | | | | | |
|---|---|---|---|---|---|---|---|---|
| R2 | 2 | 3 | 9 | 10 | 11 | 14 | 15 | 23 |
| 300 | X | X | X | X | X | X | | |
| 301 | X | X | X | X | X | X | | X |
| 302 | X | | X | X | | | | X |
| 303 | | | | | X | | | X |
| 304 | X | X | X | X | X | X | X | X |
| 305 | X | X | X | | | | | |
| 306 | X | X | | X | X | | | X |
| 307 | X | X | X | X | X | | | |
| 308 | X | X | X | | | | | |
| 309 | X | | | | X | X | | X |
| 310 | X | X | X | X | X | X | X | X |
| 311 | X | X | X | X | X | | | X |
| 312 | X | X | X | | | | | X |
| 313 | X | | | | X | | | X |
| 314 | | X | X | | | | | |
| 315 | | | | | | | | |
| 316 | X | X | X | X | X | | | X |
| 317 | X | | | X | X | X | | X |
| 318 | X | X | X | X | | | | X |
| 319 | X | X | | X | | | | X |
| 320 | X | X | | X | X | | | X |
| 321 | X | X | X | X | X | X | | X |
| 322 | X | X | X | X | X | X | X | X |
| 323 | X | X | X | X | X | X | X | X |
| 324 | X | X | X | | | X | | X |
| 325 | | | | | X | | | X |
| 326 | X | | | | | | | |
| 327 | | X | X | | X | | | |
| 328 | | | | | | | | |
| 330 | | | | | | | | |
| 331 | | | | | | | | |

TABLE 3a-continued

| R2 | | | | | |
|---|---|---|---|---|---|
| 332 | | | | | |
| 333 | | | | | |
| 334 | | X | X | X | X |
| 335 | | | | | |
| 336 | | | X | | X |
| 337 | | X | | X | X |
| 338 | | X | X | X | X |

| | R1 | | | | | | | | | | | | |
|---|---|---|---|---|---|---|---|---|---|---|---|---|---|
| R2 | 20 | 22 | 27 | 38 | 39 | 40 | 41 | 42 | 31 | 32 | 34 | 35 | 36 | 37 |
| 300 | X | | X | X | X | X | X | | X | X | X | X |
| 301 | X | | X | X | X | X | | X | X | X | X | X |
| 302 | | | | | | | | | X | X | | X |
| 303 | | | | | | | | | | X | | | X |
| 304 | X | | X | X | X | X | X | X | | X | X | X |
| 305 | X | | | X | X | X | X | | | X | X | X |
| 306 | X | | X | X | X | X | X | X | X | X | X | X |
| 307 | X | | X | X | X | X | X | X | | X | X | X |
| 308 | X | | X | X | X | X | X | X | | X | X | X | X |
| 309 | X | | X | X | X | X | X | X | | X | X | X |
| 310 | X | | X | X | X | X | X | X | X | X | X | X | X |
| 311 | | | X | X | X | X | X | | | X | X | X |
| 312 | | | X | X | X | X | X | | | X | X | X |
| 313 | | X | X | X | | X | | | | X | X |
| 314 | | X | X | X | X | | | | X | X | X |
| 315 | | | | | | | | | | | | |
| 316 | X | | X | X | X | X | X | X | | X | X | X | X |
| 317 | | X | X | X | X | | X | | | X | X |
| 318 | X | | X | | X | | X | | X | X |
| 319 | X | | X | X | X | X | X | X | X | X | X | X |
| 320 | X | | X | X | | X | X | X | X | X | X | X |
| 321 | X | | X | X | X | X | X | X | | X | X | X | X |
| 322 | X | | X | X | X | X | X | X | | X | X | X |
| 323 | X | | X | | X | X | X | X | X | X | X | X |
| 324 | | | | X | | | | | | | | |
| 325 | | | | | | | | | | | | |
| 326 | X | | | | | | | | | X | | |
| 327 | | | | | | | X | | X | | X |
| 328 | X | | | | X | | X | | | | |
| 330 | | | X | X | | | X | X | | X | X | X |
| 331 | X | | X | | X | X | X | | X | X | X |
| 332 | | | X | X | | X | X | | X | X | X |
| 333 | X | | X | | X | X | X | | X | X | X |
| 334 | | X | X | | X | X | X |
| 335 | | X | X | | X | |
| 336 | | X | | X | X |
| 337 | | X | X | | X | X |
| 338 | | X | X | | X | X |

| | R1 | | | | | | | | | | | | |
|---|---|---|---|---|---|---|---|---|---|---|---|---|---|
| R2 | 7 | 8 | 13 | 17 | 19 | 21 | 25 | 33 | 43 | 26 | 28 | 29 | 30 |
| 300 | X | X | X | | X | X | X | X | | | | | X |
| 301 | | X | X | | X | X | X | | | X | | | |
| 302 | | X | | | X | X | | X | | | | | |
| 303 | | | X | | | | | | | | | | |
| 304 | X | X | X | | X | X | X | X | | | | | X |
| 305 | | X | | | X | X | X | X | | | | | X |
| 306 | X | X | X | X | X | X | X | | | | | | X |
| 307 | | X | | | X | X | X | | | | | | |
| 308 | | X | | X | X | X | X | | | | | | X |
| 309 | X | X | X | X | X | | X | | | | X | X |
| 310 | X | X | X | X | | | X | X | | X | | | X |
| 311 | X | X | | | X | X | X | | | | | | X |
| 312 | X | | | | X | X | X | | | | | | X |
| 313 | X | X | | | X | | X | X | | | | | X |
| 314 | X | | | | X | | | | | | | | X |
| 315 | X | | | | | | | | | | | | |
| 316 | X | X | X | | X | | X | | | | | X | X |
| 317 | X | X | X | X | X | | X | | | | X | X | X |
| 318 | | X | | X | X | X | X | | | | | | |
| 319 | X | | X | | X | X | X | | | | | | X |
| 320 | X | X | X | X | X | X | | | | | | | X |
| 321 | X | X | X | X | X | X | X | | | | | X | X |
| 322 | X | X | X | | X | X | X | X | | | | X | X |
| 323 | X | X | X | | X | X | X | X | | | | X | X |

TABLE 3a-continued

| | | | | | | | | | | | |
|---|---|---|---|---|---|---|---|---|---|---|---|
| 324 | X | | X | | | | X | | | X | |
| 325 | X | | X | | | | | | | | |
| 326 | X | X | X | X | | X | X | | | | | X |
| 327 | | X | | X | X | X | | X | | | | X |
| 328 | | | | | | | X | X | | | | X |
| 330 | | | | | | | | | | | | X |
| 331 | | | | | | | X | X | | | | |
| 332 | | | | | | | X | X | | | | |
| 333 | | | | | | | X | X | | | | |
| 334 | | | | | | | | | X | X | | |
| 335 | | | | | | | | | | | | X |
| 336 | | | | | | | | | | | | X |
| 337 | | | | | | | | | | | | X |
| 338 | | | | | | | | | | | | X |

| | R1 | | | | | | | |
|---|---|---|---|---|---|---|---|---|
| R2 | 2 | 3 | 9 | 10 | 11 | 14 | 15 | 23 |
| 339 | | | X | X | X | X | | |
| 340 | | | X | X | X | X | | |
| 341 | | | X | X | X | X | | |
| 342 | | | X | X | X | X | | |
| 343 | | | | | | | | |
| 344 | | | | X | | X | | |
| 345 | | | X | | | | | |
| 346 | | | X | X | X | X | | |
| 347 | | | X | X | X | X | | |
| 348 | | | X | X | X | X | | |
| 349 | | | X | | | | | |
| 350 | | | X | X | X | | | |
| 351 | | | X | X | X | | | |
| 352 | | X | X | | X | | | |
| 353 | | | | | | | | |
| 354 | | | | | | | | |
| 355 | | | X | X | | X | | |
| 356 | | | X | X | X | X | | |
| 357 | | | X | | | | | |
| 358 | | | X | | | | | |
| 359 | | | X | X | X | X | | |
| 360 | | | X | X | X | X | | |
| 361 | | | | X | X | X | | |
| 362 | | | | X | X | X | | |
| 363 | | | | | | | | |
| 364 | | | X | | | | | |
| 365 | | | X | X | X | X | | |
| 366 | | | X | X | | | | |
| 367 | | | | X | X | X | | |
| 368 | | | | | | | | |
| 369 | | | X | X | X | | | |
| 370 | | | X | X | X | | | |
| 371 | | | X | X | X | | | |
| 372 | | | X | | | | | |
| 373 | | | X | | X | X | | |
| 374 | | | X | | | | | |
| 375 | | | X | X | X | | | |
| 376 | | | X | | X | | | |
| 377 | | | X | | | | | |

| | R1 | | | | | | | | | | | | | |
|---|---|---|---|---|---|---|---|---|---|---|---|---|---|---|
| R2 | 20 | 22 | 27 | 38 | 39 | 40 | 41 | 42 | 31 | 32 | 34 | 35 | 36 | 37 |
| 339 | | | | | X | X | | | X | X | X | | | |
| 340 | | | | | X | X | | | X | X | X | X | | |
| 341 | | | | | X | | | | X | X | X | | | |
| 342 | | | | | X | X | | | X | X | X | | | |
| 343 | | | | | | X | | | X | X | | | X | |
| 344 | | | | | X | X | | | | X | X | X | | |
| 345 | | | | | X | X | | | X | X | X | | | |
| 346 | | | | | X | X | | | X | X | X | X | | |
| 347 | | | | | X | X | | | X | X | X | X | | |
| 348 | | | | | X | | | | X | X | | | | |
| 349 | | | | | X | X | | | X | X | X | X | | |
| 350 | | | | | X | X | | | X | X | X | | | |
| 351 | | | | | X | X | | | X | X | | | | |
| 352 | | | | | X | X | | | X | X | X | X | | |
| 353 | | | | | X | | | | | | | | | |
| 354 | | | | | | X | | | X | | | | | |

TABLE 3a-continued

| | | | | | | | | | | | |
|---|---|---|---|---|---|---|---|---|---|---|---|
| 355 | | | X | X | | X | X | | X | X | | |
| 356 | | | X | X | | X | X | | X | X | | |
| 357 | | | | | | X | | | | | | |
| 358 | | | X | X | | X | X | | | | | |
| 359 | | | X | X | | X | X | | X | X | | |
| 360 | | | | | | X | | | | | | |
| 361 | | | X | X | | X | X | | X | | | |
| 362 | | | X | X | | | | | X | X | | |
| 363 | | | X | | | X | | | | | | |
| 364 | | | | | | | | | | | | |
| 365 | | | | | | | | | X | | | |
| 366 | | | | | | | | | X | | | |
| 367 | | | | | | | | | X | | | |
| 368 | | | | X | | | | | | | | |
| 369 | | | X | | | X | | | X | X | | |
| 370 | | | X | | | X | | | X | X | | |
| 371 | | | X | | | X | | | X | X | | |
| 372 | | | X | | | X | | | X | X | | |
| 373 | | | X | | | X | | | X | X | | |
| 374 | | | X | | | X | | | X | X | | |
| 375 | | | X | | | X | | | X | X | | |
| 376 | | | X | | | | | | X | | | |
| 377 | | | X | | | X | | | X | X | | |

| | R1 | | | | | | | | | | | | |
|---|---|---|---|---|---|---|---|---|---|---|---|---|---|
| R2 | 7 | 8 | 13 | 17 | 19 | 21 | 25 | 33 | 43 | 26 | 28 | 29 | 30 |
| 339 | | | | | | | | | | | | | X |
| 340 | | | | | | | | | | | | X | X |
| 341 | | | | | | | | | | | | | X |
| 342 | | | | | | | | | | | | X | X |
| 343 | | | | | | | | | | | | | X |
| 344 | | | | | | | | | | | | | |
| 345 | | | | | | | | | | | | | X |
| 346 | | | | | | | | | | | | | X |
| 347 | | | | | | | | | | | | | X |
| 348 | | | | | | | | | | | | | X |
| 349 | | | | | | | | | | | | | X |
| 350 | | | | | | | | | | | | | X |
| 351 | | | | | | | | | | | | X | X |
| 352 | | | | | | | | | | | | X | X |
| 353 | | | | | | | | | | | | | X |
| 354 | | | | | | | | | | | | | |
| 355 | | | | | | | | | | | | X | X |
| 356 | | | | | | | | | | | | | X |
| 357 | | | | | | | | | | | | | X |
| 358 | | | | | | | | | | | | | X |
| 359 | | | | | | | | | | | | X | X |
| 360 | | | | | | | | | | | | | X |
| 361 | | | | | | | | | | | | X | X |
| 362 | | | | | | | | | | | | X | X |
| 363 | | | | | | | | | | | | | X |
| 364 | | | | | | | | | | | | | |
| 365 | | | | | | | | | | | | X | X |
| 366 | | | | | | | | | | | | | |
| 367 | | | | | | | | | | | | X | X |
| 368 | | | | | | | | | | | | | |
| 369 | | | | | | | | | | | | | |
| 370 | | | | | | | | | | | | | |
| 371 | | | | | | | | | | | | | |
| 372 | | | | | | | | | | | | | |
| 373 | | | | | | | | | | | | | |
| 374 | | | | | | | | | | | | | |
| 375 | | | | | | | | | | | | | |
| 376 | | | | | | | | | | | | | |
| 377 | | | | | | | | | | | | | |

| | R1 | | | | | | | |
|---|---|---|---|---|---|---|---|---|
| R2 | 2 | 3 | 9 | 10 | 11 | 14 | 15 | 23 |
| 378 | | | | X | X | | | |
| 379 | | | | X | X | | | |
| 380 | | | X | X | | | | |
| 381 | | | | | | | | |
| 382 | | | | | | | | |
| 383 | | | | | | | | |
| 177 | X | | X | | X | X | X | X |

TABLE 3a-continued

| R2 | | | | | | | | |
|---|---|---|---|---|---|---|---|---|
| 178 | X | | X | X | X | X | X | X |
| 179 | X | | X | X | X | X | X | X |
| 264 | | | | | | | | |
| 189 | X | | X | X | X | X | X | X |
| 198 | X | | X | X | X | X | X | X |
| 200 | X | | X | | | X | | X |
| 202 | X | | X | X | X | X | | X |
| 217 | X | | X | X | X | X | X | X |
| 218 | X | | X | X | X | X | X | X |
| 219 | X | | X | X | X | X | X | X |
| 223 | X | | X | X | X | X | X | X |
| 224 | X | | X | X | X | X | X | X |
| 225 | X | | X | X | X | X | X | X |
| 226 | X | | X | X | X | X | X | X |
| 227 | X | | X | X | X | X | X | X |
| 230 | X | | X | X | X | X | X | X |
| 242 | X | | X | X | X | X | X | X |
| 245 | X | | X | X | X | X | X | X |
| 248 | X | | X | X | X | X | X | X |
| 251 | X | | X | X | X | X | X | X |
| 258 | X | | X | X | X | X | X | X |
| 260 | X | | X | X | X | X | X | X |
| 329 | | | | | | | | |
| 263 | | | | | | | | |
| 236 | X | | X | X | X | X | | X |

| | | | | | | R1 | | | | | | | | |
|---|---|---|---|---|---|---|---|---|---|---|---|---|---|---|
| R2 | 20 | 22 | 27 | 38 | 39 | 40 | 41 | 42 | 31 | 32 | 34 | 35 | 36 | 37 |
| 378 | | | | | X | | | | X | | X | X | | |
| 379 | | | | | X | | | | X | | X | X | | |
| 380 | | | | | | | | | X | | | X | | |
| 381 | | | | | | | | | X | | | X | | |
| 382 | | | | | | | | | | | | X | | |
| 383 | | | | | | | | | X | | | X | X | |
| 177 | X | | | | X | X | X | X | X | X | | X | X | |
| 178 | X | X | | | | | X | | X | X | X | | X | X |
| 179 | X | X | | | | | X | | X | X | X | | | X |
| 264 | | | X | X | X | X | | X | X | X | X | X | X | X |
| 189 | | X | | | X | X | X | X | X | X | X | | X | X |
| 198 | | X | | | X | X | X | X | X | X | X | | X | X |
| 200 | | X | | | X | X | X | X | X | X | X | | X | X |
| 202 | | X | | | X | X | X | X | X | X | X | | X | X |
| 217 | | X | | | X | X | X | X | X | X | X | | X | X |
| 218 | | X | | | X | X | X | X | X | X | X | | X | X |
| 219 | | X | | | X | X | X | X | X | X | X | | X | X |
| 223 | | X | | | X | X | X | X | X | X | X | | X | X |
| 224 | | X | | | X | X | X | X | X | X | X | | X | X |
| 225 | | X | | | X | X | X | X | X | X | X | | X | X |
| 226 | | X | | | X | X | X | X | X | X | X | | X | X |
| 227 | | X | | | X | X | X | X | X | X | X | | X | X |
| 230 | | X | | | X | X | X | X | X | X | X | | X | X |
| 242 | | X | | | X | X | X | X | X | X | X | | X | X |
| 245 | | X | | | X | X | X | X | X | X | X | | X | X |
| 248 | | X | | | X | X | X | X | X | X | X | | X | X |
| 251 | | X | | | X | X | X | X | X | X | X | | X | X |
| 258 | | X | | | X | X | X | X | X | X | X | | X | X |
| 260 | | X | | | X | X | X | X | X | X | X | | X | X |
| 329 | | | X | X | X | X | X | X | X | X | X | X | X | X |
| 263 | | X | | | | | | | | | | | | |
| 236 | | | | X | X | X | X | X | X | | | | X | X |

| | | | | R1 | | | | |
|---|---|---|---|---|---|---|---|---|
| R2 | 30 | 44 | 45 | 47 | 49 | 50 | 51 | 52 |
| 378 | | | | | | | | |
| 379 | | | | | | | | |
| 380 | | | | | | | | |
| 381 | | | | | | | | |
| 382 | | | | | | | | |
| 383 | | | | | | | | |
| 177 | | | | | | | | |
| 178 | | | | | | | | |
| 179 | | | | | | | | |
| 264 | X | | | | | | | |
| 189 | | | X | X | X | | X | |
| 198 | | | X | X | X | X | X | X |

TABLE 3a-continued

| R2 | | | | | | | | |
|---|---|---|---|---|---|---|---|---|
| 200 | | X | X | X | X | X | X | X |
| 202 | | X | X | X | X | X | X | X |
| 217 | | X | X | X | | | | X |
| 218 | | X | X | X | | | | X |
| 219 | | X | X | X | | | | X |
| 223 | | X | X | X | | | | X |
| 224 | | X | X | X | | | | X |
| 225 | | X | X | X | X | X | | X |
| 226 | | X | X | X | X | X | X | X |
| 227 | | X | X | X | | X | X | X |
| 230 | | X | X | X | X | X | X | X |
| 242 | | X | X | X | X | X | X | X |
| 245 | | X | X | X | X | X | X | X |
| 248 | | X | X | X | X | X | | X |
| 251 | | X | X | X | X | X | X | X |
| 258 | | X | X | X | X | X | X | X |
| 260 | | X | X | X | X | X | X | X |
| 329 | X | | X | X | X | X | X | X |
| 263 | | X | X | X | X | X | X | X |
| 236 | | X | | X | | X | | |

| | | | | | R1 | | | | | | |
|---|---|---|---|---|---|---|---|---|---|---|---|
| R2 | 7 | 8 | 13 | 17 | 19 | 21 | 25 | 33 | 43 | 26 | 28 | 29 |
| 378 | | | | | | | | | | | | |
| 379 | | | | | | | | | | | | |
| 380 | | | | | | | | | | | | |
| 381 | | | | | | | | | | | | |
| 382 | | | | | | | | | | | | |
| 383 | | | | | | | | | | | | |
| 177 | | | X | | X | | X | X | X | | | |
| 178 | X | | X | | X | X | X | X | X | | X | |
| 179 | X | | X | | X | X | X | X | | | X | |
| 264 | | | | | | | | | | | | |
| 189 | X | | X | | X | X | X | X | X | | X | |
| 198 | X | | X | | X | X | X | X | X | | X | |
| 200 | | | | | | X | | X | | | | |
| 202 | X | | X | | X | X | | X | X | | X | |
| 217 | X | | X | | X | X | | X | X | | X | |
| 218 | X | | X | | X | X | | | X | | X | |
| 219 | X | | X | | X | | | | X | | X | |
| 223 | X | | | | X | X | | X | | | X | |
| 224 | X | | X | | X | X | | X | | | X | |
| 225 | X | | X | | X | X | | X | | | X | |
| 226 | X | | X | | X | X | | X | | | X | |
| 227 | X | | | | X | X | | X | | | X | |
| 230 | X | | X | | X | X | | X | | | X | |
| 242 | X | | X | | X | X | | X | | | X | |
| 245 | X | | X | | X | X | | X | | | X | |
| 248 | X | | X | | X | X | | X | | | X | |
| 251 | X | | X | | X | X | | X | | | X | |
| 258 | X | | X | | X | X | | X | | | X | |
| 260 | X | | X | | X | X | | X | | | X | |
| 329 | | | | | | | | | | | | |
| 263 | | | | | | | | | | | | |
| 236 | | X | | X | | X | X | | | | X | |

| | | | | | R1 | | | | | | |
|---|---|---|---|---|---|---|---|---|---|---|---|
| R2 | 2 | 9 | 10 | 11 | 14 | 15 | 23 | 22 | 39 | 40 | 41 | 42 |
| 180 | X | X | X | | X | X | X | X | X | X | X | X |
| 181 | X | X | X | X | X | X | X | X | X | X | X | X |
| 182 | X | X | X | | X | | | X | X | X | X | X |
| 183 | X | X | X | X | X | X | X | X | X | X | X | X |
| 184 | X | X | X | | X | X | | X | X | X | X | X |
| 185 | X | X | X | | | X | X | | | | | |
| 186 | X | X | | | X | | X | | | X | X | X |
| 187 | X | X | X | X | X | X | X | X | X | X | X | X |
| 188 | X | X | X | | X | X | X | X | X | X | X | X |
| 190 | X | X | | X | X | X | X | X | X | X | X | X |
| 191 | X | X | | | X | X | X | X | X | X | X | X |
| 192 | X | X | X | X | X | X | X | X | X | X | X | X |
| 193 | X | X | X | | X | X | X | X | X | X | X | X |
| 194 | X | X | X | X | X | X | X | X | X | X | X | X |
| 195 | X | X | X | X | X | X | X | X | X | X | X | X |
| 196 | X | X | X | X | X | X | X | X | X | X | X | X |
| 197 | X | X | X | X | X | X | X | X | X | X | X | X |

TABLE 3a-continued

| R2 | | | | | | | | | | | | |
|---|---|---|---|---|---|---|---|---|---|---|---|---|
| 199 | X | X | X | X | X | X | X | X | X | X | X | X |
| 201 | X | X | X | X | X | | X | X | | | X | |
| 203 | X | X | X | X | X | X | X | X | X | | X | |
| 204 | X | X | X | X | X | X | X | X | X | X | X | X |
| 205 | X | X | X | X | X | X | X | X | X | X | X | X |
| 206 | X | X | X | X | X | | X | X | | X | X | X |
| 207 | X | X | X | X | X | X | X | X | | X | X | X |
| 208 | X | X | X | X | X | X | X | X | X | X | X | X |
| 209 | X | X | X | X | X | | X | X | | | X | |
| 210 | X | X | X | X | X | X | X | X | | | X | |
| 211 | X | X | X | X | X | X | X | X | X | X | X | X |

| | R1 | | | | | | | | | | | | |
|---|---|---|---|---|---|---|---|---|---|---|---|---|---|
| R2 | 31 | 32 | 34 | 36 | 37 | 7 | 13 | 19 | 21 | 25 | 33 | 43 | 26 |
| 180 | X | X | X | X | X | | X | X | X | | X | X | X |
| 181 | X | X | X | X | X | X | X | X | X | | X | X | |
| 182 | | X | X | X | X | X | X | | | | X | X | X |
| 183 | X | X | X | X | X | X | X | X | X | X | | X | X |
| 184 | X | X | X | | | X | X | X | X | | X | X | |
| 185 | | | | | | | X | | X | | | | |
| 186 | X | X | X | | | | | | | | X | | |
| 187 | X | X | X | X | X | X | X | X | X | | X | X | X |
| 188 | X | X | X | X | X | X | X | X | X | X | | X | X |
| 190 | X | X | X | X | X | | X | | | | X | X | X |
| 191 | X | X | X | X | X | X | X | X | X | X | X | X | X |
| 192 | X | X | X | X | X | X | X | X | X | X | X | X | |
| 193 | X | X | X | X | X | X | X | X | X | X | X | X | X |
| 194 | X | X | X | X | X | X | X | X | X | X | X | X | X |
| 195 | X | X | X | X | X | X | X | X | X | X | X | X | |
| 196 | X | X | X | X | X | X | X | X | X | X | | X | |
| 197 | X | X | X | X | X | X | X | X | X | X | X | | X |
| 199 | X | X | X | X | X | X | X | X | X | X | X | X | X |
| 201 | X | X | X | X | X | X | X | X | X | X | X | X | X |
| 203 | X | X | X | X | X | X | X | X | X | X | X | | X |
| 204 | X | X | X | X | X | X | X | X | X | X | X | X | X |
| 205 | X | X | X | X | X | X | X | X | X | X | X | X | |
| 206 | X | X | X | X | X | X | X | X | X | X | | X | X |
| 207 | X | X | X | X | X | X | X | X | X | | | X | X |
| 208 | X | X | X | X | X | X | X | X | X | X | | X | X |
| 209 | X | X | X | | | X | X | X | X | X | | X | |
| 210 | X | X | X | X | X | X | | X | X | X | X | | X |
| 211 | X | X | X | X | X | X | X | X | X | X | X | X | X |

| | R1 | | | | | | | | | | | |
|---|---|---|---|---|---|---|---|---|---|---|---|---|
| R2 | 2 | 9 | 10 | 11 | 14 | 15 | 23 | 22 | 39 | 40 | 41 | 42 |
| 212 | X | X | X | X | X | X | X | X | X | X | X | X |
| 213 | X | X | X | X | X | | X | X | | | X | |
| 214 | X | X | X | X | X | X | X | X | X | | X | X |
| 215 | X | X | | | X | X | X | | | | | |
| 216 | X | X | X | X | X | X | X | X | X | X | X | X |
| 220 | X | X | X | X | X | X | X | X | X | X | X | X |
| 221 | X | X | X | X | X | X | X | X | X | X | X | X |
| 222 | X | X | | | X | | X | X | | X | X | X |
| 228 | X | X | X | X | X | X | X | X | X | X | X | X |
| 229 | X | X | X | X | X | X | X | X | X | X | X | X |
| 231 | X | X | X | X | X | X | X | | X | X | X | X |
| 232 | X | X | X | X | X | X | X | X | X | X | X | X |
| 233 | X | X | X | X | X | X | X | X | X | X | X | X |
| 234 | X | X | X | X | X | X | X | X | | X | X | X |
| 235 | X | X | X | X | X | X | X | | X | X | X | X |
| 237 | X | X | X | X | X | X | X | | | | X | |
| 238 | X | X | X | X | X | X | X | X | X | X | X | X |
| 239 | X | X | X | X | X | X | X | | X | X | X | X |
| 240 | X | X | X | X | X | X | X | X | X | X | X | X |
| 241 | X | X | X | X | X | X | X | X | X | X | X | X |
| 243 | X | X | X | X | X | X | X | X | X | X | X | X |
| 244 | X | X | X | X | X | X | X | X | X | X | X | X |
| 246 | X | X | X | X | X | X | X | X | | X | X | |
| 247 | X | X | X | X | X | X | X | X | X | X | X | X |
| 249 | X | X | X | X | X | X | X | X | X | X | X | X |
| 250 | X | X | X | X | X | X | X | X | X | X | X | X |
| 252 | X | X | X | X | X | X | X | X | X | X | X | X |
| 253 | X | X | X | X | X | X | X | | | | X | |
| 254 | X | X | X | X | X | X | X | X | X | X | X | X |
| 255 | X | X | X | X | X | X | X | X | X | X | X | X |
| 256 | X | X | X | X | X | X | X | X | X | X | X | X |
| 257 | X | X | X | X | X | X | X | X | X | X | X | X |
| 259 | X | X | X | X | X | X | X | X | X | | X | |
| 261 | X | X | X | X | X | X | X | X | X | X | X | X |
| 262 | X | X | X | X | X | X | X | X | X | X | X | X |

| | R1 | | | | | | | | | | | | |
|---|---|---|---|---|---|---|---|---|---|---|---|---|---|
| R2 | 31 | 32 | 34 | 36 | 37 | 7 | 13 | 19 | 21 | 25 | 33 | 43 | 26 |
| 212 | X | X | X | | | X | X | X | X | X | X | X | X |
| 213 | | | | | X | X | X | X | X | X | X | X | X |
| 214 | X | X | X | X | | X | X | X | X | X | X | X | X |
| 215 | | | | | | | | | | | | | X |
| 216 | X | X | X | X | | X | X | X | X | X | X | X | X |
| 220 | X | X | X | X | X | X | X | | X | X | X | | X |
| 221 | X | X | X | X | X | X | X | | X | X | X | X | X |
| 222 | X | X | X | X | | | | X | X | X | | X | X |
| 228 | X | X | X | X | X | X | X | X | X | X | X | X | X |
| 229 | | | | | | X | X | X | X | | | | X |
| 231 | | X | X | X | X | X | X | X | | X | | X | X |
| 232 | X | X | X | X | X | X | X | X | | X | | X | X |
| 233 | X | X | X | X | X | X | X | X | | X | X | X | X |
| 234 | | X | X | X | X | X | X | X | X | X | | X | X |
| 235 | | X | X | X | X | X | X | X | X | X | X | | X |
| 237 | X | X | X | X | X | X | X | X | X | X | X | X | X |
| 238 | | X | X | X | X | X | X | X | X | X | X | X | X |
| 239 | X | X | X | X | X | X | X | X | X | X | X | | X |
| 240 | | X | X | X | X | X | X | X | X | X | | X | X |
| 241 | X | X | X | | X | X | X | X | X | X | X | | X |
| 243 | X | X | X | X | X | X | X | X | X | X | | X | X |
| 244 | X | X | X | X | X | X | X | X | X | X | | X | X |
| 246 | X | X | X | X | | X | X | X | X | X | X | X | X |
| 247 | X | X | X | | | X | X | X | X | X | | X | X |
| 249 | X | X | X | X | X | X | X | X | X | X | | | X |
| 250 | X | X | X | X | X | X | X | X | X | X | | X | X |
| 252 | X | X | X | X | X | X | X | X | X | X | | X | X |
| 253 | X | X | X | | | X | X | X | X | X | | X | X |
| 254 | X | X | X | X | X | X | X | X | X | X | X | X | X |
| 255 | X | X | X | X | X | X | X | X | X | X | X | X | X |
| 256 | X | X | X | X | X | X | X | X | X | X | X | X | X |
| 257 | X | X | X | X | X | X | X | X | X | X | X | X | X |
| 259 | X | X | X | X | X | X | X | X | X | X | | X | X |
| 261 | X | X | X | X | X | X | X | X | X | X | X | X | X |
| 262 | X | X | X | X | X | X | X | X | X | X | | X | X |

| | R1 | | | | | | | | |
|---|---|---|---|---|---|---|---|---|---|
| R2 | 2 | 3 | 9 | 10 | 11 | 14 | 15 | 23 | 22 |
| 265 | | | | | | | | | |
| 266 | X | X | X | X | X | X | X | X | |
| 267 | X | X | X | X | X | X | X | X | X |
| 268 | X | X | X | X | X | X | X | X | X |
| 269 | X | X | X | X | | X | X | X | X |
| 270 | X | X | X | X | X | | X | X | X |
| 271 | X | X | X | | | | | X | X |
| 272 | X | X | X | X | | | | X | X |
| 273 | X | X | X | X | X | X | | | X |
| 274 | | X | | | | | | | X |
| 275 | X | X | X | X | X | | X | X | X |
| 276 | X | X | X | X | X | X | X | | X |
| 277 | X | X | X | X | X | X | X | X | X |
| 278 | X | X | X | X | X | X | X | X | X |
| 279 | X | X | X | X | X | X | X | X | X |
| 280 | X | X | X | X | X | | X | | X |
| 281 | X | X | X | X | | | | X | X |
| 282 | X | X | X | X | X | X | X | X | X |
| 283 | X | X | X | X | X | X | | X | X |
| 284 | X | X | X | X | X | X | | X | X |
| 285 | X | X | X | X | X | X | | X | X |
| 286 | X | | X | | X | | | | X |
| 287 | X | | | | | | | X | X |
| 288 | X | X | X | X | X | | | X | X |
| 289 | X | X | X | X | | | | X | X |
| 290 | X | X | X | X | | | | X | X |
| 291 | X | | | | | | | | X |
| 292 | X | X | X | X | X | | | X | X |
| 293 | X | X | X | X | X | | | X | X |

TABLE 3a-continued

| | | | | | | | | | |
|---|---|---|---|---|---|---|---|---|---|
| 294 | X | X | X | | X | | | X | X |
| 295 | X | X | X | X | X | X | X | X | X |
| 296 | X | X | X | X | X | X | | X | X |
| 297 | X | X | X | X | X | X | X | X | X |
| 298 | X | X | X | X | X | | | X | X |
| 299 | X | X | | | | | | X | X |
| 300 | X | X | X | X | X | X | | | X |
| 301 | X | X | X | X | X | X | | X | X |

| | R1 | | | | | | | | | | | |
|---|---|---|---|---|---|---|---|---|---|---|---|---|
| R2 | 38 | 39 | 40 | 41 | 42 | 31 | 32 | 34 | 35 | 36 | 37 | 30 |
| 265 | | | | | | | | | | | | |
| 266 | X | X | X | X | X | | | X | X | | | X |
| 267 | X | X | X | X | X | X | X | X | X | X | X | X |
| 268 | X | X | X | X | X | X | X | X | X | X | X | X |
| 269 | X | X | X | X | X | | X | X | X | X | X | X |
| 270 | X | X | X | X | | X | X | X | X | X | X | X |
| 271 | X | | | X | X | | X | X | X | X | X | X |
| 272 | X | X | | X | X | X | X | X | | X | X | X |
| 273 | X | | X | X | X | X | X | X | X | X | X | X |
| 274 | | | | | | X | | | | | | X |
| 275 | | X | X | X | X | X | X | X | X | X | X | X |
| 276 | X | X | X | X | X | X | X | X | X | X | X | X |
| 277 | | X | X | X | X | X | X | X | | | | |
| 278 | | X | X | X | X | X | X | X | X | | X | X |
| 279 | X | X | X | X | X | X | X | X | X | X | X | X |
| 280 | | X | X | X | X | X | X | X | X | | | X |
| 281 | X | X | X | X | X | X | X | X | X | X | X | X |
| 282 | X | X | X | X | X | X | X | X | X | X | X | X |
| 283 | X | | X | X | X | X | X | X | X | X | X | X |
| 284 | X | X | X | X | X | X | X | X | X | X | X | X |
| 285 | X | X | | X | X | | X | | X | X | X | X |
| 286 | | | | X | | X | X | | X | X | | |
| 287 | X | | X | X | X | | | X | X | | | |
| 288 | X | X | X | X | X | | X | X | X | X | X | X |
| 289 | X | X | X | X | X | X | X | X | X | X | X | X |
| 290 | X | X | X | | X | X | X | X | | X | | X |
| 291 | X | X | X | | X | X | X | X | X | X | | X |
| 292 | X | X | X | X | X | X | X | X | X | X | | X |
| 293 | X | X | X | X | | X | X | X | X | X | X | X |
| 294 | X | X | X | X | | X | X | X | X | X | X | X |
| 295 | X | X | X | | X | X | X | X | | X | X | X |
| 296 | X | X | X | X | X | X | X | X | X | | | |
| 297 | X | X | X | X | X | X | X | X | X | X | | |
| 298 | X | X | X | X | X | X | X | X | X | X | | X |
| 299 | | | X | X | | X | | | | | | |
| 300 | X | X | X | X | | X | X | | X | X | X | X |
| 301 | X | X | X | X | | X | X | X | X | X | X | |

| | R1 | | | | | | | | | | |
|---|---|---|---|---|---|---|---|---|---|---|---|
| R2 | 7 | 8 | 13 | 17 | 19 | 21 | 25 | 33 | 43 | 28 | 29 |
| 265 | | | | | | | | | | | |
| 266 | | X | X | X | | X | | | | X | |
| 267 | X | X | X | X | X | X | X | | | X | X |
| 268 | X | X | X | X | X | X | X | X | | X | X |
| 269 | X | X | X | | X | X | | X | | X | X |
| 270 | X | X | X | | X | X | X | X | | X | X |
| 271 | X | X | X | X | X | X | X | | | | |
| 272 | X | X | | X | X | X | X | X | | | |
| 273 | | X | X | | X | X | X | X | | X | X |
| 274 | | X | | | X | | | | | | |
| 275 | X | | X | | X | X | X | X | | X | |
| 276 | | X | X | | X | X | X | X | | X | X |
| 277 | | | X | | X | X | X | X | | X | X |
| 278 | | X | X | | X | X | X | X | | X | X |
| 279 | | X | X | | X | X | X | X | | X | X |
| 280 | X | X | X | X | X | X | X | X | | | |
| 281 | X | X | X | | X | X | X | X | | | |
| 282 | X | X | X | X | X | X | X | X | | X | X |
| 283 | X | X | X | X | X | X | X | X | | | |
| 284 | X | X | X | X | X | X | X | | X | | |
| 285 | X | X | X | X | X | X | | | | | |
| 286 | X | X | X | | X | X | X | X | | | |
| 287 | | X | | | X | X | | X | | | |
| 288 | X | X | X | X | X | | X | | | | |

TABLE 3a-continued

| | | | | | | | | | |
|---|---|---|---|---|---|---|---|---|---|
| 289 | X | X | X | X | X | X | X | | |
| 290 | X | X | X | X | X | X | X | | |
| 291 | X | | X | X | X | | | X | |
| 292 | X | X | X | X | X | | X | X | |
| 293 | X | X | X | X | X | | X | X | |
| 294 | X | X | X | X | X | | X | X | |
| 295 | X | X | X | X | X | X | X | X | |
| 296 | X | X | X | X | X | X | X | | X |
| 297 | X | X | X | X | X | X | X | X | X |
| 298 | X | X | X | X | X | X | X | X | |
| 299 | X | | X | | X | | X | | |
| 300 | X | | X | | X | X | X | | |
| 301 | | X | X | | X | X | X | | X |

| | R1 | | | | | | | | |
|---|---|---|---|---|---|---|---|---|---|
| R2 | 2 | 3 | 9 | 10 | 11 | 14 | 15 | 23 | 22 |
| 302 | X | X | X | | | | | X | |
| 303 | | | | | X | | | X | |
| 304 | X | | | X | X | X | X | X | X |
| 305 | X | X | X | | | | | | X |
| 306 | X | X | | X | X | | | X | X |
| 307 | X | | X | X | X | | | | X |
| 308 | X | X | X | | | | | | X |
| 309 | X | | | X | | X | | X | X |
| 310 | X | X | X | X | X | X | X | X | X |
| 311 | X | X | X | X | X | | | X | |
| 312 | X | X | X | | | | | X | |
| 313 | X | | | | X | | | X | |
| 314 | | X | X | | | | | | |
| 315 | | | | | | | | | |
| 316 | X | X | X | | X | | X | X | X |
| 317 | X | | | X | X | X | | X | |
| 318 | X | X | X | X | | | | X | X |
| 319 | X | X | X | X | | | | X | X |
| 320 | X | X | X | X | X | | | X | X |
| 321 | X | X | X | X | X | X | X | X | X |
| 322 | X | X | X | X | X | X | X | X | X |
| 323 | X | X | X | X | | X | X | X | X |
| 324 | X | X | X | | | X | | X | |
| 325 | | | | | X | | | X | |
| 326 | X | | | | | X | | X | X |
| 327 | | X | X | | X | | | | |
| 328 | | | | | | | | | X |
| 330 | | | | | | | | | |
| 331 | | | | | | | | | X |
| 332 | | | | | | | | | |
| 333 | | | | | | | | | X |
| 334 | | X | X | X | X | | | | |

| | R1 | | | | | | | | | | | |
|---|---|---|---|---|---|---|---|---|---|---|---|---|
| R2 | 38 | 39 | 40 | 41 | 42 | 31 | 32 | 34 | 35 | 36 | 37 | 30 |
| 302 | | | | X | X | | X | | | | | |
| 303 | | | | | | X | | | X | | | |
| 304 | X | X | X | X | X | X | X | X | X | X | X | X |
| 305 | | | X | X | X | X | X | | | X | X | X |
| 306 | X | X | | X | X | X | X | X | X | X | | X |
| 307 | X | | | X | X | X | X | | | X | X | |
| 308 | X | X | X | X | X | X | X | X | X | X | X | X |
| 309 | X | X | X | X | X | X | X | X | | X | X | X |
| 310 | X | X | X | X | X | X | X | X | X | X | X | X |
| 311 | X | X | X | X | X | X | | | | X | X | X |
| 312 | X | X | X | | | X | X | | X | X | X | X |
| 313 | X | X | | | X | | | X | | X | X | X |
| 314 | | X | X | X | | | X | X | | X | X | X |
| 315 | | | | | | | | | | | | |
| 316 | X | X | X | X | X | X | X | X | X | X | X | X |
| 317 | X | X | X | X | | X | | X | X | X | | X |
| 318 | X | | | X | | X | | | X | X | | X |
| 319 | X | | X | | X | X | X | X | X | X | X | X |
| 320 | X | | X | | X | X | X | X | X | X | X | X |
| 321 | X | X | X | X | X | X | X | X | X | X | X | X |
| 322 | X | X | X | X | X | X | X | X | X | X | X | X |
| 323 | X | | X | X | X | X | X | X | X | X | X | X |
| 324 | | X | | | | | | | | | | |
| 325 | | | | | | | | | | | | |

TABLE 3a-continued

|     | | | | | | | | | | |
| --- | --- | --- | --- | --- | --- | --- | --- | --- | --- | --- |
| 326 | | | | | | | X | | X | X |
| 327 | | | | | | X | X | | X | X |
| 328 | | | X | | | X | | | | X |
| 330 | X | X | X | | X | X | X | X | X | X |
| 331 | | X | | X | | X | X | | X | X |
| 332 | | X | | X | | X | X | | X | X |
| 333 | | X | | X | | X | X | | X | X |
| 334 | | X | X | | X | X | | X | | X |

|    | R1 | | | | | | | | | |
| -- | -- | -- | -- | -- | -- | -- | -- | -- | -- | -- |
| R2 | 7 | 8 | 13 | 17 | 19 | 21 | 25 | 33 | 43 | 28 | 29 |
| 302 | | X | | | X | X | | X | | | |
| 303 | | | | X | | | | | | | |
| 304 | X | X | X | | X | X | X | X | | | |
| 305 | | X | | | X | X | X | X | | | |
| 306 | X | X | X | X | X | X | X | | | | |
| 307 | | X | | | X | X | X | | | | |
| 308 | | X | | X | X | X | X | X | | | |
| 309 | X | X | X | X | X | | X | | | X | |
| 310 | X | X | X | X | | | X | X | | X | |
| 311 | X | X | | | X | X | X | | | | |
| 312 | X | | | | X | X | | | | | |
| 313 | X | X | | | X | | X | X | | | |
| 314 | X | | | | | X | | | | | |
| 315 | X | | | | | | | | | | |
| 316 | X | X | X | | X | | X | X | | | X |
| 317 | X | X | X | X | X | | | | | X | X |
| 318 | | X | | X | X | X | X | | | | |
| 319 | X | | X | X | X | | X | | | | |
| 320 | X | X | X | X | X | | X | X | | | |
| 321 | X | X | X | X | X | X | X | X | | X | X |
| 322 | X | X | X | | X | X | X | X | | X | X |
| 323 | X | X | X | | X | X | X | X | | X | |
| 324 | X | | X | | | | | X | | | X |
| 325 | X | | X | | | | | | | | |
| 326 | X | X | X | X | | | X | | | | |
| 327 | | X | X | X | X | X | | X | | | |
| 328 | | | | | | | | X | X | | |
| 330 | | | | | | | | | | | |
| 331 | | | | | | | | X | X | | |
| 332 | | | | | | | | X | X | | |
| 333 | | | | | | | | X | X | | |
| 334 | | | | | | | | | | | X |

|    | R1 | | | | |
| -- | -- | -- | -- | -- | -- |
| R2 | 9 | 10 | 11 | 14 | 39 |
| 335 | | | | | X |
| 336 | | X | | X | |
| 337 | X | | X | X | X |
| 338 | X | X | X | X | X |
| 339 | X | X | X | X | X |
| 340 | X | X | | X | X |
| 341 | X | X | X | X | X |
| 342 | X | X | X | X | X |
| 343 | | | | | |
| 344 | | X | | X | X |
| 345 | X | | | | X |
| 346 | | X | X | X | X |
| 347 | X | X | X | X | X |
| 348 | X | X | X | X | X |
| 349 | | X | | | X |
| 350 | | X | X | X | X |
| 351 | | X | X | X | X |
| 352 | X | X | | X | X |
| 353 | | | | | |
| 354 | | | | | |
| 355 | X | X | | X | X |
| 356 | X | X | X | X | X |
| 357 | | X | | | |
| 358 | X | | | | X |

|    | R1 | | | | | | |
| -- | -- | -- | -- | -- | -- | -- | -- |
| R2 | 40 | 42 | 31 | 34 | 35 | 30 | 29 |
| 335 | X | | X | | | X | |
| 336 | X | X | X | | | X | |
| 337 | X | X | X | | | X | |
| 338 | X | X | X | | | X | |
| 339 | X | X | X | X | | X | |
| 340 | X | X | X | X | X | X | X |
| 341 | | X | X | X | | X | |
| 342 | X | X | X | X | | X | X |
| 343 | X | X | X | | X | X | |
| 344 | X | | X | X | X | | |
| 345 | X | X | X | X | X | X | |
| 346 | X | X | X | X | X | X | |
| 347 | X | X | X | X | X | X | |
| 348 | | X | X | | | X | |
| 349 | X | | X | X | X | X | |
| 350 | X | X | X | X | | X | |
| 351 | X | X | X | X | | X | X |
| 352 | X | X | X | X | X | X | X |
| 353 | X | | | | | X | |
| 354 | X | X | | | | | |
| 355 | X | X | X | | X | X | X |
| 356 | X | X | X | X | | X | |
| 357 | | X | | | | X | |
| 358 | X | X | X | | | X | |

|    | R1 | | | | |
| -- | -- | -- | -- | -- | -- |
| R2 | 9 | 10 | 11 | 14 | 39 |
| 359 | X | X | X | X | X |
| 360 | X | X | | X | |
| 361 | | X | X | X | X |
| 362 | X | X | X | X | X |
| 363 | | | | | X |
| 364 | X | | | | |
| 365 | X | X | X | X | |
| 366 | X | X | | | |
| 367 | | X | X | X | |
| 368 | | | | | |
| 369 | X | X | X | | X |
| 370 | X | X | X | | X |
| 371 | X | X | X | | X |
| 372 | X | | | | X |
| 373 | X | X | X | | X |
| 374 | X | | | | X |
| 375 | X | X | | X | X |
| 376 | X | | | X | X |
| 377 | X | | | | X |
| 378 | | X | | X | X |
| 379 | | X | | X | X |
| 380 | | X | X | | |
| 381 | | | | | |
| 382 | | | | | |
| 383 | | | | | |

|    | R1 | | | | | | |
| -- | -- | -- | -- | -- | -- | -- | -- |
| R2 | 40 | 42 | 31 | 34 | 35 | 30 | 29 |
| 359 | X | X | X | X | X | X | X |
| 360 | | X | | | | X | |
| 361 | X | X | X | X | | X | X |
| 362 | X | | X | X | | X | X |
| 363 | | X | | | | X | |
| 364 | | | | | | | |
| 365 | | | | X | | X | X |
| 366 | | | | X | | | |
| 367 | | | | X | | X | X |
| 368 | X | | | | | | |
| 369 | | | X | X | X | | |
| 370 | | | X | X | X | | |
| 371 | | | X | X | X | | |
| 372 | | | X | X | X | | |
| 373 | | | X | X | X | | |
| 374 | | | X | X | X | | |

TABLE 3a-continued

| R2  |   |   |   |   |
|-----|---|---|---|---|
| 375 |   | X | X | X |
| 376 |   |   |   | X |
| 377 |   | X | X | X |
| 378 |   | X | X | X |
| 379 |   | X | X |   |
| 380 |   | X |   | X |
| 381 |   | X |   | X |
| 382 |   |   |   | X |
| 383 |   | X | X | X |

|     | R1 |   |    |    |    |    |    |    |
|-----|----|---|----|----|----|----|----|----|
| R2  | 2  | 9 | 10 | 11 | 14 | 15 | 23 | 20 |
| 177 | X  | X |    | X  | X  | X  | X  | X  |
| 178 | X  | X | X  | X  | X  | X  | X  | X  |
| 179 | X  | X | X  | X  | X  | X  | X  |    |
| 264 |    |   |    |    |    |    |    |    |
| 189 | X  | X | X  | X  | X  | X  | X  |    |
| 198 | X  | X | X  | X  | X  | X  | X  |    |
| 200 | X  | X |    |    |    | X  | X  |    |
| 202 | X  | X | X  | X  | X  |    | X  |    |
| 217 | X  | X | X  | X  | X  | X  | X  |    |
| 218 | X  | X | X  | X  | X  | X  | X  |    |
| 219 | X  | X | X  | X  | X  | X  | X  |    |
| 223 | X  | X | X  | X  | X  | X  | X  |    |
| 224 | X  | X | X  | X  | X  | X  | X  |    |
| 225 | X  | X | X  | X  | X  | X  | X  |    |
| 226 | X  | X | X  | X  | X  | X  | X  |    |
| 227 | X  | X | X  | X  | X  | X  | X  |    |
| 230 | X  | X | X  | X  | X  | X  | X  |    |
| 242 | X  | X | X  | X  | X  | X  | X  |    |
| 245 | X  | X | X  | X  | X  | X  | X  |    |
| 248 | X  | X | X  | X  | X  | X  | X  |    |
| 251 | X  | X | X  | X  | X  | X  | X  |    |
| 258 | X  | X | X  | X  | X  | X  | X  |    |
| 260 | X  | X | X  | X  | X  | X  | X  |    |
| 329 |    |   |    |    |    |    |    |    |
| 263 |    |   |    |    |    |    |    |    |
| 236 | X  | X | X  | X  | X  | X  | X  |    |

|     | R1 |    |    |    |    |    |    |    |    |    |    |    |    |
|-----|----|----|----|----|----|----|----|----|----|----|----|----|----|
| R2  | 22 | 27 | 38 | 39 | 40 | 41 | 42 | 31 | 32 | 34 | 35 | 36 | 37 | 30 |
| 177 | X  |    |    | X  | X  | X  |    | X  | X  | X  |    | X  | X  |    |
| 178 | X  |    |    |    |    | X  |    | X  | X  | X  |    | X  | X  |    |
| 179 | X  |    |    |    | X  |    |    | X  | X  | X  |    |    | X  |    |
| 264 |    | X  | X  | X  | X  |    | X  | X  | X  | X  | X  | X  | X  | X  |
| 189 | X  |    |    | X  | X  | X  | X  | X  | X  | X  |    | X  | X  |    |
| 198 | X  |    |    | X  | X  | X  | X  | X  | X  | X  |    | X  | X  |    |
| 200 | X  |    |    | X  | X  | X  | X  | X  | X  | X  |    | X  | X  |    |
| 202 | X  |    |    | X  | X  | X  | X  | X  | X  | X  |    | X  | X  |    |
| 217 | X  |    |    | X  | X  | X  | X  | X  | X  | X  |    | X  | X  |    |
| 218 | X  |    |    | X  | X  | X  | X  | X  | X  | X  |    | X  | X  |    |
| 219 | X  |    |    | X  | X  | X  | X  | X  | X  | X  |    | X  | X  |    |
| 223 | X  |    |    | X  | X  | X  | X  | X  | X  | X  |    | X  | X  |    |
| 224 | X  |    |    | X  | X  | X  | X  | X  | X  | X  |    | X  | X  |    |
| 225 | X  |    |    | X  | X  | X  | X  | X  | X  | X  |    | X  | X  |    |
| 226 | X  |    |    | X  | X  | X  | X  | X  | X  | X  |    | X  | X  |    |
| 227 | X  |    |    | X  | X  | X  | X  | X  | X  | X  |    | X  | X  |    |
| 230 | X  |    |    | X  | X  | X  | X  | X  | X  | X  |    | X  | X  |    |
| 242 | X  |    |    | X  | X  | X  | X  | X  | X  | X  |    | X  | X  |    |
| 245 | X  |    |    | X  | X  | X  | X  | X  | X  | X  |    | X  | X  |    |
| 248 | X  |    |    | X  | X  | X  | X  | X  | X  | X  |    | X  | X  |    |
| 251 | X  |    |    | X  | X  | X  | X  | X  | X  | X  |    | X  | X  |    |
| 258 | X  |    |    | X  | X  | X  | X  | X  | X  | X  |    | X  | X  |    |
| 260 | X  |    |    | X  | X  | X  | X  | X  | X  | X  |    | X  | X  |    |
| 329 |    |    | X  | X  | X  | X  | X  | X  | X  | X  | X  | X  | X  | X  |
| 263 |    | X  |    |    |    |    |    |    |    |    |    |    |    |    |
| 236 |    |    |    | X  | X  | X  | X  | X  | X  |    |    | X  | X  |    |

|     | R1 |    |    |    |    |    |    |
|-----|----|----|----|----|----|----|----|
| R2  | 44 | 45 | 47 | 49 | 50 | 51 | 52 |
| 177 |    |    |    |    |    |    |    |
| 178 |    |    |    |    |    |    |    |
| 179 |    |    |    |    |    |    |    |

TABLE 3a-continued

|     |   |   |   |   |   |   |   |
|-----|---|---|---|---|---|---|---|
| 264 |   |   |   |   |   |   |   |
| 189 | X | X | X |   |   | X |   |
| 198 | X | X | X | X | X | X | X |
| 200 | X | X | X | X | X | X | X |
| 202 | X | X | X | X |   | X | X |
| 217 | X | X | X |   |   | X |   |
| 218 | X | X | X |   |   | X |   |
| 219 | X | X | X |   |   | X |   |
| 223 | X | X | X |   |   | X |   |
| 224 | X | X | X |   |   | X |   |
| 225 | X | X | X | X | X | X | X |
| 226 | X | X | X | X | X | X | X |
| 227 | X | X | X |   | X | X | X |
| 230 | X | X | X | X | X | X | X |
| 242 | X | X | X | X |   | X | X |
| 245 | X | X | X |   |   | X | X |
| 248 | X | X | X |   | X | X | X |
| 251 | X | X | X | X | X | X | X |
| 258 | X | X | X | X | X | X | X |
| 260 |   | X | X | X | X | X | X |
| 329 | X | X | X | X | X | X | X |
| 263 | X | X | X | X | X | X | X |
| 236 | X |   | X |   |   | X |   |

|     | R1 |    |    |    |    |    |    |    |
|-----|----|----|----|----|----|----|----|----|
| R2  | 7  | 13 | 19 | 21 | 25 | 33 | 43 | 26 |
| 177 |    | X  | X  |    | X  | X  | X  |    |
| 178 | X  | X  | X  | X  | X  | X  | X  | X  |
| 179 | X  | X  | X  | X  | X  | X  |    | X  |
| 264 |    |    |    |    |    |    |    |    |
| 189 | X  | X  | X  | X  | X  | X  | X  | X  |
| 198 | X  | X  | X  | X  | X  | X  | X  | X  |
| 200 |    |    |    | X  |    | X  |    |    |
| 202 | X  | X  | X  | X  | X  |    |    | X  |
| 217 | X  | X  | X  | X  | X  | X  |    | X  |
| 218 | X  | X  | X  |    | X  | X  |    | X  |
| 219 | X  | X  | X  |    |    |    |    | X  |
| 223 | X  | X  | X  | X  | X  | X  |    | X  |
| 224 | X  | X  | X  | X  | X  | X  |    | X  |
| 225 | X  | X  | X  | X  | X  | X  |    | X  |
| 226 | X  | X  | X  | X  | X  | X  |    | X  |
| 227 | X  | X  | X  | X  | X  | X  |    | X  |
| 230 | X  | X  | X  | X  | X  | X  |    | X  |
| 242 | X  | X  | X  | X  | X  | X  |    | X  |
| 245 | X  | X  | X  | X  | X  | X  |    | X  |
| 248 | X  | X  | X  | X  | X  | X  |    | X  |
| 251 | X  | X  | X  | X  | X  | X  |    | X  |
| 258 | X  | X  | X  | X  | X  | X  |    | X  |
| 260 | X  | X  | X  | X  | X  | X  |    | X  |
| 329 |    |    |    |    |    |    |    |    |
| 263 |    |    |    |    |    |    |    |    |
| 236 |    | X  | X  | X  | X  |    |    | X  |

|     | R1 |    |    |    |    |    |    |    |
|-----|----|----|----|----|----|----|----|----|
| R2  | 22 | 44 | 45 | 47 | 49 | 50 | 51 | 52 |
| 384 |    | X  | X  | X  | X  | X  | X  | X  |
| 385 |    | X  | X  | X  | X  | X  | X  | X  |
| 386 |    | X  | X  | X  | X  | X  | X  | X  |
| 387 |    | X  | X  | X  | X  | X  | X  | X  |
| 388 |    | X  | X  | X  | X  | X  | X  | X  |
| 389 |    | X  | X  | X  | X  | X  | X  | X  |
| 390 |    | X  | X  | X  | X  | X  | X  | X  |
| 391 |    | X  | X  | X  | X  | X  | X  | X  |
| 392 |    | X  | X  | X  | X  | X  | X  | X  |
| 393 |    | X  | X  | X  | X  | X  | X  | X  |
| 394 |    | X  | X  | X  | X  | X  | X  | X  |
| 395 |    | X  | X  | X  | X  | X  | X  | X  |
| 396 |    | X  | X  | X  | X  | X  | X  | X  |
| 397 |    | X  | X  | X  | X  | X  | X  | X  |
| 398 |    | X  | X  | X  | X  | X  | X  | X  |
| 399 |    | X  | X  | X  | X  | X  | X  | X  |
| 400 |    | X  | X  | X  | X  | X  | X  | X  |
| 401 |    | X  | X  | X  | X  | X  | X  | X  |
| 402 |    | X  | X  | X  | X  | X  | X  | X  |
| 403 |    | X  | X  | X  | X  | X  | X  | X  |

TABLE 3a-continued

| | | | | | | | |
|---|---|---|---|---|---|---|---|
| 404 | X | X | X | X | X | X | X |
| 405 | X | X | X | X | X | X | X |
| 406 | X | X | X | X | X | X | X |
| 407 | X | X | X | X | X | X | X |
| 408 | X | X | X | X | X | X | X |
| 409 | X | X | X | X | X | X | X |
| 410 | X | X | X | X | X | X | X |
| 411 | X | X | X | X | X | X | X |
| 412 | X | X | X | X | X | X | X |
| 413 | X | X | X | X | X | X | X |
| 414 | X | X | X | X | X | X | X |
| 415 | X | X | X | X | X | X | X |
| 416 | X | X | X | X | X | X | X |
| 417 | X | X | X | X | X | X | X |
| 418 | X |   | X |   | X | X | X |
| 419 | X | X | X | X | X | X | X |
| 420 | X |   | X | X | X | X | X |
| 421 | X | X | X | X | X | X | X |
| 422 | X | X | X | X | X | X | X |
| 423 | X | X | X | X | X | X | X |
| 424 | X | X | X | X | X | X | X |
| 425 | X | X | X | X | X | X | X |
| 426 | X | X | X | X | X | X | X |
| 427 | X | X | X | X | X | X | X |
| 428 | X | X | X | X | X | X | X |
| 429 | X | X | X | X | X | X | X |
| 430 | X | X | X | X | X | X | X |
| 431 | X | X | X | X | X | X | X |
| 432 | X | X | X | X | X | X | X |
| 434 |   | X | X | X | X | X | X |
| 437 |   | X | X | X | X | X | X |
| 433 |   |   | X |   |   | X | X |
| 435 |   |   | X |   |   | X | X |
| 436 |   |   | X |   |   | X | X |
| 438 |   |   | X |   |   | X | X |

Table 3b

Table 3b is directed to compounds of the formula (IIIB):

$$\text{(IIIB)}$$

wherein $R^1$ and $R^2$ are as defined in Table 3b.

An "X" in the box formed by the intersection of the $R^2$ and the $R^1$ row represents an $R^2$ and the $R^1$ combination of a compound of formula IIIB that is excluded from the definitions of the compounds of formula I (and formula IIA). For example, compounds of formula IIIB wherein $R^2$ is moiety 3 (see Table 2 for definition) and $R^1$ is moiety 45 (see Table 1 for definition) are excluded from the definition of formula I (and formula IIA)(there is an "X" in the box formed by the intersection of the $R^2$ column and the $R^1$ row).

If there is no "X" in the box, then that compound is within the definition of the compounds of formula I (and formula IIA). For example, compounds of formula IIIB wherein moeity $R^2$ is 3 and moiety $R^1$ is 44 (no "X" in the box formed by the intersection of the $R^2$ column and the $R^1$ row) are within the definition of the compounds of formula I (and formula IIA).

TABLE 3b

| | R1 | | | | | | | | |
|---|---|---|---|---|---|---|---|---|---|
| R2 | 45 | 46 | 47 | 48 | 49 | 50 | 51 | 52 | 44 |
| 3 | X | X | X | X | X | X | X | X |   |
| 5 | X | X | X | X | X | X | X | X |   |
| 16 | X | X | X | X |   | X | X | X |   |
| 20 | X | X | X | X | X | X | X | X |   |
| 22 | X | X | X | X | X | X | X | X |   |
| 30 | X | X | X | X | X | X | X | X |   |
| 35 | X | X | X |   | X | X | X | X |   |
| 44 | X | X | X | X |   | X | X | X |   |
| 47 | X | X | X | X | X | X | X | X |   |
| 48 | X | X | X | X | X | X | X | X |   |
| 55 | X | X | X | X | X | X | X | X |   |
| 59 | X | X | X | X | X | X | X | X |   |
| 60 | X | X | X | X | X | X | X | X |   |
| 64 | X | X | X | X | X | X | X | X |   |
| 68 | X | X | X | X | X | X | X | X |   |
| 83 | X | X | X |   | X | X | X | X |   |
| 84 | X | X | X | X | X | X | X | X |   |
| 85 | X | X | X | X | X | X | X | X |   |
| 133 |   |   |   |   | X | X | X | X |   |
| 134 | X | X | X | X | X | X | X | X |   |
| 135 | X | X | X | X | X | X | X | X |   |
| 136 | X | X | X | X | X | X | X | X |   |
| 138 | X | X | X | X | X | X | X | X |   |
| 139 | X | X | X | X | X | X | X | X |   |
| 140 | X | X | X | X | X | X | X | X |   |
| 141 | X | X |   | X | X | X | X | X |   |
| 144 | X | X | X | X | X | X | X | X |   |
| 146 | X | X | X | X | X | X | X | X |   |
| 152 | X | X | X | X | X | X | X | X |   |
| 157 | X | X | X | X |   | X | X | X |   |
| 167 | X | X | X | X | X | X | X | X |   |
| 175 | X | X | X | X |   | X | X | X |   |
| 189 | X | X | X |   | X | X | X | X | X |
| 198 | X | X | X | X | X | X | X | X |   |
| 200 | X | X | X | X | X | X | X | X |   |
| 202 | X | X | X | X | X | X | X | X |   |
| 217 | X | X | X |   | X | X | X | X | X |
| 218 | X | X | X |   | X | X | X | X | X |
| 219 | X | X | X |   | X | X | X | X |   |
| 223 | X | X | X |   | X | X | X | X | X |
| 224 | X | X | X |   | X | X | X | X | X |
| 225 | X | X | X | X | X | X | X | X |   |
| 226 | X | X | X | X | X | X | X | X |   |
| 227 | X | X | X | X | X | X | X | X |   |
| 230 | X | X | X | X | X | X | X | X |   |
| 236 | X | X | X | X | X | X | X | X |   |
| 242 | X | X |   | X | X | X | X | X |   |
| 245 | X |   |   | X | X | X | X | X |   |
| 248 | X | X | X | X |   | X | X | X |   |
| 251 | X | X | X | X | X | X | X | X |   |
| 258 | X | X | X | X |   | X | X | X |   |
| 260 | X | X | X | X | X | X | X | X |   |
| 263 | X | X | X | X | X | X | X | X |   |
| 329 | X | X | X | X | X | X | X | X |   |
| 384 | X | X | X | X | X | X | X | X |   |
| 385 | X | X | X | X | X | X | X | X |   |
| 386 | X | X | X | X |   | X | X | X |   |
| 387 | X | X | X |   | X | X | X | X |   |
| 388 | X | X | X | X | X | X | X | X |   |
| 389 | X | X | X | X |   | X | X | X |   |
| 390 | X | X | X |   | X | X | X | X |   |
| 391 | X | X | X | X | X | X | X | X |   |
| 392 | X | X |   | X | X | X | X | X |   |
| 393 | X |   |   | X | X | X | X | X |   |
| 394 | X |   |   | X | X | X | X | X |   |
| 395 | X | X |   | X | X | X | X | X |   |
| 396 | X | X | X | X | X | X | X | X |   |
| 397 | X | X | X | X | X | X | X | X |   |
| 398 | X | X | X | X | X | X | X | X |   |
| 399 | X | X | X | X | X | X | X | X |   |
| 400 | X | X | X | X |   | X | X | X |   |
| 401 | X | X | X | X |   | X | X | X |   |
| 402 | X | X |   | X | X | X | X | X |   |
| 403 | X |   | X |   | X | X | X | X |   |
| 404 | X | X | X | X | X | X | X | X |   |

TABLE 3b-continued

| R2 | 45 | 46 | 47 | 48 | 49 | 50 | 51 | 52 | 44 |
|---|---|---|---|---|---|---|---|---|---|
| 405 | X | X | X | X | X | X | X | X | |
| 406 | X | | X | X | X | X | X | X | |
| 407 | X | X | X | X | X | X | X | X | |
| 408 | X | X | X | X | X | X | X | X | |
| 409 | X | X | X | X | X | X | X | X | |
| 410 | X | X | X | X | X | X | X | X | |
| 411 | X | X | X | X | X | X | X | X | |
| 412 | X | X | X | X | X | X | X | X | |
| 413 | X | X | X | X | X | X | X | X | |
| 414 | X | X | X | X | X | X | X | X | |
| 415 | X | X | X | X | X | X | X | X | |
| 416 | X | X | X | X | X | X | X | X | |
| 417 | X | X | X | X | X | X | X | X | |
| 418 | X | X | X | X | X | X | X | X | |
| 419 | X | X | X | X | X | X | X | X | |
| 420 | X | | X | X | X | X | X | X | |
| 421 | X | X | X | X | X | X | X | X | |
| 422 | X | X | X | X | X | X | X | X | |
| 423 | X | X | X | X | X | X | X | X | |
| 424 | X | X | X | X | X | X | X | X | |
| 425 | X | X | X | X | | X | X | X | |
| 426 | X | X | X | X | | X | X | X | |
| 427 | X | X | X | X | X | X | X | X | |
| 428 | X | X | X | X | X | X | X | X | |
| 429 | X | X | X | X | X | X | X | X | |
| 430 | X | X | X | X | X | X | X | X | |
| 431 | X | X | X | X | X | X | X | X | |
| 432 | X | X | X | X | | X | X | X | |
| 433 | X | | X | | X | X | X | X | |
| 434 | X | | X | X | X | X | X | X | |
| 435 | X | X | X | | X | X | X | X | |
| 436 | X | | X | | | X | X | X | |
| 437 | X | X | X | | X | X | X | X | |
| 438 | X | | X | | | X | X | X | |
| 469 | X | X | X | X | X | X | X | X | |
| 470 | X | X | X | X | X | X | X | X | |
| 471 | X | X | X | X | | X | X | X | |
| 472 | X | | X | X | X | X | X | X | |
| 473 | X | X | X | X | X | | X | X | |
| 474 | X | X | X | X | X | X | X | X | |
| 475 | X | | X | | X | X | X | X | |
| 476 | X | X | X | X | X | X | X | X | |
| 477 | X | X | X | X | X | X | X | X | |
| 478 | X | X | X | X | X | X | X | X | |
| 479 | X | X | X | X | X | X | X | X | |
| 480 | X | X | X | X | X | X | X | X | |
| 481 | X | X | X | X | X | X | X | X | |
| 482 | X | X | X | X | X | X | X | X | |
| 483 | X | X | X | X | X | X | X | X | |
| 484 | X | X | X | X | X | X | X | X | |
| 485 | X | X | | X | X | X | X | X | |
| 486 | X | | X | X | X | X | X | X | |
| 487 | X | X | X | X | X | X | X | X | |
| 488 | | | | | | X | X | X | |
| 489 | X | X | X | X | X | X | | X | |
| 490 | X | X | X | X | X | X | X | X | |
| 491 | X | X | X | X | X | X | X | X | |
| 492 | X | X | X | X | X | X | X | X | |
| 493 | | X | X | X | X | X | X | X | |
| 494 | X | X | X | X | X | X | X | X | X |
| 495 | X | X | X | X | X | X | X | | |
| 496 | | X | X | X | X | X | | X | |
| 497 | X | X | X | X | X | X | | X | |
| 498 | X | X | X | | X | | X | X | |
| 500 | X | X | X | | X | X | X | X | X |
| 501 | X | X | X | | X | X | X | X | X |
| 502 | X | X | X | | X | X | X | X | X |
| 503 | X | X | X | | X | X | X | X | X |
| 504 | X | X | X | | X | X | X | X | X |
| 505 | X | X | X | | X | | X | X | |
| 506 | X | X | X | | X | | X | X | X |
| 507 | X | X | X | | X | | X | X | X |
| 508 | X | X | X | | X | | X | X | X |
| 509 | X | X | X | | X | X | X | X | X |
| 510 | X | X | X | | X | X | X | X | X |
| 511 | X | X | X | | X | | X | X | X |
| 512 | X | X | X | | X | X | X | X | X |
| 513 | X | X | X | | X | X | X | X | X |
| 514 | X | X | X | | X | X | X | X | X |
| 515 | X | X | X | | X | X | X | X | X |
| 516 | X | X | X | | X | X | X | X | X |
| 517 | X | X | X | | X | X | X | X | X |
| 518 | X | X | X | | X | X | X | X | |
| 519 | X | X | X | | X | X | X | X | X |
| 520 | X | X | X | | X | X | X | X | X |
| 521 | | X | X | | X | X | X | X | |
| 522 | | X | X | | X | | X | X | |
| 523 | X | X | X | | X | | | X | |
| 524 | X | X | X | | X | X | X | X | |
| 525 | X | X | X | | X | X | X | X | X |
| 526 | X | X | X | | X | X | X | X | X |
| 527 | X | X | X | | X | X | X | X | X |
| 528 | X | X | X | | X | X | X | X | X |
| 529 | X | X | X | | | X | X | X | X |
| 530 | X | X | X | | X | X | X | X | X |
| 531 | X | X | X | | X | X | | X | X |
| 532 | X | X | X | | X | X | | X | X |
| 533 | X | X | X | | X | X | | X | X |
| 534 | X | X | X | | X | | X | X | X |
| 535 | | X | X | | X | | X | X | X |
| 536 | | X | X | | X | | X | X | X |

Table 3c

Table 3c is directed to compounds of the formula (IIIC):

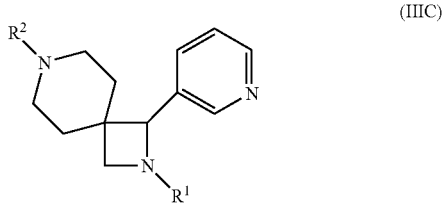

(IIIC)

wherein $R^1$ and $R^2$ are as defined in Table 3c.

An "X" in the box formed by the intersection of the $R^2$ and the $R^1$ row represents an $R^2$ and $R^1$ combination of a compound of formula IIIC that is excluded from the definition of the compounds of formula I (and formula IIA). For example, compounds of formula IIIC wherein $R^2$ is moiety 3 (see Table 2 for definition) and $R^1$ is moiety 44 (see Table 1 for definition) are excluded from the definition of formula I (and formula IIA) (there is an "X" in the box formed by the intersection of the $R^2$ column and the $R^1$ row).

If there is no "X" in the box, then that compound is within the definition of the compounds of formula I (and formula IIA). For example, compounds of formula IIIC wherein moiety $R^2$ is 3 and moiety $R^1$ is 50 (no "X" in the box formed by the intersection of the $R^2$ column and the $R^1$ row) are within the definition of the compounds of formula I (and formula IIA).

TABLE 3c

| R2 | R1 44 | 46 | 47 | 51 | 50 |
|---|---|---|---|---|---|
| 3 | X | X | X | X | |
| 5 | X | X | X | X | |
| 16 | X | X | X | X | |
| 20 | X | X | X | X | |
| 22 | X | X | X | X | |
| 30 | X | X | X | X | |
| 35 | X | X | X | X | |
| 44 | X | X | X | X | |
| 47 | X | X | X | X | |
| 48 | X | X | X | X | |
| 55 | X | X | X | X | |
| 59 | X | X | X | X | |
| 60 | X | X | X | X | |
| 64 | X | X | X | X | |
| 68 | X | X | X | X | |
| 83 | X | | | X | |
| 84 | X | X | X | X | |
| 85 | X | X | | X | |
| 133 | X | | X | | |
| 134 | X | X | X | X | |
| 135 | X | X | X | X | |
| 136 | X | X | X | X | |
| 138 | X | X | X | X | |
| 139 | X | X | X | X | |
| 140 | X | X | X | X | |
| 141 | X | X | X | X | |
| 144 | X | X | X | X | |
| 146 | X | X | X | X | |
| 152 | X | X | X | X | |
| 157 | X | X | X | X | |
| 167 | X | X | X | X | |
| 175 | X | X | X | X | |
| 189 | X | X | X | X | X |
| 198 | X | X | X | X | |
| 200 | X | X | X | X | |
| 202 | X | X | X | X | |
| 217 | X | X | X | X | X |
| 218 | X | X | X | X | X |
| 219 | X | X | X | X | X |
| 223 | X | X | X | X | X |
| 224 | X | X | X | X | X |
| 225 | X | X | X | X | |
| 226 | X | X | X | X | |
| 227 | X | X | X | X | |
| 230 | X | X | X | X | |
| 236 | X | X | X | X | X |
| 242 | X | X | X | X | |
| 245 | X | X | | X | |
| 248 | X | X | X | X | |
| 251 | X | X | X | X | |
| 258 | X | X | X | X | |
| 260 | X | X | X | X | |
| 263 | X | X | X | X | |
| 329 | X | X | X | X | |
| 384 | X | X | X | X | |
| 385 | X | X | X | X | |
| 386 | X | X | X | X | |
| 387 | X | X | X | X | |
| 388 | X | X | X | X | |
| 389 | X | X | X | X | |
| 390 | X | X | X | X | |
| 391 | X | X | X | X | |
| 392 | X | X | X | X | |
| 393 | X | X | X | X | |
| 394 | X | | X | X | |
| 395 | X | X | X | X | |
| 396 | X | X | X | X | |
| 397 | X | X | X | X | |
| 398 | X | X | X | X | |
| 399 | X | X | X | X | |
| 400 | X | X | X | X | |
| 401 | X | X | X | X | |
| 402 | X | X | X | X | |
| 403 | X | X | X | X | |
| 404 | X | X | X | X | |
| 405 | X | X | X | X | |
| 406 | X | X | X | X | |
| 407 | X | X | X | X | |
| 408 | X | X | X | X | |
| 409 | X | X | X | X | |
| 410 | X | X | X | X | |
| 411 | X | X | X | X | |
| 412 | X | X | X | X | |
| 413 | X | X | | X | |
| 414 | X | | X | X | |
| 415 | X | X | X | X | |
| 416 | X | X | X | X | |
| 417 | X | X | X | X | |
| 418 | X | | | X | |
| 419 | X | X | X | X | |
| 420 | X | X | X | X | |
| 421 | X | X | X | X | |
| 422 | X | X | X | X | |
| 423 | X | X | X | X | |
| 424 | X | X | X | X | |
| 425 | X | X | X | X | |
| 426 | X | X | X | X | |
| 427 | X | X | X | X | |
| 428 | X | X | X | X | |
| 429 | X | X | X | X | |
| 430 | X | X | X | X | |
| 431 | X | X | X | X | |
| 432 | X | X | X | X | |
| 433 | X | | | X | |
| 434 | X | X | X | X | |
| 435 | X | | | X | |
| 436 | X | | | X | |
| 437 | X | X | X | X | |
| 438 | X | | | X | |
| 469 | X | X | X | | |
| 470 | X | X | X | X | |
| 471 | X | X | X | X | |
| 472 | X | X | X | X | |
| 473 | X | X | X | X | |
| 474 | X | X | X | X | |
| 475 | X | X | X | | |
| 476 | X | X | | X | |
| 477 | X | X | X | X | |
| 478 | X | X | X | X | |
| 479 | X | X | X | X | |
| 480 | X | X | X | X | |
| 481 | X | X | | X | |
| 482 | X | X | X | X | |
| 483 | X | X | X | X | |
| 484 | X | X | X | X | |
| 485 | X | X | X | X | |
| 486 | X | X | X | X | |
| 487 | X | | | | |
| 488 | X | | | | |
| 489 | X | X | X | X | |
| 490 | X | X | X | X | |
| 491 | X | X | X | X | |
| 492 | X | X | X | X | |
| 493 | X | X | X | X | |
| 494 | X | X | X | X | |
| 495 | X | | | | |
| 496 | | X | X | X | |
| 497 | | X | X | X | |
| 498 | | X | X | X | |
| 500 | X | X | X | X | X |
| 501 | X | X | X | X | X |
| 502 | X | X | X | X | X |
| 503 | X | X | X | X | X |
| 504 | X | X | X | X | X |
| 505 | X | X | X | X | X |
| 506 | X | X | X | X | X |
| 507 | X | X | X | X | X |
| 508 | X | X | X | X | X |
| 509 | X | X | X | X | X |
| 510 | X | X | X | X | X |

TABLE 3c-continued

| | R1 | | | | |
|---|---|---|---|---|---|
| R2 | 44 | 46 | 47 | 51 | 50 |
| 511 | X | X | X | X | X |
| 512 | X | X | X | X | X |
| 513 | X | X | X | X | X |
| 514 | X | X | X | X | X |
| 515 | X | X | X | X | X |
| 516 | X | X | X | X | X |
| 517 | X | X | X | X | X |
| 518 | X | X | X | X | X |
| 519 | X | X | X | X | X |
| 520 | X | X | X | X | X |
| 521 | X | X | X | X | X |
| 522 | X | X | X | X | X |
| 523 | X | X | X | X | X |
| 524 | X | X | X | X | X |
| 525 | X | X | X | X | X |
| 526 | X | X | X | X | X |
| 527 | X | X | X | X | X |
| 528 | X | X | X | X | X |
| 529 | X | X | X | X | |
| 530 | X | X | X | | X |
| 531 | X | X | X | | X |
| 532 | X | X | X | | |
| 533 | X | X | X | | X |
| 534 | X | X | X | X | X |
| 535 | X | X | | X | X |
| 536 | X | X | | X | X |

Table 3d

Table 3d is directed to compounds of the formula (IIID):

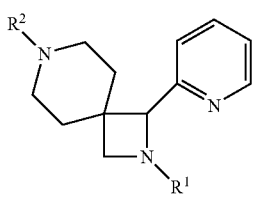

wherein $R^1$ and $R^2$ are as defined in Table 3d.

An "X" in the box formed by the intersection of the $R^2$ and the $R^1$ row represents an $R^2$ and the $R^1$ combination of a compound of formula IIID that is excluded from the definition of the compounds of formula I (and formula IIA). For example, compounds of formula IIID wherein $R^2$ is moiety 3 (see Table 2 for definition) and $R^1$ is moiety 46 (see Table 1 for definition) are excluded from the definition of formula I (formula IIA)(there is an "X" in the box formed by the intersection of the $R^2$ column and the $R^1$ row).

If there is no "X" in the box, then that compound is within the definition of the compounds of formula I (and formula IIA). For example, compounds of formula IIID wherein moiety $R^2$ is 83 and moiety $R^1$ is 46 (no "X" in the box formed by the intersection of the $R^2$ column and the $R^1$ row) are within the definition of the compounds of formula I (and formula IIA).

TABLE 3d

| | R1 | |
|---|---|---|
| R2 | 46 | 48 |
| 3 | X | X |
| 5 | X | X |
| 16 | X | X |
| 20 | X | X |
| 22 | X | X |
| 30 | X | X |
| 35 | X | X |
| 44 | X | X |
| 47 | X | X |
| 48 | X | X |
| 55 | X | X |
| 59 | X | X |
| 60 | X | X |
| 64 | X | X |
| 68 | X | X |
| 83 | | X |
| 84 | X | X |
| 85 | | X |
| 133 | | X |
| 134 | X | X |
| 135 | X | X |
| 136 | X | X |
| 138 | X | X |
| 139 | X | X |
| 140 | X | X |
| 141 | X | X |
| 144 | X | X |
| 146 | X | X |
| 152 | X | X |
| 157 | X | X |
| 167 | X | X |
| 175 | X | X |
| 189 | X | X |
| 198 | X | X |
| 200 | X | X |
| 202 | X | X |
| 217 | X | X |
| 218 | X | X |
| 219 | X | X |
| 223 | X | X |
| 224 | X | X |
| 225 | X | X |
| 226 | X | X |
| 227 | X | X |
| 230 | X | X |
| 236 | X | X |
| 242 | X | X |
| 245 | | X |
| 248 | X | X |
| 251 | X | X |
| 258 | X | X |
| 260 | X | X |
| 263 | X | X |
| 329 | X | X |
| 384 | X | X |
| 385 | X | X |
| 386 | X | X |
| 387 | X | X |
| 388 | X | X |
| 389 | X | X |
| 390 | X | X |
| 391 | X | X |
| 392 | X | X |
| 393 | X | X |
| 394 | X | X |
| 395 | X | X |
| 396 | X | X |
| 397 | X | X |
| 398 | X | X |
| 399 | X | X |
| 400 | X | X |
| 401 | X | X |
| 402 | X | X |
| 403 | X | X |
| 404 | X | X |

TABLE 3d-continued

| R2 | R1 46 | R1 48 |
|---|---|---|
| 405 | X | X |
| 406 | X | X |
| 407 | X | X |
| 408 | X | X |
| 409 | X | X |
| 410 | X | X |
| 411 | X | X |
| 412 | X | X |
| 413 | X | X |
| 414 | X | X |
| 415 | X | X |
| 416 | X | X |
| 417 | X | X |
| 418 | X | X |
| 419 | X | X |
| 420 | X | X |
| 421 |  | X |
| 422 | X | X |
| 423 | X | X |
| 424 | X | X |
| 425 | X | X |
| 426 | X | X |
| 427 | X | X |
| 428 | X | X |
| 429 | X | X |
| 430 | X | X |
| 431 | X | X |
| 432 | X | X |
| 433 |  | X |
| 434 | X | X |
| 435 |  | X |
| 436 |  | X |
| 437 | X | X |
| 438 |  | X |
| 469 | X | X |
| 470 | X | X |
| 471 | X | X |
| 472 | X | X |
| 473 | X |  |
| 474 | X | X |
| 475 | X |  |
| 476 | X | X |
| 477 | X | X |
| 478 | X | X |
| 479 | X | X |
| 480 | X | X |
| 481 | X | X |
| 482 | X | X |
| 483 | X | X |
| 484 | X | X |
| 485 | X | X |
| 486 | X | X |
| 487 |  | X |
| 489 | X | X |
| 490 | X | X |
| 491 | X | X |
| 492 | X | X |
| 493 | X | X |
| 494 |  | X |
| 495 | X | X |
| 496 | X | X |
| 497 |  | X |
| 498 | X |  |
| 500 | X | X |
| 501 | X | X |
| 502 | X | X |
| 503 | X | X |
| 504 | X | X |
| 505 | X | X |
| 506 | X | X |
| 507 | X | X |
| 508 | X | X |
| 509 | X | X |
| 510 | X | X |
| 511 | X | X |
| 512 | X | X |
| 513 | X | X |
| 514 | X | X |
| 515 | X | X |
| 516 | X | X |
| 517 | X | X |
| 518 | X | X |
| 519 | X | X |
| 520 | X | X |
| 521 | X | X |
| 522 | X | X |
| 523 | X | X |
| 524 | X | X |
| 525 | X | X |
| 526 | X | X |
| 527 | X | X |
| 528 | X | X |
| 529 | X | X |
| 530 | X | X |
| 531 | X | X |
| 532 | X | X |
| 533 | X | X |
| 534 | X | X |
| 535 | X |  |
| 536 | X |  |

Table 4a

Table 4a is directed to compounds of the formula (IVA):

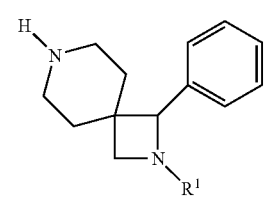

(IVA)

wherein R¹ is as defined in Table 4a.

The compounds defined by Table 4a are excluded from the definition of the compounds of formula I (and formula IIA).

TABLE 4a

| R1 | R1 |
|---|---|
| 19 | 67 |
| 21 | 68 |
| 22 | 69 |
| 25 | 70 |
| 29 | 71 |
| 31 | 72 |
| 34 | 73 |
| 35 | 74 |
| 43 | 75 |
| 53 | 76 |
| 54 | 77 |
| 55 | 78 |
| 56 | 79 |
| 57 | 80 |
| 58 | 81 |
| 59 | 82 |
| 60 | 83 |
| 61 | 84 |
| 62 | 85 |

TABLE 4a-continued
| R1 | R1 |
|---|---|
| 63 | 86 |
| 64 | 87 |
| 65 | 88 |
| 66 | 89 |
| 67 | 90 |
|  | 91 |
|  | 93 |
Representative compounds of the invention include, for example, the compounds in Table 5. The compounds in Table 5 had Cav 3.2 (Ionworks) $IC_{50}$ within the range of 24 to 33000 nM.
TABLE 5
| isomer | Compound |
|---|---|
| A | 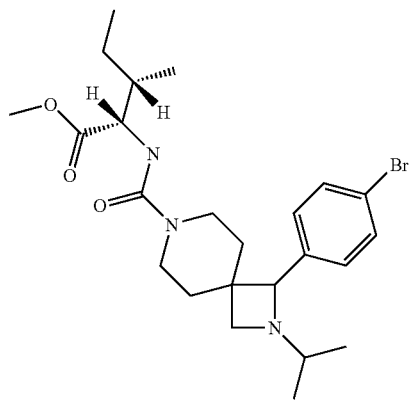 (1) |
| A | 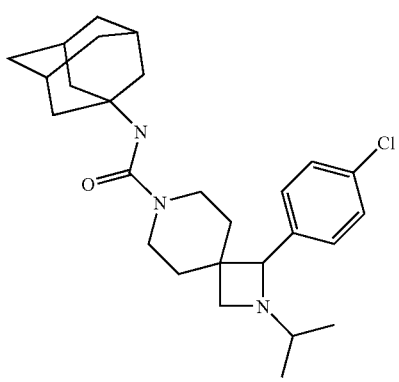 (2) |
TABLE 5-continued
| isomer | Compound |
|---|---|
| A | 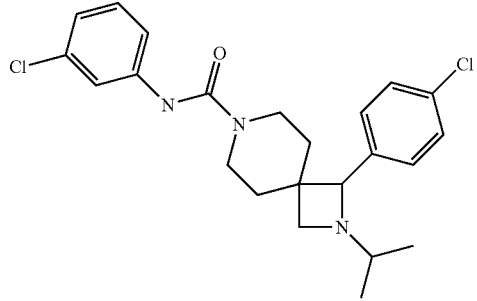 (3) |
| A | 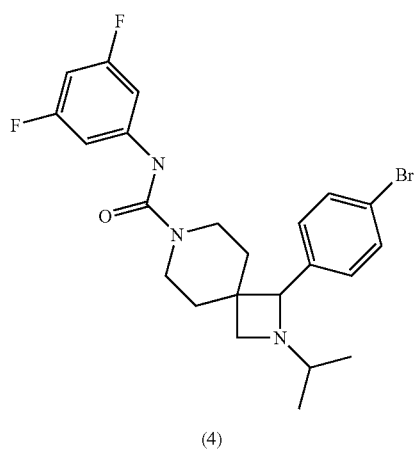 (4) |
| A | 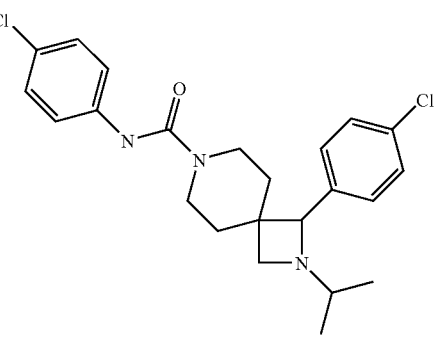 (5) |
| A | 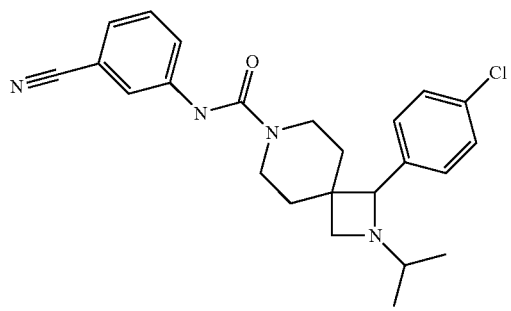 (6) |

TABLE 5-continued
| isomer | Compound |
|---|---|
| | 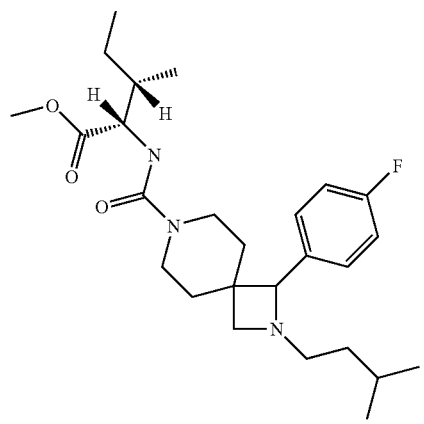<br>(7) |
| A | 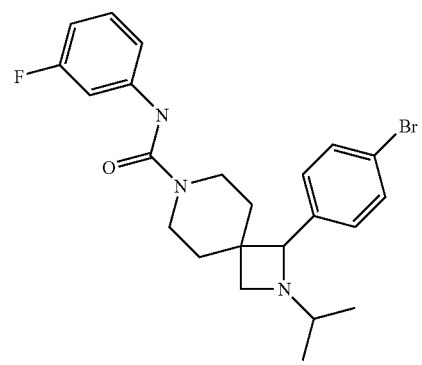<br>(8) |
| A | 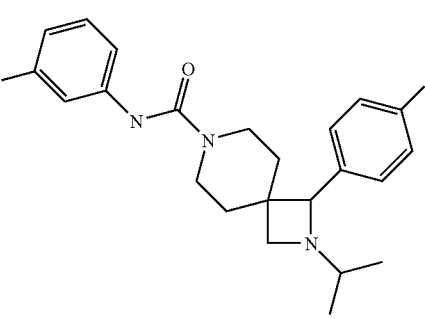<br>(9) |
| | 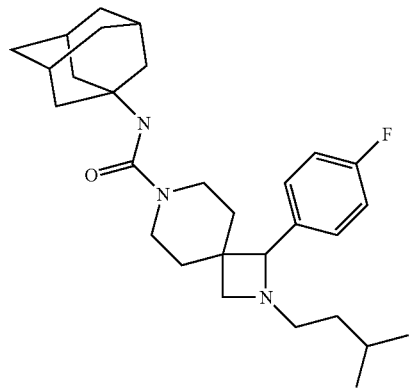<br>(10) |
| | 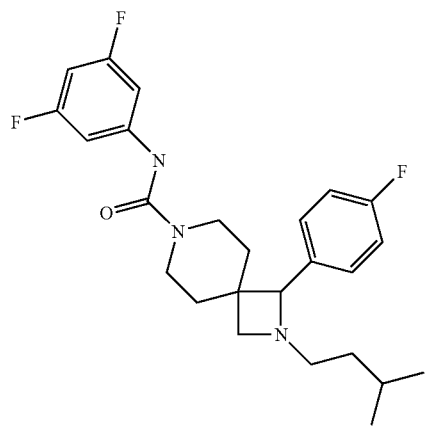<br>(11) |
| | 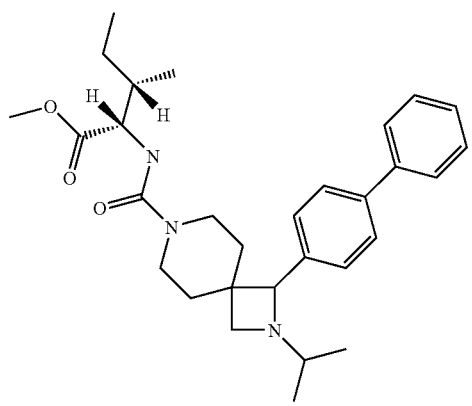<br>(12) |

TABLE 5-continued
| isomer | Compound |
|---|---|
| A | 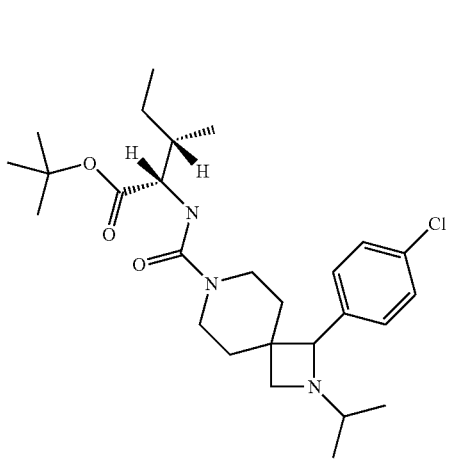<br>(13) |
| B | 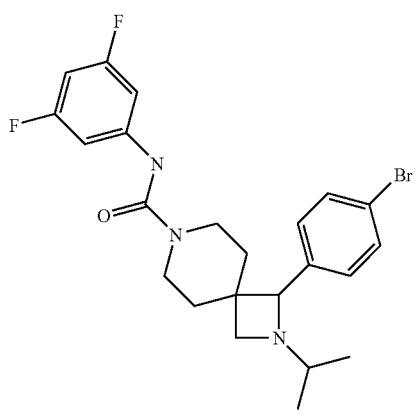<br>(14) |
| | 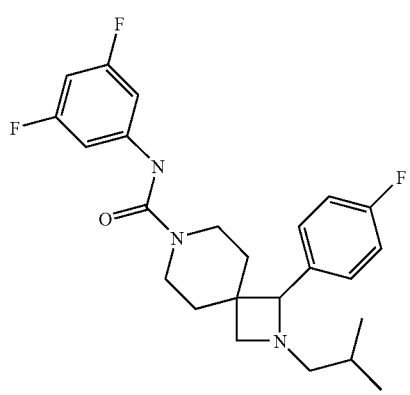<br>(15) |
TABLE 5-continued
| isomer | Compound |
|---|---|
| | 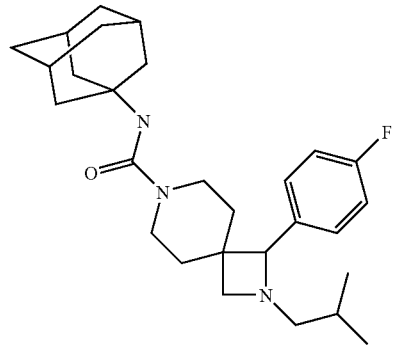<br>(16) |
| A | 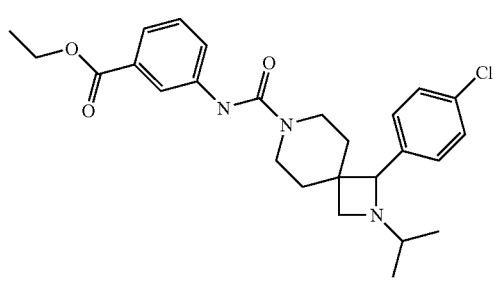<br>(17) |
| A | 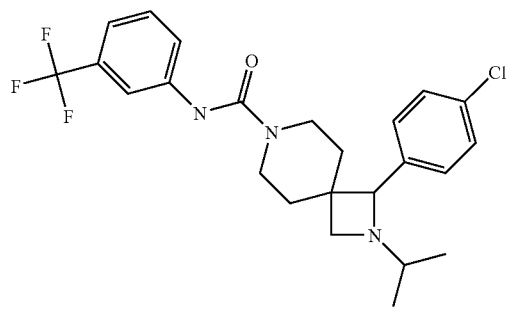<br>(18) |
| A | 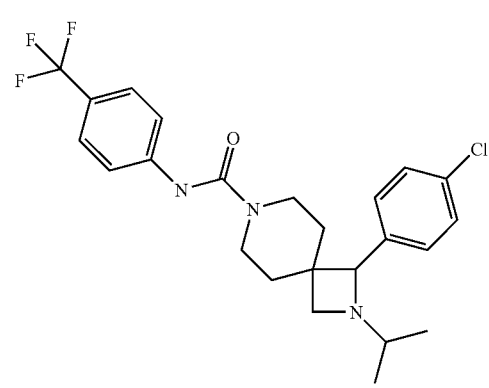<br>(19) |

TABLE 5-continued
| isomer | Compound |
|---|---|
| A | 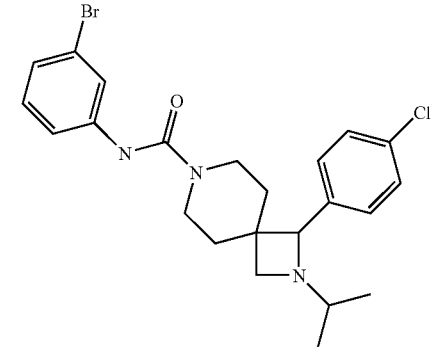 (20) |
|  | 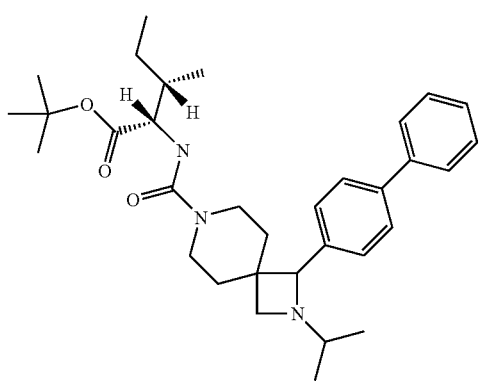 (21) |
| A | 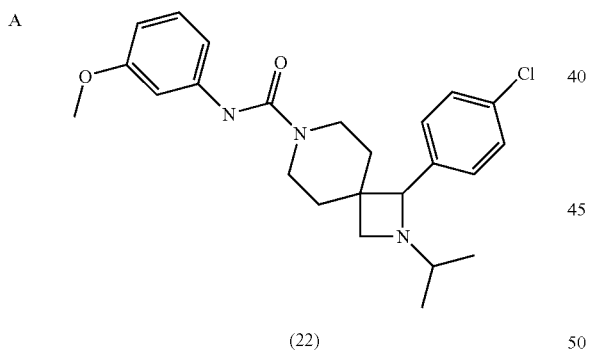 (22) |
| B | 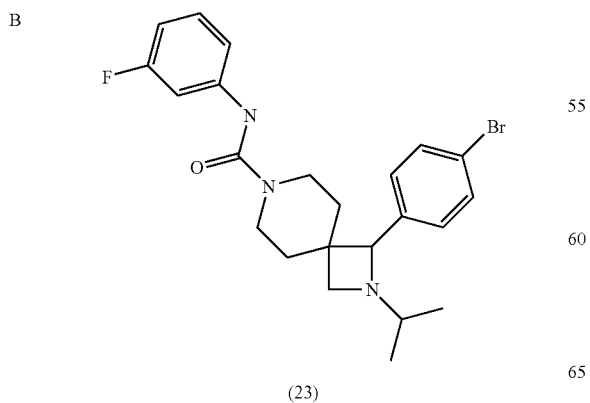 (23) |
TABLE 5-continued
| isomer | Compound |
|---|---|
|  | 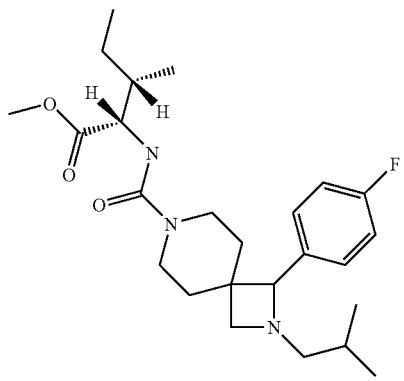 (24) |
|  | 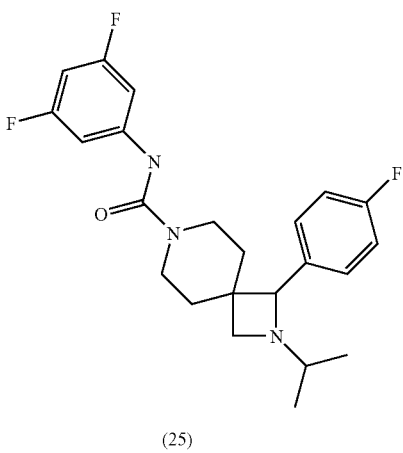 (25) |
| A | 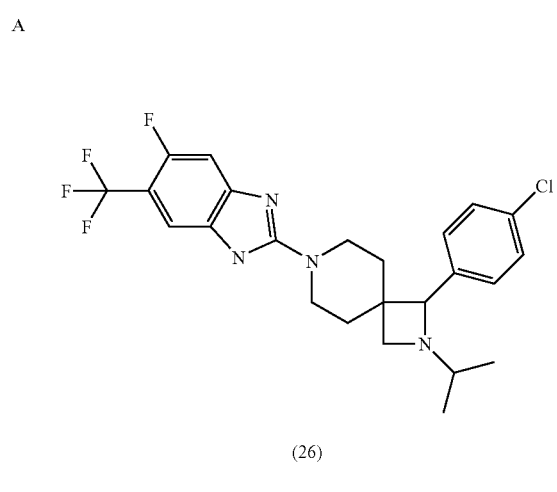 (26) |

TABLE 5-continued
| isomer | Compound |
|---|---|
| A | 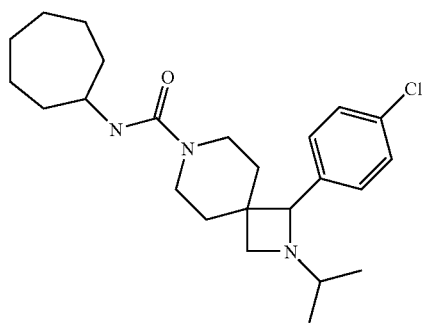 (27) |
| | 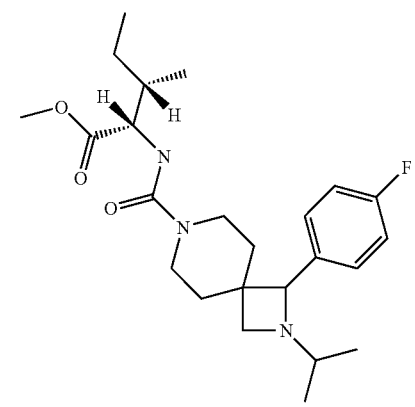 (28) |
| | 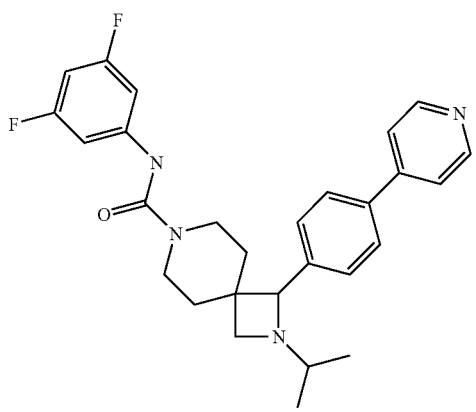 (29) |
TABLE 5-continued
| isomer | Compound |
|---|---|
| A | 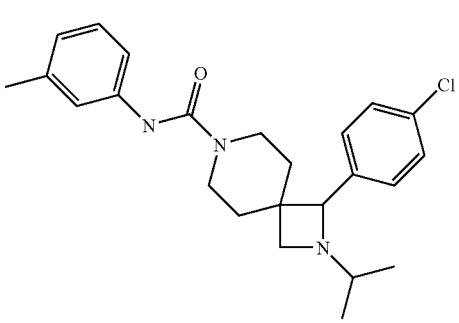 (30) |
| | 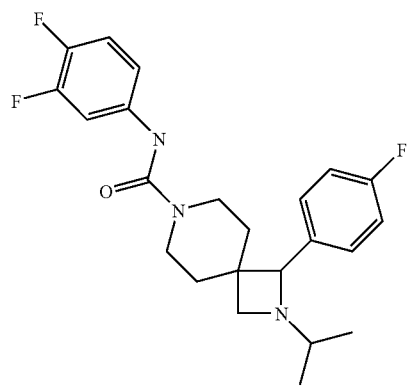 (31) |
| B | 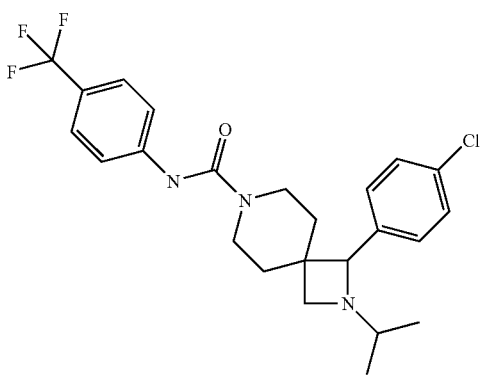 (32) |

TABLE 5-continued
| isomer | Compound |
|---|---|
| A | 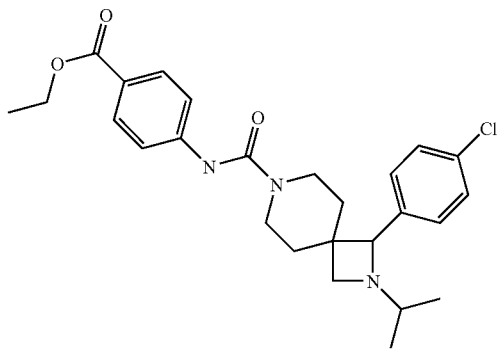<br>(33) |
|  | 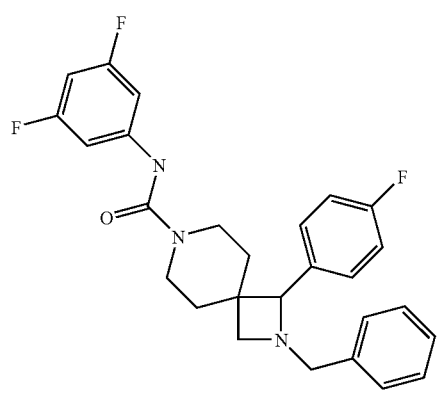<br>(34) |
|  | 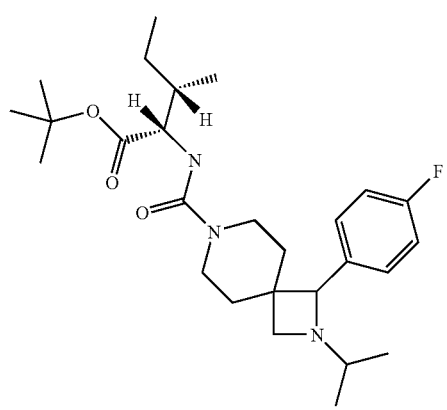<br>(35) |
|  | 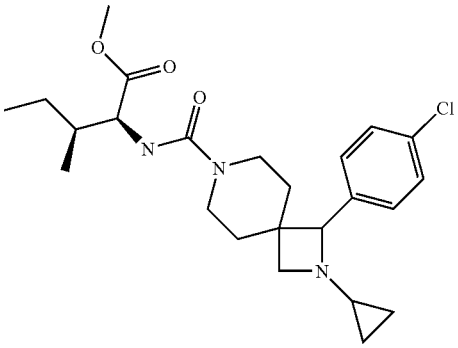<br>(36) |
| A | 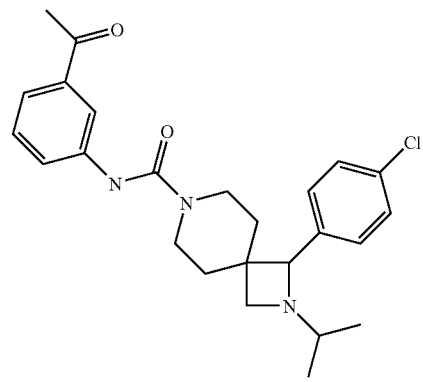<br>(37) |
|  | 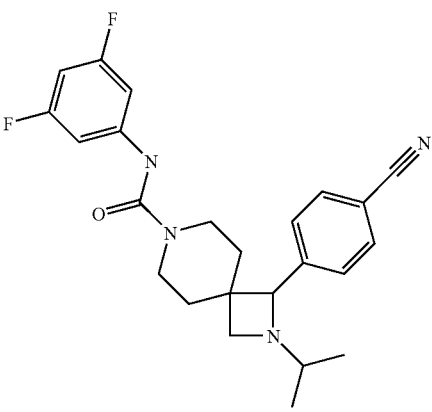<br>(38) |

TABLE 5-continued
| isomer | Compound |
|---|---|
| A | 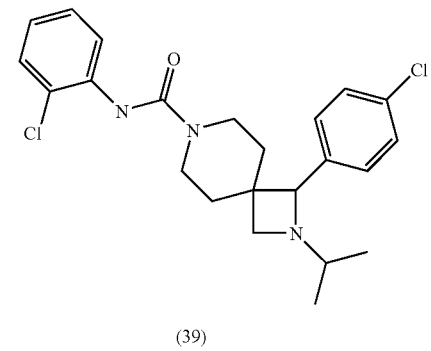<br>(39) |
| A | 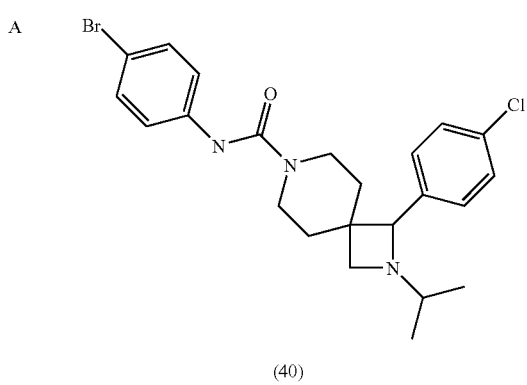<br>(40) |
| | 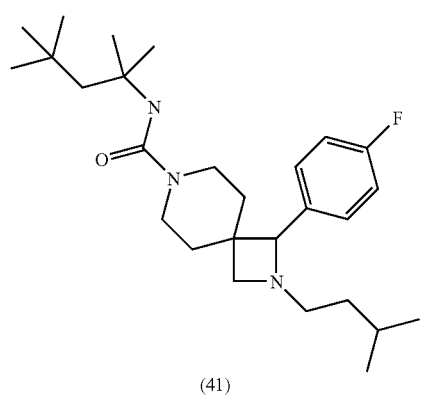<br>(41) |
| | 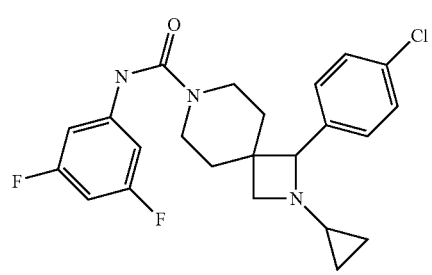<br>(42) |
TABLE 5-continued
| isomer | Compound |
|---|---|
| | 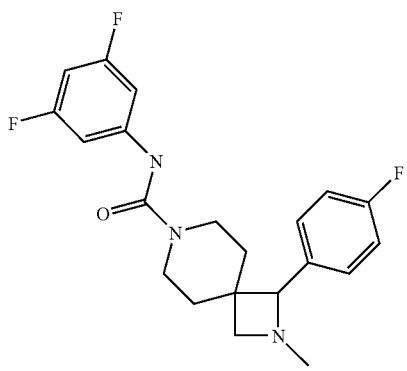<br>(43) |
| B | 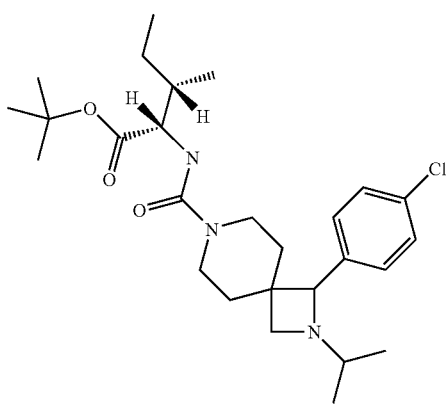<br>(44) |
| A | 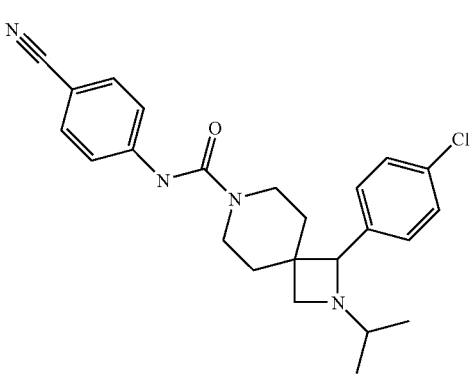<br>(45) |

TABLE 5-continued
| isomer | Compound |
|---|---|
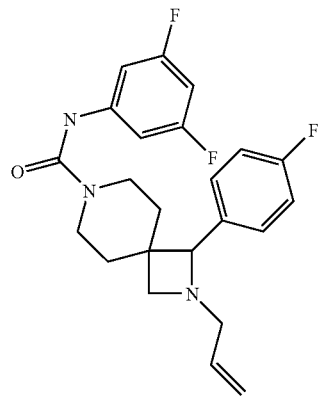
(46)
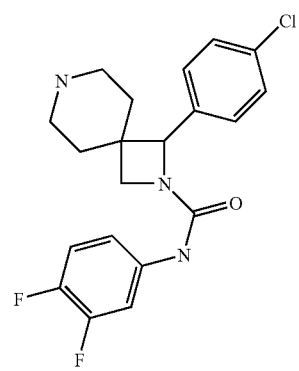
(47)
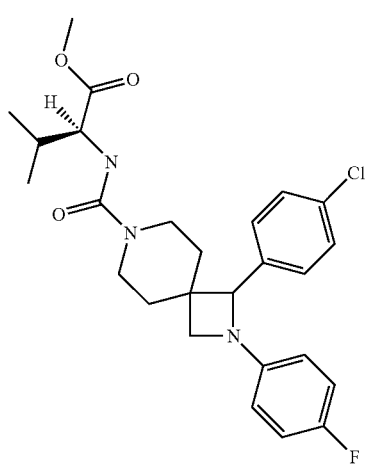
(48)
TABLE 5-continued
| isomer | Compound |
|---|---|
| B | |
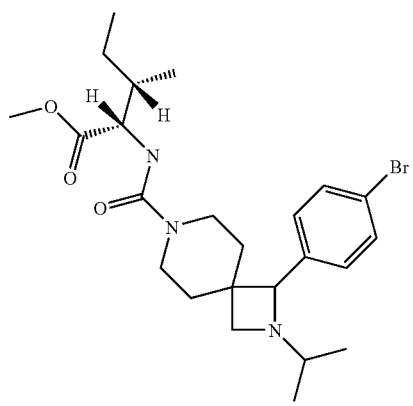
(49)
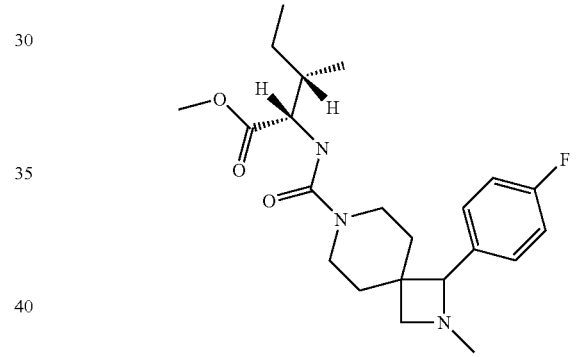
(50)
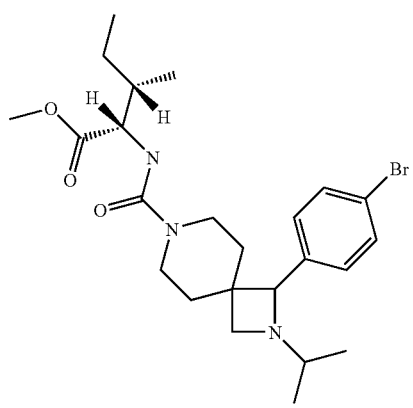
(51)

TABLE 5-continued
| isomer | Compound |
|---|---|
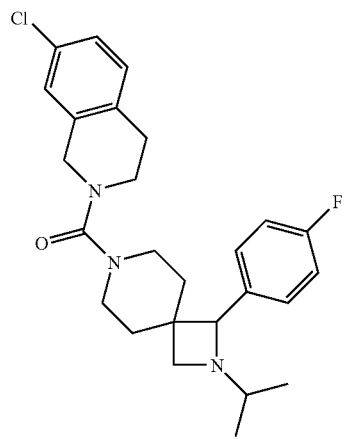
(52)
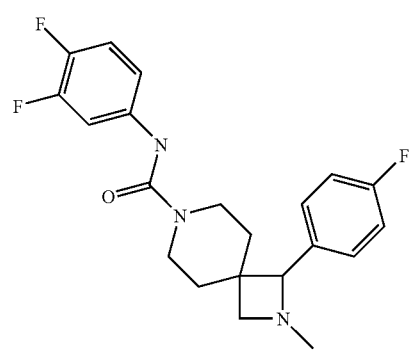
(53)
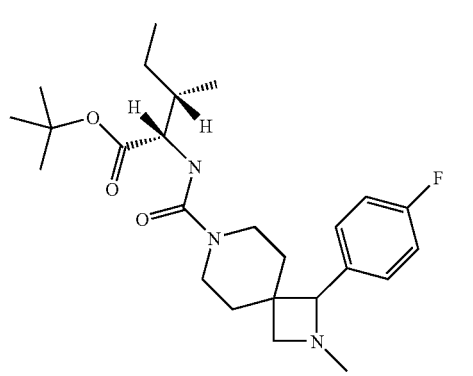
(54)
TABLE 5-continued
| isomer | Compound |
|---|---|
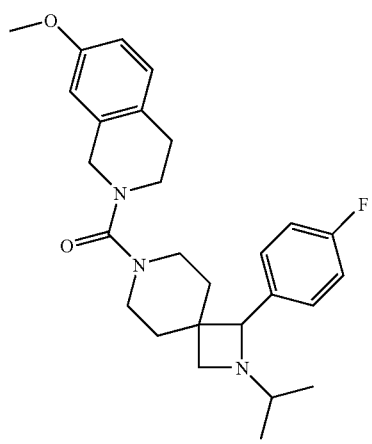
(55)
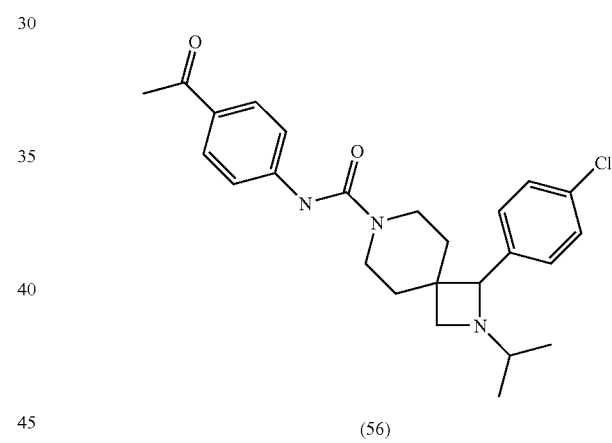
(56)
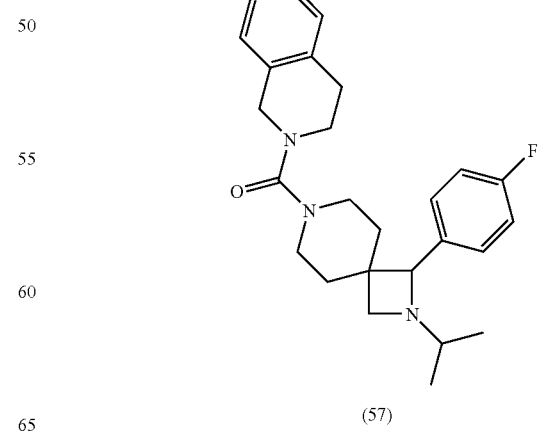
(57)

TABLE 5-continued
| isomer | Compound |
|---|---|
|  | (58) |
| B | (59) |
| A | (60) |
|  | (61) |
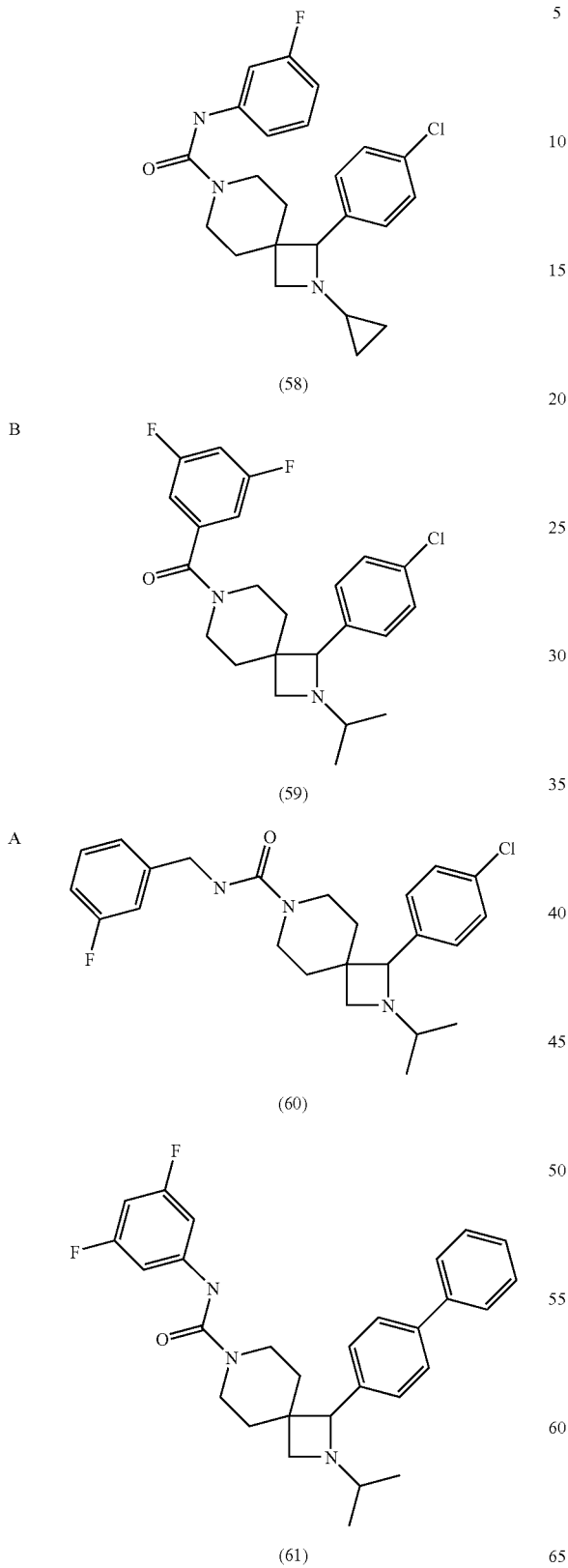
TABLE 5-continued
| isomer | Compound |
|---|---|
|  | (62) |
|  | (63) |
| A | (64) |
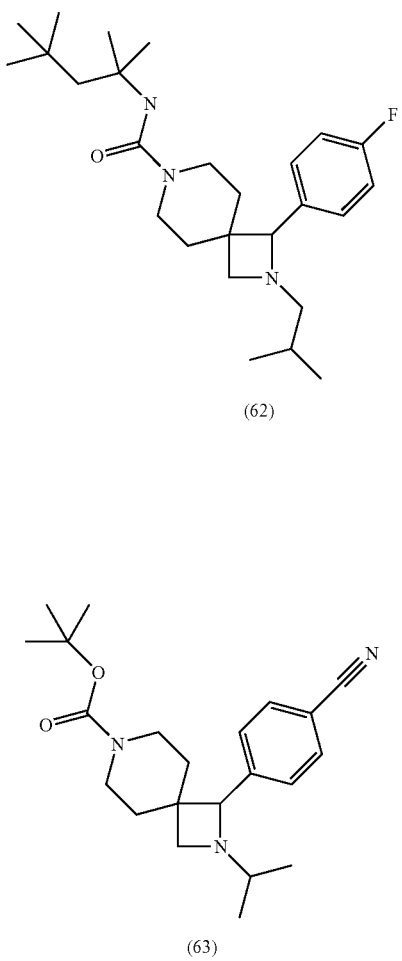

TABLE 5-continued
| isomer | Compound |
|---|---|
| | 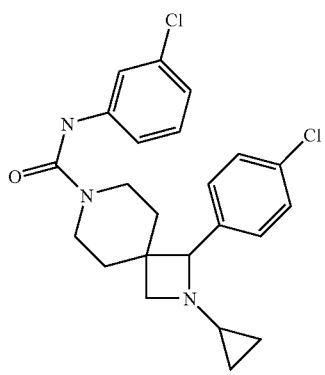 (65) |
| A | |
| | 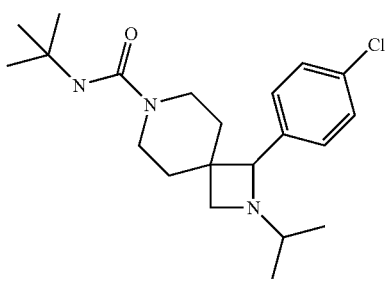 (66) |
| | 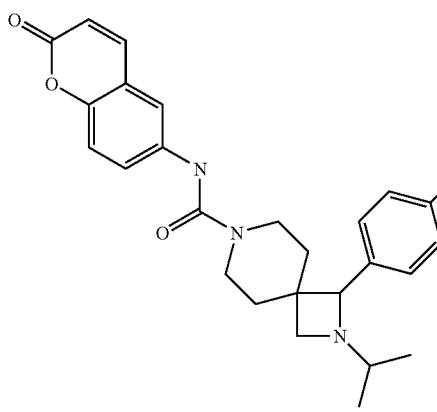 (67) |
TABLE 5-continued
| isomer | Compound |
|---|---|
| | 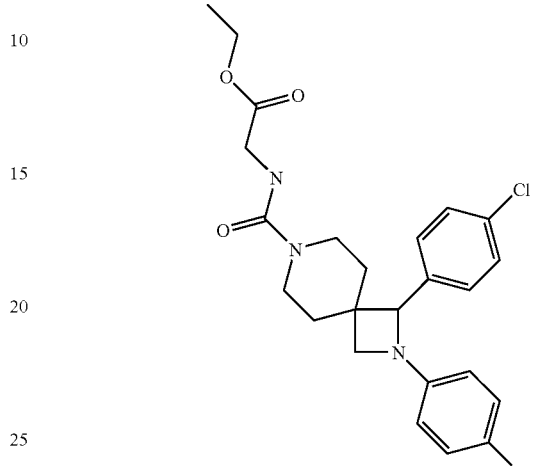 (68) |
| | 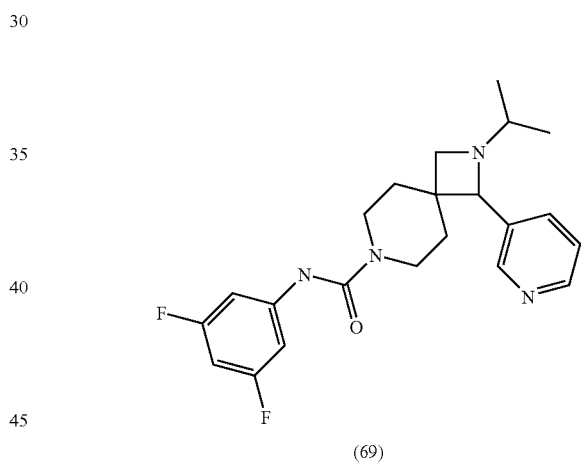 (69) |
| | 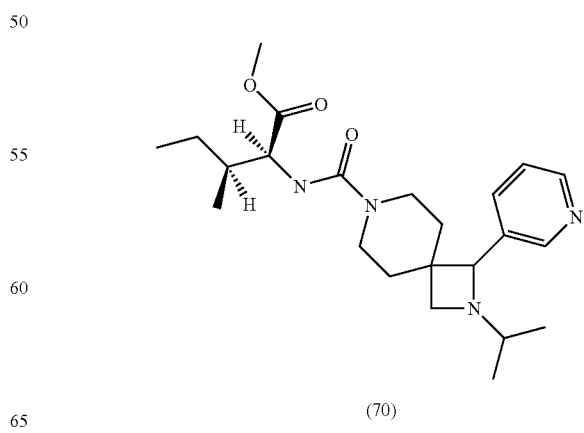 (70) |

TABLE 5-continued
| isomer | Compound |
|---|---|
| A | 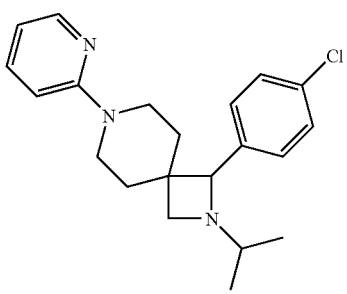<br>(71) |
|  | 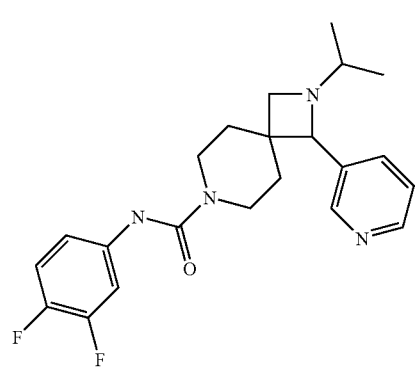<br>(72) |
| A | 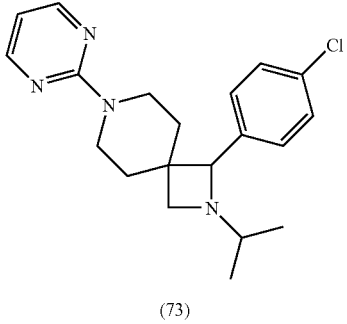<br>(73) |
| B | 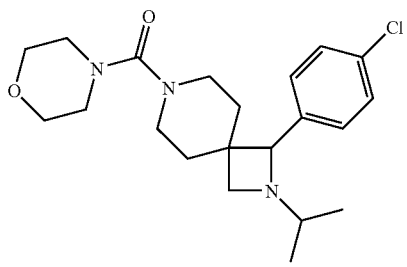<br>(74) |
|  | 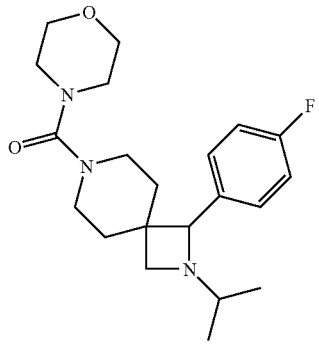<br>(75) |
|  | 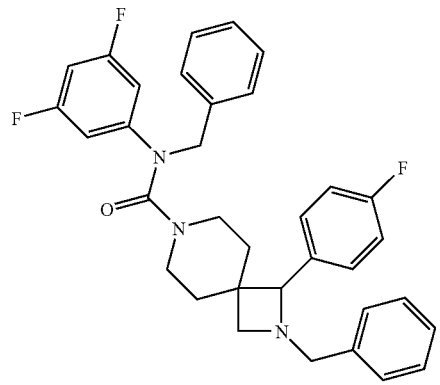<br>(76) |
|  | 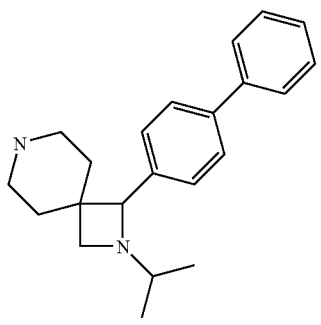<br>(77) |
|  | 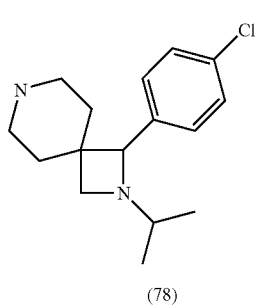<br>(78) |

TABLE 5-continued
| isomer | Compound |
|---|---|
| A | 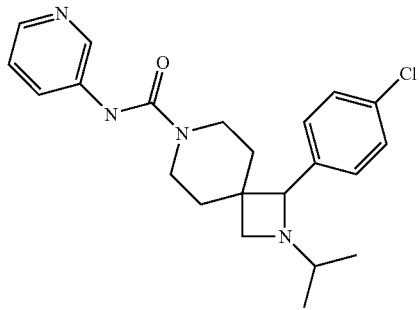<br>(79) |
| B | 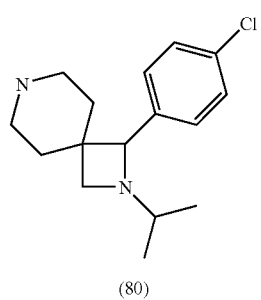<br>(80) |
|  | 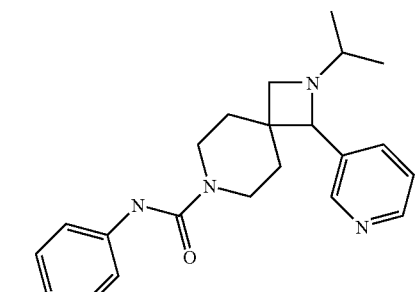<br>(81) |
| A | 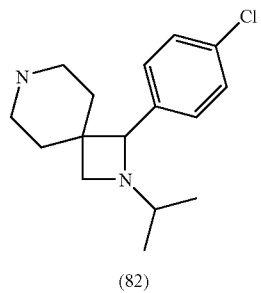<br>(82) |
TABLE 5-continued
| isomer | Compound |
|---|---|
|  | 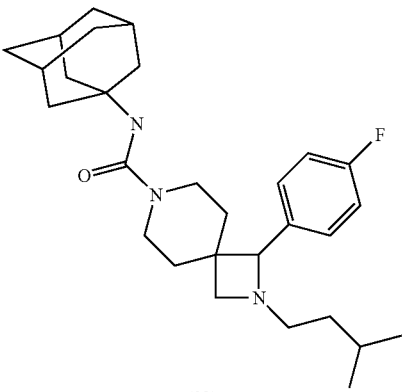<br>(83) |
|  | 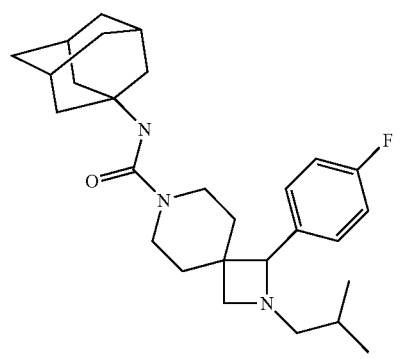<br>(84) |
|  | 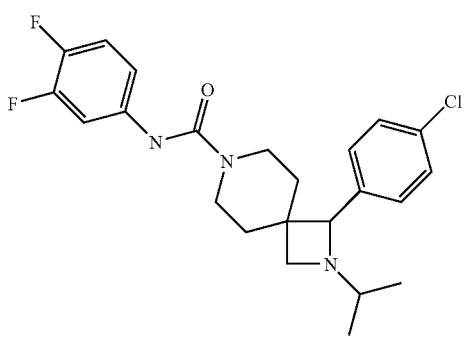<br>(85) |
|  | 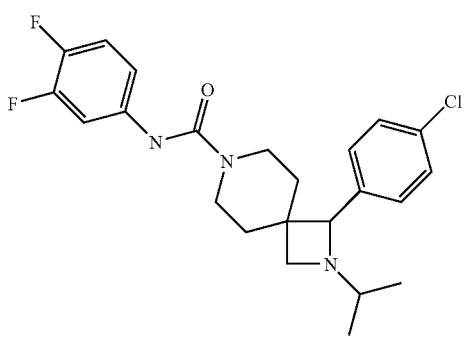<br>(86) |

TABLE 5-continued
| isomer | Compound |
|---|---|
| | 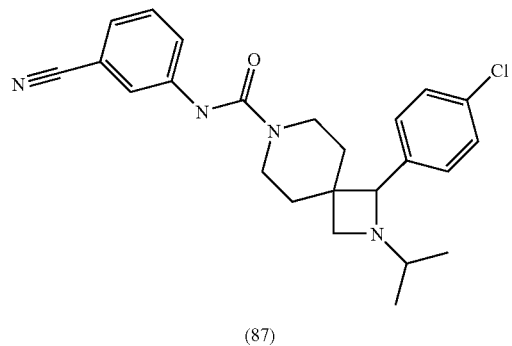 (87) |
| | 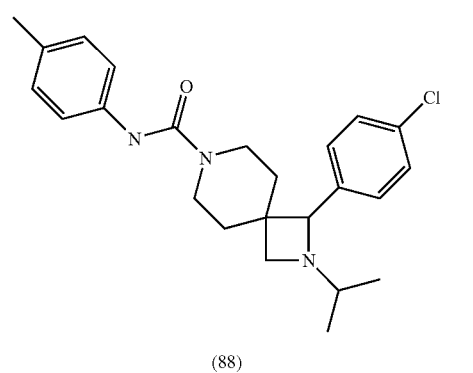 (88) |
| | 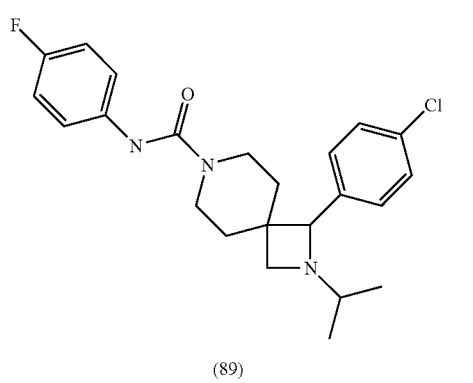 (89) |
| | 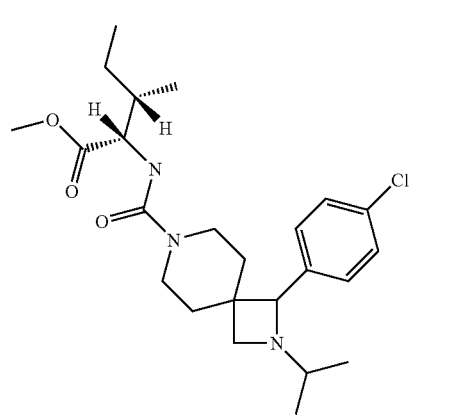 (90) |
| | 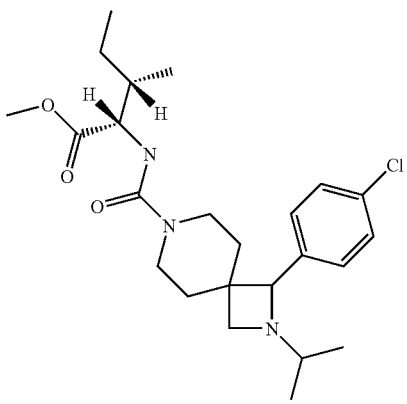 (91) |
| | 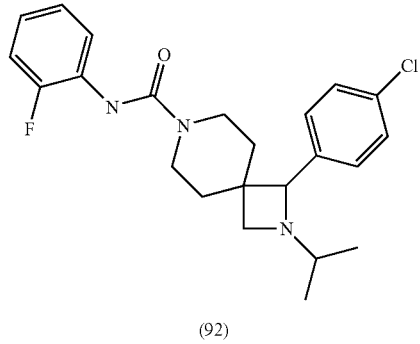 (92) |
| | 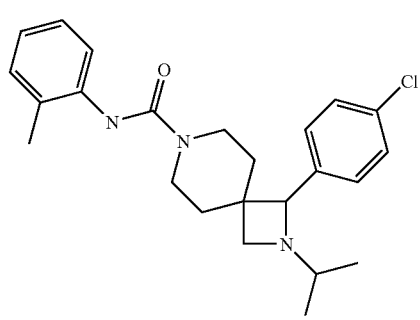 (93) |
| | 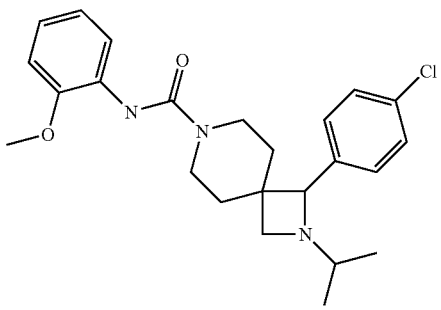 (94) |

TABLE 5-continued
| isomer | Compound |
|---|---|
| | 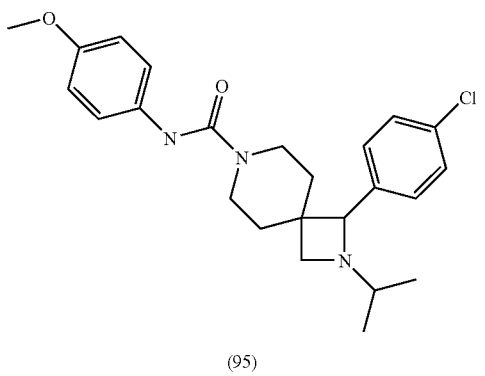<br>(95) |
| | 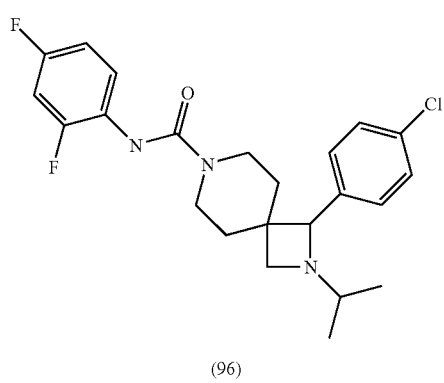<br>(96) |
| | 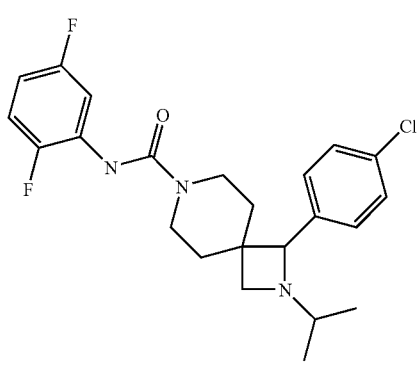<br>(97) |
| | 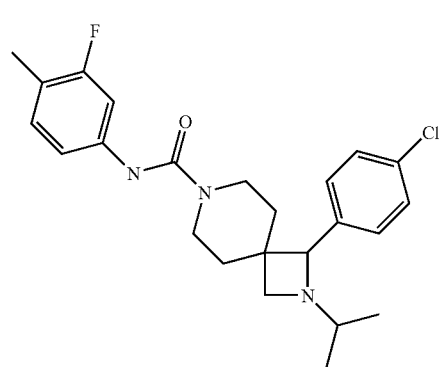<br>(98) |
| | 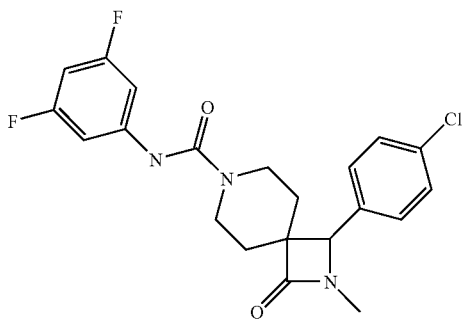<br>(99) |
| | 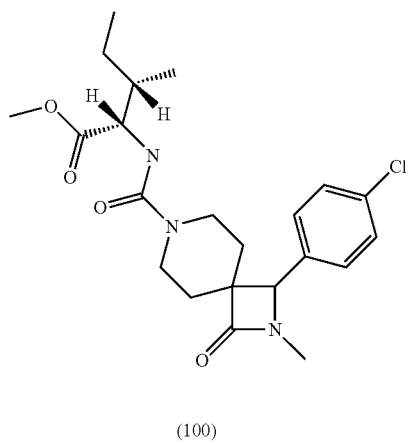<br>(100) |
| | 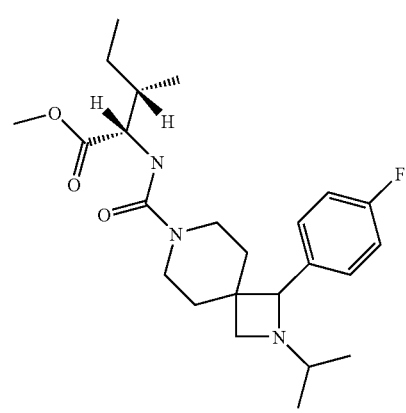<br>(101) |

TABLE 5-continued
| isomer | Compound |
|---|---|
|  | 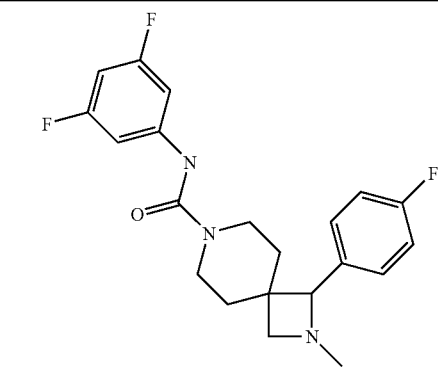 (102) |
|  | 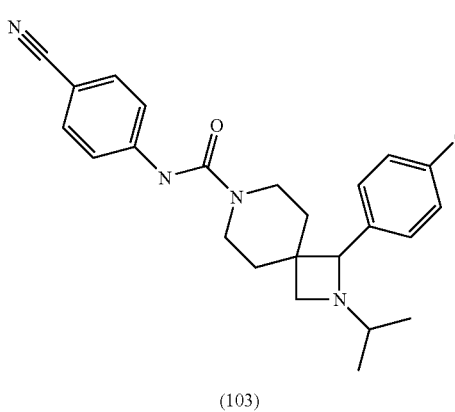 (103) |
|  | 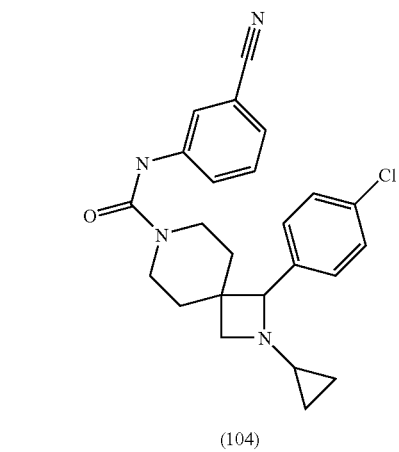 (104) |
|  | 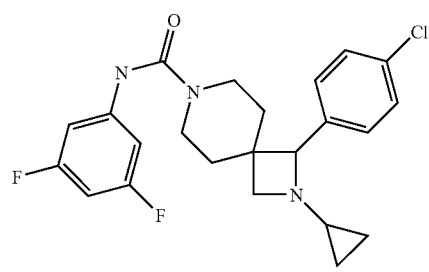 (105) |
TABLE 5-continued
| isomer | Compound |
|---|---|
|  | 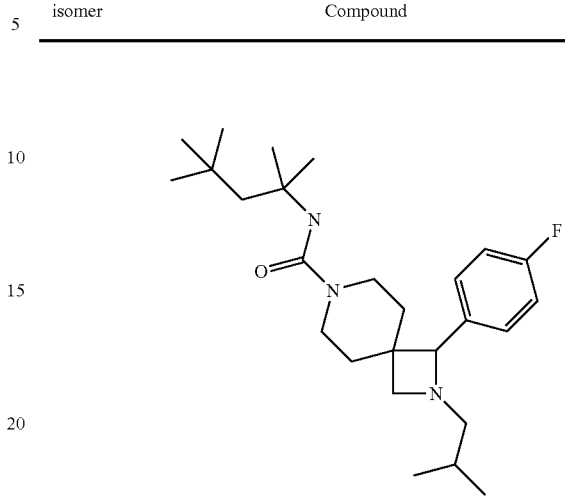 (106) |
|  | 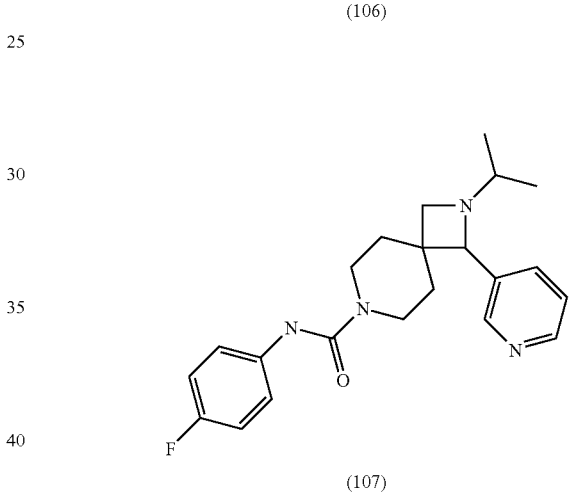 (107) |
Representative compounds of the invention include, for example, the compounds in Table 6 The compounds in Table 6 had a GPR119 cAMP $EC_{50}$ in the range of 516 to 13600 nM.
TABLE 6
| Compound |
|---|
| (108) 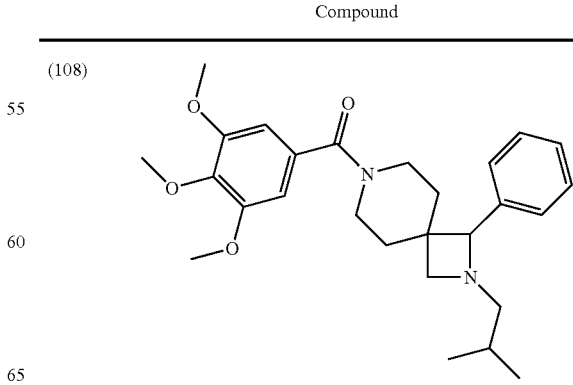 |

TABLE 6-continued
| Compound |
|---|
| (109) 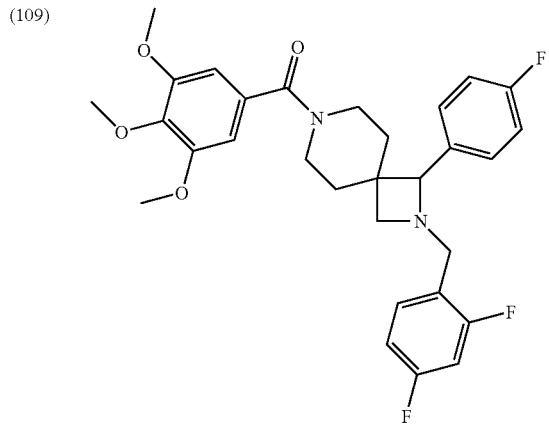 |
| (110) 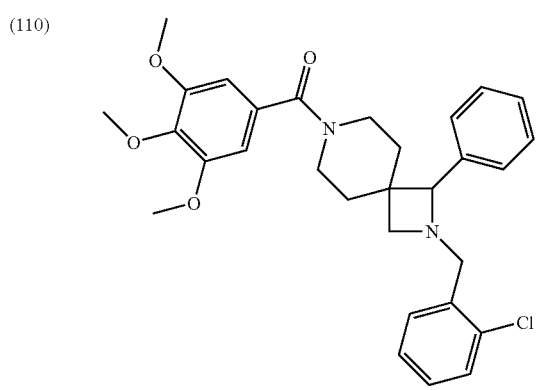 |
| (111) 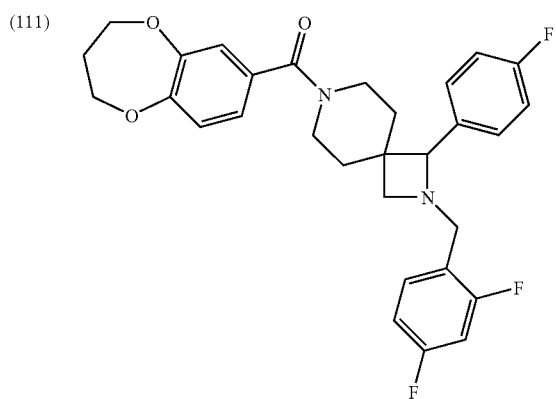 |
| (112) 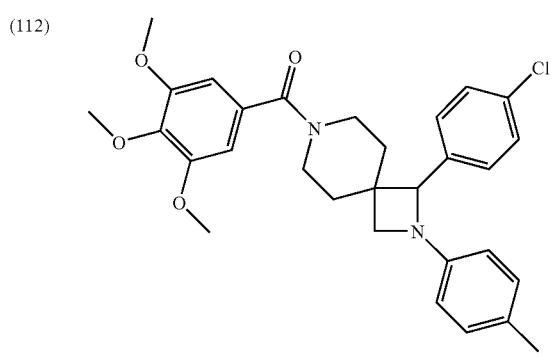 |
| (113) 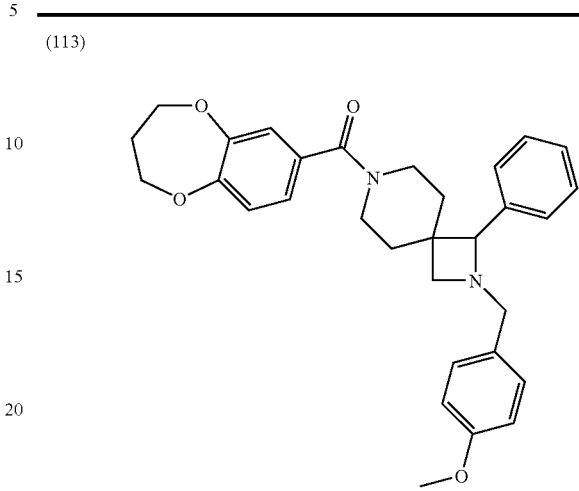 |
| (114) 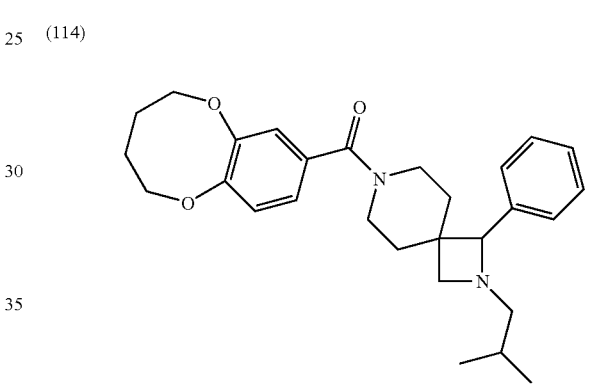 |
| (115) 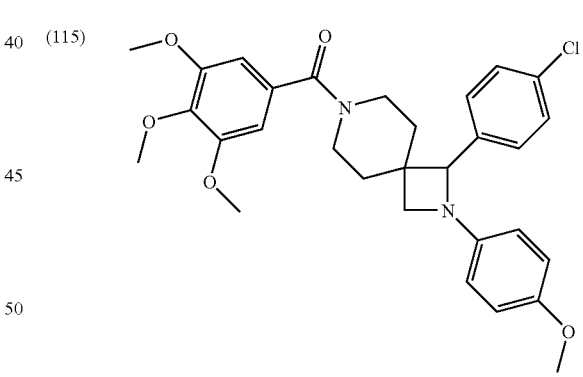 |
| (116) 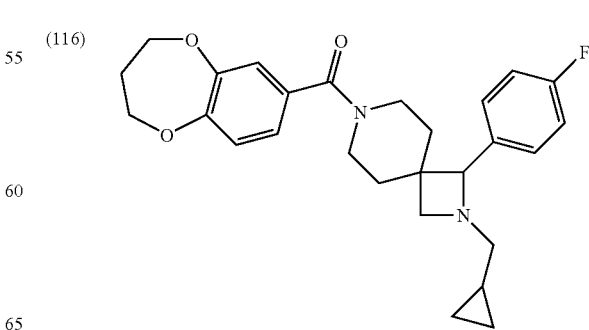 |

TABLE 6-continued
Compound
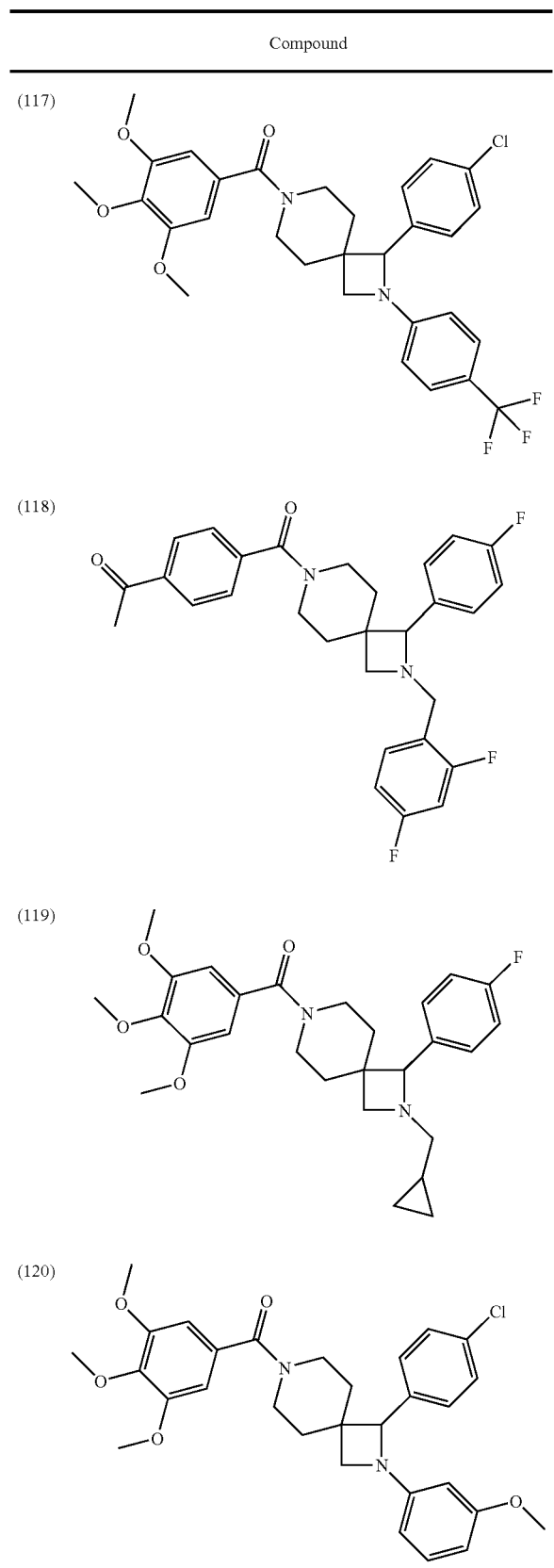
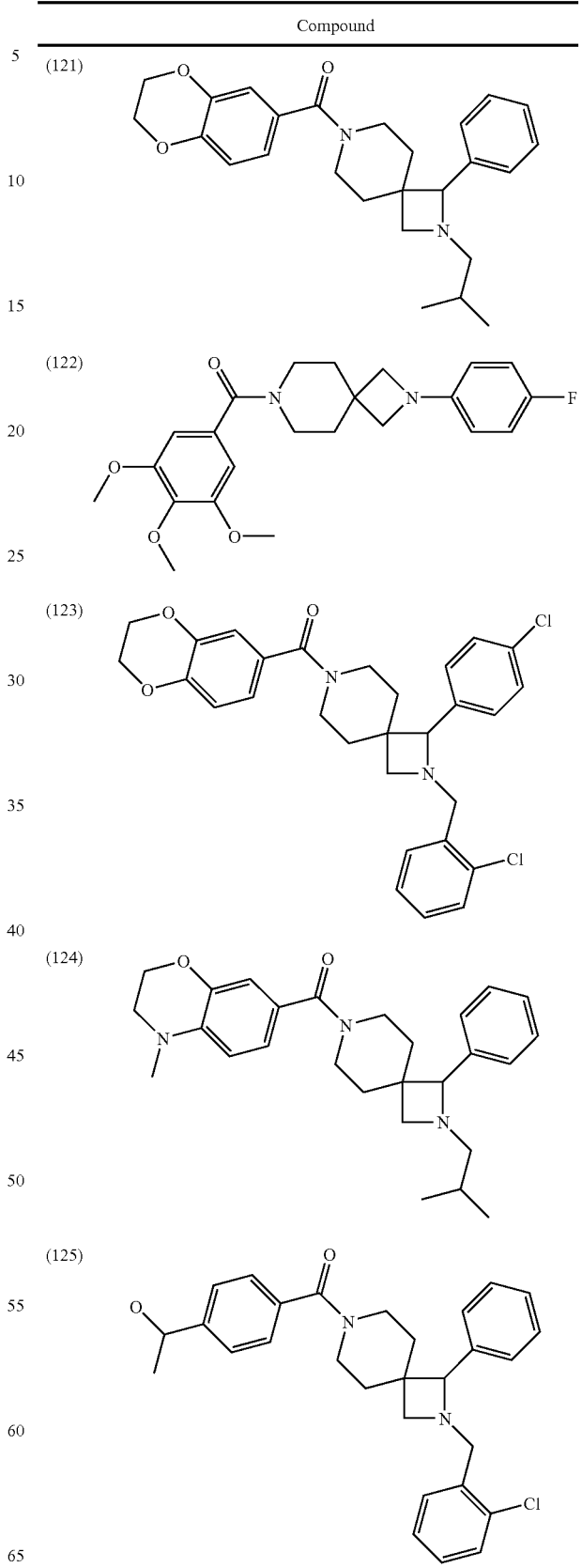

TABLE 6-continued

Compound (126)

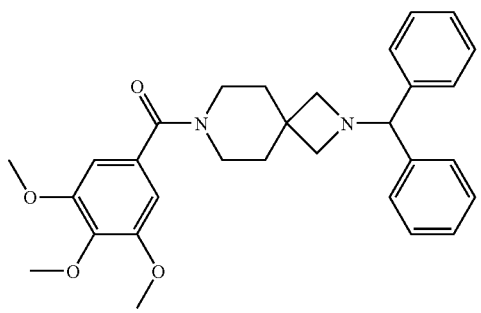

(127)

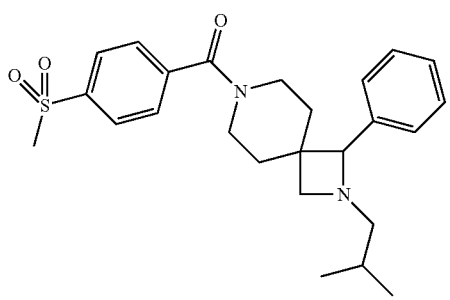

(128)

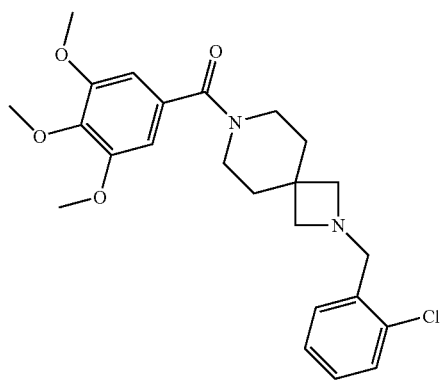

(129)

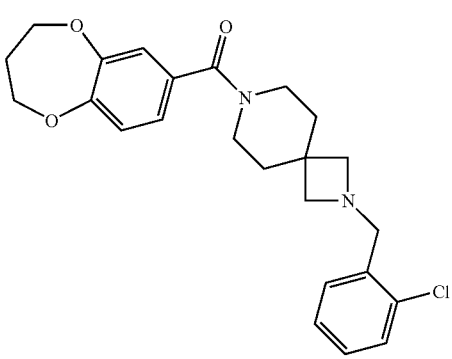

TABLE 6-continued

Compound (130)

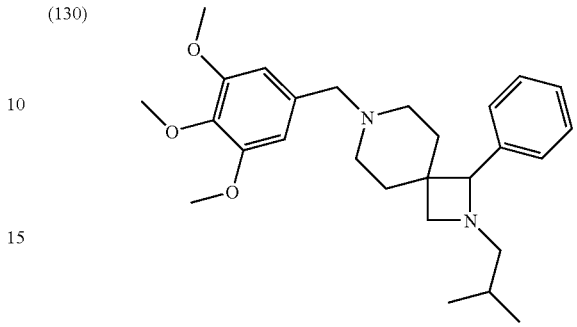

(131)

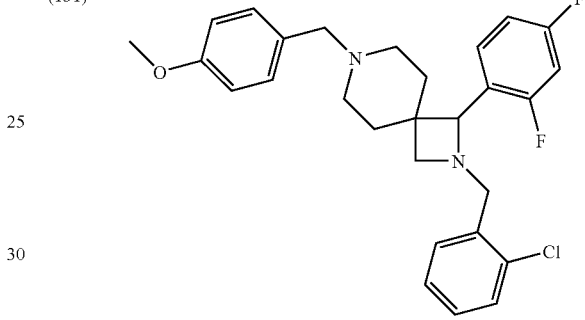

(141)

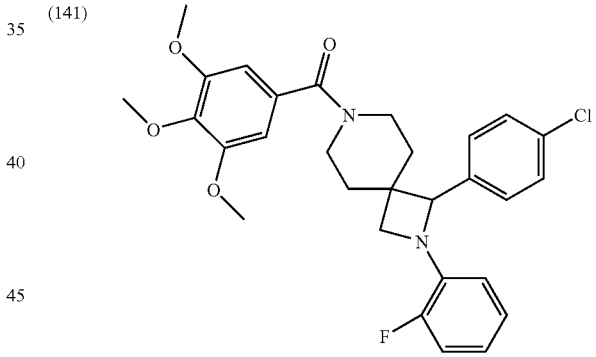

isomer A

As used above, and throughout this disclosure, the following terms, unless otherwise indicated, shall be understood to have the following meanings:

"At least one" compound of formula I means 1, 2, 3 or 4 different compounds, but preferably one compound of formula I is used in the claimed methods. Similarly, when "at least one" is used in connection with the additional agents used in the combinations, 1, 2, 3 or 4 additional agents are contemplated, but preferably one or two, more preferably one additional agent is used.

The "A" linker in the definition of $R^2$ and $R^{2a}$ is read from left to right, i.e., the left side is connected to the nitrogen of the spirocyclic-ring attached to the azetidinone, and the right side is connected to the $R^6$. For example when A is —C(O)—NH—, the partial structure is represented as

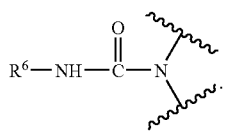

"Patient" includes both human and animals. A "patient" is a human or non-human mammal. In one embodiment, a patient is a human. In another embodiment, a patient is a non-human mammal, including, but not limited to, a monkey, dog, baboon, rhesus, mouse, rat, horse, cat or rabbit. In another embodiment, a patient is a companion animal, including but not limited to a dog, cat, rabbit, horse or ferret. In one embodiment, a patient is a dog. In another embodiment, a patient is a cat.

"PG" means protecting group.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched, Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkenylene" means a difunctional group obtained by removal of a hydrogen from an alkenyl group that is defined above. Non-limiting examples of alkenylene include —CH=CH—, —C(CH$_3$)=CH—, and —CH=CHCH$_2$—.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzothiadiazolyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Benzofused cycloalkyl", "benzofused cycloalkenyl", "benzofused heterocycloalkyl", and "benzofused heterocycloalkenyl" mean cycloalkyl, cycloalkenyl, heterocycloalkyl or heterocycloalkenyl rings fused to a benzene ring at two adjacent carbon atoms of the non-aromatic rings, for example:

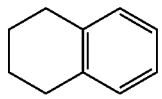 and 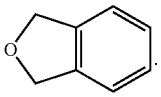

The rings are joined to the rest of the molecule by a bond to the non-aromatic ring.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —O—C(O)-alkyl, —O—C(O)-aryl, —O—C(O)-cycloalkyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system Examples of such moieties are —(CH$_2$)$_3$—, —(CH$_2$)$_4$—, —O—CH$_2$—O—, —O(CH$_2$)$_2$—O, —O(CH$_2$)$_3$—O, —NH—NH—NH—, —NH—S—NH—, —NH—O—NH—, or —NH—NH—C(O)—, and the like which form moieties such as, for example:

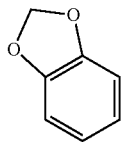 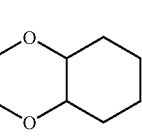 and

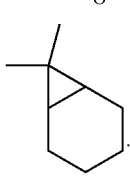

When R$^1$, R$^2$ and/or R$^3$ is an aryl or heteroaryl ring, the ring system substituent can also be a sugar, a polyol, a glucuronide or a sugar carbamate.

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" or "heterocycloalkyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 or 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" or "heterocycloalkyl" may also be substituted by a moiety which simultaneously replaces two available hydrogens on the same carbon atom on a ring system (e.g., carbonyl). An example of such moiety is:

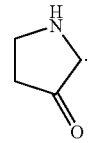

"Heterocyclylalkyl" or "heterocycloalkylalkyl" means a heterocyclyl moiety as defined above linked via an alkyl moiety (defined above) to a parent core. Non-limiting examples of suitable heterocyclylalkyl include piperidinylmethyl, piperazinylmethyl and the like.

"Heterocyclenyl" or "heterocycloalkenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain 5 to 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluorodihydrofuranyl, 7-oxabicyclo[2.2.1]heptenyl, dihydrothiophenyl, dihydrothiopyranyl, and the like. "Heterocyclenyl" may also be substituted by a moiety which simultaneously replaces two available hydrogens on the same carbon atom on a ring system (e.g., carbonyl). An example of such moiety is:

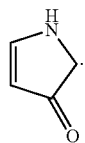

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

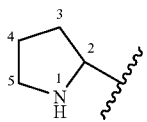

there is no —OH attached directly to carbons marked 2 and 5.

It should also be noted that tautomeric forms such as, for example, the moieties:

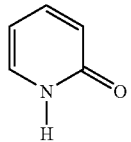 and 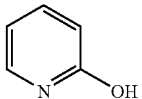

are considered equivalent in certain embodiments of this invention.

"Heteroaralkyl" or "heteroarylalkyl" means a heteroarylalkyl- group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl- group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S(O$_2$)— group. Preferred groups are those in which the alkyl group is lower alkyl. The bond to the parent moiety is through the sulfonyl.

"Arylsulfonyl" means an aryl-S(O$_2$)— group. The bond to the parent moiety is through the sulfonyl.

"Polyol" means a compound or residue having a plurality of —OH groups; in particular, polyols are alkyl groups in which a plurality of C—H bonds are replaced by C—OH bonds. Typical polyols include glycerol, erythritol, sorbitol, xylitol, mannitol, and inositol. Linear polyol residues generally have the empirical formula —C$_y$H$_{2y+1}$O$_y$, and cyclic polyol residues generally have the formula —C$_y$H$_{2y-1}$O$_y$— Polyols wherein y is 3, 4, 5 or 6 are preferred. Cyclic polyols also include reduced sugars such as glucitol.

"Sugar" means a carbohydrate comprised of one or two saccharose groups. Monosaccharide sugars, also known as simple sugars, are composed of chains of 2-7 carbon atoms, wherein one of the carbons carries aldehydic or ketonic oxygen, which may be combined in acetal or ketal forms. The remaining carbons usually have hydrogen atoms and hydroxyl groups, or protecting groups for hydroxyl, such as acetate. Typical monosaccharides considered "sugars" in the present invention are arabinose, ribose, xylose, xylulose, deoxyribose, galactose, glucose, mannose, fructose, sorbose, tagatose, fucose, quinovose, rhamnose, manno-heptulose and sedoheptulose. Typical disaccharides are sucrose, lactose, maltose and cellobiose. Unless specifically modified, the term "sugar" refers to both D-sugars and L-sugars. The sugar may be protected. The sugar can be attached through an oxygen or a carbon.

Reduced C-attached sugars or C-glycosyl compounds are also encompassed by the invention. The reduced sugars (e.g., glucitol) can be classified as either polyols or sugars, and are also known as alditols. Alditols are polyols having the general formula $HOCH_2[CH(OH)]_xCH_2OH$.

"Glucuronide" means a glycoside of glucuronic acid.

"Sugar carbamate" means a mono-, di- or oligo-saccharide in which one or more hydroxyl groups are derivatized as carbamates, particularly as phenyl carbamates or substituted phenyl carbamates.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound after being obtained from a purification process or processes described herein or well known to the skilled artisan (e.g., chromatography, recrystallization and the like), in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I or IIA, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press, The term "prodrug" means a compound (e.g., a drug precursor) that is transformed in vivo to yield a compound of Formula (I) or (IIA) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula I or IIA or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)-aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$(C_1-C_2)$alkylamino$(C_2-C_3)$alkyl (such as β-dimethylaminoethyl), carbamoyl-$(C_1-C_2)$alkyl, N,N-di $(C_1-C_2)$alkylcarbamoyl-(C1-C2)alkyl and piperidino-, pyrrolidino- or morpholino$(C_2-C_3)$ alkyl, and the like.

Similarly, if a compound of Formula I or IIA contains an alcohol functional group, a prodrug can be formed by the replacement of the hydrogen atom of the alcohol group with a group such as, for example, $(C_1-C_6)$alkanoyloxymethyl, 1-$((C_1-C_6)$alkanoyloxy)ethyl, 1-methyl-1-$((C_1-C_6)$alkanoyloxy)ethyl, $(C_1-C_6)$alkoxycarbonyloxymethyl, N—$(C_1-C_6)$ alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula I or IIA incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$alkyl, $(C_3-C_7)$ cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N—$(C_1-C_6)$alkylaminoalkyl, —$C(Y^4)Y^5$ wherein $Y^4$ is H or methyl and $Y^5$ is mono-N— or di-N,N—$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.,* 93 (3), 601-611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.,* 5 (1), article 12 (2004); and A. L. Bingham et al., *Chem. Commun.,* 603-604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I or IIA can form salts which are also within the scope of this invention. Reference to a compound of Formula I or IIA herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I or IIA contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I or IIA may be formed, for example, by reacting a compound of Formula I or IIA with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates), and the like. Additionally, acids which are generally considered suitable for the formation of pharmaceutically useful salts from basic pharmaceutical compounds are discussed, for example, by P. Stahl et at, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66 (1) 1-19; P. Gould, *International J. of Pharmaceutics* (1986) 33 201-217; Anderson et al, *The Practice of Medicinal Chemistry* (1996), Academic Press, New York, and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino), (2) sulfonate esters, such as alkyl or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

Compounds of Formula I or IIA, and salts, solvates, esters and prodrugs thereof, may exist in their tautomeric form (for example, as an amide or imino ether). All such tautomeric forms are contemplated herein as part of the present invention.

The compounds of Formula I or IIA may contain asymmetric or chiral centers, and, therefore, exist in different stereoisomeric forms. It is intended that all stereoisomeric forms of the compounds of Formula I or IIA as well as mixtures thereof, including racemic mixtures, form part of the present invention. In addition, the present invention embraces all geometric and positional isomers. For example, if a compound of Formula I or IIA incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula I may be atropisomers (e.g., substituted biaryls) and are considered as part of this invention. Enantiomers can also be separated by use of chiral HPLC column.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula I or IIA incorporates a double bond or a fused ring, both the cis- and trans-forms, as well as mixtures, are embraced within the scope of the invention. Also, for example, all keto-enol and imine-enamine forms of the compounds are included in the invention).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula I or IIA (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their ease of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labelled compounds of Formula I or IIA can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I or IIA, and of the salts, solvates, esters and prodrugs of the compounds of Formula for IIA, are intended to be included in the present invention.

Those skilled in the art will appreciate that for some of the compounds of Formula I, one isomer will show greater pharmacological activity than other isomers.

One to three compounds of formula I or IIA can be administered in the methods of the invention, preferably one.

For preparing pharmaceutical compositions from the compounds described for use in the methods of this invention, inert, pharmaceutically acceptable carriers can be either solid or liquid. Solid form preparations include powders, tablets, dispersible granules, capsules, cachets and suppositories. The powders and tablets may be comprised of from about 5 to about 70 percent active ingredient. Suitable solid carriers are known in the art e.g. magnesium carbonate, magnesium stearate, talc, sugar, lactose. Tablets, powders, cachets and capsules can be used as solid dosage forms suitable for oral administration.

For preparing suppositories, a low melting wax such as a mixture of fatty acid glycerides or cocoa butter is first melted, and the active ingredient is dispersed homogeneously therein as by stirring. The molten homogeneous mixture is then poured into convenient sized molds, allowed to cool and thereby solidify.

Liquid form preparations include solutions, suspensions and emulsions. As an example may be mentioned water or water-propylene glycol solutions for parenteral injection.

Liquid form preparations may also include solutions for intranasal administration.

Aerosol preparations suitable for inhalation may include solutions and solids in powder form, which may be in combination with a pharmaceutically acceptable carrier, such as an inert compressed gas.

Also included are solid form preparations which are intended to be converted, shortly before use, to liquid form preparations for either oral or parenteral administration. Such liquid forms include solutions, suspensions and emulsions.

The compounds for use in the present invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound of formula I or IIA is administered orally.

Preferably, the pharmaceutical preparation is in unit dosage form. In such form, the preparation is subdivided into unit doses containing appropriate quantities of the active component, e.g., an effective amount to achieve the desired purpose.

The quantity of active compound of formula I or IIA in a unit dose of preparation may be varied or adjusted from about 0.1 mg to 1000 mg, more preferably from about 1 mg to 300 mg, according to the particular application.

The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small increments until the optimum effect under the circumstances is reached. For convenience, the total daily dosage may be divided and administered in portions during the day if desired.

The amount and frequency of administration of the compounds of formula I or IIA will be regulated according to the judgment of the attending clinician considering such factors as age, condition and size of the patient as well as severity of the symptoms being treated. A typical recommended dosage regimen for compounds of formula I or IIA is oral administration of from 10 mg to 2000 mg/day preferably 10 to 1000 mg/day, in two to four divided doses to provide relief from the diseases or conditions listed above.

The doses and dosage regimen of the other agents used in the treatment of diseases or conditions listed above will be determined by the attending clinician in view of the approved doses and dosage regimen in the package insert, taking into consideration the age, sex and condition of the patient and the severity of the disease. When administered in combination, the compound(s) of formula I or IIA and the other agent(s) for treating diseases or conditions listed above can be administered simultaneously or sequentially. This is particularly useful when the components of the combination are preferably given on different dosing schedules, e.g., one component is administered once daily and another every six hours, or when the preferred pharmaceutical compositions are different, e.g. one is preferably a tablet and one is a capsule. A kit comprising the separate dosage forms is therefore advantageous.

Additional agents useful for treating pain include non-opioid (also known as non-steroidal anti-inflammatories) analgesics such as acetylsalicylic acid, choline magnesium trisalicylate, acetaminophen, ibuprofen, fenoprofen, diflusinal, and naproxen; opioid analgesics such as morphine, hydromorphone, methadone, levorphanol, fentanyl, oxycodone, and oxymorphone; steroids such as prednisolone, fluticasone, triamcinolone, beclomethasone, mometasone, budisamide, betamethasone, dexamethasone, prednisone, flunisolide and cortisone; COX-I inhibitors such as aspirin and piroxicam; COX-II inhibitors such as rofecoxib, celecoxib, valdecoxib and etoricoxib; agents useful for treating inflammatory bowel disease such as IL-10, steroids, and azulfidine; and agents useful for treating rheumatoid arthritis such as methotrexate, azathioprine, cyclophosphamide, steroids and mycophenolate mofetil.

Especially preferred agents for treating neuropathic pain are opioid and non-opioid analgesics, including acetylsalicylic acid, choline magnesium trisalicylate, acetaminophen, ibuprofen, fenoprofen, diflusinal, naproxen, morphine, hydromorphone, methadone, levorphanol, fentanyl, oxycodone, and oxymorphone. Especially preferred agents for treating inflammatory pain are steroids and non-opioid analgesic agents.

Examples of the drugs for use in combination with compounds of formula I or IIA for treating Type II diabetes include sulfonylureas, insulin sensitizers (such as PPAR agonists, DPPIV inhibitors, PTP-1B inhibitors and glucokinase activators), α-glucosidase inhibitors, insulin secretagogues, hepatic glucose output lowering compounds, and insulin.

The activators or agonists of PPAR are discussed above Non-limiting examples of sulfonylurea drugs include glipizide, tolbutamide, glyburide, glimepiride, chlorpropamide, acetohexamide, gliamilide, gliclazide, glibenclamide and tolazamide. Insulin sensitizers include PPAR-γ agonists described in detail above, preferably troglitazone, rosiglitazone, pioglitazone and englitazone; biguanidines such as metformin and phenformin; DPPIV inhibitors such as sitagliptin, saxagliptin, denagliptin and vildagliptin; PTP-1B inhibitors; and glucokinase activators. α-Glucosidase inhibitors that can be useful in treating type II diabetes include miglitol, acarbose, and voglibose. Hepatic glucose output lowering drugs include Glucophage and Glucophage XR. Insulin secretagogues include sulfonylurea and non-sulfonylurea drugs such as GLP-1, exendin, GIP, secretin, glipizide, chlorpropamide, nateglinide, meglitinide, glibenciamide, repaglinide and glimepiride. Insulin includes all formulations of insulin, including long acting and short acting forms of insulin.

Compounds of the invention may be administered in combination with anti-obesity agents for the treatment of diabetes. Examples of anti-obesity agents include CB1 antagonists or inverse agonists such as rimonabant, neuropeptide Y antagonists, MCR4 agonists, MCH receptor antagonists, histamine H3 receptor antagonists or inverse agonists, leptin, appetite suppressants such as sibutramine, and lipase inhibitors such as xenical.

For treating diabetes, compounds of the invention may also be administered in combination with antihypertensive agents, for example β-blockers and calcium channel blockers (for example diltiazem, verapamil, nifedipine, amlopidine, and mybefradil), ACE inhibitors (for example captopril, lisinopril, enalapril, spirapril, ceranopril, zefenopril, fosinopril, cilazopril, and quinapril), AT-1 receptor antagonists (for example losartan, irbesartan, and valsartan), renin inhibitors and endothelin receptor antagonists (for example sitaxsentan).

Certain meglitinide drugs lower blood glucose levels by stimulating the release of insulin from the pancreas. This action is dependent upon functioning β cells in the pancreatic islets Insulin release is glucose-dependent and diminishes at low glucose concentrations. The meglitinide drugs close ATP-dependent potassium channels in the β cell membrane by binding at characterizable sites. This potassium channel blockade depolarizes the β cell, which leads to an opening of calcium channels. The resulting increased calcium influx induces insulin secretion. Non-limiting examples of suitable meglitinide drugs include repaglinide and nateglinide.

Non-limiting examples of suitable antidiabetic medications that sensitize the body to the insulin that is already present include certain biguanides and certain glitazones or thiazolidinediones. Certain suitable biguanides lower blood sugar by decreasing hepatic glucose production, decreasing intestinal absorption of glucose and improving insulin sensitivity (increasing peripheral glucose uptake and utilization). A non-limiting example of a suitable biguanide is metformin. Non-limiting examples of metformin include metformin hydrochloride (N,N-dimethylimidodicarbonimidic diamide hydrochloride, such as GLUCOPHAGE® Tablets from Bristol-Myers Squibb); metformin hydrochloride with glyburide, such as GLUCOVANCE™ Tablets from Bristol-Myers Squibb); buformin.

Non-limiting examples of antidiabetic medications that slow or block the breakdown of starches and certain sugars and are suitable for use in the compositions of the present invention include alpha-glucosidase inhibitors and certain peptides for increasing insulin production. Alpha-glucosidase inhibitors help the body to lower blood sugar by delaying the digestion of ingested carbohydrates, thereby resulting in a smaller rise in blood glucose concentration following meals. Non-limiting examples of suitable alpha-glucosidase inhibitors include acarbose; miglitol; camiglibose; certain polyamines as disclosed in WO 01/47528 (incorporated herein by reference); voglibose. Non-limiting examples of suitable peptides for increasing insulin production including amlintide (CAS Reg. No. 122384-88-7 from Amylin; pramlintide, exendin, certain compounds having Glucagon-like peptide-1 (GLP-1) agonistic activity as disclosed in WO 00/07617 (incorporated herein by reference).

Non-limiting examples of additional antidiabetic medications include orally administrable insulin. Non-limiting examples of suitable orally administrable insulin or insulin containing compositions include AL-401 from AutoImmune, and certain compositions as disclosed in U.S. Pat. Nos. 4,579,730; 4,849,405; 4,963,526; 5,642,868; 5,763,396; 5,824,638; 5,843,866; 6,153,632; 6,191,105; and WO 85/05029 (each of which is incorporated herein by reference).

The antidiabetic medications are administered in a therapeutically effective amount to treat the specified condition, for example in a daily dose preferably ranging from about 1 to about 3000 mg per day, and more preferably about 50 to about 2000 mg per day, given in a single dose or 2-4 divided doses. The exact dose, however, is determined by the attending clinician and is dependent on such factors as the potency of the compound administered, the age, weight, condition and response of the patient.

General Methods

The general methods described in this paragraph were used unless stated otherwise in the examples below. All solvents and reagents were used as received. Proton NMR spectra were obtained using a Varian XL-400 (400 MHz) instrument and were reported as parts per million (ppm) downfield from $Me_4Si$. LCMS analysis was performed using an Applied Biosystems API-100 mass spectrometer equipped with a Shimadzu SCL-10A LC column: Altech platinum C18, 3 um, 33 mm×7 mm ID; gradient flow: 0 min, 10% $CH_3CN$; 5 min, 95% $CH_3CN$; 7 min, 95% $CH_3CN$; 7.5 min, 10% $CH_3CN$; 9 min, stop. Flash column chromatography was performed using Selecto Scientific flash silica gel, 32-63 mesh Analytical and preparative TLC was performed using Analtech Silica gel GF plates. Chiral HPLC was performed using a Varian PrepStar system equipped with a Chiralpak OD column (Chiral Technologies).

In the Schemes and examples that follow, the following abbreviations are used: Ac (acetyl); Me (methyl); Et (ethyl); Ph (phenyl); Bn (benzyl); Boc (tert-butoxycarbonyl); DCE (dichloroethane); DMSO ($d_6$-dimethylsulfoxide); DIPEA (diisopropylethylamine); Dioxane (1,4-dioxane); EtOAc (ethyl acetate); EtOH (ethanol); Ether (diethyl ether); HOBT (1-hydroxybenzotriazole hydrate); IPA (isopropyl alcohol); LCMS (liquid chromatography mass spectrometry); LDA (lithium diisopropylamide); LHMSD (lithium bis(trimethylsilyl)amide); MeOH (methanol); RT (Room temperature, about 25° C.); $SiO_2$ (silica gel for flash chromatography); TFA (trifluoroacetic acid); TLC (thin layer chromatography); THF (tetrahydrofuran).

The compounds of the invention can be made according to the processes described below. The compounds of this invention are also exemplified in the examples below, which examples should not be construed as limiting the scope of the disclosure. Alternative mechanistic pathways and analogous structures within the scope of the invention may be apparent to those skilled in the art.

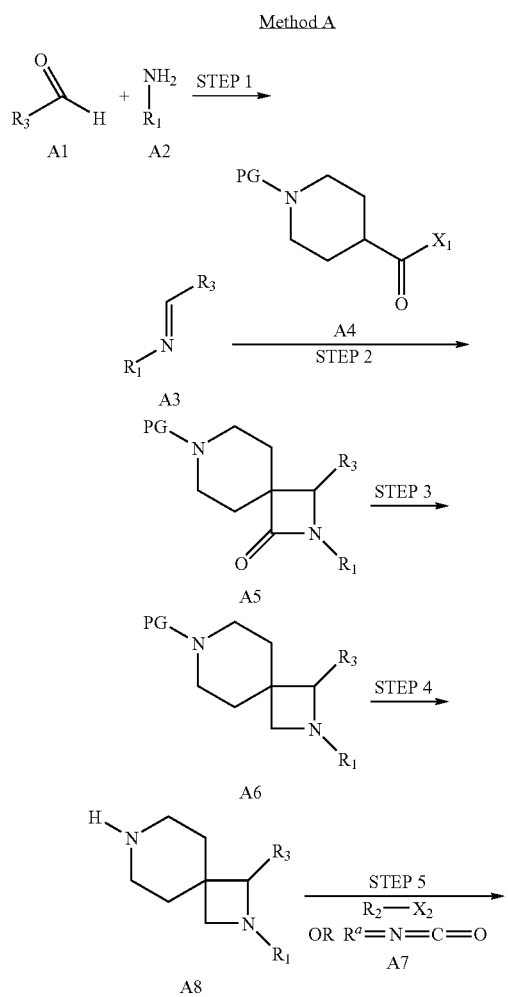

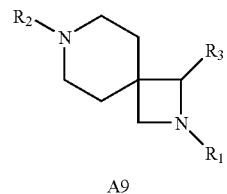

Compounds of formula A1 in a solvent such as toluene or isopropanol can be treated with a compound of formula A2 to provide a compound of formula A3. A Compound of formula A4 (where X1 is a halogen or alkoxy group such as OEt) can be treated with a base such as LDA or LHMDS at −78° C. followed by compound of formula A3 at room temperature to provide compound of formula A5. A Compound of formula A5 can be converted into compound of formula A6 by treatment with reagents such as LiAlH4/AlCl3, diborane or a mixture of diphenylsilane and hydridocarbonyltris(triphenylphosphine) rhodium to reduce the lactam carbonyl. Removal of the protecting group from A6 (for example where PG=Boc, by the treatment with HCl-dioxane) provides A8. which by the treatment with compound of formula A7 (where for example, R2-X2 can be a carboxylic acid, an alkyl or aryl halide) or an isocyanate in the presence of an appropriate base or coupling agent such as a carbodimide as needed is converted into compounds of formula A9.

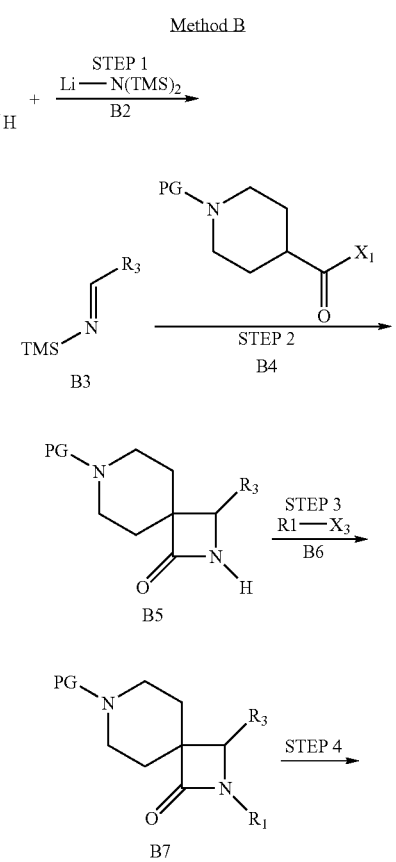

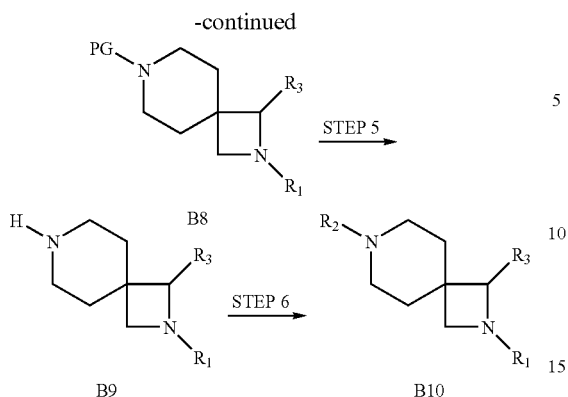

Compound of formula B1 can be treated with a compound of formula B2 to provide compound of formula B3. Compound of formula B4 can be treated with a base such as LDA or LHMDS at −78° C. followed by treatment with a compound of formula B3 at room temperature to provide compound of formula B5. Compound of formula B6 (where X3 is a leaving group such as halogen or triflate, for example) can be converted into a compound of formula B7 by the treatment with a compound of formula B5 and a base such as NaH. Compound B7 is then reduced with reagents such as LiAlH, LiAH4/AlCl3, diborane or a mixture of diphenylsilane and hydridocarbonyltris(triphenylphosphine) rhodium to provide compound B8, which is elaborated into B9 and B10 following the procedures of step 4 and step 5 in Method A.

One skilled in the art will appreciate that by replacing the starting materials A4, or B4 with rings of different sizes will provide access to compounds such as:

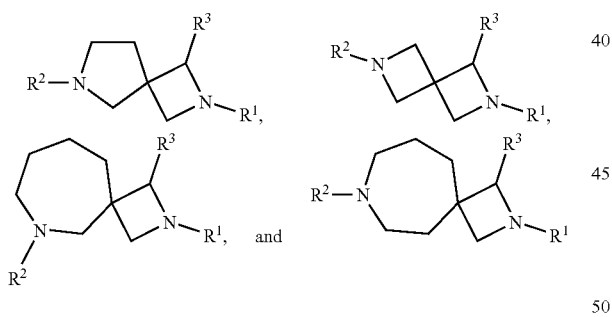

EXAMPLE 1

Preparation of 1-(4-Chlorophenyl)-N-cycloheptyl-2-isopropyl-2,7-diazaspiro[3.5]nonane-7-carboxamide, Hydrochloride

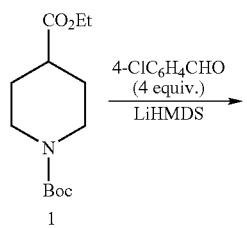

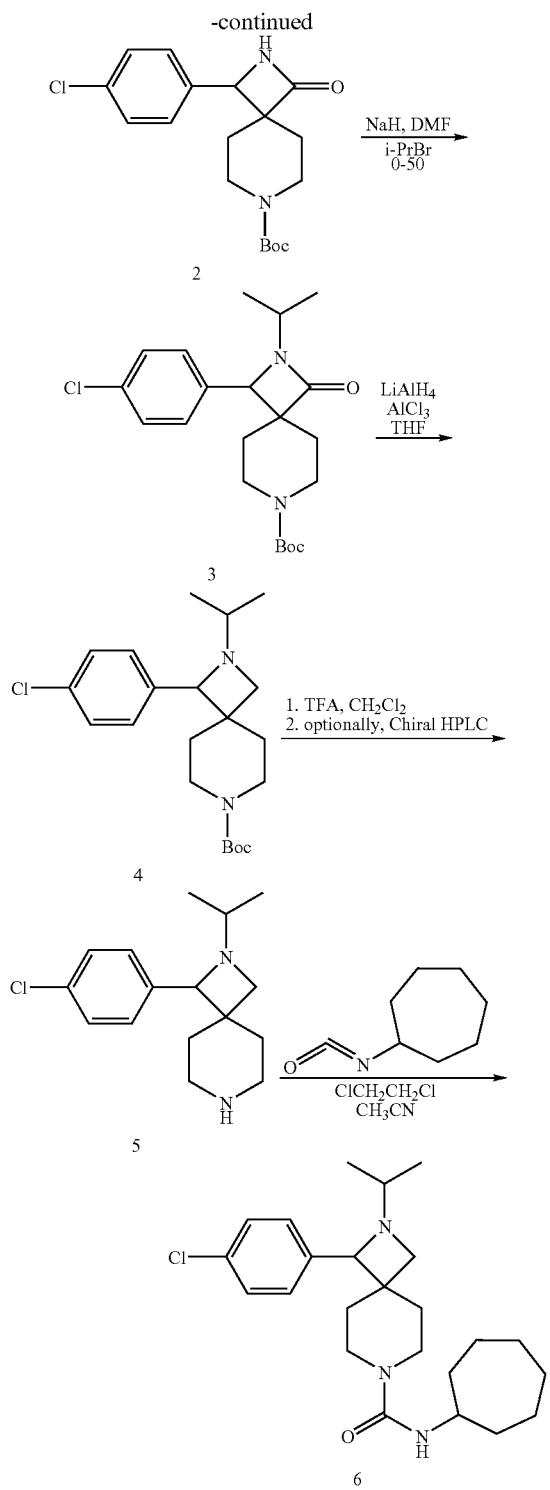

Step A: Preparation of 1,1-Dimethylethyl 1-oxo-3-(4-chlorophenyl)-2,7-diazaspiro[3.5]nonane-7-carboxylate (2)

In a dry 250 mL, 3-necked flask, add 4-chlorobenzaldehyde (6-51 g) and dry THF (20 mL) and cool to −30 C. Add 1M lithium bis(trimethylsilyl)amide in THF (47 mL) dropwise keeping the temperature at ~30 C. Then, warm the reaction mixture to 0 C for 30 min. (Solution A)

In a dry 250 mL flask, under a nitrogen atmosphere, add diisopropylamine (6.1 mL) and dry THF (10 mL) and cool to 0 C. Add 2.5 M n-butyl lithium in hexane (17.4 mL, 43.5 mmole) dropwise and let stir at −60 C for 25 min. Then, add a solution of ethyl 1-tert-butoxycarbonylpiperidine-4-carboxylate (1) (9.3 g) in dry THF (10 mL) dropwise maintaining the temperature at −65 to −55 C for 90 min. (Solution B) Add solution A to solution B dropwise maintaining temperature at −55 to −65 C for 2.5 h. Warm to RT and stir overnight. Quench with sat, NH$_4$Cl (50 mL) dropwise at 25-30 C. Partition with EtOAc. Concentrate the dried (MgSO4) EtOAc solution in vacuo to give an amber foam (14.72 g). Dissolve the amber foam in EtOAc (15 mL) at ~55° C. Add hexane (3×10 mL) and let stand overnight. Collect the crystals and dry in a vacuum oven to give the title compound as a yellow solid (7.67 g).

Step B: Preparation of 1,1-Dimethylethyl 1-oxo-3-(4-chlorophenyl)-2-isopropyl-2,7-diazaspiro[3.5]nonane-7-carboxylate (3)

In a dry 100 mL 3-necked flask, add 1,1-dimethylethyl 1-oxo-3-(4-chlorophenyl) -2,7-diazaspiro[3.5]nonane-7-carboxylate (7.0 g) and dry DMF (50 mL) and cool to ~2 C. Add portionwise sodium hydride in 60% oil dispersion (1.10 g) keeping temperature at 2-5 C. After 5 min., add portionwise 2-bromopropane (2.6 mL) keeping temperature 3 to 8° C. Warm mixture to 50° C. After 4.5 h, cool to ~20° C. and add ice water (400 mL). Extract with EtOAc (2×499 mL). Extract EtOAc with brine (50 mL). Concentrate the dried (MgSO$_4$) EtOAc in vacuo to give the title compound as an amber oil (8.80 g). Add EtOAc:hexane (1:2, 20 mL) and keep overnight at RT to give the title compound as a yellow solid (5.75 g).

Step C: Preparation of 1,1-Dimethylethyl 1-(4-chlorophenyl)-2-isopropyl-2,7-diazaspiro[3.5]nonane-7-carboxylate (4)

Under a nitrogen atmosphere, in a dry 500 mL 3-necked flask, add LiAlH4 (0.87 g) and THF (dried over Mol sieves) (96 mL) and cool to 10 C (ice bath). Add AlCl3 (3.33 g) portionwise keeping the temperature at ~10 C. Heat to 50-60 C for 30 min., then cool to −40 to −50 C, Add 1,1-dimethylethyl 1-oxo-3-(4-chlorophenyl)-2-isopropyl-2,7-diazaspiro[3.5]nonane-7-carboxylate (5.75 g in dry THF (150 mL). Warm the reaction mixture to −20 C and monitor at 15 min intervals until starting material is gone (~60 min.). At −30 C, quench the reaction mixture at ~−30 C with 10% NaOH, then warm to room temperature. Extract with diethyl ether (2×300 mL). Extract the diethyl ether with brine, Concentrate the dried (MgSO4) Et2O in vacuo to give the title compound as a viscous oil (9.79 g). Add EtOAc (5 mL) and hexane (25 ml) and let stand at RT to give the title compound as a white solid (0.031 g). Filtrate (4.47 g) in EtOAc (30 mL) and hexane (30 mL) gave additional compound (3.56 g) which was placed on an Analogix system: Column of silica gel (115 g) and eluted with hexane/EtOAc, 20 mL fractions collected. Concentration of fraction 54-145 gave the title compound (2.94 g) as a white solid.

Step D: Preparation of 1-(4-Chlorophenyl)-2-isopropyl-2,7-diazaspiro[3.5]nonane (5)

Under a nitrogen atmosphere, treat 1,1-dimethylethyl 1-(4-chlorophenyl)-2-isopropyl-2,7-diazaspiro[3.5]nonane-7-carboxylate (2.74 g) in dry CH$_2$Cl$_2$ (10 mL) with trifluoroacetic acid (2×5 mL) at RT for 45 min. Concentrate the reaction mixture in vacuo. Add CH$_2$Cl$_2$ (10 mL) and concentrate in vacuo (three times) to give a viscous colorless oil (5.76 g). Partition this oil between CH$_2$Cl$_2$ and 1N NaOH. Concentrate the dried (MgSO$_4$) CH$_2$Cl$_2$ solution in vacuo to give the title compound (1.37 g) as a viscous oil.

Step E: Separation of 1-(4-Chlorophenyl)-2-isopropyl-2,7-diazaspiro[3.5]nonane (5) Isomer A and (5) Isomer B

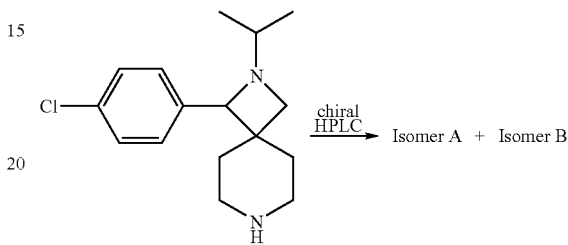

A racemic mixture of N-[[1-(4-chlorophenyl)-2-isopropyl-2,7-diazaspiro[3.5]nonane (0.50 g) was dissolved in isopropanol (1 mL) hexane (3 mL) was separated by HPLC on a Chiralpak OD column with 1% diethylamine in hexane/isopropanol 90/10 (75 mL/min) to give Isomer A (16.8 min.) and isomer B (45.1 min.) which upon evaporation of the solvent gave a white solids (0.22 grams of each).

| Ex. No. | Structure | MW |
|---|---|---|
| 1.1 | Isomer A | 278.8 |
| 1.2 | Isomer B | 278.8 |

Step F: Preparation of 1-(4-Chlorophenyl) N-cycloheptyl-2-isopropyl-2,7-diazaspiro[3.5]nonane-7-carboxamide, Hydrochloride (6)

Treat 1-(4-Chlorophenyl)-2-isopropyl-2,7-diazaspiro[3.5]nonane, Isomer A (0.015 g) in ClCH$_2$CH$_2$Cl (1 mL) and acetonitrile (1 mL) with cycloheptyl isocyanate (18 uL), and the resulting mixture stirred at RT for 424 h. P—S Trisamine (Argoonaut, 4.64 mmol/g) (120 g) and ClCH₂CH₂Cl (2 mL) were added and the resulting mixture was shaken to 20 h. The reaction mixture was filtered, the resin washed with CH2Cl2 (2 mL). The resulting filtrate was concentrated in vacuo and then placed on a silica gel plate (1000 u) and eluted with CH$_2$Cl$_2$:MeOH (95:5) to give of 1-(4-chlorophenyl)-2-isopropyl-2,7-diazaspiro[3.5]nonane-7-carboxamide, white residue (0.0208 g). Add MeOH (0.5 mL) and 0.1N HCl in MeOH (1 mL), and concentrate in vacuo to give the title compound, as a white solid (0.0222 g).

EXAMPLE 2

Preparation of 1,1-Dimethylethyl 1-(4-chlorophenyl)-2-cyclopropyl-2,7-diazaspiro[3.5]nonane-7-carboxylate (10)

Step A: Preparation of 1,1-Dimethylethyl 1-oxo-3-(4-chlorophenyl)-2-cyclopropyl-2,7-diazaspiro[3.5]nonane-7-carboxylate (9)

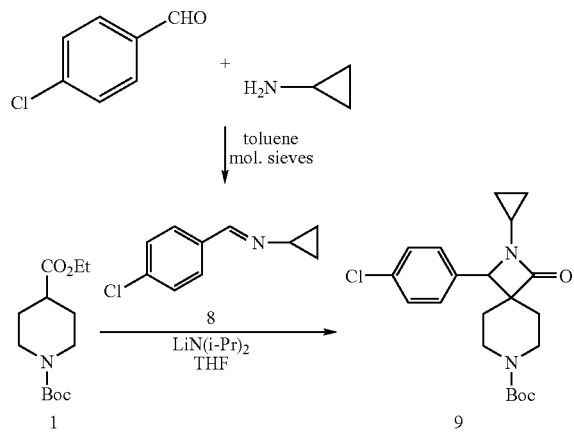

Under a nitrogen atmosphere, react 4-chlorobenzaldehyde (14.0 g) and cyclopropylamine (5.7 g) in anhydrous toluene (50 mL) in the presence of molecular sieves for 48 h. Filter the reaction mixture and concentrate the filtrate in vacuo at 60 C to give 4-chlorobenzylidene cyclopropylamine (By as a crystalline solid (15.98 g).

Cool to 0 to −10 C, a solution of diisopropylamine (6.0 mL) in THF (10 mL) and add n-butyllithium (2.5 M, 16.6 mL) dropwise. After 1 h, the reaction mixture was cooled to −78 C. Add a solution of ethyl 1-tert-butoxycarbonylpiperidine-4-carboxylate (1) (10 g) in anhydrous THF (20 mL) dropwise, and stir the resulting solution at −78 C for 1.5 h. Add 4-chlorobenzylidene cyclopropylamine (8) (6.69 g) in THF (40 mL) and stir for 1 h. Warm the reaction mixture to room temperature and stir overnight. Quench the reaction mixture with saturated ammonium chloride solution and extract with EtOAc. Partition the EtOAc solution with 1N HCl, then salt solution. Concentrate the dried (MgSO4) EtOAc solution in vacuo to give an amber oil (13.83 g). Absorb the amber oil (12.8 g) on Purasil 60A 230-400 mesh (~30 mL), place in a syringe cartridge, and elute onto a Redi Sep Normal Phase Disposable Column (330 g, ISCO). Elute with hexane (one column volume) then hexane/EtOAc gradient (0% to 55% EtOAc) at 65 mL/min. Collect the title compound and concentrate the fractions in vacuo to give the title compound (9) (3.49 g).

Step B: Preparation of 1,1-Dimethylethyl 1-(4-chlorophenyl)-2-cyclopropyl-2,7-diazaspiro[3.5]nonane-7-carboxylate (10)

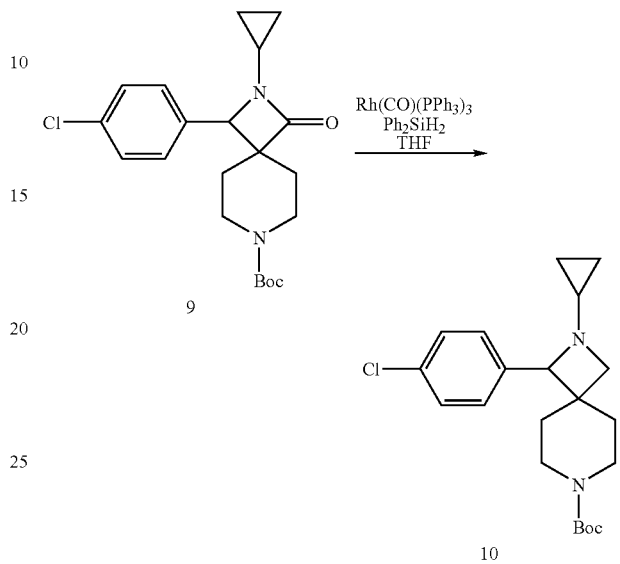

Under a nitrogen atmosphere, treat 1,1-dimethylethyl 1-oxo-3-(4-chlorophenyl)-2-cyclopropyl-2,7-diazaspiro[3.5]nonane-7-carboxylate (9) (0.76 g) in anhydrous THF (2 mL) with RhH(CO)(PPH3)3 (18 mg) and then, diphenylsilane (9.1 mL). The resulting mixture was shaken at room temperature for 2 h. Place the reaction mixture on silica gel plates (12, 1000 u) and elute with hexane/EtOAc 85/15 to give a colorless residue (0.700 g). Place this material on silica gel plates (12, 1000 u) and elute with hexane/EtOAc 85/15 to give the title compound (10) as a colorless foam (0.58 g)

EXAMPLE 2a

2-{[1-(4-Chloro-phenyl)-2-cyclopropyl-2,7-diazaspiro[3.5]nonane-7-carbonyl]-amino}-3-methylpentanoic acid methyl ester

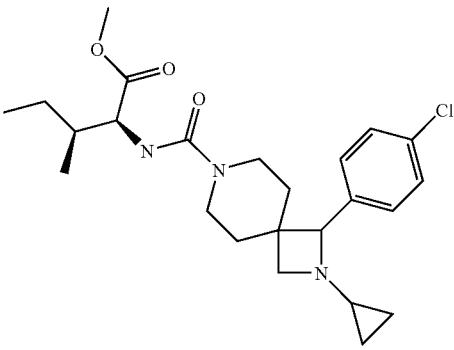

Treat the compound from Example 2 with TFA according to the procedure of step D in Example 1 and treat the resultant product from this reaction with (2S,3S)-2-isocyanato-3-methylvaleric acid, methyl ester according to the procedure Example 1 step E to give the title compound which is characterized by LCMS. (MWT 448).

EXAMPLE 3

Preparation of 2-(2,4-Difluoro-benzyl)-1-(4-fluoro-phenyl)-2,7-diaza-spiro[3.5]nonane-7-carboxylic acid tert-butyl ester

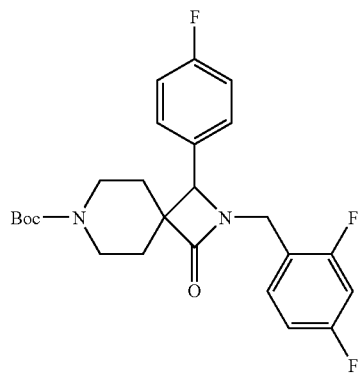

2-(2,4-Difluoro-benzyl)-1-(4-fluoro-phenyl)-3-oxo-2,7-diaza-spiro[3.5]nonane-7-carboxylic acid tert-butyl ester Step 1:

Follow the procedure of Example 1 Step 1 using p-fluorobenzaldehyde in place of p-chloro-benzaldehyde. Take this product (1.0 g, 2.8 mmol) in DMF (10 mL) under an atmosphere of nitrogen, add sodium hydride (60% dispersion in oil) (0.13 g, 3.4 mmol). Stir for 10 min and add α-bromo-2, 4-difluorotoluene (0.58 g, 2.84 mmol). Stir at room temperature overnight. Concentrate and purify reaction mixture by prep TLC using 30% EtOAc in hexanes to obtain the title compound as a white solid (1.20 g).

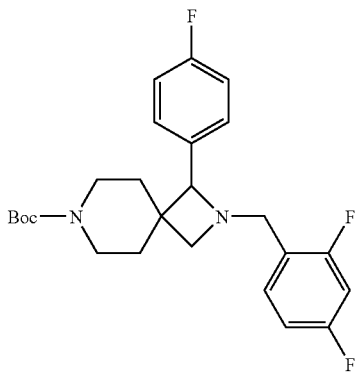

2-(2,4-Difluoro-benzyl)-1-(4-fluoro-phenyl)-2,7-diaza-spiro[3.5]nonane-7-carboxylic acid tert-butyl ester Step 2:

To the product of Step 1 (0-969) 2.13 mmol) in THF (5 mL) under an atmosphere of nitrogen, add diphenylsilane (0.98 mL, 5.3 mmol) and add hydridocarbonyltris(triphenylphosphine) rhodium (1) (0.14 g, 0114 mmol). Stir for 1 h. Purify reaction mixture by prep TLC using 30% EtOAc in hexanes to obtain the title compound as a white solid (0.83 g).

EXAMPLE 4

1-(4-Chloro-phenyl)-2-p-tolyl-2,7-diaza-spiro[3.5]nonane-7-carboxylic acid tert-butyl ester

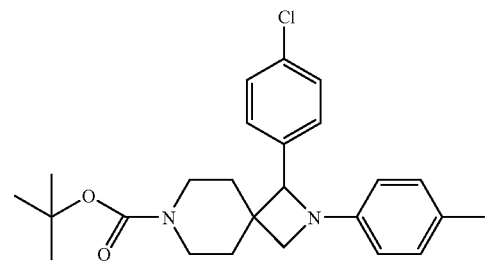

To the product of Example 1 step 1 (0.60 g, 1.71 mmol) in a sealed tube, add 1,4-dioxane (4 mL), add methyl 4-iodobenzoate (0.54 g, 2.1 mmol), add copper(I) iodide (0.17 g, 0.090 mmol), add N,N'-dimethylethylenediamine (0.018 mL, 0.17 mmol) and add $K_3PO_4$ (0.55 g, 2.6 mmol). Seal tube and heat to 60° C. and stir 24 h. Allow to cool, filter through a pad of celite and concentrate. Purify by prep TLC using 20% EtOAc in hexanes to a white solid (0.82 g). Treat this with RhH(CO)(PPH3)3 and diphenylsilane according to the procedure of Example 2 Step B to give the title compound which was characterized by LCMS. (MWT 426)

EXAMPLE 5

Preparation of 2-(2-Chloro-benzyl)-3-(2,4-difluorophenyl)-7-(4-methoxy-benzyl)-2,7-diaza-spiro[3.5]nonan-1-one

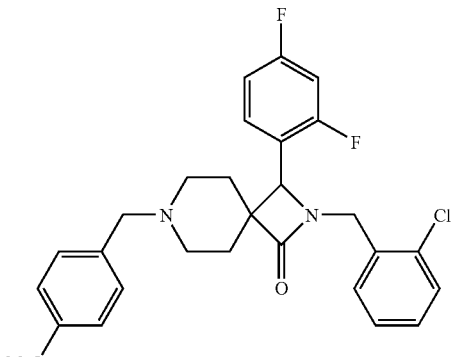

Using the procedure of Example 2 with 2,4-difluorobenzlaldehyde, and 2-chlorobenzylamine obtain the product from steps A and B. Remove the Boc protecting group with TFA according to the procedure of Step D in Example 1 and treat the resultant product (0.525 g, 1.39 mmol) in EtOH (12 mL), with 4-methoxybenzyl chloride (0.207 mL, 1.53 mmol) and potassium carbonate (0.231 g, 0.1.67 mmol). Stir for 14 h. Filter through a pad of celite and concentrate. Purify reaction mixture by prep TLC using 3% $CH_3OH$ in $CH_2Cl_2$ to obtain the title compound as a tan solid (0.400 g).

EXAMPLE 6

2-Isobutyl-1-phenyl-7-(3,4,5-trimethoxy-benzyl)-2,7-diaza-spiro[3.5]nonane

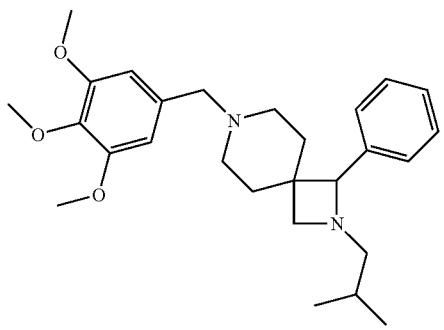

Using essential the same process as in Example 2, using benzaldehyde, LiHMDS, isobutylbromide and 3,4,5-trimethoxy-benzylchloride the title compound is prepared an characterized by LCMS (MWT 438.6).

Using Method A or Method B along with the procedures described in the examples above with the appropriate aldehyde (A1 or B1), amine (A2 or B2), the halide (B6) and the isocyanate reagents the compounds in Table 7 are prepared and identified by LCMS. (Unless otherwise noted Method A is used when $R^1$ is Aryl and Method B is used when $R^1$ is alkyl or substituted alkyl)

TABLE 7

| Isomer | Structure | MWT | Isomer | Structure | MWT |
|---|---|---|---|---|---|
|  |  | 382.5 | A |  | 440.0 |
|  |  | 400.5 | A |  | 398.9 |
|  |  | 400.5 | A |  | 378.0 |

TABLE 7-continued

| Isomer | Structure | MWT | Isomer | Structure | MWT |
|---|---|---|---|---|---|
| | (structure) | 416.6 | A | (structure) | 430.0 |
| A | (structure) | 415.9 | | (structure) | 433.6 |
| A | (structure) | 412.0 | | (structure) | 405.5 |
| A | (structure) | 432.4 | A | (structure) | 476.8 |

TABLE 7-continued

| Isomer | Structure | MWT | Isomer | Structure | MWT |
|---|---|---|---|---|---|
| A | | 423.0 | | | 475.7 |
| A | | 428.0 | | | 447.6 |
| A | | 470.0 | | | 417.5 |
| A | | 470.0 | | | 389.4 |

TABLE 7-continued

| Isomer | Structure | MWT | Isomer | Structure | MWT |
|---|---|---|---|---|---|
| | | 417.5 | | | 467.7 |
| | | 389.4 | | | 445.7 |
| A | | 432.4 | A | | 476.8 |
| A | | 432.4 | A | | 418.0 |

TABLE 7-continued

| Isomer | Structure | MWT | Isomer | Structure | MWT |
|---|---|---|---|---|---|
| A | | 423.0 | A | | 494.5 |
| A | | 440.0 | A | | 460.4 |
| | | 445.5 | | | 461.6 |
| | | 447.6 | | | 453.6 |

TABLE 7-continued
| Isomer | Structure | MWT | Isomer | Structure | MWT |
|---|---|---|---|---|---|
| | 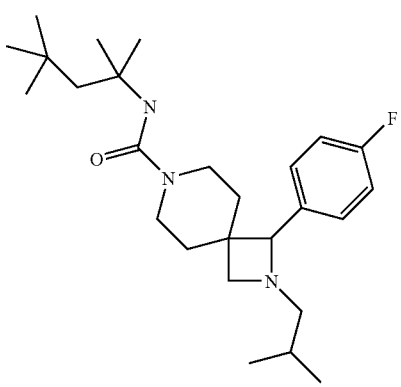 | 431.6 | A | 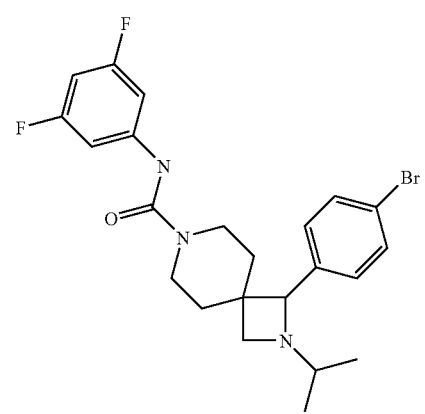 | 478.4 |
| | 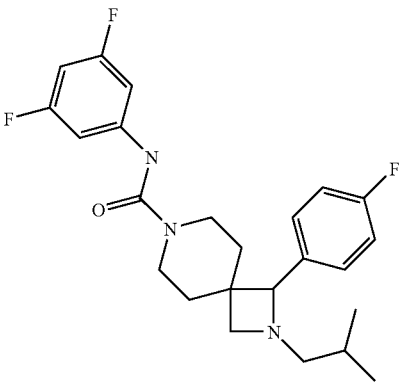 | 431.5 | B | 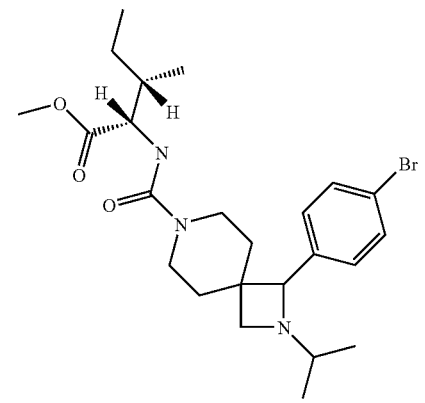 | 494.5 |
| | 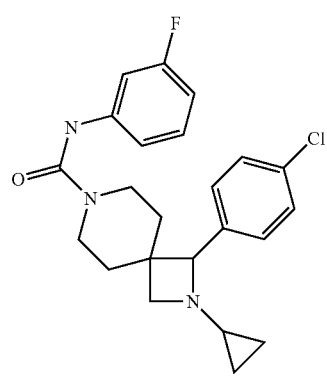 | 413.9 | B | 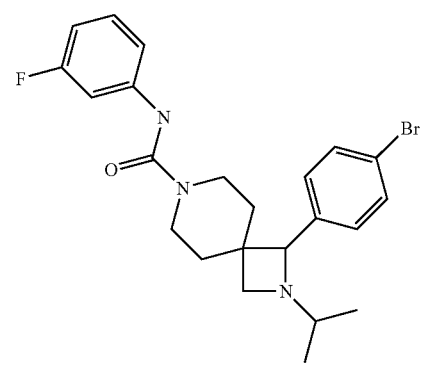 | 460.4 |

TABLE 7-continued

| Isomer | Structure | MWT | Isomer | Structure | MWT |
|---|---|---|---|---|---|
|  |  | 420.9 | B |  | 478.4 |
|  |  | 430.4 |  |  | 415.5 |
|  |  | 431.9 | B |  | 466.0 |
|  |  | 448.0 | A |  | 466.0 |

TABLE 7-continued

| Isomer | Structure | MWT | Isomer | Structure | MWT |
|---|---|---|---|---|---|
| A | 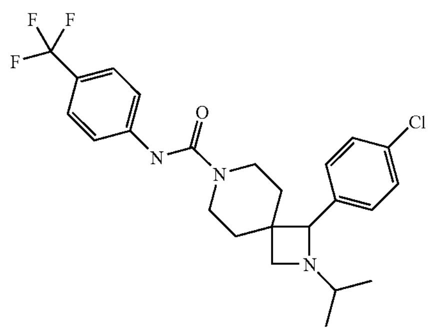 | 466.0 | | 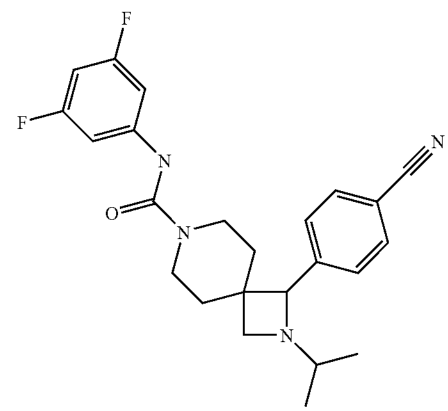 | 424.5 |
| | | 465.5 | | | 491.7 |
| | | 492.1 | | | 533.8 |

TABLE 7-continued
| Isomer | Structure | MWT | Isomer | Structure | MWT |
|---|---|---|---|---|---|
|  |  | 449.5 |  |  | 460.0 |
|  | 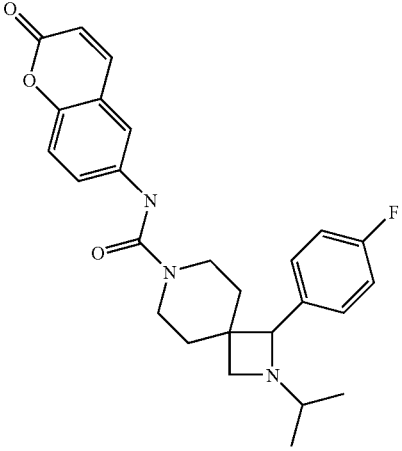 |  |  | 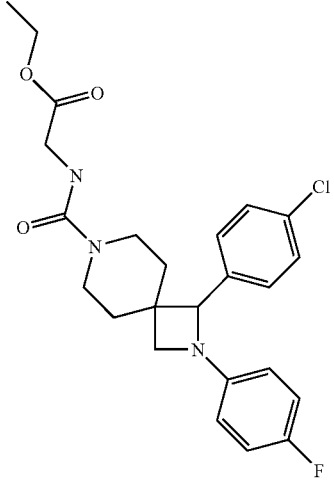 |  |
| A |  | 492.1 |  |  | 488.0 |
|  | 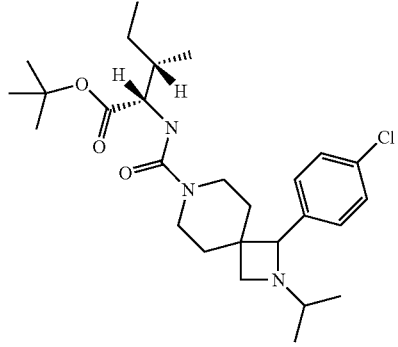 |  |  | 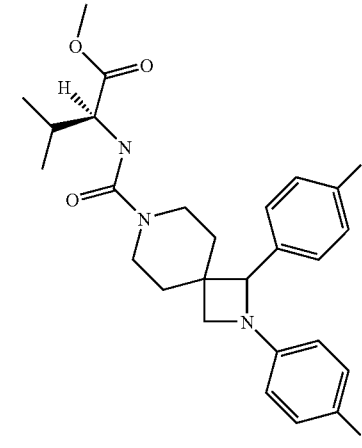 |  |
| A |  | 456.1 |  |  | 476.6 |
|  | 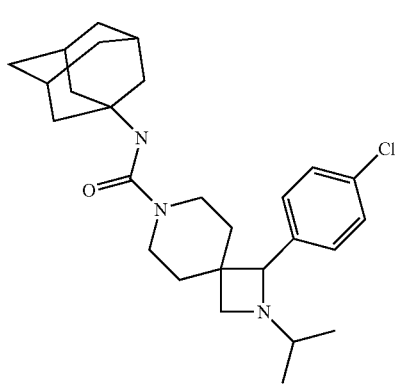 |  |  | 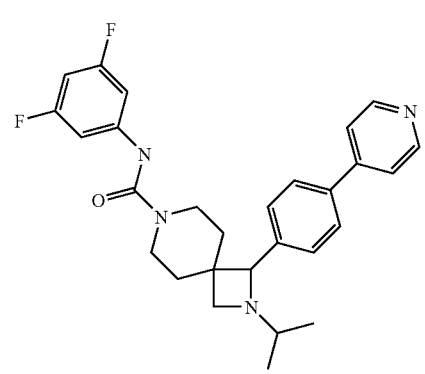 |  |

TABLE 7-continued

| Isomer | Structure | MWT | Isomer | Structure | MWT |
|---|---|---|---|---|---|
|  | 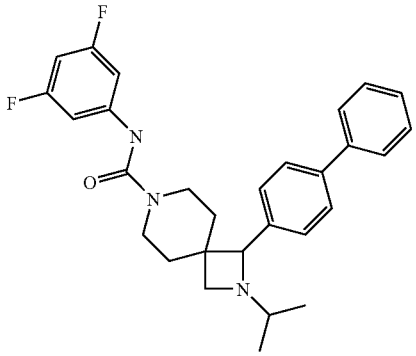 | 475.6 |  |  |  |

Using Method A or Method B along with the procedures described in the examples above with the appropriate aldehyde (A1 or B1), amine (A2 or B2), halide (B6) and carboxylic acids or acid chloride reagents the following compounds of Table 8 are prepared and identified by LCMS. (Unless otherwise noted Method A is used when $R^1$ is Aryl and Method B is used when $R^1$ is alkyl or substituted alkyl)

TABLE 8

| Structure | MWT | Structure | MWT |
|---|---|---|---|
| 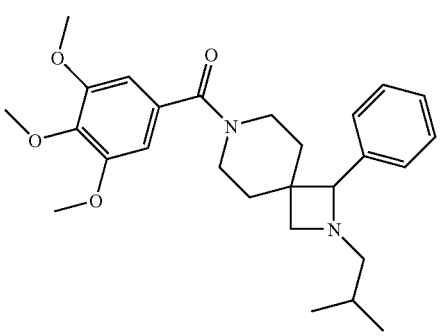 | 452.6 | 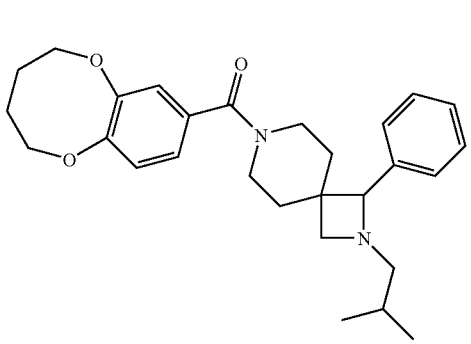 | 448.6 |
| 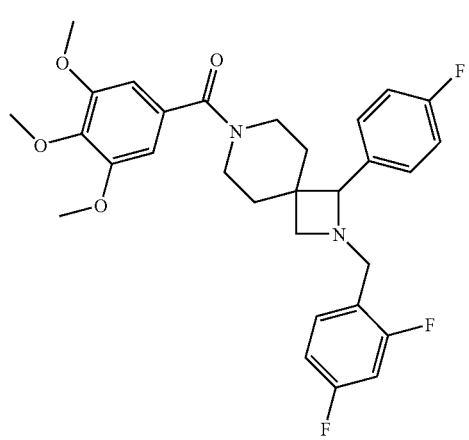 | 540.6 | 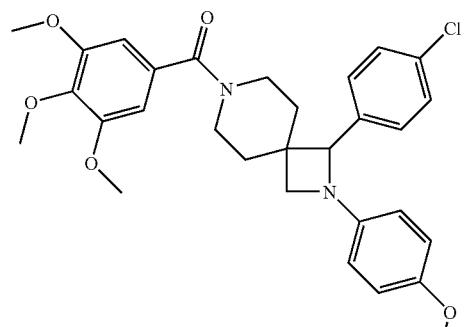 | 537.1 |

TABLE 8-continued

| Structure | MWT | Structure | MWT |
|---|---|---|---|
| | 521.1 | | 450.6 |
| 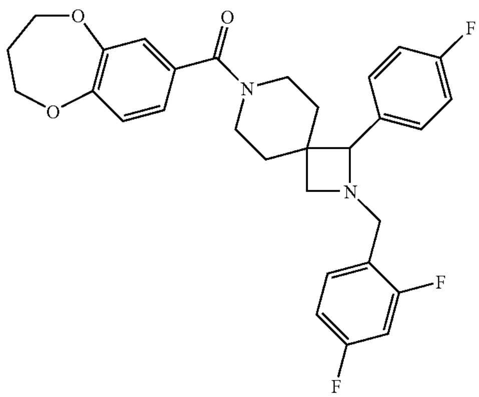 | 522.6 | 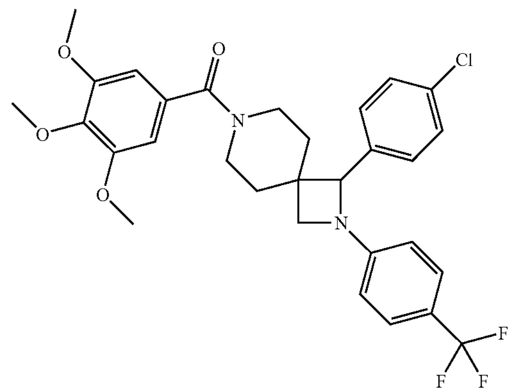 | 575.0 |
| | 521.1** | | 492.5 |
| 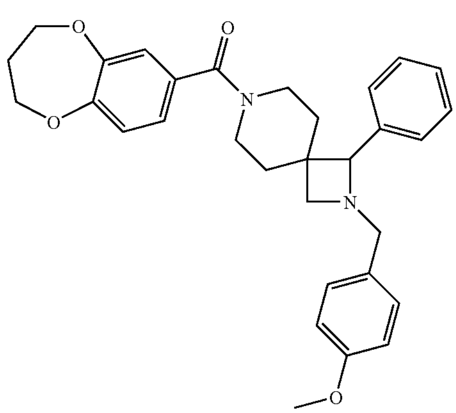 | 498.6 | 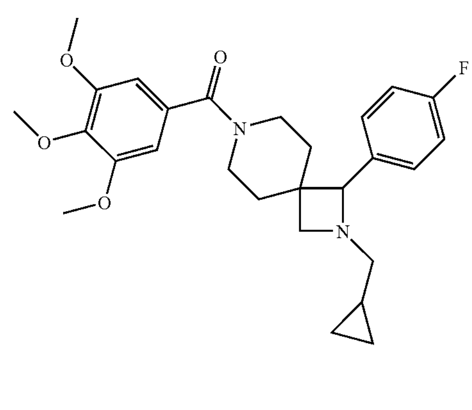 | 468.6 |

TABLE 8-continued
| Structure | MWT | Structure | MWT |
|---|---|---|---|
| 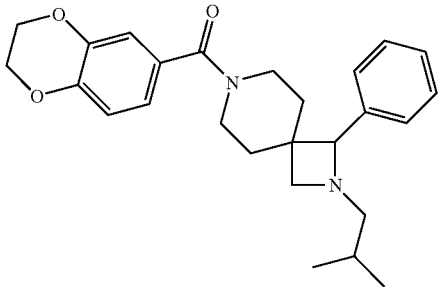 | 420.6 | 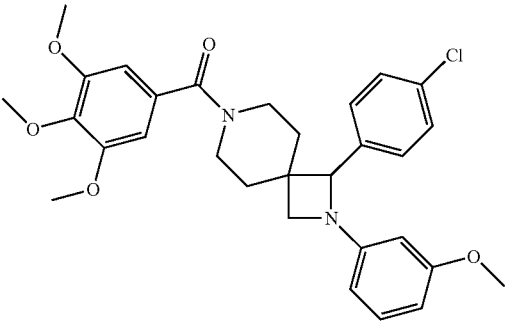 | 537.1* |
| 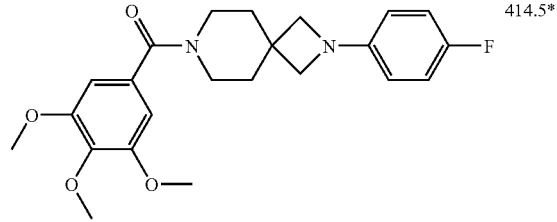 | 414.5* | 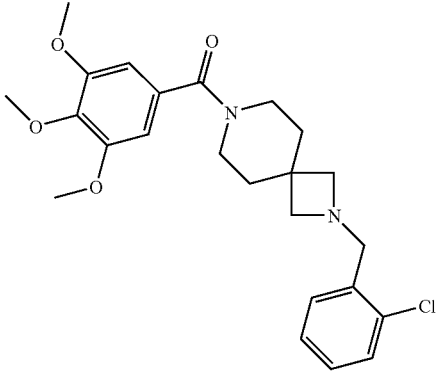 | 445.0 |
| 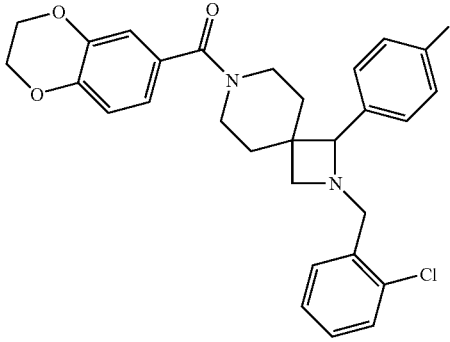 | 523.5 | 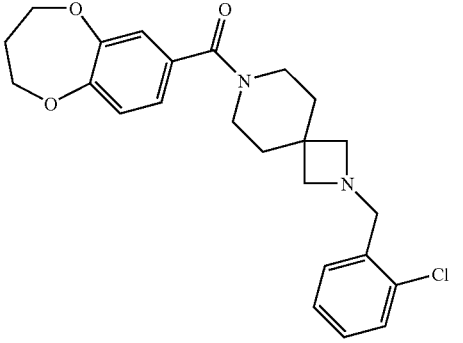 | 426.9 |
| 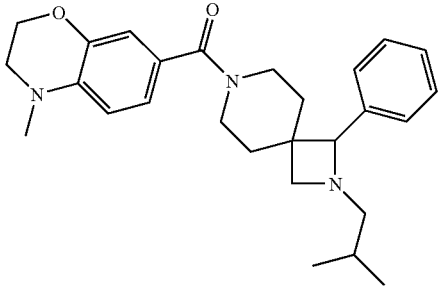 | 433.6 | 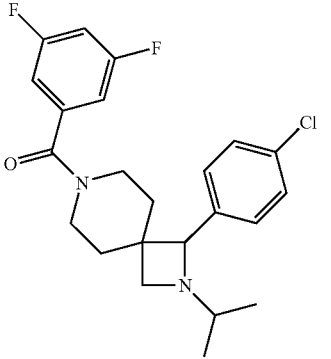 | 418.9 |

TABLE 8-continued

| Structure | MWT | Structure | MWT |
|---|---|---|---|
| 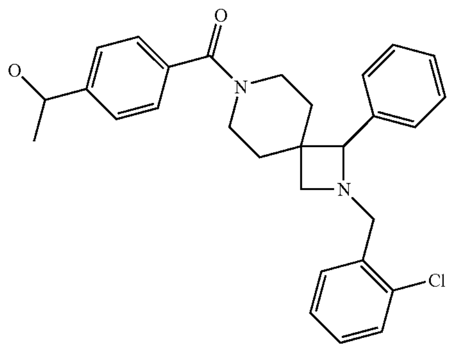 | 475.0 | 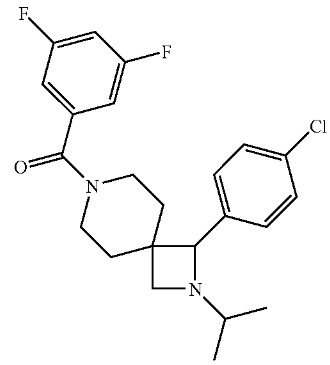 | 418.9 |
| 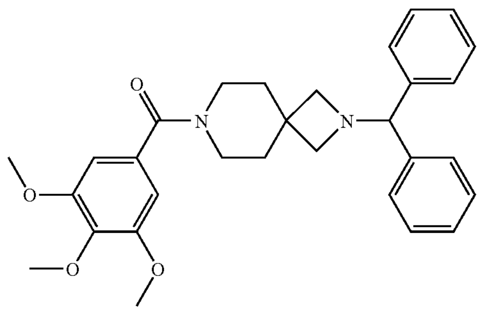 | 486.6 | 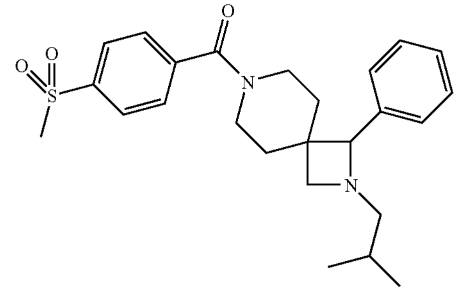 | 440.6 |

*compound prepared by Method B
**compound prepared by Method B using the product of Example 4

Following procedures similar to those described above, as indicated in Table 8A, the compounds in Table 8A were prepared. The Retention Times were obtained under the following conditions: C18 column (4.6×50 mm), Flow rate 1 mL/min, 5 minute gradient (90% water, 10% acetonitrile) to (5% water, 95% acetonitrile) water and acetonitrile contain 0.05% TFA.

TABLE 8A

| | Compound | Procedure | M + 1 | Time |
|---|---|---|---|---|
| (132) | | Ex. 2 Method A | 479 | 3.17 |
| (133) | | Ex. 2 Method A | 463 | 3.16 |

TABLE 8A-continued

| | Compound | Procedure | M + 1 | Time |
|---|---|---|---|---|
| (134) | | Ex. 1 Method B | 423 | 2.80, 2.97 |
| (135) | | Ex. 1 Method B | 458 | 3.16 |
| (136) | | Ex. 1 Method B | 416 | 2.87 |
| (137) | | Ex. 2 Method A | 479 | 3.27 |
| (138) | | Ex. 2 Method A | 463 | 3.16 |

TABLE 8A-continued
| | Compound | Procedure | M + 1 | Time |
|---|---|---|---|---|
| (139) | 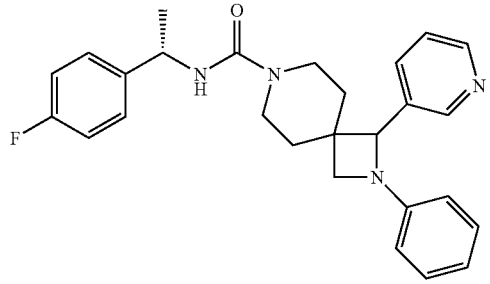 | Ex. 2 Method A | 445 | 3.04 |
| (140) | 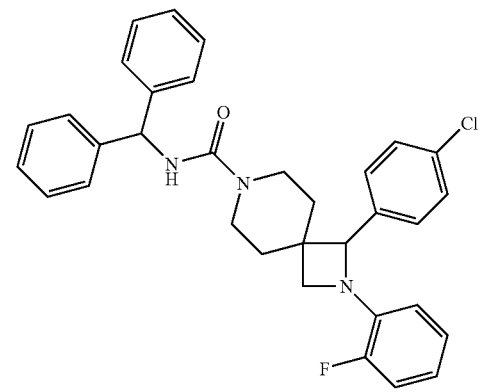 | Ex. 2 Method A | 541.3 | 5.5 |
| (141) | 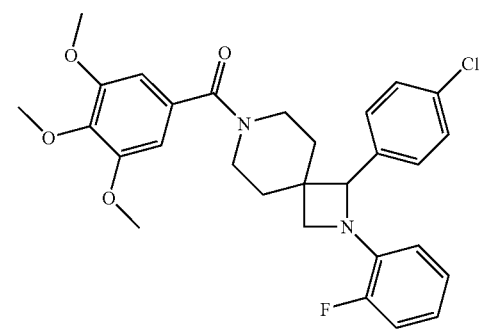<br>Isomer B | Method for the compounds in Table 8 | 526.3 | 5.14 |
| (141) | 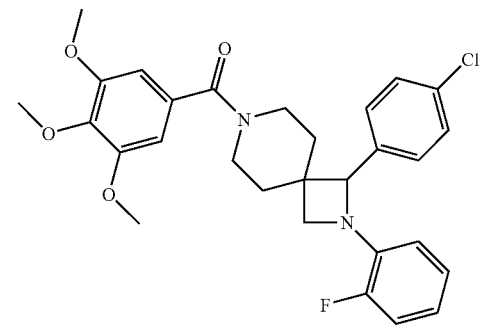<br>Isomer A | Method for the compounds in Table 8 | 526.3 | 5.15 |

TABLE 8A-continued

| Compound | Procedure | M + 1 | Time |
|---|---|---|---|
| (142) | Ex. 2 Method A | 541.3 | 5.49 |
| (143) Isomer A | Ex. 1 Step E | 332 | 2.16 |
| (143) Isomer B | Ex. 1 Step E | 332 | 2.17 |
| (144) Isomer B | Ex. 2 Method A | 487 | 3.68 |

TABLE 8A-continued
| Compound | Procedure | M + 1 | Time |
|---|---|---|---|
| 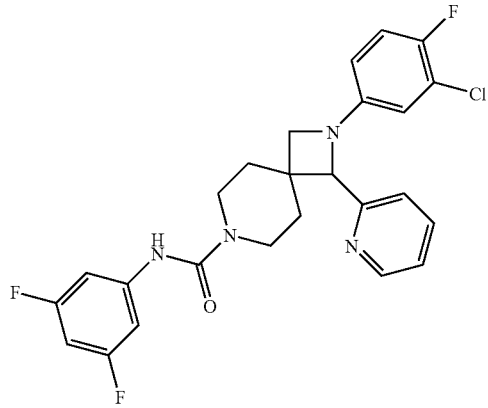 | Ex. 2 Method A | 487 | 3.58 |
| (145) 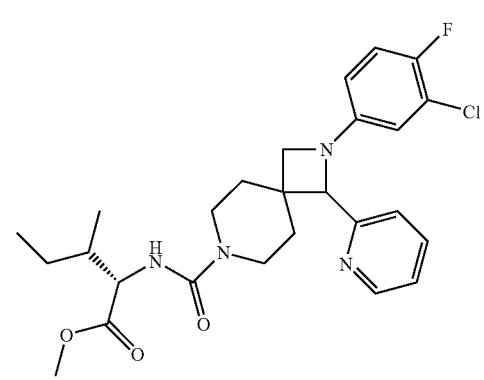<br>Isomer A | Ex. 2 Method A | 503 | 3.46 |
| (145) 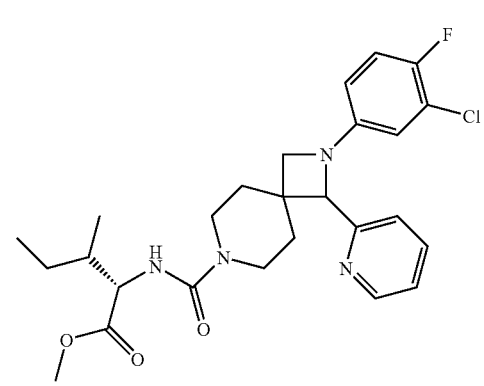<br>Isomer B | Ex. 2 Method A | 503 | 3.46 |

TABLE 8A-continued
| Compound | Procedure | M + 1 | Time |
|---|---|---|---|
| (146) 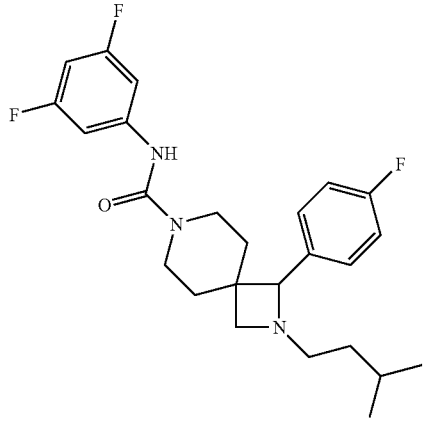 Isomer A | Ex. 1 Method B | 446 | 3.55 |
| (146) 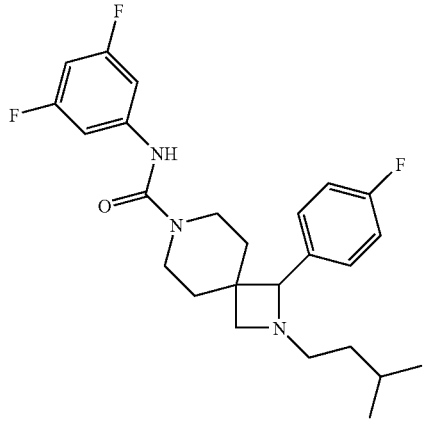 Isomer B | Ex. 1 Method B | 446 | 3.51 |
| (147) 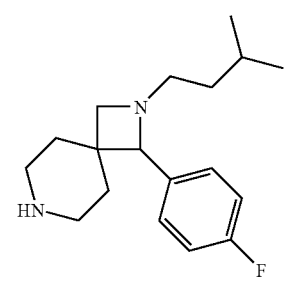 Isomer A | Ex. 1 Step E | 291 | 1.98, 0.78 |
| (147) 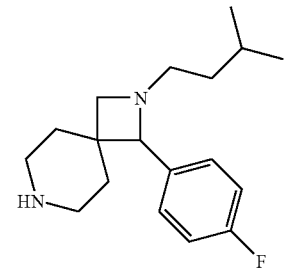 Isomer B | Ex. 1 Step E | 291 | 1.90, 0.75 |

TABLE 8A-continued

| Compound | | Procedure | M + 1 | Time |
|---|---|---|---|---|
| (148) | 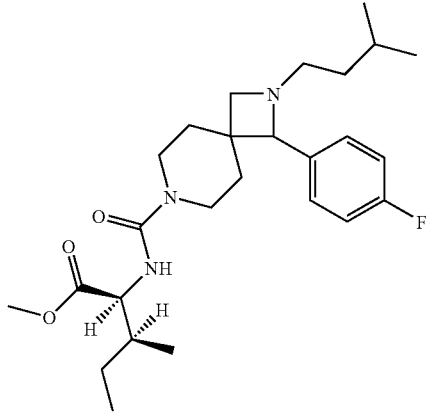<br>Isomer A | Ex. 1<br>Method B | 462 | 3.39 |
| (148) | 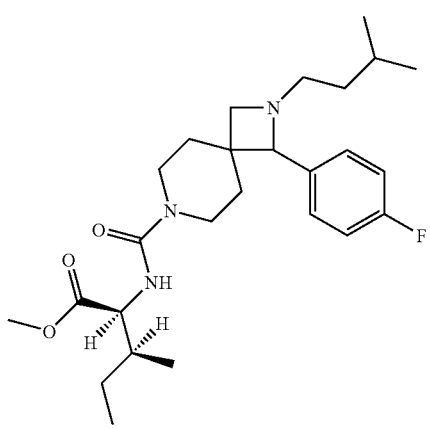<br>Isomer B | Ex. 1<br>Method B | 462 | 3.4 |

Assays

Methods for Evaluating Functional Effects on Ion Channels

Functional evaluation of voltage-gated ion channels was used to determine potency and/or single concentration efficacy of proprietary compounds. Two different methodologies were used to measure ion currents: the IonWorks HT (Molecular Devices, Sunnyvale, Calif.) a moderate throughput voltage clamp screening platform that utilizes 96-well compound plates and conventional whole cell patch clamp for lower throughput, higher fidelity determinations.

Cell Lines

HEK cells were transiently transfected and then selected for stable heterologous expression of different channel proteins of interest. Calcium channel cell lines expressed a resting potassium current, human $K_{ir}2.1$, and the pore forming α-subunit of voltage-gated calcium channels. In the case of $Ca_v2.1$ cells the auxiliary subunit, $β_2a$, was also expressed. Calcium channel lines that were used to generate the data in this document expressed either human $Ca_v3.2$, rat $Ca_v3.2$ or human $Ca_v2.1$. The human heart sodium channel, $hNa_v1.5$, was stably expressed in CHO cells. These cells were licensed from the University of Pennsylvania.

Cell lines were grown at 37° C. in humidified incubators, equilibrated with 95% air/5% $CO_2$. CHO cells were grown in Ham's F-12 medium. HEK cells were grown in DMEM. All media were supplemented with 10% heat-inactivated fetal bovine serum, penicillin, streptomycin and appropriate selection antibiotics (zeocin, geneticin and/or hygromycin). Cells were passaged when 80% confluent or less.

Ionworks Screen for hCaV3.2

The extracellular buffer for experiments using this instrument contained the following (mM) (NaCl 125, HEPES 10, KCl 5.4, $CaCl_2$ 1.8, $MgCl_2$ 1.8, 0.2 $BaCl_2$ pH 7.35). The IonWorks uses amphotericin to gain electrical access to the cell interior. The internal solution contained (mM concentrations): 130 K-gluconate, 20 KCl, 5 HEPES-KOH (pH 7.25), 2 $CaCl_2$, 1 $MgCl_2$. Amphotericin added at 5 mg in 65 ml when present (in 650 µl DMSO). All internal and external solutions for this experiment contain 1% DMSO. Cells were acutely trypsinized from a T-75 flask and resuspended in extracellular buffer at a density of $2 \times 10^5$ cells/ml.

Experiments were performed at room temperature, Transmembrane potential was held at −100 mV for 5 seconds prior to running the voltage protocol. During this time leak currents were measured during a step to −110 mV (200 milliseconds). T-type calcium currents were activated with a 250 millisecond step to −20 mV. This depolarization step was repeated for a total of 10 pulses with an interpulse interval of 1 second. Data were excluded if the following acceptance criteria were not met: total resistance for the pre-compound scan >65 MΩ, pre-compound current >250 pA, post compound total resistance >50 MΩ.

T-type currents were measured as the peak inward current minus the current at the end of the 250 msec step to −20 mV. After the recoding configuration was established there was a pre-compound measurement of current amplitude Compound was added as a 3× solution containing 1% DMSO. After incubation with compound for 10 minutes currents were measured again. The current amplitude after compound addition was divided by the pre-compound current for pulse 10 to determine the traction of current remaining after compound addition. For each compound, 8-point concentration-effect relationships were measured with ½ log serial dilutions. These data were then transferred into GraphPad Prism (v 4) and non-linear regression analysis was used to estimate the $IC_{50}$ for each test compound, Conventional Whole Cell Patch Clamp Cells were plated onto 9 mm diameter circular coverglass in the appropriate growth medium and placed in a 37° C. incubator until used. Whole cell patch clamp studies were conducted at room temperature using conventional methods, PCLAMP software (v8 or 9) was used in conjunction with a compatible A/D D/A board, a Pentium III personal computer and either a Multiclamp 700 or an AxoPatch 1D amplifier was used to generate voltage clamp protocols, acquire data and measure currents.

At the time of study, a piece of coverglass with attached cells was transferred to a recording chamber on the stage of an inverted microscope and the whole cell configuration of patch clamp was established. The recording chamber was gravity perfused with extracellular solution at a flow rate of approximately 3 ml/min. Patch electrodes had resistances of 2-3 MΩ when filled with pipette solution. The extracellular solution was a HEPES-buffered saline (149 NaCl, 10 HEPES-NaOH (pH 7.4), 10 glucose, 5 CsCl, 2 $MgCl_2$, 5 $CaCl_2$; concentrations in mM). The pipette solution contained (mM concentrations) 115 CsCl, 10 HEPES-CsOH (pH 7.3), 4 MgATP, 10 EGTA, osmolarity to 310 mM with sucrose). All solutions contained 0.1% DMSO.

The holding potential was −100 mV for all protocols. Interpulse interval was 15 seconds. The time course of $hCa_v3.2$ or $rCa_v3.2$ current was examined with a 200 millisecond test pulse to −35 mV. $Ca_v3.2$ currents were measured as the peak current 10-30 milliseconds after the voltage was stepped to −35 mV. P/N 4 leak subtraction was used. The amplifier low pass filter was set to 10 kHz and the data were sampled at 10 kHz. Data were filtered offline with a Gaussian filter with a −3 dB cutoff of 280 Hz. The voltage protocol for hCaV2.1 currents differed only in terms of the voltage for the depolarizing test potential. For $hCa_v2.1$ currents were activated with a 200 millisecond step to 0 mV. $hCa_v2.1$ currents were measured from the leak-subtracted traces as the average current between 190 and 200 milliseconds after the step to 0 mV. The voltage protocol for sodium currents included a 150 millisecond hyperpolarizing pulse to −140 mV to optimize channel availability, followed by a 20 millisecond test pulse to −20 mV. Sodium currents were measured from leak subtracted traces as the peak transient inward current.

All drug effects were measured after a steady-state effect was achieved. Concentration-effect relationships were derived by exposing each cell to only a single concentration of test article. For non-linear regression analysis the post-compound current amplitude was normalized to the pre-compound current amplitude for each cell. If a given current was inhibited by >50% at a concentration of 10 μM or less, the data for multiple concentrations of compound and corresponding vehicle and time control cells were entered into GraphPad Prism (v 4) for non-linear regression analysis to determine the $IC_{50}$.

The actions of the compounds of formula I and IIA for the treatment or prevention of pain may be assessed by various animal models, for example, by the following tests:

Formalin test: Mice are gently restrained and 30 μl of formalin solution (1.5% in saline) is injected subcutaneously into the plantar surface of the right hind paw of the mouse, using a microsyringe with a 27 gauge needle. After the formalin injection, the mouse is immediately put back into the Plexiglas observation chamber (30×20×20 cm) and the nociceptive response of the animal to formalin injection is observed for a period of 60 min. The duration of licking and flinching of the injected paw is recorded and quantified every 5 min for the total observation period. The recording of the early phase (first phase) starts immediately and lasts for 5 min. The late phase (second phase) starts about 10-15 min after formalin injection.

L5 and L6 spinal nerve ligation of the sciatic nerve (neuropathic pain model): The peripheral neuropathy is produced by ligating the L5 and L6 spinal nerves of the right sciatic nerve, based on the method previously of Kim and Chung (1992). Briefly, rats are anaesthetized with chloral hydrate (400 mg/kg, i.p.), placed in a prone position and the right paraspinal muscles separated from the spinous processes at the L4-S2 levels. The L5 transverse process is carefully removed with a small rongeur to identify the L4-L5 spinal nerves. The right L5 and L6 spinal nerves are isolated and tightly ligated with 7/0 silk thread. A complete hemostasis is confirmed and the wound sutured.

Chronic constriction injury (CCI) of the sciatic nerve (neuropathic pain model): Surgery is performed according to the method described by Bennett & Xie (1987). Rats are anaesthetized with chloral hydrate (400 mg/kg, i.p.) and the common sciatic nerve is exposed at the level of the mid-thigh. Proximally, at about 1 cm from the nerve trifurcation, four loose ligatures (4/0 silk) spaced 1 mm are tied around the nerve. The ligature delays, but does not arrest, circulation through the superficial epineural vasculature. The same procedure is performed except for ligature placement (sham surgery) in a second group of animals.

Carrageenan (inflammatory pain model): The right hind paw of each animal is injected at subplantar level with 0.1 mL of carrageenan (25 GA needle). Pre-tests are determined prior to carrageenan or drug administration. In the POST-TREATMENT protocol, rats are tested 3 hours after carrageenan treatment to establish the presence of hyperalgesia and then at different times after drug administration. In the PRE-TREATMENT protocol, one hour after drug administration, rats are treated with carrageenan and they are tested starting from 3 hours later.

Freund's adjuvant-induced arthritic model (inflammatory pain model): Animals receive a single subplantar injection of 100 mL of a 500 mg dose of heat-killed and dried *Mycobacterium tuberculosis* (H37 Ra, Difco Laboratories, Detroit, Mich., USA) in a mixture of paraffin oil and an emulsifying agent, mannide monooleate (complete Freund's adjuvant). Control animals are injected with 0.1 mL mineral oil (incomplete Freund's adjuvant).

Measurement of tactile allodynia (behavioral test): Behavioral tests are conducted by observer blinded to the treatment during the light cycle to avoid circadian rhythm fluctuation.

Tactile sensitivity is evaluated using a series of calibrated Semmes-Weinstein (Stoelting, Ill.) von Frey filaments, bending force ranging from 0.25 to 15 g. Rats are placed in a transparent plastic box endowed with a metal mesh floor and are habituated to this environment before experiment initiation. The von Frey filaments are applied perpendicularly to the midplantar surface of the ipsilateral hind paws and the mechanical allodynia is determined by sequentially increasing and decreasing the stimulus strength ("up-down" paradigm of the filament presentation). Data are analysed with a Dixon non-parametric test (Chaplan et al. 1994). Paw licking or vigorously shaking after stimulation is considered pain-like responses.

Thermal hyperalgesia (behavioral test): Thermal hyperalgesia to radiant heat is assessed by measuring the withdrawal latency as an index of thermal nociception (Hargreaves et al., 1998). The plantar test (Basile, Comerio, Italy) is chosen because of its sensitivity to hyperalgesia. Briefly, the test consists of a movable infrared source placed below a glass plane onto which the rat is placed. Three individual perspex boxes allow three rats to be tested simultaneously. The infrared source is placed directly below the plantar surface of the hind paw and the paw withdrawal latency (PWL) is defined as the time taken by the rat to remove its hind paw from the heat source. PWLs are taken three times for both hind paws of each rat and the mean value for each paw represented the thermal pain threshold of rat. The radiant heat source is adjusted to result in baseline latencies of 10-12 sec. The instrument cut-off is fixed at 21 sec to prevent tissue damage.

Weight bearing (behavioral test): An incapacitance tester is employed for determination of hind paw weight distribution. Rats are placed in an angled plexiglass chamber positioned so that each hind paw rested on a separate force plate. The weight bearing test represents a direct measure of the pathological condition of the arthritic rats without applying any stress or stimulus, thus this test measures a spontaneous pain behaviour of the animals.

GPR119 Screening Assay:

Reagent Preparation:

| | |
|---|---|
| Stimulation Buffer: | 100 ml HBSS (GIBCO # 14025-092) + 100 mg BSA (MP Biomedicals faction V, #103703) = 0.1% + 500 ul 1M HEPES (Cellgro #25-060-CI) = 5 mM + 75 ul RO-20 (Sigma B8279; 20 mM stock in DMSO stored in aliquots at −20 C.) = 15 uM (made fresh daily) |

B84 (N-[4-(methylsulfonyl)phenyl]-5-nitro-6-[4-(phenylthio)-1-piperidinyl]-4-pyrimidinamine, see WO 2004/065380): A 10 mM stock solution of the test compound in DMSO was prepared, aliquoted and stored at −20 C. For Totals—Dilute 1:33.3 in DMSO then 1:50 in Stimulation Buffer=6 uM in 2% DMSO(=3 uM B84 and 1% DMSO final). For Dose Response Curve–3 ul stock+7 ul DMSO+490 ul Stim Buffer=60 uM in 2% DMSO (=30 uM B84 and 1% DMSO final). (made fresh daily).

Cell Line:

Human clone 3: HEK 293 cells stable transfected with human-SP9215(GPR119)/pcDNA3.1 and also stable for pCRELuc, Stratagene. Cells are maintained in DMEM containing 10% FBS (Invitrogen #02-4006Dk, lot #1272302, heat inactivated), 1×MEM, 1× Pen/Strep, 0.1 mg/ml Hygromycin B, and 0.5 mg/ml G418. Cells are split 1:8 twice per week.

cAMP Kit: LANCE™ cAMP 384 kit, Perkin Elmer #AD0263

Compound Dilutions:

Add DMSO to vials containing compounds to yield a 1 mg/ml solution.

1. Dilute compounds to 60 μM in Stimulation buffer. Make ½ log dilutions into Stimulation buffer containing 2% DMSO using the epMotion robot. 10 point dose response curve 1 nM to 30 uM.
2. Compounds are run in quadruplicate, 2 separate dilutions for each, sets 1 and 1a.

Assay Procedure:

1. The afternoon before the assay, replace the media in the flask of Human clone 3 cells with Optimem. (Gibco #11058-021) NOTE: cells should be in culture 6-8 days.
2. Next morning, pipet the cells gently off the flask using HBSS (RT).
3. Pellet the cells (1300 rpm, 7 min, RT) and resuspend in Stimulation Buffer at 2.5×10 e6/ml (=5-8,000 cell/6 ul). Add 1:100 dilution of Alexa Fluor 647-anti cAMP antibody (provided in the kit) directly to the cell suspension.
4. Into white 384-well plates (Matrix) add 6 ul of 2×B84, cmpds or stim buffer for nsb. They all contain 2% DMSO (=1% DMSO final).
5. Add 6 ul of the cell suspension to the wells. Incubate 30 minutes RT.
6. For the std curve add 6 ul cAMP std solution diluted in Stim Buffer+2% DMSO according to kit directions (1000-3 nM). Add 6 ul of 1:100 anti-cAMP dilution in Stim Buffer to std wells.
7. Make Detection Mix according to kit instructions and incubate 15 min RT.
8. Add 12 ul Detection Mix to all the wells, Mix gently by tapping and incubate 2-3 hrs RT.
9. Read on the Envision under the protocol "Lance/Delphia cAMP"
10. Values (nM) for each sample are determined by extrapolation from the std curve. % Control, Fold and EC50 (Control=3 uM B84) are determined for each compound, averaging sets 1 and 1a.

Using the above assays, the compounds in Table 5, and compounds (132)-(139) and Isomers A and B of compounds (143)-(148) in Table 8A, had Cav 3.2 (Ionworks) $IC_{50}$ within the range of 24 to 33000 nM. The compounds in Table 6 had a GPR119 cAMP $IC_{50}$ in the range of 882 to 13600 nM.

Table 9 provides GPR119 cAMP $EC_{50}$ data in nM for compounds of this invention.

TABLE 9
| Compound | GPR 119 cAMP EC50 nM |
|---|---|
| 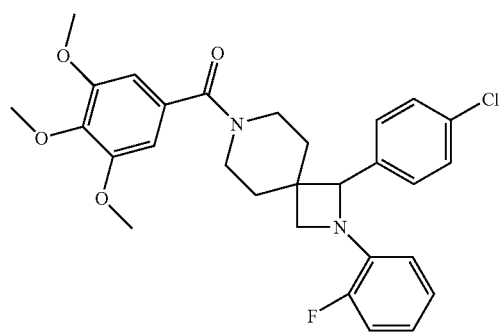<br>(141) isomer A | 516 |
| 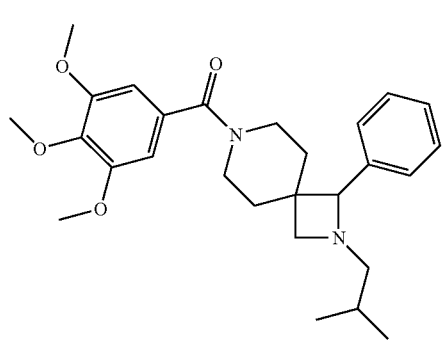 | 882 |
| 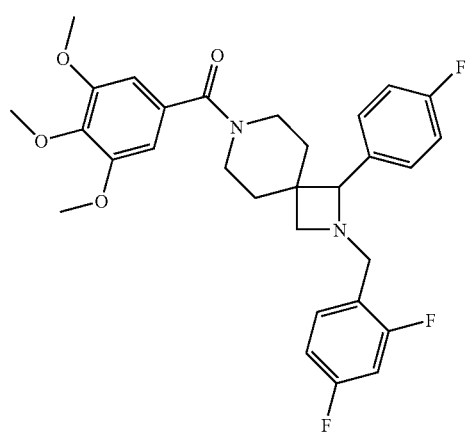 | 1200 |
TABLE 9-continued
| Compound | GPR 119 cAMP EC50 nM |
|---|---|
| 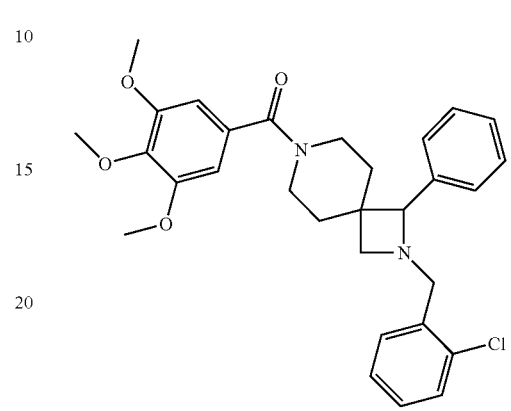 | 1260 |
| 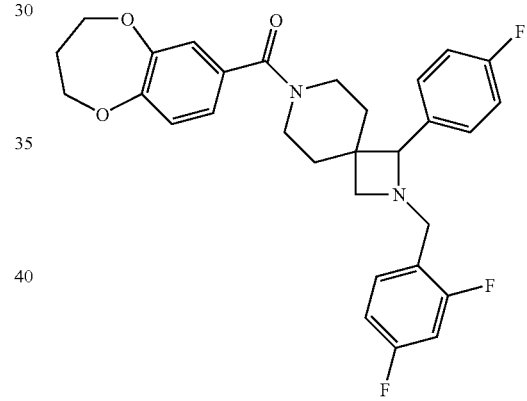 | 1300 |
| 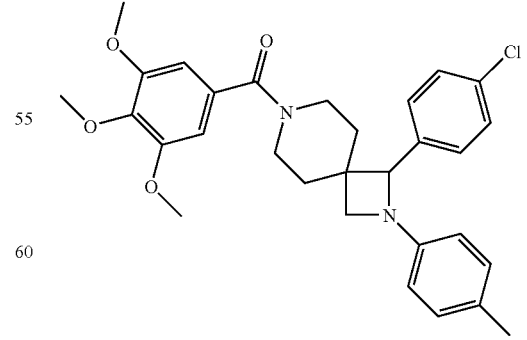 | 1340 |
Table 10 provides Cav3.2 IC$_{50}$ data in nM for compounds of this invention.

TABLE 10

| Isomer | Compound | IW hCav3.2 IC50 nM |
|---|---|---|
| A | | 24<br>82* |
| A | | 38 |
| A | | 44 |
| A | | 49 |

TABLE 10-continued
| Isomer | Compound | IW hCav3.2 IC50 nM |
|---|---|---|
| A | 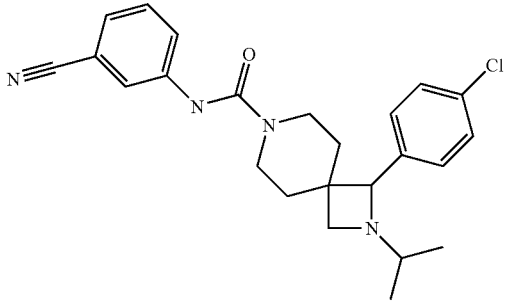 | 50 |
|  | 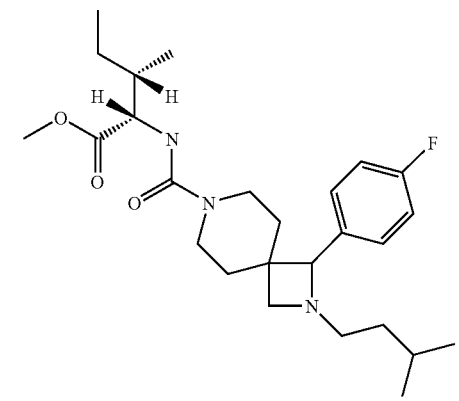 | 58 |
| A | 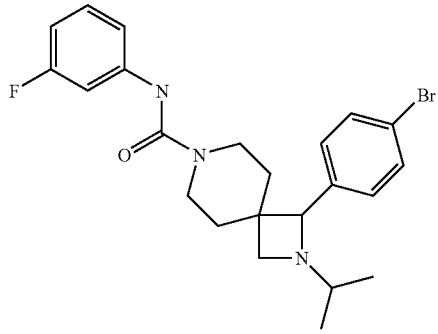 | 58 |
| A | 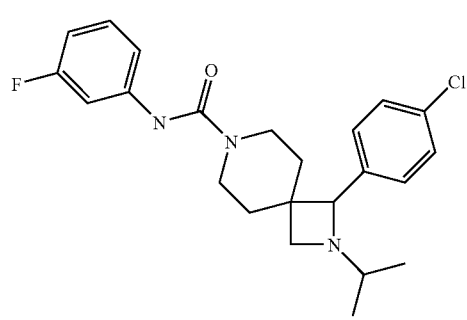 | 64 |

TABLE 10-continued
| Isomer | Compound | IW hCav3.2 IC50 nM |
|---|---|---|
| | 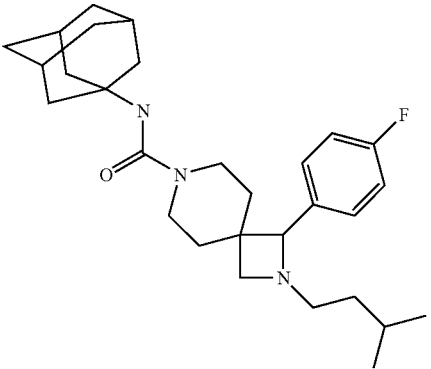 | 68 202* |
| | 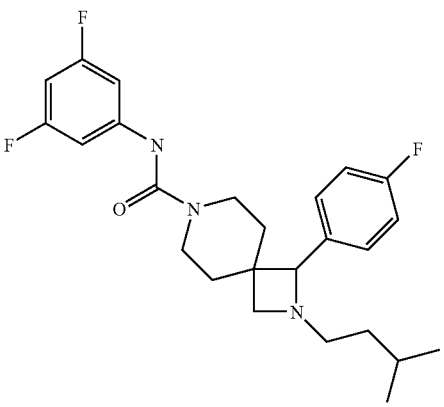 | 70 |
| | 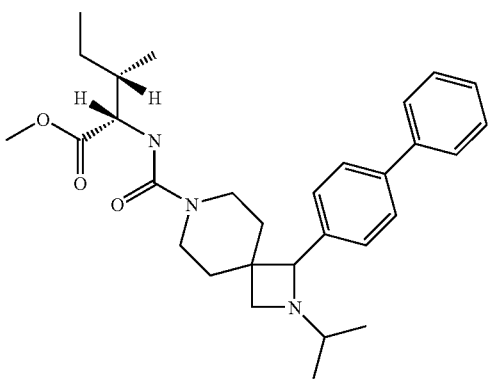 | 76 |
| A | 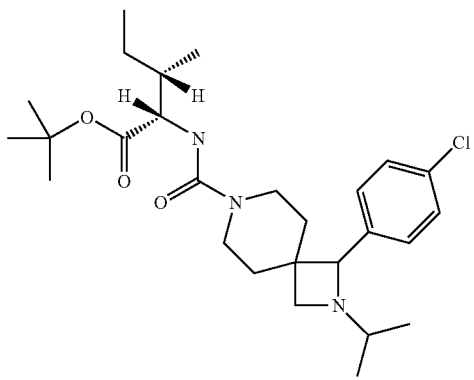 | 85 |

TABLE 10-continued

| Isomer | Compound | IW hCav3.2 IC50 nM |
|---|---|---|
| A | 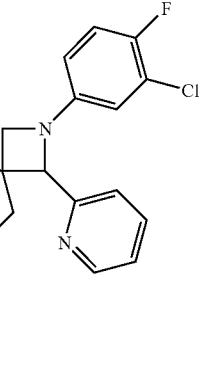 (144) Isomer A | 60 |
| A | 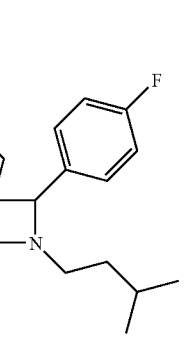 (146) Isomer A | 76 |
| A | 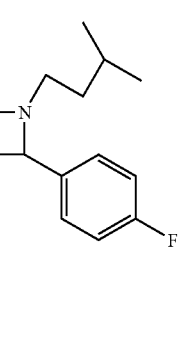 (148) Isomer A | 45 |

*IC50 in nM for the CaV3.2 Voltage clamp assay

To Measure NPC1L1 the Following Binding Assays would be Used:

HEK-293 cells expressing human NPC1L1 can be plated into 384-well black/clear plates (BD Biosciences, Bedford Mass.) for binding experiments the following day. Cell growth media (DMEM, 10% fetal calf serum, 1 mg/ml geneticin, 100 Units/ml penicillin) can be aspirated. Cell growth media (20 ml) containing 250 nM BODIPY-labeled glucuronidated ezetimibe can be added to each well. Cell growth media (20 ml) containing the indicated concentration of compound can then be added to the wells. Unlabeled glucuronidated ezetimibe (100 mM) can be used to determine nonspecific binding. The binding reaction can be allowed to proceed for 4 h at 37 C. Subsequently the cell growth media can be aspirated and the cells can be washed once with PBS. The remaining fluorescent labeled glucuronidated ezetimibe bound to the cells can be quantified using a FlexStation plate reader (Molecular Devices, Sunnyvale Calif.) to measure fluorescence intensity. Ki values can be determined from competition binding curves (n=4 for each point) using Prism and Activity Base software.

To Measure Inhibition of Cholesterol Absorption the Following In Vivo Assay Would be Used:

Male rats can be dosed by oral gavage with 0.25 ml corn oil or compound in corn oil; 0.5 h later, each rat can be given 0.25 ml of corn oil orally with 2 µCi $^{14}$C-Cholesterol, 1.0 mg cold cholesterol.

2 h later, the rats can be anesthetized with 100 mg/kg IP of Inactin, and a 10 ml blood sample can be collected from the abdominal aorta. The small intestine can be removed, divided into 3 sections, and each rinsed with 15 ml of cold saline. The rinses can be pooled. The liver can be removed, weighed, and three ~350 mg aliquots can be removed. 5 ml 1N NaOH can be added to each intestinal piece, 1 ml to each liver aliquot to dissolve at 40° overnight. 2×1 ml aliquots of the SI digests and the liver digests can be neutralized with 0.25 ml 4N HCl and counted. 2×1 ml aliquots of plasma and intestinal rinses can be counted.

Embodiments of this invention include those in paragraphs:

1. Compounds of formula (I);
2. The compound as described in paragraph (1.) wherein:
(A) $R^1$ is selected from the group consisting of: H, alkyl, substituted alkyl, cycloalkyl, aryl, substituted aryl, arylalkyl, heteroaryl, substituted heteroaryl, heteroarylalkyl, diphenyl methyl, cycloalkylalkyl and -alkylene-C(O)N(alkyl)$_2$;
(B) $R^2$ is selected from the group consisting of: H, alkyl, substituted alkyl, cycloalkyl, aryl, substituted aryl, arylalkyl, heteroarylalkyl, substituted heteroarylalkyl, heterocycloalkyl, heterocycloalkylalkyl, $R^6$-A-, alkyl-O—C(O)—, (alkyl)$_2$-N-alkylene-C(O)—, CN-alkylene-C(O)—, alkyl-O-alkylene-C(O)—, alkyl-C(O)-alkylene-C(O)—, alkyl-NH—C(O)—, alkyl-O—C(O)-alkylene-C(O)—,

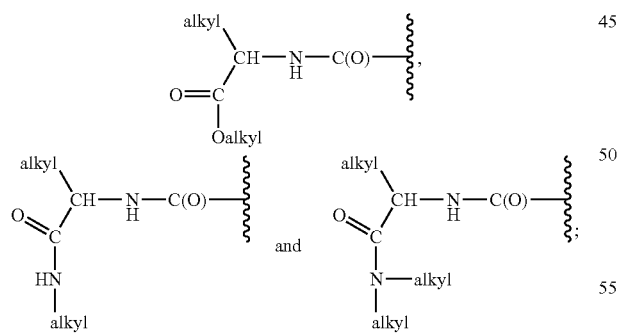

(C) $R^3$ is selected from the group consisting of: H, alkyl, substituted alkyl, cycloalkyl, aryl, substituted aryl, arylalkyl, arylalkenyl, arylalkynyl, arylalkyl-NH—, arylalkoxy, heteroaryl, substituted heteroaryl, heteroarylalkyl, heteroarylalkenyl, and heteroarylalkynyl;

(D) Each occurrence of $R^4$ is independently selected from the group consisting of: —CH$_2$—, —CH(alkyl)- and —C(alkyl)$_2$ wherein each alkyl for each $R^4$ is independently selected;

(E) Each occurrence of $R^5$ is independently selected from the group consisting of: —CH$_2$—, —CH(alkyl)- and —C(alkyl)$_2$ wherein each alkyl for each $R^5$ is independently selected; or (F) Each occurrence of $R^4$ is independently selected from the group consisting of: —CH$_2$—, —CH(alkyl)- and —C(alkyl)$_2$ wherein each alkyl for each $R^4$ is independently selected; each occurrence of $R^5$ is independently selected from the group consisting of: —CH$_2$—, —CH(alkyl)- and —C(alkyl)$_2$- wherein each alkyl for each $R^5$ is independently selected; and wherein a ring carbon of said $R^4$ is bound to a ring carbon of said $R^5$ by a CH$_2$—CH$_2$— group;

(G) u is an integer from 0 to 3;

(H) v is an integer from 0 to 3, such that the sum of u and v is from 3 to 5;

(I) $R^6$ is selected from the group consisting of: alkyl, aryl, heteroaryl, substituted heteroaryl, cycloalkyl, cycloalkylalkyl, heterocycloalkyl, cycloalkenyl, heterocycloalkenyl, benzofused cycloalkyl, benzofused heterocycloalkyl, and benzofused heterocycloalkenyl;

(J) A is selected from the group consisting of: —C(O)—, —C(O)-alkylene-, —C(O)-alkylene-O—, —C(O)—CH$_2$—N(alkyl)-C(O)—, -alkylene-, -alkenylene-, —C(O)-alkenylene-, —C(O)—NH—, —C(O)—NH-alkylene-, and

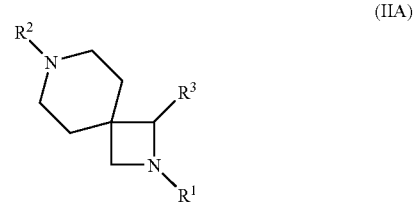

(K) wherein the compounds defined by an "X" in Tables 3a, 3b, 3c, and 3d, and the compounds defined in Table 4a are excluded from the definition of the compounds of formula I;

3. The compound as described in paragraph (1.) having the formula IIA:

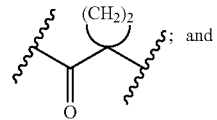

(IIA)

wherein the compounds defined by an "X" in Tables 3a, 3b, 3c, 3d and the compounds in Table 4a are excluded from the compounds of formula IIA;

4. The compound as described in paragraph (1.) wherein $R^3$ is selected from the group consisting of: (A) phenyl, (B) substituted phenyl, (C) heteroaryl, and (D) substituted heteroaryl wherein there are 1 to 3 substituents independently selected from the group consisting of: halo and —CN;

5. The compound as described in paragraph (1.) wherein $R^3$ is selected from the group consisting of: (A) phenyl, (B) substituted phenyl wherein there are 1 to 3 substituents independently selected from the group consisting of: Br, F, Cl and —CN, (C) heteroaryl selected from the group consisting of: pyridyl and pyrimidinyl, and (D) substituted heteroaryl selected from the group consisting of substituted pyridyl and substituted pyrimindinyl wherein there are 1 to 3 substituents independently selected from the group consisting of: Br, F, and Cl and —CN;

6. The compound as described in paragraph (1.) wherein $R^3$ is selected from the group consisting of:

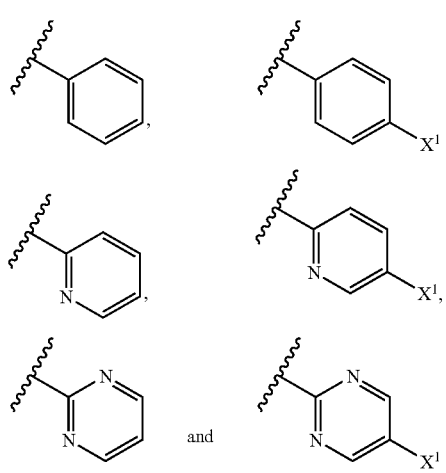

wherein $X^1$ is selected from the group consisting of: Br, F, and Cl and —CN;

7. The compound as described in paragraph (1.) wherein $R^3$ is selected from the group consisting of:

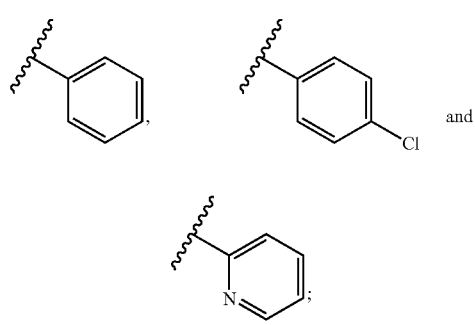

8. The compound of claim 3 wherein $R^3$ is selected from the group consisting of: (A) phenyl, (B) substituted phenyl, (C) heteroaryl, and (D) substituted heteroaryl wherein there are 1 to 3 substituents independently selected from the group consisting of: halo and —CN;

9. The compound as described in paragraph (3.) wherein $R^3$ is selected from the group consisting of: (A) phenyl, (B) substituted phenyl wherein there are 1 to 3 substituents independently selected from the group consisting of: Br, F, Cl and —CN, (C) heteroaryl selected from the group consisting of: pyridyl and pyrimidinyl, and (D) substituted heteroaryl selected from the group consisting of substituted pyridyl and substituted pyrimindinyl wherein there are 1 to 3 substituents independently selected from the group consisting of: Br, F, and Cl and —CN;

10. The compound as described in paragraph (3.) wherein $R^3$ is selected from the group consisting of:

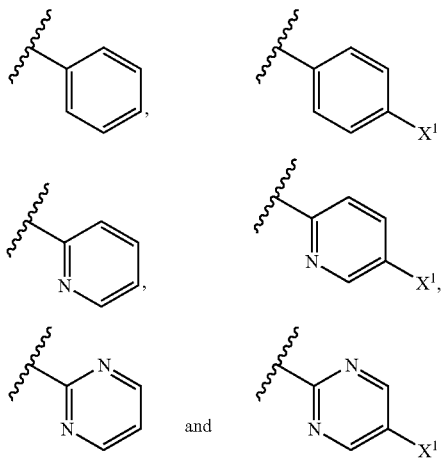

wherein $X^1$ is selected from the group consisting of: Br, F, and Cl and —CN.

11. The compound as described in paragraph (3.) wherein $R^3$ is selected from the group consisting of:

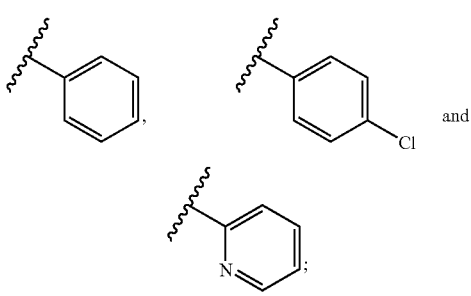

12. The compound as described in paragraph (3.) wherein $R^1$ is selected from the group consisting of: methyl, i-propyl, —CH$_2$CH(CH$_3$)$_2$, —CH$_2$CH$_2$(CH$_3$)$_2$,

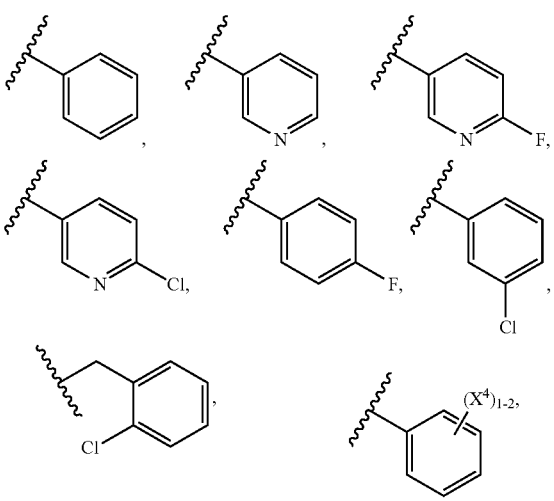

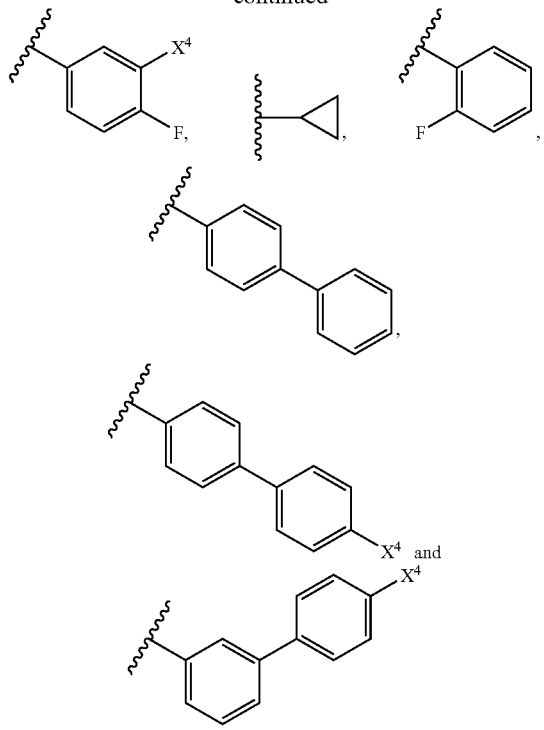

wherein each X⁴ is independently selected from the group consisting of: Br, Cl, CN and —CF₃;

13. The compound as described in paragraph (1.) wherein R² is selected from the group consisting of: alkyl(—C(O)Oalkyl)-NH—C(O)— and R⁶-A-, wherein A is selected from the group consisting of: —C(O)—NH—, —C(O)— or —C(O)-alkylene-, and R⁶ is an optionally substituted group selected from the group consisting of: aryl, heteroaryl, cycloalkyl, cycloalkylalkyl, heterocycloalkyl, cycloalkenyl, heterocycloalkenyl, benzofused cycloalkyl, benzofused heterocycloalkyl, and benzofused heterocycloalkenyl;

14. The compound as described in paragraph (13.) wherein R⁶ is selected from the group consisting of: phenyl, naphthyl, pyridyl, substituted phenyl, and substituted naphthyl, wherein said substituted groups are substituted with 1 to 3 substituents independently selected from the group consisting of: alkyl F, Cl, Br, —CF₃, CN, alkoxy, phenoxy and —CO₂alkyl;

15. The compound as described in paragraph (14.) of claim 14 wherein said substituents are independently selected from the group consisting of: alkyl, F, Cl, Br, CN;

16. The compound as described in paragraph (14.) wherein said substituted phenyl is selected from the group consisting of:

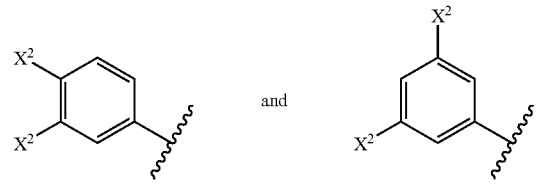

wherein each X² is independently selected from the group consisting of: alkyl, F, Cl, and Br, —CF₃, CN, alkoxy, phenoxy and —CO₂alkyl;

17. The compound as described in paragraph (14.) wherein said substituted phenyl is selected from the group consisting of:

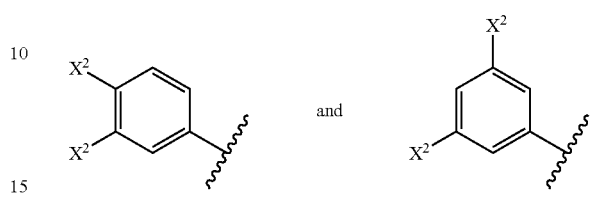

wherein each X² is independently selected from the group consisting of: F, Cl, Br and CN;

18. The compound as described in paragraph (17.) wherein said substituted phenyls are selected from the group consisting of:

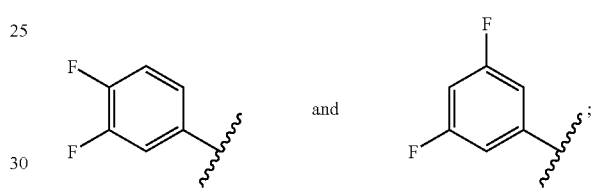

19. The compound as described in paragraph (13.) wherein said R⁶ heteroaryl is a substituted heteroaryl substituted with 1 to 3 substituents independently selected from the group consisting of: alkyl, halo F, Cl, Br, —CF₃, CN, alkoxy, phenoxy and —CO₂alkyl;

20. The compound as described in paragraph (19.) wherein said substituents are independently selected from the group consisting of: F, Cl, Br and CN;

21. The compound as described in paragraph (19.) wherein said substituted heteroaryl is

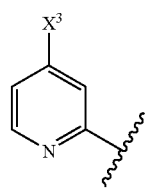

wherein X³ is independently selected from the group consisting of: alkyl, F, Cl, Br, —CF₃, CN, alkoxy, phenoxy and —CO₂alkyl;

22. The compound as described in paragraph (21.) wherein X³ is independently selected from the group consisting of: F, Cl, Br and CN;

23. The compound as described in paragraph (13.) wherein said cycloalkyl is selected from the group consisting of: cyclopentyl, cyclohexyl, and cycloheptyl;

24. The compound as described in paragraph (13.) wherein said cycloalkenyl is dihydropyran;

25. The compound as described in paragraph (13.) wherein R² is selected from the group consisting of:

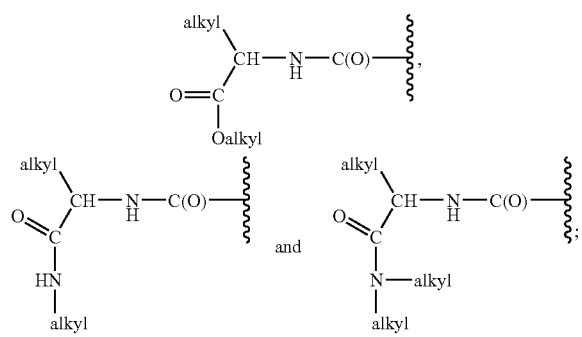

26. The compound as described in paragraph (13.) wherein $R^2$ is selected from the group consisting of: alkyl(—C(O)Oalkyl)-NH—C(O)— and $R^6$-A-, wherein A is selected from the group consisting of: —C(O)—NH—, —C(O)— or —C(O)-alkylene-, and $R^6$ is an optionally substituted group selected from the group consisting of: aryl, heteroaryl, cycloalkyl, cycloalkylalkyl, heterocycloalkyl, cycloalkenyl, heterocycloalkenyl, benzofused cycloalkyl, benzofused heterocycloalkyl, and benzofused heterocycloalkenyl;

27. The compound as described in paragraph (26.) wherein $R^6$ is selected from the group consisting of: phenyl, naphthyl, pyridyl, substituted phenyl, and substituted naphthyl, wherein said substituted groups are substituted with 1 to 3 substituents independently selected from the group consisting of: alkyl, F, Cl, Br, —$CF_3$, CN, alkoxy, phenoxy and —$CO_2$alkyl;

28. The compound as described in paragraph (27.) of claim 27 wherein said substituents are independently selected from the group consisting of: alkyl, F, Cl, Br, CN;

29. The compound as described in paragraph (27.) wherein said substituted phenyl is selected from the group consisting of:

wherein each $X^2$ is independently selected from the group consisting of: alkyl, F, Cl, and Br, —$CF_3$, CN, alkoxy, phenoxy and —$CO_2$alkyl;

30. The compound as described in paragraph (27.) wherein said substituted phenyl is selected from the group consisting of:

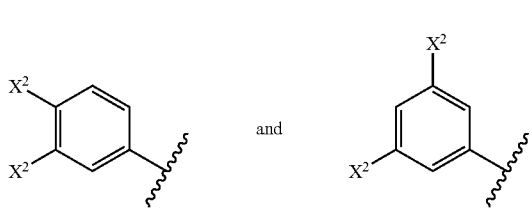

wherein each $X^2$ is independently selected from the group consisting of: F, Cl, Br and CN;

31. The compound as described in paragraph (30.) wherein said substituted phenyls are selected from the group consisting of:

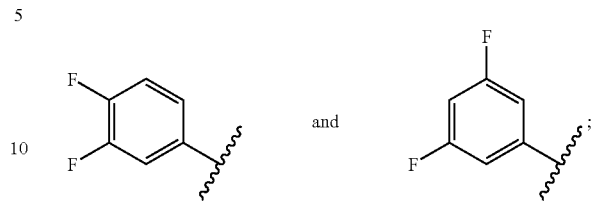

32. The compound as described in paragraph (26.) wherein said $R^6$ heteroaryl is a substituted heteroaryl substituted with 1 to 3 substituents independently selected from the group consisting of: alkyl, halo F, Cl, Br, —$CF_3$, CN, alkoxy, phenoxy and —$CO_2$alkyl;

33. The compound as described in paragraph (32.) of claim 32 wherein said substituents are independently selected from the group consisting of: F, Cl, Br and CN;

34. The compound as described in paragraph (32.) of claim 32 wherein said substituted heteroaryl is

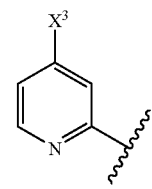

wherein $X^3$ is independently selected from the group consisting of: alkyl, F, Cl, Br, —$CF_3$, CN, alkoxy, phenoxy and —$CO_2$alkyl;

35. The compound of claim 34 wherein $X^3$ is independently selected from the group consisting of: F, Cl, Br and CN.

36. The compound as described in paragraph (26.) wherein said cycloalkyl is selected from the group consisting of: cyclopentyl, cyclohexyl, and cycloheptyl;

37. The compound as described in paragraph (26.) wherein said cycloalkenyl is dihydropyran;

38. The compound as described in paragraph (26.) wherein $R^2$ is:

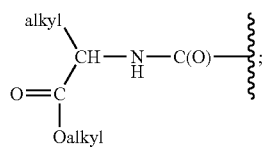

39. The compound as described in paragraph (1.) wherein:
$R^1$ is selected from the group consisting of: H, alkyl, substituted alkyl, cycloalkyl, aryl and substituted aryl;
$R^3$ is selected from the group consisting of: aryl and substituted aryl; and
$R^2$ is selected from the group consisting of: H, aryl-NH—C(O)—, alkyl-NH—C(O)—, alkyl-O—C(O)—, alkyl-O—C(O)-alkylene-NH—C(O)—, and alkyl(—C(O)Oalkyl)-NH—C(O)—;

40. The compound as described in paragraph (3.) wherein:

R$^1$ is selected from the group consisting of: H, alkyl, substituted alkyl cycloalkyl, aryl and substituted aryl;

R$^3$ is selected from the group consisting of, aryl and substituted aryl; and

R$^2$ is selected from the group consisting of: H, aryl—NH—C(O)—, alkyl-NH—C(O)—, alkyl-O—C(O)—, alkyl-O—C(O)-alkylene-NH—C(O)—, and alkyl(—C(O)Oalkyl)-NH—C(O)—;

41. The compound as described in paragraph (1.) wherein:

R$^1$ is selected from the group consisting of: H, isopropyl, methyl, phenyl, 4-fluorophenyl, 2-chlorophenyl and cyclopropyl;

R$^3$ is selected from the group consisting of: 4-chlorophenyl, phenyl, 4-bromophenyl, and 4-benzyloxy-phenyl; and R$^2$ is selected from the group consisting of: H, 3,5-dichloro-phenyl-NH—C(O)—, 3,4-di-fluoro-phenyl-NH—C(O)—, 4-chloro-phenyl-NH—C(O)—, 3,5-difluoro-phenyl-NH—C(O)—, 4-fluoro-phenyl-NH—C(O)—, (CH$_3$)$_2$C—CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—, 2-CF$_3$-phenyl-NHC(O)—, 2-chloro-6-methyl-phenyl-NHC(O)—, 2,6-dichloro-phenyl-NHC(O)—, t-Bu-phenyl-NHC(O)—,

42. The compound as described in paragraph (1) wherein:

R$^1$ is selected from the group consisting of: H, isopropyl, methyl, phenyl, 4-fluorophenyl, 2-chlorophenyl and cyclopropyl;

R$^3$ is selected from the group consisting of: 4-chlorophenyl, phenyl, 4-bromophenyl, and 4-benzyloxy-phenyl; and R$^2$ is selected from the group consisting of: H, 3,5-dichloro-phenyl-NH—C(O)—, 3,4-di-fluoro-phenyl-NH—C(O)—, 4-chloro-phenyl-NH—C(O)—, 3,5-difluoro-phenyl-NH—C(O)—, 4-fluoro-phenyl-NH—C(O)—, (CH$_3$)$_2$C—CH$_2$—C(CH$_3$)$_2$—NH—C(O)—, phenyl-NH—C(O)—, 2-methyl-phenyl-NH—C(O)—, 4-(CH$_3$—O—C(O)-)phenyl-NH—C(O)—, 2-cyano-phenyl-NH—C(O)—, 2-chloro-phenyl-NH—C(O)—, 2-fluoro-phenyl-NH—C(O)—, t-Bu-O—C(O)—, 4-isopropyl-phenyl-NH—C(O)—, 2-CF$_3$-phenyl-NHC(O)—, 2-chloro-6-methyl-phenyl-NHC(O)—, 2,6-dichloro-phenyl-NHC(O)—, t-Bu-phenyl-NHC(O)—,

43. The compound as described in paragraph (3.) wherein:

(A) R$^1$ is selected from the group consisting of: (1) alkyl, (2) alkenyl, (3) cycloalkyl, (4) aryl, (5) halo substituted phenyl, (6) arylalkyl-, and (7) —C(O)NQ$^B$ wherein Q$^B$ is selected from the group consisting of: substituted phenyl;

(B) R$^2$ is selected from the group consisting of:

(1) —C(O)NHQ$^A$ wherein Q$^A$ is selected from the group consisting of:
  (a) cycloalkyl,
  (b) alkyl substituted with —C(O)—O-alkyl,
  (c) substituted aryl,
  (d) alkyl,
  (e) substituted arylalkyl,
  (f) substituted heterocycloalkenylbenzo,
  (g) heteroaryl, (2) H, (3) substituted benzoheterocycloakyl-C(O)—, (4) —C(O)O-alkyl, (5) heterocycloalkyl, and (6) —C(O)NQ$^C$Q$^D$ wherein Q$^C$ and Q$^D$ are each independently selected from the group consisting of: H, Q$^A$ (as defined in (B)(1)), substituted aryl, and arylalkyl; and (C) R$^3$ is selected from the group consisting of:
  (1) substituted phenyl,
  (2) heteroaryl;

44. The compound as described in paragraph (3.) wherein:

(A) R$^1$ is selected from the group consisting of: i-propyl, methyl, —(CH$_2$)$_2$CH(CH$_3$)$_2$), —CH$_2$CH(CH$_3$)$_2$), —CH$_2$CH=CH$_2$, cyclopropyl, phenyl, p-F-phenyl, benzyl, and —C(O)NQ$^B$ wherein Q$^B$ is phenyl substituted with halo;

(B) R$^2$ is selected from the group consisting of:

(1) —C(O)NHQ$^A$ wherein Q$^A$ is selected from the group consisting of: adamantyl and cycloheptyl, —CH(C(O)OCH$_3$)CH(CH$_3$)$_2$, —CH(C(O)OCH$_3$)CH(CH$_3$)CH$_2$CH$_3$, —CH(C(O)Ot-butyl)CH(CH$_3$)CH$_2$CH$_3$, —CH(C(O)OCH$_3$)CH(CH$_3$)$_2$, and CH$_2$C(O)OCH$_2$CH$_3$, 3,5-di-F-phenyl, 3-F-phenyl, p-Cl-phenyl, m-Cl-phenyl, o-Cl-phenyl, m-Br-phenyl, p-Br-phenyl), m,p-di-F-phenyl, p-F-phenyl, o-F-phenyl, o,p-di-F-phenyl, o,m-di-F-phenyl), m-CN-phenyl, p-CN-phenyl, m-CF$_3$-phenyl, p-CF$_3$-phenyl, m-methoxyphenyl, m-CH$_3$CH$_2$OC(O)-phenyl, m-methylphenyl, m-CH$_3$O-phenyl, p-methylphenyl, o-methylphenyl, o-methoxyphenyl, p-methoxyphenyl, and m-F-p-methyl-phenyl), —CH(CH$_3$)$_2$CH$_2$C (CH$_3$)$_3$, t-butyl, halo substituted benzyl, pyridyl and (2) 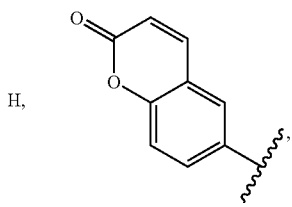

(3) 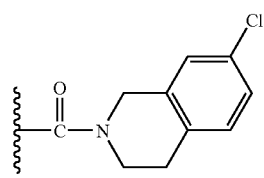

(4) 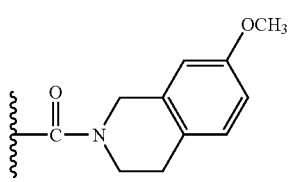

(5) —C(O)Ot-butyl,
(6) morpholinyl), and
(7) —C(O)NQ$^C$Q$^D$ wherein Q$^C$ and Q$^D$ are each independently selected from the group consisting of: H, Q$^A$, halo substituted phenyl, and benzyl); and
(C) R$^3$ is selected from the group consisting of: p-Cl-phenyl, p-Br-phenyl, and p-F-phenyl, phenyl-phenyl-, pyridyl-phenyl-, p-CN-phenyl, and pyridyl;

45. The compound as described in paragraph (3.) wherein:
(A) R$^1$ is selected from the group consisting of:
  (1) alkyl,
  (2) substituted arylalkyl,
  (3) cycloalkylalkyl, and
  (4) substituted alkyl;
(B) R$^2$ is selected from the group consisting of:
  (1) —C(O)aryl wherein said aryl is substituted with 1 to 3 substituents independently selected from the group consisting of: alkoxy, alkyl-C(O)—, and —SO$_2$alkyl,
  (2) —C(O)benzoheterocycloalkyl,
  (3) substituted heterocycloalkyl, and
  (4) substituted arylalkyl; and
(C) R$^3$ is selected from the group consisting of: H, aryl, and substituted aryl;

46. The compound as described in paragraph (1.) wherein:
(A) R$^1$ is selected from the group consisting of: —CH$_2$CH (CH$_3$)$_2$), o,p-di-F-benzyl, o-Cl-benzyl, and o,p-di-F-benzyl, p-methylphenyl, p-methoxyphenyl, m-methoxyphenyl, p-CF$_3$-phenyl, and p-F-phenyl), cyclopropyl-CH$_2$—, and —CH(phenyl)$_2$;
(B) R$^2$ is selected from the group consisting of: o,m,p-trimethoxyphenyl-C(O)—, —C(O)-(p-CH$_3$C(O)phenyl), —C(O)-(p-SO$_2$CH$_3$-phenyl),

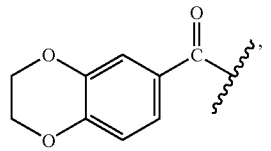

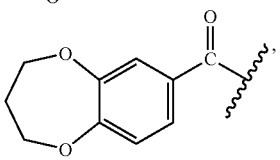

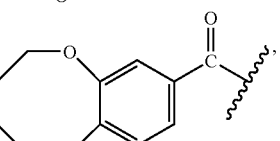

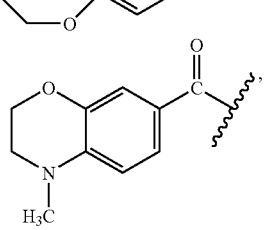

and p-methoxybenzyl; and
(C) R$^3$ is selected from the group consisting of: H, phenyl, p-F-phenyl, p-Cl-phenyl, and o,p-di-F-phenyl;

47. A compound selected from the group consisting of compounds 1 to 148;

48. A compound selected from the group consisting of the compounds in Tables 5, 6, 7, 8, 8A, 9 and 10;

49. The compound as described in paragraph (48.) wherein said compound is selected from the group consisting of the compounds of Table 9;

50. The compound as described in paragraph (48.) wherein said compound is selected from the group consisting of the compounds of Table 10;

51. The compound as described in paragraph (1.) in pure and isolated form;

52. A pharmaceutical composition comprising at least one compound as described in paragraph (1.) and a pharmaceutically acceptable carrier;

53. A pharmaceutical composition comprising at least one compound as described in paragraph (3.) and a pharmaceutically acceptable carrier;

54. A method of treating pain comprising administering to a patient in need of such treatment an effective amount of at least one compound as described in paragraph (1.);

55. A method of treating pain comprising administering to a patient in need of such treatment an effective amount of a compound as described in paragraph (1.);

56. A method of treating pain comprising administering to a patient in need of such treatment an effective amount of a compound as described in paragraph (3.), 57. The method as described in paragraph (55.) wherein said pain is inflammatory pain;

58. The method as described in paragraph (56.) wherein said pain is inflammatory pain;

59. The method as described in paragraph (55.) wherein said pain is chronic pain;

60. The method as described in paragraph (56.) wherein said pain is chronic pain;

61. The method as described in paragraph (55.) wherein said pain is neuropathic pain;

62. The method as described in paragraph (56.) wherein said pain is neuropathic pain;

63. A method of treating pain comprising administering to a patient in need of such treatment an effective amount of a compound as described in paragraph (1.) in combination with an effective amount of at least one additional agents for treating pain;

64. A method of treating pain comprising administering to a patient in need of such treatment an effective amount of a compound as described in paragraph (3.) in combination with an effective amount of at least one additional agent for treating pain;

65. The method as described in paragraph (63.) wherein said additional agent for treating pain is selected from the group consisting of: non-opioid analgesics, opioid analgesics, steroids, COX-I inhibitors, COX-II inhibitors, agents useful for treating inflammatory bowel disease, and agents useful for treating rheumatoid arthritis;

66. The method as described in paragraph (64.) wherein said additional agent for treating pain is selected from the group consisting of: non-opioid analgesics, opioid analgesics, steroids, COX-I inhibitors, COX-II inhibitors, agents useful for treating inflammatory bowel disease, and agents useful for treating rheumatoid arthritis;

67. The method as described in paragraph (63.) wherein said additional agent for treating pain is selected from the group consisting of:
non-opioid analgesics selected from the group consisting of: acetylsalicylic acid, choline magnesium trisalicylate, acetaminophen, ibuprofen, fenoprofen, diflusinal, and naproxen;
opioid analgesics selected from the group consisting of: morphine, hydromorphone, methadone, levorphanol, fentanyl, oxycodone, and oxymorphone;
steroids selected from the group consisting of: prednisolone, fluticasone, triamcinolone, beclomethasone, mometasone, budisamide, betamethasone, dexamethasone, prednisone, flunisolide and cortisone;
COX-I inhibitors selected from the group consisting of: aspirin and piroxicam;
COX-II inhibitors selected from the group consisting of: rofecoxib, celecoxib, valdecoxib and etoricoxib;
agents useful for treating inflammatory bowel disease selected from the group consisting of: as IL-10, steroids, and azulfidine; and
agents useful for treating rheumatoid arthritis selected from the group consisting of: methotrexate, azathioprine, cyclophosphamide, steroids and mycophenolate mofetil;

68. The method as described in paragraph (64.) wherein said additional agent for treating pain is selected from the group consisting of:
non-opioid analgesics selected from the group consisting of: acetylsalicylic acid, choline magnesium trisalicylate, acetaminophen, ibuprofen, fenoprofen, diflusinal, and naproxen;
opioid analgesics selected from the group consisting of: morphine, hydromorphone, methadone, levorphanol, fentanyl, oxycodone, and oxymorphone;
steroids selected from the group consisting of: prednisolone, fluticasone, triamcinolone, beclomethasone, mometasone, budisamide, betamethasone, dexamethasone, prednisone, flunisolide and cortisone;
COX-I inhibitors selected from the group consisting of: aspirin and piroxicam;
COX-II inhibitors selected from the group consisting of: rofecoxib, celecoxib, valdecoxib and etoricoxib;
agents useful for treating inflammatory bowel disease selected from the group consisting of: as IL-10, steroids, and azulfidine; and
agents useful for treating rheumatoid arthritis selected from the group consisting of: methotrexate, azathioprine, cyclophosphamide, steroids and mycophenolate mofetil;

69. The method as described in paragraph (63.) wherein said additional agent for treating pain is selected from the group consisting of: acetylsalicylic acid, choline magnesium trisalicylate, acetaminophen, ibuprofen, fenoprofen, diflusinal, naproxen, morphine, hydromorphone, methadone, levorphanol, fentanyl, oxycodone, and oxymorphone;

70. The method as described in paragraph (63.) wherein said additional agent for treating pain is selected from the group consisting of: steroids and non-opioid analgesic agents;

71. The method as described in paragraph (64.) wherein said additional agent for treating pain is selected from the group consisting of: acetylsalicylic acid, choline magnesium trisalicylate, acetaminophen, ibuprofen, fenoprofen, diflusinal, naproxen, morphine, hydromorphone, methadone, levorphanol, fentanyl, oxycodone, and oxymorphone;

72. The method as described in paragraph (64.) wherein said additional agent for treating pain is selected from the group consisting of: steroids and non-opioid analgesic agents;

73. A method of treating diabetes comprising administering to a patient in need of such treatment an effective amount of at least one compound as described in paragraph (1.);

74. A method of treating diabetes comprising administering to a patient in need of such treatment an effective amount of at least one compound as described in paragraph (3.);

75. A method of treating diabetes comprising administering to a patient in need of such treatment an effective amount of at least one compound as described in paragraph (1.) in combination with an effective amount of at least one other drug for treating diabetes;

76. A method of treating diabetes comprising administering to a patient in need of such treatment an effective amount of at least one compound as described in paragraph (3.) in combination with an effective amount of at least one other drug for treating diabetes;

77. The method as described in paragraph (75.) wherein said other drug for treating diabetes is selected from the group consisting of: sulfonylureas, insulin sensitizers, α-glucosidase inhibitors, insulin secretagogues, hepatic glucose output lowering compounds, and insulin;

78. The method as described in paragraph (76.) wherein said other drug for treating diabetes is selected from the group consisting of: sulfonylureas, insulin sensitizers, α-glucosidase inhibitors, insulin secretagogues, hepatic glucose output lowering compounds, and insulin;

79. The method as described in paragraph (77.) wherein said insulin sensitizers are selected from the group consisting of: PPAR agonists, DPPIV inhibitors, PTP-1B inhibitors and glucokinase activators;

80. The method as described in paragraph (78.) wherein said insulin sensitizers are selected from the group consisting of: PPAR agonists, DPPIV inhibitors, PTP-1B inhibitors and glucokinase activators;

81. A kit comprising in a single package at least one compound as described in paragraph (1.) in a pharmaceutical composition, and at least one separate pharmaceutical composition comprising at least one additional agent for treating pain;

82. A kit comprising in a single package at least one compound as described in paragraph (3.) in a pharmaceutical composition, and at least one separate pharmaceutical composition comprising at least one additional agent for treating pain;

83. A kit comprising in a single package at least one compound of claim 1 in a pharmaceutical composition, and at least one separate pharmaceutical composition comprising at least one additional drug for treating diabetes;

84. A kit comprising in a single package at least one compound as described in paragraph (3.) in a pharmaceutical composition, and at least one separate pharmaceutical composition comprising at least one additional drug for treating diabetes;

85. A method for inhibiting the absorption of cholesterol comprising administering to a patient in need of such treatment an effective amount of at least one compound as described in paragraph (1.);

86. A method for inhibiting the absorption of cholesterol comprising administering to a patient in need of such treatment an effective amount of at least one compound as described in paragraph (1.) in combination with an effective amount of at least one additional agent for treating a disorder of lipid metabolism;

87. A method for inhibiting the absorption of cholesterol comprising administering to a patient in need of such treatment an effective amount of at least one compound as described in paragraph (1.) in combination with an effective amount of at least one nicotinic acid receptor agonist;

88. A method for inhibiting the absorption of cholesterol comprising administering to a patient in need of such treatment an effective amount of at least one compound as described in paragraph (1.) in combination with an effective amount of at least one inhibitor of HMG-CoA reductase;

89. A method for inhibiting the absorption of cholesterol comprising administering to a patient in need of such treatment an effective amount of at least one compound as described in paragraph (1.) in combination with an effective amount of at least one inhibitor of CETP;

90. A method for inhibiting the absorption of cholesterol comprising administering to a patient in need of such treatment an effective amount of at least one compound as described in paragraph (1.) in combination with an effective amount of at least one NPC1L1 antagonist;

91. A method for inhibiting the absorption of cholesterol comprising administering to a patient in need of such treatment an effective amount of at least one compound as described in paragraph (1.) in combination with an effective amount of at least one inhibitor of HMG-CoA reductase, and in combination with an effective amount of at least one NPC1L1 antagonist; and 92. A kit comprising in a single package at least one compound as described in paragraph (1.) in a pharmaceutical composition, and at least one separate pharmaceutical composition comprising at least one additional drug for inhibiting the absorption of cholesterol.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

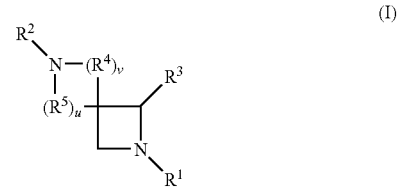

or a pharmaceutically acceptable salt, solvate, prodrug or stereoisomer thereof, wherein:

$R^1$ is selected from the group consisting of: (1) aryl and (2) substituted aryl, and wherein:

the substituted aryl moieties are each independently substituted with one or more substituents independently selected from the group consisting of: (a) —(C=N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl;

$R^2$ is —C(O)NHQ$^A$ wherein Q$^A$ is substituted aryl, and wherein:

the substituted aryl is substituted with one or more substituents independently selected from the group consisting of: (a) —(C=N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl;

$R^3$ is selected from the group consisting of: (1) heteroaryl and (2) substituted heteroaryl; and wherein:

the substituted heteroaryl is substituted with one or more substituents independently selected from the group consisting of: (a) —(C=N—O-alkyl)CH₃, (b) —NC(O)NH₂, (c) —NC(O)NH(alkyl), (d) —NC(O)N(alkyl)₂, (e) —SO₂NH₂, (f) —SO₂NH(alkyl), (g) —SO₂N(alkyl)₂, (h) —CF₃, (i) —OH, (j) -halo, (k) —CN, (l) -alkoxy, (m) —C(O)O-alkyl, (n) —S(O)alkyl, (o) —SO₂-alkyl, (p) —P(O)(O-alkyl)₂, and (q) alkyl; and Each $R^4$ is —CH₂—, and v is 2;

Each $R^5$ is —CH₂—, and u is 2; and wherein for compound of formula IIIC:

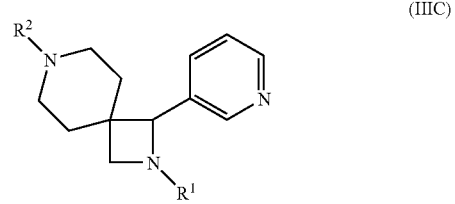

when R¹ is
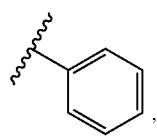,
then
R² is not:
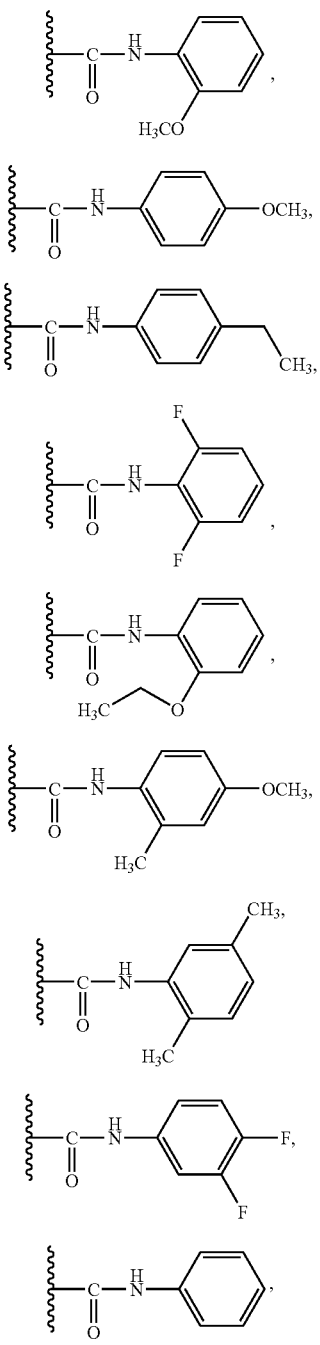
-continued
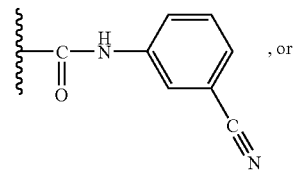
wherein for compound of formula IIIC:
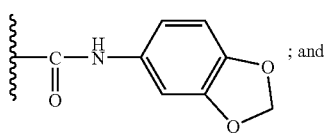
(IIIC)
when R¹ is
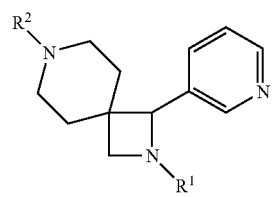,
then
R² is not:
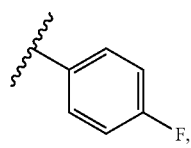
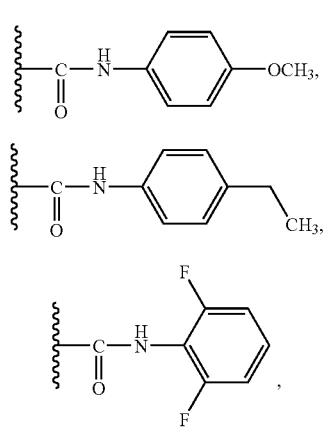

-continued
146 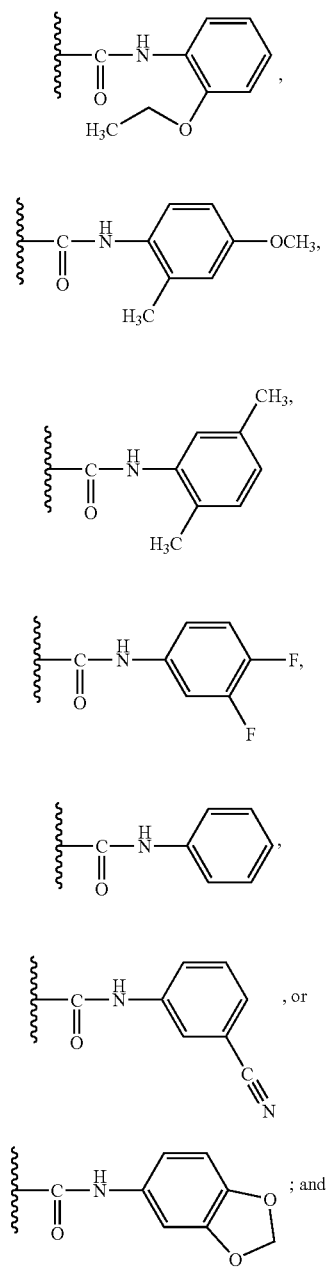
152
157
167
175
475
476
; and
wherein for compound of formula IIIC:
(IIIC)
when R¹ is
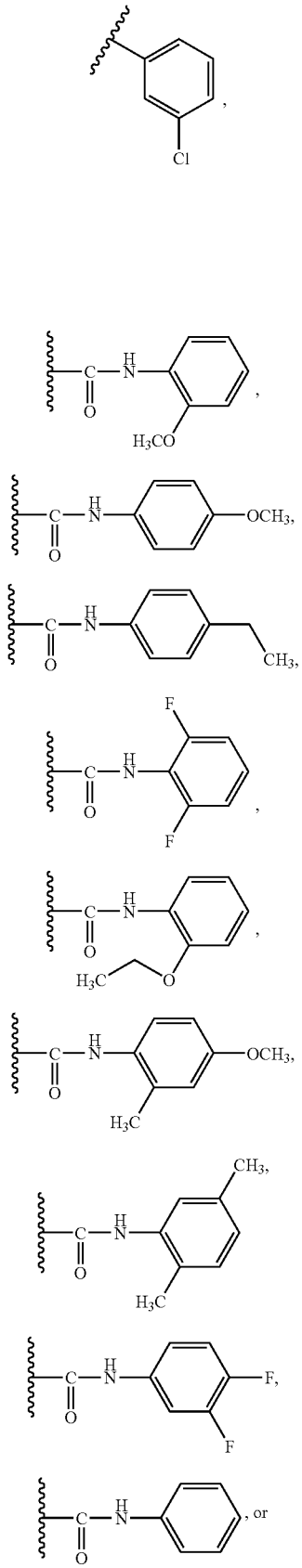
then
R² is not:

-continued
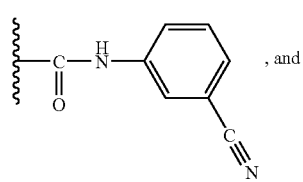, and
wherein for compound of formula IIID:
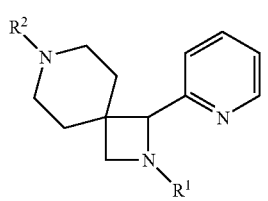 (IIID)
when R¹ is
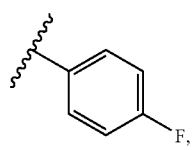,
then
R² is not:
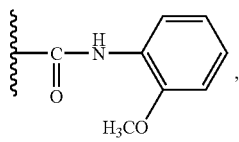,
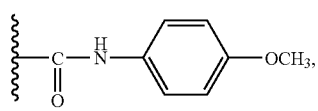,
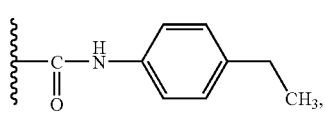,
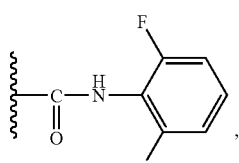,
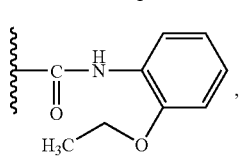,
-continued
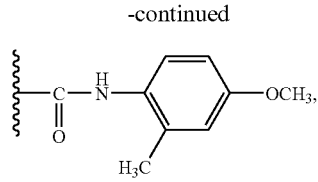,
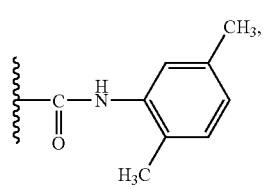,
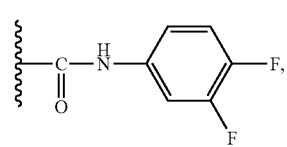,
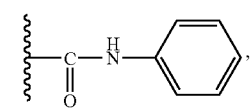,
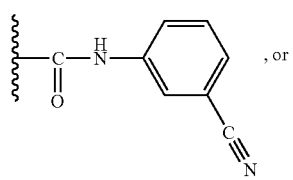, or
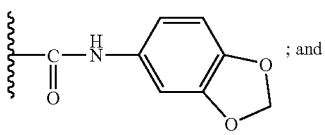; and
wherein for compound of formula IIID:
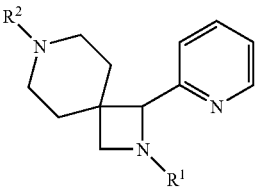 (IIID)
when R¹ is
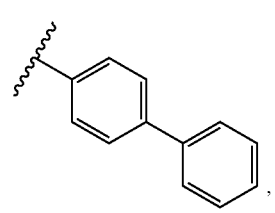, then
R² is not:
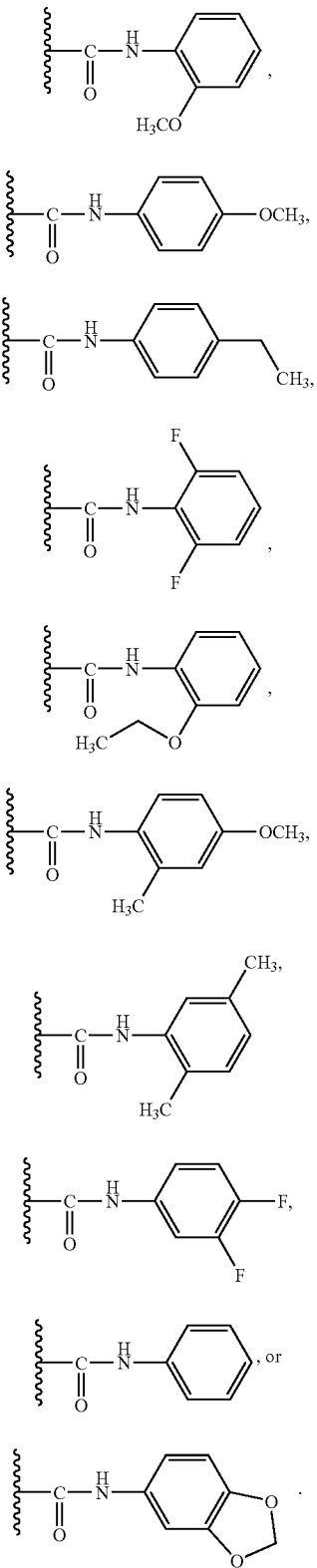
2. The compound of claim 1 wherein R³ is selected from the group consisting of:
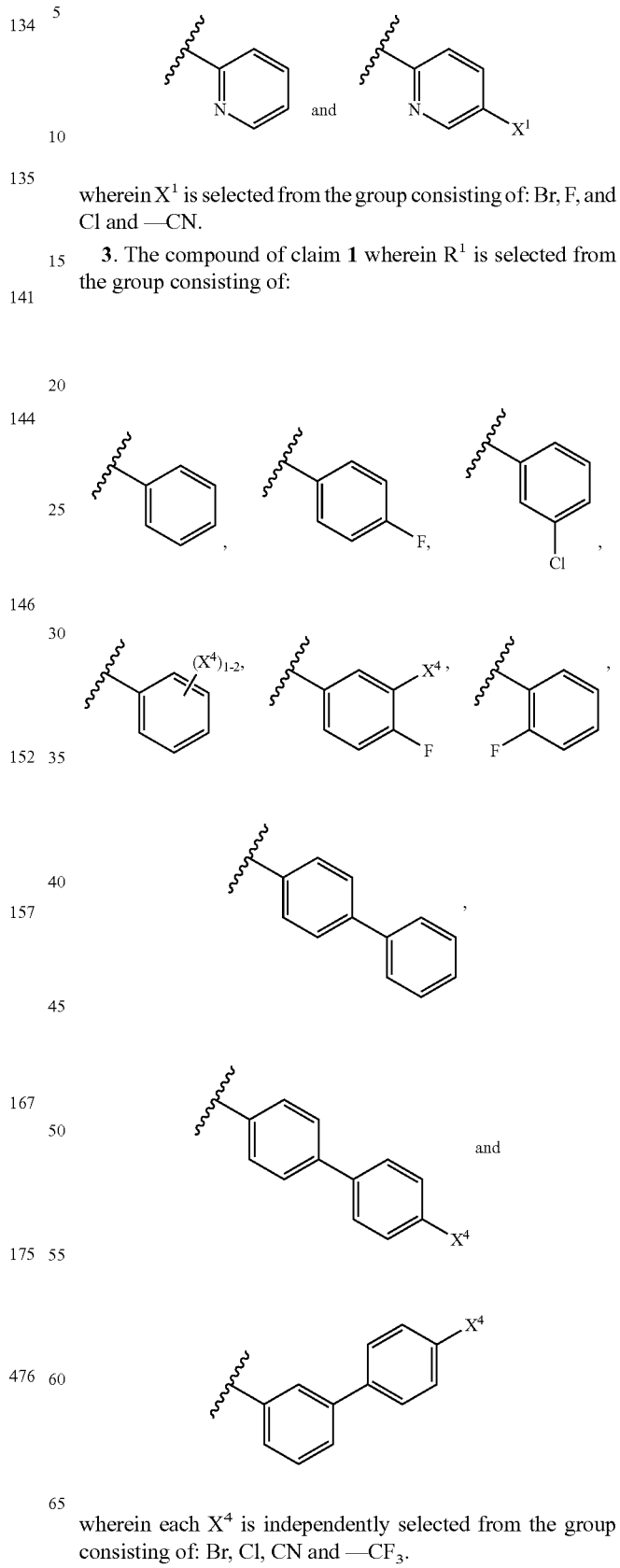
wherein X¹ is selected from the group consisting of: Br, F, and Cl and —CN.
3. The compound of claim 1 wherein R¹ is selected from the group consisting of:
wherein each X⁴ is independently selected from the group consisting of: Br, Cl, CN and —CF₃.

4. A compound of the formula:

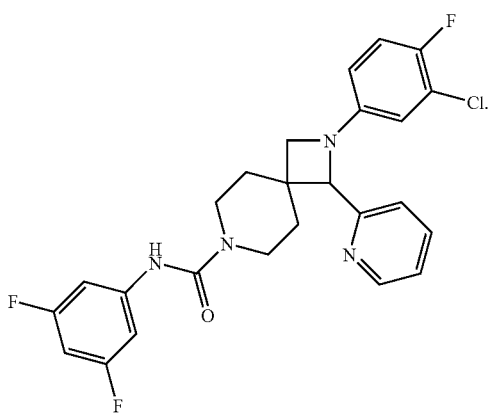

5. A pharmaceutical composition comprising:
at least one compound of claim 1 and a pharmaceutically acceptable carrier.

6. A compound of the formula:

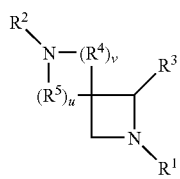
(I)

or a pharmaceutically acceptable salt, solvate, prodrug or stereoisomer thereof, wherein:
$R^1$ is halo substituted phenyl;
$R^2$ is —C(O)NHQ$^A$ wherein Q$^A$ is halo substituted phenyl;
$R^3$ is pyridyl;
Each $R^4$ is —CH$_2$—, and v is 2;
Each $R^5$ is —CH$_2$—, and u is 2; and
wherein for compounds of formula IIIC:

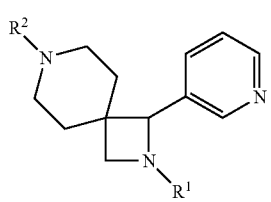
(IIIC)

when $R^1$ is

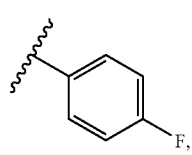
46 then
$R^2$ is not:

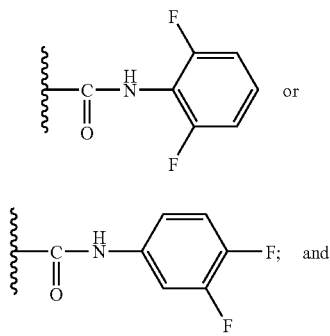
144 or

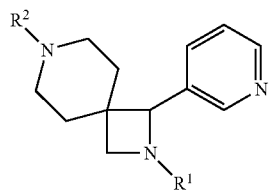
167 and wherein for compounds of formula IIIC:

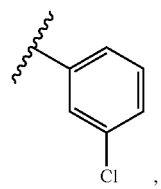
(IIIC)

when $R^1$ is

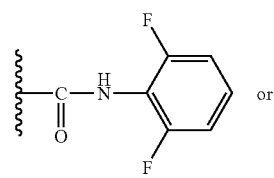
47 then
$R^2$ is not:

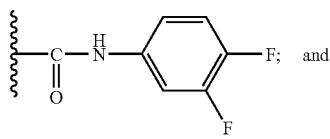
144 or

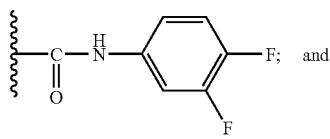
167 and wherein for compounds of formula IIID:
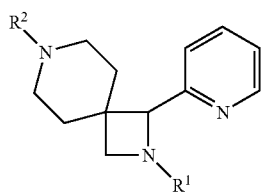
(IIID)
when R¹ is
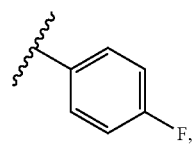
then
R² is not:
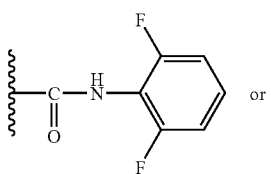
144
or
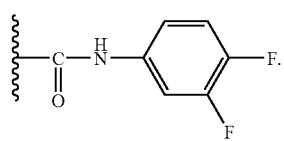
167
* * * * *